(12) United States Patent
Inouye et al.

(10) Patent No.: US 9,075,058 B2
(45) Date of Patent: Jul. 7, 2015

---

(54) COELENTERAZINE ANALOGUES AND COELENTERAMIDE ANALOGUES

(71) Applicants: JNC Corporation, Chiyoda-ku, Tokyo (JP); National University Corporation Tokyo Medical and Dental University, Bunyo-ku, Tokyo (JP)

(72) Inventors: Satoshi Inouye, Yokohama (JP); Yuiko Sahara, Yokohama (JP); Takamitsu Hosoya, Bunkyo-ku (JP)

(73) Assignees: JNC CORPORATION, Tokyo (JP); NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 0 days.

(21) Appl. No.: 14/609,539

(22) Filed: Jan. 30, 2015

(65) Prior Publication Data

US 2015/0153344 A1    Jun. 4, 2015

Related U.S. Application Data

(62) Division of application No. 14/324,962, filed on Jul. 7, 2014, which is a division of application No. 14/095,421, filed on Dec. 3, 2013, now Pat. No. 8,883,432, which is a division of application No. 13/080,385, filed on Apr. 5, 2011, now Pat. No. 8,642,281.

(30) Foreign Application Priority Data

Apr. 6, 2010    (JP) ................. 2010-088175

(51) Int. Cl.
| | | |
|---|---|---|
| *C12N 9/96* | (2006.01) | |
| *G01N 33/53* | (2006.01) | |
| *C12Q 1/66* | (2006.01) | |
| *C12Q 1/68* | (2006.01) | |
| *C07D 241/12* | (2006.01) | |
| *G01N 33/573* | (2006.01) | |
| *C07D 241/20* | (2006.01) | |
| *C07D 409/04* | (2006.01) | |
| *C07D 495/04* | (2006.01) | |
| *C07D 495/14* | (2006.01) | |
| *C07D 409/14* | (2006.01) | |
| *G01N 21/64* | (2006.01) | |

(52) U.S. Cl.
CPC ............ *G01N 33/573* (2013.01); *C07D 241/20* (2013.01); *C07D 409/04* (2013.01); *C07D 495/04* (2013.01); *C07D 495/14* (2013.01); *C07D 409/14* (2013.01); *G01N 21/6428* (2013.01); *G01N 2333/90241* (2013.01); *G01N 2333/43595* (2013.01)

(58) Field of Classification Search
USPC .................. 544/336; 435/6.11, 7.1, 8, 188
See application file for complete search history.

(56) References Cited

U.S. PATENT DOCUMENTS

| | | |
|---|---|---|
| 2004/0219527 A1 | 11/2004 | Golz et al. |
| 2005/0054838 A1 | 3/2005 | Otsuka et al. |
| 2006/0023432 A1 | 2/2006 | Hockel et al. |
| 2006/0234324 A1 | 10/2006 | Inouye et al. |
| 2006/0246534 A1 | 11/2006 | Inouye et al. |
| 2008/0002038 A1 | 1/2008 | Suwa |
| 2008/0020384 A1 | 1/2008 | Ohmiya et al. |
| 2011/0288280 A1 | 11/2011 | Hosoya et al. |
| 2012/0035070 A1 | 2/2012 | Inouye et al. |

FOREIGN PATENT DOCUMENTS

| | | |
|---|---|---|
| EP | 1666488 A1 | 6/2006 |
| GB | 2426761 A | 12/2006 |
| JP | 2005-073533 A | 3/2005 |
| JP | 2005-515977 A | 6/2005 |
| JP | 2006-271327 A | 10/2006 |
| JP | 2006-0308501 A | 11/2006 |
| JP | 2008-000073 A | 1/2008 |
| JP | 2008-000074 A | 1/2008 |
| JP | 2008-026298 A | 2/2008 |
| JP | 2008-054689 A | 3/2008 |
| WO | 03040100 A1 | 5/2003 |
| WO | 2006051311 A1 | 5/2006 |
| WO | 2010090318 A | 8/2010 |
| WO | 2010090319 A1 | 8/2010 |

OTHER PUBLICATIONS

Office Action issued for the corresponding JP application No. 2010-088175 on Jun. 3, 2014 with English translation.
Maciej Adamozyk et al., "Synthesis of 3,7-dihydromidazol[1,2]pyrazine-3-ones and their chemiluminescent properties" Tetrahedron, vol. 59, No. 41, 2003, pp. 8129-8142.
Osamu Shimomura et al., "The relative rate of aequorin regeneration from apoaeguorin and coelenterazine analogues", Biochemical Journal, vol. 296, No. 3, 1993, pp. 549-551.
Search Report mailed Jul. 21, 2011 issued in GB Application No. 1105683.5.
Great Britain Search Report issued Dec. 14, 2011 issued in GB Application No. 1105683.5.
Shimomura, In: "The Jellyfish Aequorea and Other Luminous Coelenterates", in Bioluminescence, Chemical Principles and Methods (2006) pp. 90-158, World Scientific Pub. Co.
Shimomura et al. "Extraction, Purification and Properties of Aequorin, a Bioluminescent Protein from the Luminous Hydromedusam, Aequorea", (Jun. 1962) J. Cell. Comp, Physiol. 59, pp. 223-239.

(Continued)

*Primary Examiner* — Kristin Vajda
(74) *Attorney, Agent, or Firm* — Drinker Biddle & Reath LLP

(57) ABSTRACT

Coelenterazine analogs with different luminescence properties from conventional ones and coelenteramide analogs with different fluorescence properties from conventional ones have been desired. The invention provides coelenterazine analogs modified at the 8-position of coelenterazine and coelenteramide analogs modified at the 2- or 3-position of coelenteramide.

9 Claims, 8 Drawing Sheets
(1 of 8 Drawing Sheet(s) Filed in Color)

(56) References Cited

OTHER PUBLICATIONS

Head et al. "The crystal structure of the photoprotein aequorin at 2.3 Å resolution", (May 2000) Nature 405, pp. 372-376.

Inouye et al. "Cloning and sequence analysis of cDNA for the luminescent protein aequorin", (Jan. 1985)Proc. Natl. Acad. Sci. USA. 82, pp. 3154-3158.

Shimomura & Johnson, "Structure of Light-Emitting Moiety of Aequorin", (1972) Biochemistry 11, pp. 1602-1608.

Shimomura & Johnson, "Chemical Nature of the Light Emitter in Bioluminescence of Aequorin", (1973) Tetrahedron Lett., V. 31, pp. 2963-2966.

Shimomura & Johnson, "Regeneration of the photoprotein aequorin", (1975) Nature 256, pp. 236-238.

Shimomura, "Cause of spectral variation in the luminescence of semissynthetic aequorins", (1995) Biochem. J. 306, pp. 537-543.

Inouye, "Blue fluorescent protein from the calcium-sensitive photoprotein aequorin is a heat resistant enzyme, catalyzing the oxidation of cóelenterazine", (Oct. 2004) FEBS Lett. 577, pp. 105-110.

Inouye et al "Expression of Apoaequorin Complementary DNA in *Escherichia coli*", (Jul. 1986) Biochemistry 25, pp. 8425-8429.

Inouye et al. "Overexpression and Purification of the Recombinant Ca2+—Building Protein, Apoaequorin1", (1989) J. Biochem. 105, pp. 473-477.

Shimomura & Inouye, "The in Situ Regeneration and Extraction of Recombinant Aequorin from *Escherichia coli* Cells and the Purfication of Extracted Aequorin", (Feb. 199) Protein Express. Purif. 16, pp. 91-95.

Shimomura et al. "Recombinant aequorin and recombinant semi-synthetic aequorins", (1990) Biochem. J. 270, pp. 309-312.

Shimomura et al. "Semi-synthetic aequorin", (1988) Biochem. J. 251, pp. 405-410.

Shimomura et al. "Semi-synthetic aequorins with improved sensitivity to Ca2+ ions", (1989) Biochem. J. 261, pp. 913-920.

Inouye & Shimomura, "The Use of Renilla Luciferase, Oplophorus Luciferase, and Apoaequorin as Bioluminescent Reporter Protein in the Presence of Coelenterazine Analogues as Substate", (1997) Biochem. Biophys. Res. Commun. 233, pp. 349-353.

Toma et al. "The crystal structure of semi-synthetic aequorins", (2005) Protein Science 14, pp. 409-416.

Ohashi et al. "NMR Analysis of the Mq2+-Binding Properties of Aequorin, a Ca 2+-Binding Photoprotein", (2005) J. Biochem. 138, pp. 613-620.

Inouye & Sasaki, "Blue fluorescent protein from the calcium-sensitive photoprotein aequorin: Catalytic properties for the oxidation of coelenterazine as an oxygenase", (Mar. 2008) FEBS Lett. 580, pp. 1977-1982.

Inouye & Sasaki, "Imidazole-assisted catalysis of luminescence reation in blue fluorescent protein from the photoprotein aequorin", (Jan. 2007) Biochem, Biophys. Res. Commun. 354, pp. 650-655.

Inouye & Hosoya, "Reconstitution of blue fluorescent protein from recombinant apoaequorin and synthetic coelenteramide", (2009) Biochem. Biophys. Res. Commun. 386, pp. 617-622.

SEQUENCE LISTING

```
<160> NUMBER OF SEQ ID NOS: 12

<210> SEQ ID NO 1
<211> LENGTH: 591
<212> TYPE: DNA
<213> ORGANISM: Aequorea victoria
<220> FEATURE:
<221> NAME/KEY: CDS
<222> LOCATION: (1)..(591)

<400> SEQUENCE: 1 atg aca agc aaa caa tac tca gtc aag ctt aca tca gac ttc gac aac        48
Met Thr Ser Lys Gln Tyr Ser Val Lys Leu Thr Ser Asp Phe Asp Asn
1               5                  10                  15 cca aga tgg att gga cga cac aag cat atg ttc aat ttc ctt gat gtc        96
Pro Arg Trp Ile Gly Arg His Lys His Met Phe Asn Phe Leu Asp Val
            20                  25                  30 aac cac aat gga aaa atc tct ctt gac gag atg gtc tac aag gca tct       144
Asn His Asn Gly Lys Ile Ser Leu Asp Glu Met Val Tyr Lys Ala Ser
        35                  40                  45 gat att gtc atc aat aac ctt gga gca aca cct gag caa gcc aaa cga       192
Asp Ile Val Ile Asn Asn Leu Gly Ala Thr Pro Glu Gln Ala Lys Arg
    50                  55                  60 cac aaa gat gct gta gaa gcc ttc ttc gga gga gct gga atg aaa tat       240
His Lys Asp Ala Val Glu Ala Phe Phe Gly Gly Ala Gly Met Lys Tyr
65                  70                  75                  80 ggt gtg gaa act gat tgg cct gca tat att gaa gga tgg aaa aaa ttg       288
Gly Val Glu Thr Asp Trp Pro Ala Tyr Ile Glu Gly Trp Lys Lys Leu
                85                  90                  95 gct act gat gaa ttg gag aaa tac gcc aaa aac gaa cca acg ctc atc       336
Ala Thr Asp Glu Leu Glu Lys Tyr Ala Lys Asn Glu Pro Thr Leu Ile
            100                 105                 110 cgt ata tgg ggt gat gct ttg ttt gat atc gtt gac aaa gat caa aat       384
Arg Ile Trp Gly Asp Ala Leu Phe Asp Ile Val Asp Lys Asp Gln Asn
        115                 120                 125 gga gcc att aca ctg gat gaa tgg aaa gca tac acc aaa gct gct ggt       432
Gly Ala Ile Thr Leu Asp Glu Trp Lys Ala Tyr Thr Lys Ala Ala Gly
    130                 135                 140 atc atc caa tca tca gaa gat tgc gag gaa aca ttc aga gtg tgc gat       480
Ile Ile Gln Ser Ser Glu Asp Cys Glu Glu Thr Phe Arg Val Cys Asp
145                 150                 155                 160 att gat gaa agt gga caa ctc gat gtt gat gag atg aca aga caa cat       528
Ile Asp Glu Ser Gly Gln Leu Asp Val Asp Glu Met Thr Arg Gln His
                165                 170                 175 tta gga ttt tgg tac acc atg gat cct gct tgc gaa aag ctc tac ggt       576
Leu Gly Phe Trp Tyr Thr Met Asp Pro Ala Cys Glu Lys Leu Tyr Gly
            180                 185                 190 gga gct gtc ccc taa                                                   591
Gly Ala Val Pro
        195

<210> SEQ ID NO 2
```

```
<211> LENGTH: 196
<212> TYPE: PRT
<213> ORGANISM: Aequorea victoria

<400> SEQUENCE: 2

Met Thr Ser Lys Gln Tyr Ser Val Lys Leu Thr Ser Asp Phe Asp Asn
1               5                   10                  15

Pro Arg Trp Ile Gly Arg His Lys His Met Phe Asn Phe Leu Asp Val
            20                  25                  30

Asn His Asn Gly Lys Ile Ser Leu Asp Glu Met Val Tyr Lys Ala Ser
        35                  40                  45

Asp Ile Val Ile Asn Asn Leu Gly Ala Thr Pro Glu Gln Ala Lys Arg
    50                  55                  60

His Lys Asp Ala Val Glu Ala Phe Phe Gly Gly Ala Gly Met Lys Tyr
65                  70                  75                  80

Gly Val Glu Thr Asp Trp Pro Ala Tyr Ile Glu Gly Trp Lys Lys Leu
                85                  90                  95

Ala Thr Asp Glu Leu Glu Lys Tyr Ala Lys Asn Glu Pro Thr Leu Ile
            100                 105                 110

Arg Ile Trp Gly Asp Ala Leu Phe Asp Ile Val Asp Lys Asp Gln Asn
        115                 120                 125

Gly Ala Ile Thr Leu Asp Glu Trp Lys Ala Tyr Thr Lys Ala Ala Gly
    130                 135                 140

Ile Ile Gln Ser Ser Glu Asp Cys Glu Glu Thr Phe Arg Val Cys Asp
145                 150                 155                 160

Ile Asp Glu Ser Gly Gln Leu Asp Val Asp Glu Met Thr Arg Gln His
                165                 170                 175

Leu Gly Phe Trp Tyr Thr Met Asp Pro Ala Cys Glu Lys Leu Tyr Gly
            180                 185                 190

Gly Ala Val Pro
        195

<210> SEQ ID NO 3
<211> LENGTH: 597
<212> TYPE: DNA
<213> ORGANISM: Clytia gregaria
<220> FEATURE:
<221> NAME/KEY: CDS
<222> LOCATION: (1)..(597)

<400> SEQUENCE: 3 atg gct gac act gca tca aaa tac gcc gtc aaa ctc aga ccc aac ttc      48
Met Ala Asp Thr Ala Ser Lys Tyr Ala Val Lys Leu Arg Pro Asn Phe
1               5                   10                  15 gac aac cca aaa tgg gtc aac aga cac aaa ttt atg ttc aac ttt ttg      96
Asp Asn Pro Lys Trp Val Asn Arg His Lys Phe Met Phe Asn Phe Leu
            20                  25                  30 gac att aac ggc gac gga aaa atc act ttg gat gaa atc gtc tcc aaa     144
Asp Ile Asn Gly Asp Gly Lys Ile Thr Leu Asp Glu Ile Val Ser Lys
        35                  40                  45 gct tcg gat gac att tgc gcc aaa ctt gga gca aca cca gaa cag acc     192
Ala Ser Asp Asp Ile Cys Ala Lys Leu Gly Ala Thr Pro Glu Gln Thr
    50                  55                  60 aaa cgt cac cag gat gct gtc gaa gct ttc ttc aaa aag att ggt atg     240
Lys Arg His Gln Asp Ala Val Glu Ala Phe Phe Lys Lys Ile Gly Met
65                  70                  75                  80 gat tat ggt aaa gaa gtc gaa ttc cca gct ttt gtt gat gga tgg aaa     288
Asp Tyr Gly Lys Glu Val Glu Phe Pro Ala Phe Val Asp Gly Trp Lys
                85                  90                  95
```

```
gaa ctg gcc aat tat gac ttg aaa ctt tgg tct caa aac aag aaa tct      336
Glu Leu Ala Asn Tyr Asp Leu Lys Leu Trp Ser Gln Asn Lys Lys Ser
            100                 105                 110 ttg atc cgc gac tgg gga gaa gct gtt ttc gac att ttt gac aaa gac      384
Leu Ile Arg Asp Trp Gly Glu Ala Val Phe Asp Ile Phe Asp Lys Asp
        115                 120                 125 gga agt ggc tca atc agt ttg gac gaa tgg aag gct tat gga cga atc      432
Gly Ser Gly Ser Ile Ser Leu Asp Glu Trp Lys Ala Tyr Gly Arg Ile
130                 135                 140 tct gga atc tgc tca tca gac gaa gac gcc gaa aag acc ttc aaa cat      480
Ser Gly Ile Cys Ser Ser Asp Glu Asp Ala Glu Lys Thr Phe Lys His
145                 150                 155                 160 tgc gat ttg gac aac agt ggc aaa ctt gat gtt gat gag atg acc aga      528
Cys Asp Leu Asp Asn Ser Gly Lys Leu Asp Val Asp Glu Met Thr Arg
                165                 170                 175 caa cat ttg gga ttc tgg tac acc ttg gac ccc aac gct gat ggt ctt      576
Gln His Leu Gly Phe Trp Tyr Thr Leu Asp Pro Asn Ala Asp Gly Leu
            180                 185                 190 tac ggc aat ttt gtt cct taa                                          597
Tyr Gly Asn Phe Val Pro
        195

<210> SEQ ID NO 4
<211> LENGTH: 198
<212> TYPE: PRT
<213> ORGANISM: Clytia gregaria

<400> SEQUENCE: 4

Met Ala Asp Thr Ala Ser Lys Tyr Ala Val Lys Leu Arg Pro Asn Phe
 1               5                  10                  15

Asp Asn Pro Lys Trp Val Asn Arg His Lys Phe Met Phe Asn Phe Leu
            20                  25                  30

Asp Ile Asn Gly Asp Gly Lys Ile Thr Leu Asp Glu Ile Val Ser Lys
        35                  40                  45

Ala Ser Asp Asp Ile Cys Ala Lys Leu Gly Ala Thr Pro Glu Gln Thr
    50                  55                  60

Lys Arg His Gln Asp Ala Val Glu Ala Phe Phe Lys Lys Ile Gly Met
65                  70                  75                  80

Asp Tyr Gly Lys Glu Val Glu Phe Pro Ala Phe Val Asp Gly Trp Lys
                85                  90                  95

Glu Leu Ala Asn Tyr Asp Leu Lys Leu Trp Ser Gln Asn Lys Lys Ser
            100                 105                 110

Leu Ile Arg Asp Trp Gly Glu Ala Val Phe Asp Ile Phe Asp Lys Asp
        115                 120                 125

Gly Ser Gly Ser Ile Ser Leu Asp Glu Trp Lys Ala Tyr Gly Arg Ile
130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
            180                 185                 190

Tyr Gly Asn Phe Val Pro
        195

<210> SEQ ID NO 5
<211> LENGTH: 657
```

```
<212> TYPE: DNA
<213> ORGANISM: Clytia gregaria
<220> FEATURE:
<221> NAME/KEY: CDS
<222> LOCATION: (1)..(657)

<400> SEQUENCE: 5 atg tcg gct tta gct gca aga tca aga ttg caa cgc aca gca aat ttt    48
Met Ser Ala Leu Ala Ala Arg Ser Arg Leu Gln Arg Thr Ala Asn Phe
1               5                   10                  15 cac acc agc ata ctg ttg gct aca gat tca aaa tac gcg gtc aaa ctc    96
His Thr Ser Ile Leu Leu Ala Thr Asp Ser Lys Tyr Ala Val Lys Leu
                20                  25                  30 gat cct gat ttt gca aat cca aaa tgg atc aac aga cac aaa ttt atg   144
Asp Pro Asp Phe Ala Asn Pro Lys Trp Ile Asn Arg His Lys Phe Met
            35                  40                  45 ttc aac ttt ttg gac ata aac ggt aat ggg aaa atc aca tta gat gaa   192
Phe Asn Phe Leu Asp Ile Asn Gly Asn Gly Lys Ile Thr Leu Asp Glu
50                  55                  60 atc gtc tcc aaa gct tca gac gac att tgt gct aaa ctg gat gca aca   240
Ile Val Ser Lys Ala Ser Asp Asp Ile Cys Ala Lys Leu Asp Ala Thr
65                  70                  75                  80 cca gaa cag acc aaa cgt cac cag gat gct gtt gaa gcg ttt ttc aag   288
Pro Glu Gln Thr Lys Arg His Gln Asp Ala Val Glu Ala Phe Phe Lys
                85                  90                  95 aaa atg ggc atg gat tat ggt aaa gaa gtt gca ttc cca gaa ttt att   336
Lys Met Gly Met Asp Tyr Gly Lys Glu Val Ala Phe Pro Glu Phe Ile
            100                 105                 110 aag gga tgg gaa gag ttg gcc gaa cac gac ttg gaa ctc tgg tct caa   384
Lys Gly Trp Glu Glu Leu Ala Glu His Asp Leu Glu Leu Trp Ser Gln
        115                 120                 125 aac aaa agt aca ttg atc cgt gaa tgg gga gat gct gtt ttc gac att   432
Asn Lys Ser Thr Leu Ile Arg Glu Trp Gly Asp Ala Val Phe Asp Ile
    130                 135                 140 ttc gac aaa gac gca agt ggc tca atc agt tta gac gaa tgg aag gct   480
Phe Asp Lys Asp Ala Ser Gly Ser Ile Ser Leu Asp Glu Trp Lys Ala
145                 150                 155                 160 tac gga cga atc tct gga atc tgt cca tca gac gaa gac gct gag aag   528
Tyr Gly Arg Ile Ser Gly Ile Cys Pro Ser Asp Glu Asp Ala Glu Lys
                165                 170                 175 acg ttc aaa cat tgt gat ttg gac aac agt ggc aaa ctt gat gtt gat   576
Thr Phe Lys His Cys Asp Leu Asp Asn Ser Gly Lys Leu Asp Val Asp
            180                 185                 190 gag atg acc agg caa cat tta ggc ttc tgg tac aca ttg gat cca act   624
Glu Met Thr Arg Gln His Leu Gly Phe Trp Tyr Thr Leu Asp Pro Thr
        195                 200                 205 tct gat ggt ctt tat ggc aat ttt gtt ccc taa                       657
Ser Asp Gly Leu Tyr Gly Asn Phe Val Pro
    210                 215

<210> SEQ ID NO 6
<211> LENGTH: 218
<212> TYPE: PRT
<213> ORGANISM: Clytia gregaria

<400> SEQUENCE: 6

Met Ser Ala Leu Ala Ala Arg Ser Arg Leu Gln Arg Thr Ala Asn Phe
1               5                   10                  15

His Thr Ser Ile Leu Leu Ala Thr Asp Ser Lys Tyr Ala Val Lys Leu
                20                  25                  30

Asp Pro Asp Phe Ala Asn Pro Lys Trp Ile Asn Arg His Lys Phe Met
```

```
                35                  40                  45
Phe Asn Phe Leu Asp Ile Asn Gly Asn Gly Lys Ile Thr Leu Asp Glu
    50                  55                  60

Ile Val Ser Lys Ala Ser Asp Ile Cys Ala Lys Leu Asp Ala Thr
65                  70                  75                  80

Pro Glu Gln Thr Lys Arg His Gln Asp Ala Val Glu Ala Phe Phe Lys
                85                  90                  95

Lys Met Gly Met Asp Tyr Gly Lys Glu Val Ala Phe Pro Glu Phe Ile
            100                 105                 110

Lys Gly Trp Glu Glu Leu Ala Glu His Asp Leu Glu Leu Trp Ser Gln
        115                 120                 125

Asn Lys Ser Thr Leu Ile Arg Glu Trp Gly Asp Ala Val Phe Asp Ile
    130                 135                 140

Phe Asp Lys Asp Ala Ser Gly Ser Ile Ser Leu Asp Glu Trp Lys Ala
145                 150                 155                 160

Tyr Gly Arg Ile Ser Gly Ile Cys Pro Ser Asp Glu Asp Ala Glu Lys
                165                 170                 175

Thr Phe Lys His Cys Asp Leu Asp Asn Ser Gly Lys Leu Asp Val Asp
            180                 185                 190

Glu Met Thr Arg Gln His Leu Gly Phe Trp Tyr Thr Leu Asp Pro Thr
        195                 200                 205

Ser Asp Gly Leu Tyr Gly Asn Phe Val Pro
    210                 215

<210> SEQ ID NO 7
<211> LENGTH: 597
<212> TYPE: DNA
<213> ORGANISM: Mitrocoma cellularia
<220> FEATURE:
<221> NAME/KEY: CDS
<222> LOCATION: (1)..(597)

<400> SEQUENCE: 7 atg tca atg ggc agc aga tac gca gtc aag ctt acg act gac ttt gat     48
Met Ser Met Gly Ser Arg Tyr Ala Val Lys Leu Thr Thr Asp Phe Asp
1               5                   10                  15 aat cca aaa tgg att gct cga cac aag cac atg ttc aac ttc ctt gac     96
Asn Pro Lys Trp Ile Ala Arg His Lys His Met Phe Asn Phe Leu Asp
                20                  25                  30 atc aat tca aat ggc caa atc aat ctg aat gaa atg gtc cat aag gct    144
Ile Asn Ser Asn Gly Gln Ile Asn Leu Asn Glu Met Val His Lys Ala
            35                  40                  45 tca aac att atc tgc aag aag ctt gga gca aca gaa gaa caa acc aaa    192
Ser Asn Ile Ile Cys Lys Lys Leu Gly Ala Thr Glu Glu Gln Thr Lys
        50                  55                  60 cgt cat caa aag tgt gtc gaa gac ttc ttt ggg gga gct ggt ttg gaa    240
Arg His Gln Lys Cys Val Glu Asp Phe Phe Gly Gly Ala Gly Leu Glu
65                  70                  75                  80 tat gac aaa gat acc aca tgg cct gag tac atc gaa gga tgg aag agg    288
Tyr Asp Lys Asp Thr Thr Trp Pro Glu Tyr Ile Glu Gly Trp Lys Arg
                85                  90                  95 ttg gct aag act gaa ttg gaa agg cat tca aag aat caa gtc aca ttg    336
Leu Ala Lys Thr Glu Leu Glu Arg His Ser Lys Asn Gln Val Thr Leu
            100                 105                 110 atc cga tta tgg ggt gat gct ttg ttc gac atc att gac aaa gat aga    384
Ile Arg Leu Trp Gly Asp Ala Leu Phe Asp Ile Ile Asp Lys Asp Arg
        115                 120                 125 aat gga tcg gtt tcg tta gac gaa tgg atc cag tac act cat tgt gct    432
Asn Gly Ser Val Ser Leu Asp Glu Trp Ile Gln Tyr Thr His Cys Ala
```

```
                Asn Gly Ser Val Ser Leu Asp Glu Trp Ile Gln Tyr Thr His Cys Ala
                    130                 135                 140 ggc atc caa cag tca cgt ggg caa tgc gaa gct aca ttt gca cat tgc       480
Gly Ile Gln Gln Ser Arg Gly Gln Cys Glu Ala Thr Phe Ala His Cys
145                 150                 155                 160 gat tta gat ggt gac ggt aaa ctt gat gtg gac gaa atg aca aga caa       528
Asp Leu Asp Gly Asp Gly Lys Leu Asp Val Asp Glu Met Thr Arg Gln
                165                 170                 175 cat ttg gga ttt tgg tat tcg gtc gac cca act tgt gaa gga ctc tac       576
His Leu Gly Phe Trp Tyr Ser Val Asp Pro Thr Cys Glu Gly Leu Tyr
            180                 185                 190 ggt ggt gct gta cct tat taa                                           597
Gly Gly Ala Val Pro Tyr
            195

<210> SEQ ID NO 8
<211> LENGTH: 198
<212> TYPE: PRT
<213> ORGANISM: Mitrocoma cellularia

<400> SEQUENCE: 8

Met Ser Met Gly Ser Arg Tyr Ala Val Lys Leu Thr Thr Asp Phe Asp
1               5                   10                  15

Asn Pro Lys Trp Ile Ala Arg His Lys His Met Phe Asn Phe Leu Asp
            20                  25                  30

Ile Asn Ser Asn Gly Gln Ile Asn Leu Asn Glu Met Val His Lys Ala
        35                  40                  45

Ser Asn Ile Ile Cys Lys Lys Leu Gly Ala Thr Glu Glu Gln Thr Lys
50                  55                  60

Arg His Gln Lys Cys Val Glu Asp Phe Phe Gly Gly Ala Gly Leu Glu
65                  70                  75                  80

Tyr Asp Lys Asp Thr Thr Trp Pro Glu Tyr Ile Glu Gly Trp Lys Arg
                85                  90                  95

Leu Ala Lys Thr Glu Leu Glu Arg His Ser Lys Asn Gln Val Thr Leu
            100                 105                 110

Ile Arg Leu Trp Gly Asp Ala Leu Phe Asp Ile Ile Asp Lys Asp Arg
        115                 120                 125

Asn Gly Ser Val Ser Leu Asp Glu Trp Ile Gln Tyr Thr His Cys Ala
    130                 135                 140

Gly Ile Gln Gln Ser Arg Gly Gln Cys Glu Ala Thr Phe Ala His Cys
145                 150                 155                 160

Asp Leu Asp Gly Asp Gly Lys Leu Asp Val Asp Glu Met Thr Arg Gln
                165                 170                 175

His Leu Gly Phe Trp Tyr Ser Val Asp Pro Thr Cys Glu Gly Leu Tyr
            180                 185                 190

Gly Gly Ala Val Pro Tyr
            195

<210> SEQ ID NO 9
<211> LENGTH: 588
<212> TYPE: DNA
<213> ORGANISM: Obelia longissima
<220> FEATURE:
<221> NAME/KEY: CDS
<222> LOCATION: (1)..(588)

<400> SEQUENCE: 9 atg tct tca aaa tac gca gtt aaa ctc aag act gac ttt gat aat cca        48
Met Ser Ser Lys Tyr Ala Val Lys Leu Lys Thr Asp Phe Asp Asn Pro
1               5                   10                  15
```

```
                1               5                   10                  15
      cga tgg atc aaa aga cac aag cac atg ttt gat ttc ctc gac atc aat        96
      Arg Trp Ile Lys Arg His Lys His Met Phe Asp Phe Leu Asp Ile Asn
                      20                  25                  30 gga aat gga aaa atc acc ctc gat gaa att gtg tcc aag gca tct gat       144
      Gly Asn Gly Lys Ile Thr Leu Asp Glu Ile Val Ser Lys Ala Ser Asp
                      35                  40                  45 gac ata tgt gcc aag ctc gaa gcc aca cca gaa caa aca aaa cgc cat       192
      Asp Ile Cys Ala Lys Leu Glu Ala Thr Pro Glu Gln Thr Lys Arg His
              50                  55                  60 caa gtt tgt gtt gaa gct ttc ttt aga gga tgt gga atg gaa tat ggt       240
      Gln Val Cys Val Glu Ala Phe Phe Arg Gly Cys Gly Met Glu Tyr Gly
      65                  70                  75                  80 aaa gaa att gcc ttc cca caa ttc ctc gat gga tgg aaa caa ttg gcg       288
      Lys Glu Ile Ala Phe Pro Gln Phe Leu Asp Gly Trp Lys Gln Leu Ala
                              85                  90                  95 act tca gaa ctc aag aaa tgg gca aga aac gaa cct act ctc att cgt       336
      Thr Ser Glu Leu Lys Lys Trp Ala Arg Asn Glu Pro Thr Leu Ile Arg
                      100                 105                 110 gaa tgg gga gat gct gtc ttt gat att ttc gac aaa gat gga agt ggt       384
      Glu Trp Gly Asp Ala Val Phe Asp Ile Phe Asp Lys Asp Gly Ser Gly
                      115                 120                 125 aca atc act ttg gac gaa tgg aaa gct tat gga aaa atc tct ggt atc       432
      Thr Ile Thr Leu Asp Glu Trp Lys Ala Tyr Gly Lys Ile Ser Gly Ile
              130                 135                 140 tct cca tca caa gaa gat tgt gaa gcg aca ttt cga cat tgc gat ttg       480
      Ser Pro Ser Gln Glu Asp Cys Glu Ala Thr Phe Arg His Cys Asp Leu
      145                 150                 155                 160 gac aac agt ggt gac ctt gat gtt gac gag atg aca aga caa cat ctt       528
      Asp Asn Ser Gly Asp Leu Asp Val Asp Glu Met Thr Arg Gln His Leu
                              165                 170                 175 gga ttc tgg tac act ttg gac cca gaa gct gat ggt ctc tat ggc aac       576
      Gly Phe Trp Tyr Thr Leu Asp Pro Glu Ala Asp Gly Leu Tyr Gly Asn
                      180                 185                 190 gga gtt ccc taa                                                       588
      Gly Val Pro
              195

<210> SEQ ID NO 10
<211> LENGTH: 195
<212> TYPE: PRT
<213> ORGANISM: Obelia longissima

<400> SEQUENCE: 10

Met Ser Ser Lys Tyr Ala Val Lys Leu Lys Thr Asp Phe Asp Asn Pro
1               5                   10                  15

Arg Trp Ile Lys Arg His Lys His Met Phe Asp Phe Leu Asp Ile Asn
                20                  25                  30

Gly Asn Gly Lys Ile Thr Leu Asp Glu Ile Val Ser Lys Ala Ser Asp
            35                  40                  45

Asp Ile Cys Ala Lys Leu Glu Ala Thr Pro Glu Gln Thr Lys Arg His
        50                  55                  60

Gln Val Cys Val Glu Ala Phe Phe Arg Gly Cys Gly Met Glu Tyr Gly
65                  70                  75                  80

Lys Glu Ile Ala Phe Pro Gln Phe Leu Asp Gly Trp Lys Gln Leu Ala
                85                  90                  95

Thr Ser Glu Leu Lys Lys Trp Ala Arg Asn Glu Pro Thr Leu Ile Arg
            100                 105                 110
```

```
Glu Trp Gly Asp Ala Val Phe Asp Ile Phe Asp Lys Asp Gly Ser Gly
            115                 120                 125

Thr Ile Thr Leu Asp Glu Trp Lys Ala Tyr Gly Lys Ile Ser Gly Ile
    130                 135                 140

Ser Pro Ser Gln Glu Asp Cys Glu Ala Thr Phe Arg His Cys Asp Leu
145                 150                 155                 160

Asp Asn Ser Gly Asp Leu Asp Val Asp Glu Met Thr Arg Gln His Leu
                165                 170                 175

Gly Phe Trp Tyr Thr Leu Asp Pro Glu Ala Asp Gly Leu Tyr Gly Asn
            180                 185                 190

Gly Val Pro
        195

<210> SEQ ID NO 11
<211> LENGTH: 627
<212> TYPE: DNA
<213> ORGANISM: Beroe abyssicola
<220> FEATURE:
<221> NAME/KEY: CDS
<222> LOCATION: (1)..(627)

<400> SEQUENCE: 11
```

| | | | | | | | | | | | | | | | | |
|---|---|---|---|---|---|---|---|---|---|---|---|---|---|---|---|---|
| atg | act | gaa | cgt | ctg | aac | gag | cag | aac | aac | gag | agt | tac | cgc | tac | ctg | 48 |
| Met | Thr | Glu | Arg | Leu | Asn | Glu | Gln | Asn | Asn | Glu | Ser | Tyr | Arg | Tyr | Leu | |
| 1 | | | | 5 | | | | | 10 | | | | | 15 | | |
| aga | agc | gtg | gga | aac | cag | tgg | cag | ttc | aac | gta | gag | gac | ctc | cac | ccc | 96 |
| Arg | Ser | Val | Gly | Asn | Gln | Trp | Gln | Phe | Asn | Val | Glu | Asp | Leu | His | Pro | |
| | | | 20 | | | | | 25 | | | | | 30 | | | |
| aag | atg | ttg | tcc | cgt | ctc | tac | aag | aga | ttc | gat | act | ttc | gat | cta | gac | 144 |
| Lys | Met | Leu | Ser | Arg | Leu | Tyr | Lys | Arg | Phe | Asp | Thr | Phe | Asp | Leu | Asp | |
| | | 35 | | | | | 40 | | | | | 45 | | | | |
| agt | gac | ggt | aag | atg | gag | atg | gac | gag | gtc | ttg | tac | tgg | ccc | gac | agg | 192 |
| Ser | Asp | Gly | Lys | Met | Glu | Met | Asp | Glu | Val | Leu | Tyr | Trp | Pro | Asp | Arg | |
| | 50 | | | | | 55 | | | | | 60 | | | | | |
| atg | agg | cag | ctg | gta | aac | gct | act | gat | gag | cag | gtt | gag | aag | atg | cgg | 240 |
| Met | Arg | Gln | Leu | Val | Asn | Ala | Thr | Asp | Glu | Gln | Val | Glu | Lys | Met | Arg | |
| 65 | | | | | 70 | | | | | 75 | | | | | 80 | |
| gat | gct | gtg | aga | gtt | ttc | ttt | ttg | cac | aag | gga | gtg | gag | cca | gta | aac | 288 |
| Asp | Ala | Val | Arg | Val | Phe | Phe | Leu | His | Lys | Gly | Val | Glu | Pro | Val | Asn | |
| | | | | 85 | | | | | 90 | | | | | 95 | | |
| ggt | ctc | ctc | aga | gag | gac | tgg | gtg | gaa | gct | aac | aga | gtc | ttc | gct | gag | 336 |
| Gly | Leu | Leu | Arg | Glu | Asp | Trp | Val | Glu | Ala | Asn | Arg | Val | Phe | Ala | Glu | |
| | | | 100 | | | | | 105 | | | | | 110 | | | |
| gct | gag | aga | gaa | aga | gag | cga | cga | gga | gaa | cct | tct | ctt | atc | gca | ctt | 384 |
| Ala | Glu | Arg | Glu | Arg | Glu | Arg | Arg | Gly | Glu | Pro | Ser | Leu | Ile | Ala | Leu | |
| | | 115 | | | | | 120 | | | | | 125 | | | | |
| ctc | tcc | aac | tct | tac | tac | gat | gta | ctg | gat | gat | gac | ggt | gat | ggt | act | 432 |
| Leu | Ser | Asn | Ser | Tyr | Tyr | Asp | Val | Leu | Asp | Asp | Asp | Gly | Asp | Gly | Thr | |
| | 130 | | | | | 135 | | | | | 140 | | | | | |
| gtt | gac | gtc | gat | gaa | tta | aag | acc | atg | atg | aaa | gca | ttt | gat | gtg | ccc | 480 |
| Val | Asp | Val | Asp | Glu | Leu | Lys | Thr | Met | Met | Lys | Ala | Phe | Asp | Val | Pro | |
| 145 | | | | | 150 | | | | | 155 | | | | | 160 | |
| cag | gaa | gct | gcc | tac | acc | ttc | ttc | gag | aag | gca | gac | act | gac | aag | agt | 528 |
| Gln | Glu | Ala | Ala | Tyr | Thr | Phe | Phe | Glu | Lys | Ala | Asp | Thr | Asp | Lys | Ser | |
| | | | | 165 | | | | | 170 | | | | | 175 | | |
| gga | aag | ttg | gag | aga | aca | gaa | cta | gtt | cat | ctc | ttt | aga | aag | ttt | tgg | 576 |
| Gly | Lys | Leu | Glu | Arg | Thr | Glu | Leu | Val | His | Leu | Phe | Arg | Lys | Phe | Trp | |
| | | | 180 | | | | | 185 | | | | | 190 | | | |
| atg | gag | cct | tac | gat | cca | cag | tgg | gac | gga | gtc | tac | gct | tat | aag | tac | 624 |
| Met | Glu | Pro | Tyr | Asp | Pro | Gln | Trp | Asp | Gly | Val | Tyr | Ala | Tyr | Lys | Tyr | |

```
                   195                 200                 205
taa                                                                      627

<210> SEQ ID NO 12
<211> LENGTH: 208
<212> TYPE: PRT
<213> ORGANISM: Beroe abyssicola

<400> SEQUENCE: 12

Met Thr Glu Arg Leu Asn Glu Gln Asn Asn Glu Ser Tyr Arg Tyr Leu
1               5                   10                  15

Arg Ser Val Gly Asn Gln Trp Gln Phe Asn Val Glu Asp Leu His Pro
            20                  25                  30

Lys Met Leu Ser Arg Leu Tyr Lys Arg Phe Asp Thr Phe Asp Leu Asp
        35                  40                  45

Ser Asp Gly Lys Met Glu Met Asp Glu Val Leu Tyr Trp Pro Asp Arg
    50                  55                  60

Met Arg Gln Leu Val Asn Ala Thr Asp Glu Gln Val Glu Lys Met Arg
65                  70                  75                  80

Asp Ala Val Arg Val Phe Phe Leu His Lys Gly Val Glu Pro Val Asn
                85                  90                  95

Gly Leu Leu Arg Glu Asp Trp Val Glu Ala Asn Arg Val Phe Ala Glu
            100                 105                 110

Ala Glu Arg Glu Arg Glu Arg Arg Gly Glu Pro Ser Leu Ile Ala Leu
            115                 120                 125

Leu Ser Asn Ser Tyr Tyr Asp Val Leu Asp Asp Asp Gly Asp Gly Thr
130                 135                 140

Val Asp Val Asp Glu Leu Lys Thr Met Met Lys Ala Phe Asp Val Pro
145                 150                 155                 160

Gln Glu Ala Ala Tyr Thr Phe Phe Glu Lys Ala Asp Thr Asp Lys Ser
                165                 170                 175

Gly Lys Leu Glu Arg Thr Glu Leu Val His Leu Phe Arg Lys Phe Trp
            180                 185                 190

Met Glu Pro Tyr Asp Pro Gln Trp Asp Gly Val Tyr Ala Tyr Lys Tyr
            195                 200                 205
```

COELENTERAZINE ANALOGUES AND COELENTERAMIDE ANALOGUES

CROSS REFERENCE TO RELATED APPLICATIONS

This application is a divisional application of U.S. application Ser. No. 14/324,962 filed Jul. 7, 2014, which is a divisional application of U.S. application Ser. No. 14/095,421, filed Dec. 3, 2013, now U.S. Pat. No. 8,883,432, which is a divisional application of U.S. application Ser. No. 13/080,385, filed on Apr. 5, 2011, now U.S. Pat. No. 8,642,281, which claims benefit of Japanese Patent Application No. 2010-088175, filed on Apr. 6, 2010 under 35 U.S.C. §119.

REFERENCE TO A SEQUENCE LISTING

A Sequence Listing containing SEQ ID NOs: 1-12 is incorporated herein by reference.

TECHNICAL FIELD

The present invention relates to coelenterazine analog, coelenteramide analog, calcium-binding photoprotein, fluorescent protein, and the like.

BACKGROUND ART

A calcium-binding photoprotein is one of the proteins responsible for bioluminescence. This photoprotein emits light upon specific interaction with $Ca^2$. The calcium-binding photoprotein is a complex of a protein having the catalytic function of oxygenation and a peroxide of luciferin as a light emitting substrate. In the calcium-binding photoprotein, the protein having the catalytic function of oxygenation refers to as an apoprotein. The peroxide of a luciferin is coelenterazine peroxide (2-hydroperoxycoelenterazine). The calcium-binding photoprotein including aequorin, clytin-I, clytin-II, mitrocomin, obelin, etc. are known and present in coelenterates. Among these photoproteins, aequorin is a photoprotein isolated from the luminous jellyfish *Aequorea aequorea* (1: Shimomura, In: *Bioluminescence. Chemical Principles* and *Methods*, (2006) pp 90-158, World Scientific Pub. Co.; 2: Shimomura et al., (1962) *J. Cell. Comp. Physiol.* 59, pp 223-240). Aequorin is a non-covalent complex of apoaequorin (21.4 kDa), which is an apoprotein, and a hydroperoxide of coelenterazine (3: Head et al., (2000) *Nature*, 405 372-376). Apoaequorin is composed of 189 amino acid residues in a single polypeptide chain and has three EF-hand motifs characteristic of $Ca^{2+}$-binding sites (4: Inouye et al., (1985) *Proc. Natl. Acad. Sci. USA.* 82, 3154-3158). In the presence of $Ca^{2+}$, aequorin emits blue light ($\lambda$=≈460 nm) by an intramolecular reaction and decomposes itself into apoaequorin, coelenteramide and $CO_2$ (5: Shimomura & Johnson (1972) *Biochemistry* 11, 1602-1608; 6: Shimomura & Johnson (1973) *Tetrahedron Lett.* 2963-2966). The complex of $Ca^{2+}$-binding apoaequorin with coelenteramide obtained by this decomposition is known as blue fluorescent protein (BFP) (7: Shimomura & Johnson (1975) *Nature* 256, 236-238). The fluorescence and luminescence spectra of this BFP are identical to the bioluminescence spectra of aequorin (8: Shimomura (1995) *Biochem. J.* 306, 537-543; 9: Inouye (2004) *FEBS Lett.* 577, 105-110).

Recombinant aequorin can be obtained by incubating recombinant apoaquorin prepared from *Escherichia coli* with coelenterazine in the presence of EDTA and a reducing reagent (10: Inouye et al. (1986) *Biochemistry* 25, 8425-8429; 11: Inouye et al. (1989) *J. Biochem.* 105, 473-477). This recombinant aequorin is highly purified (12: Shimomura & Inouye (1999) *Protein Express. Purif* 16, 91-95). The luminescence properties of recombinant aequorin are identical to that of native aequorin (13: Shimomura et al. (1990) *Biochem. J.* 270, 309-312).

Approximately 50 types of coelenterazine analogs (CTZ analogs) were hitherto synthesized and some of them were actually used to prepare semi-synthetic aequorins (e.g., 13: Shimomura et al. (1990) *Biochem. J.* 270, 309-312, 14: Shimomura O. et al. (1988) *Biochem. J.* 251, 405-410, 15: Shimomura O. et al. (1989) *Biochem. J.* 261, 913-920, 16: Inouye S. & Shimomura O. (1997) *Biochem. Biophys. Res. Commun.* 233, 349-353).

The crystal structures of aequorin and semi-synthetic aequorins have been determined (3: Head et al. (2000) *Nature* 405, 372-376; 17: Toma et al. (2005) *Protein Science* 14, 409-416), and the binding properties of $Mg^{2+}$ to EF-hand motif of aequorin were also investigated by NMR analysis (18: Ohashi et al. (2005) 1 J. Biochem. 38, 613-620).

Recently, BFP was quantitatively prepared from the purified recombinant aequorin (9: Inouye, *FEBS Lett.* 577 (2004) 105-110; 19: Inouye & Sasaki, *FEBS Lett.* 580 (2006) 1977-1982). BFP was found to have a substantial luminescence activity, catalyzing the oxidation of coelenterazine like a luciferase. The luminescence activity of BFP is about 10 times higher than that of $Ca^{2+}$-binding apoaequorin (9: Inouye, *FEBS Lett.* 577 (2004) 105-110). Thus, BFP is a novel bifunctional protein having both fluorescence and luciferase activities. BFP is further converted into green fluorescent protein (gFP) having the fluorescence emission maximum peak at around 470 nm by the treatment of EDTA.

gFP is a non-covalent complex of apoaequorin with coelenteramide and aequorin can be obtained by incubation of gFP with coelenterazine at 25° C. in the absence of a reducing reagent (9: Inouye (2004) *FEBS Lett.* 577, 105-110). By incubation of BFP or gFP with various coelenterazine analogs in the presence of EDTA and dithiothreitol (DTT), semi-synthetic aequorins could be also prepared (19: Inouye & Sasaki (2006) *FEBS Lett.* 580, 1977-1982). Furthermore, the luminescence activity of BFP as a luciferase is stimulated by the addition of imidazole at the concentrations of 30 to 300 mM using coelenterazine and its analog as a substrate (20: Inouye & Sasaki (2007) *Biochem. Biophys. Res. Commun.* 354, 650-655).

In the development of use of BFP and gFP, there are some problems that the catalytic domain for oxygenation of coelenterazine, which is important basic information, or amino acid residues in BFP and gFP still remain to be elucidated. In order to solve these problems and in the development of use, it is necessary to easily prepare several tens milligrams of BFP and gFP and succeed. The present inventors have also established a method for preparing semi-synthetic gFP and semi-synthetic BFP from apoaequorin and chemically synthesized coelenteramide (21: Inouye & Hosoya (2009) *Biochem. Biophys. Res. Commun.* 386, 617-622). Semi-synthetic BFP prepared by this method shows a luciferase activity using coelenterazine as a substrate, similar to BFP prepared from aequorin by Ca2+-triggered luminescence reaction. The emission spectrum of semi-synthetic BFP is blue with around 470 nm.

When/As an in vivo probe to be used, a probe having the maximum wavelength of fluorescence closer to that of the near infrared region (longer than 600 nm) has been desired. In semi-synthetic BFP and semi-synthetic gFP prepared from coelenteramide analogs and apoaequorin from native aequorin, however, those having a maximum wavelength of fluorescence at 485 nm or longer have not yet been reported.

REFERENCES

1: Shimomura, In: Bioluminescence, Chemical principles and methods (2006) pp 90-158, World Scientific Pub. Co.
2: Shimomura et al. (1962) *J. Cell. Comp. Physiol.* 59, 223-240
3: Head et al. (2000) *Nature* 405, 372-376
4: Inouye et al. (1985) *Proc. Natl. Acad. Sci. USA.* 82, 3154-3158
5: Shimomura & Johnson (1972) *Biochemistry* 11, 1602-1608
6: Shimomura & Johnson (1973) *Tetrahedron Lett.* 2963-2966
7: Shimomura & Johnson (1975) *Nature* 256, 236-238
8: Shimomura (1995) *Biochem. J.* 306, 537-543
9: Inouye (2004) *FEBS Lett.* 577, 105-110
10: Inouye et al (1986) *Biochemistry* 25, 8425-8429
11: Inouye et al. (1989) *J. Biochem.* 105 473-477
12: Shimomura & Inouye (1999) *Protein Express. Purif.* 16, 91-95
13: Shimomura et al. (1990) *Biochem. J.* 270, 309-312
14: Shimomura et al. (1988) *Biochem. J.* 251, 405-410
15: Shimomura et al. (1989) *Biochem. J.* 261, 913-920
16: Inouye S. & Shimomura O. (1997) *Biochem. Biophys. Res. Commun.* 233, 349-353
17: Toma et al. (2005) *Protein Science* 14, 409-416
18: Ohashi et al. (2005) *J. Biochem.* 138, 613-620
19: Inouye & Sasaki (2006) *FEBS Lett.* 580, 1977-1982
20: Inouye & Sasaki (2007) *Biochem. Biophys. Res. Commun.* 354, 650-655
21: Inouye & Hosoya (2009) *Biochem. Biophys. Res. Commun.* 386, 617-622

DISCLOSURE OF INVENTION

Under the foregoing circumstances, coelenterazine analogs showing different luminescence properties from conventional ones have also been desired.

Furthermore, coelenteramide analogs showing different fluorescence properties from conventional ones and fluorescent proteins containing such coelenteramide analogs have been desired.

In order to solve the above problems, the present inventors have made extensive investigations and, as a result, have found that coelenterazine analogs modified at the 8-position of coelenterazine show different luminescence properties from those of known compounds, that coelenteramide analogs modified at the 2- or 3-position of coelenteramide show different luminescence properties from those of known compounds, and so on. Thus, the present invention has come to be accomplished.

The present invention provides the following coelenterazine analogs, coelenteramide analogs, calcium-binding photoproteins, fluorescent proteins, and so on.

[1] A compound represented by general formula (1) shown below:

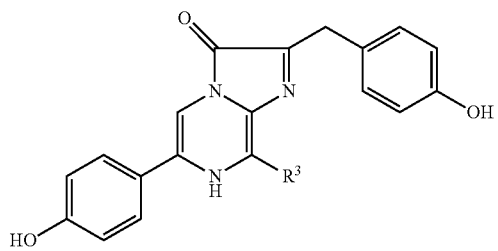

wherein $R^3$ is hydrogen atom, bromine atom and any one selected from the groups represented by formulas below:

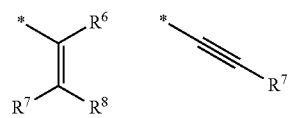

wherein each of $R^6$, $R^7$ and $R^8$ independently represents hydrogen atom, a substituted or unsubstituted alkyl having 1 to 6 carbon atoms, a substituted or unsubstituted aryl, or a substituted or unsubstituted heteroaryl; and $R^6$ and $R^8$ may be combined together to form a substituted or unsubstituted aryl or substituted or unsubstituted heteroaryl with the carbon atom bound to each of $R^6$ and $R^8$.

[2] The compound according to [1] above, which is selected from the compounds shown below.

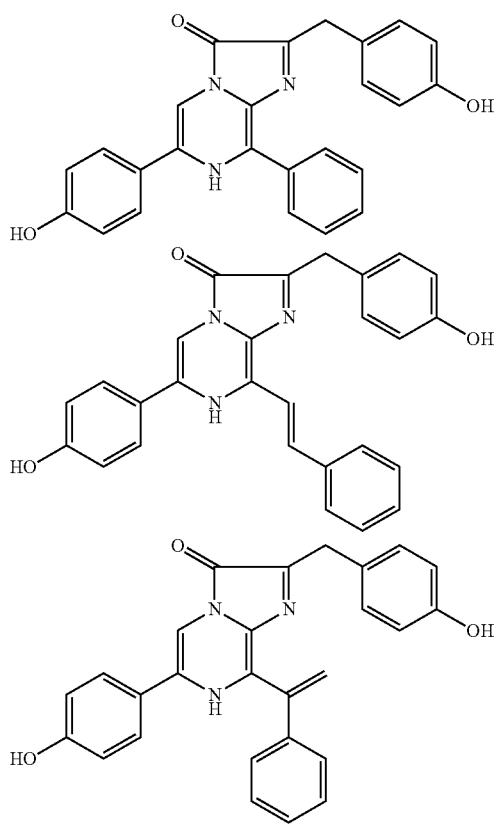

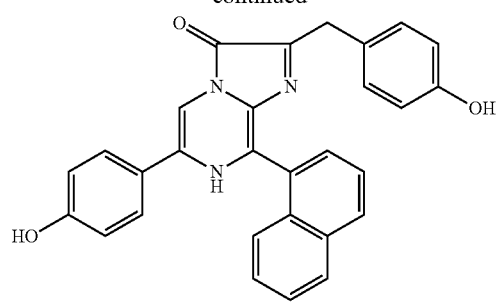
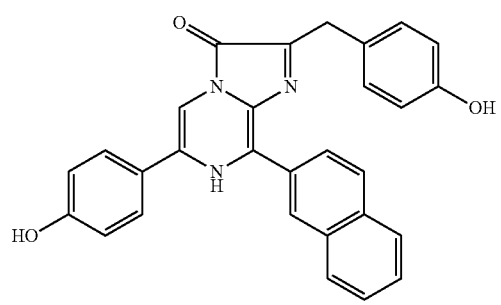
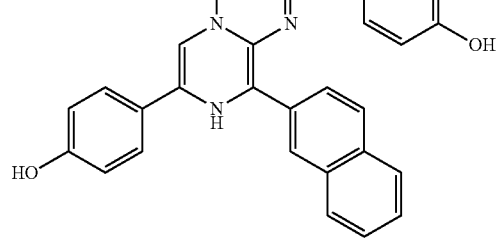
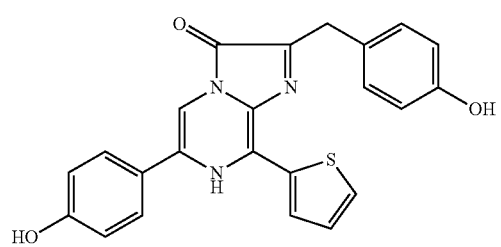
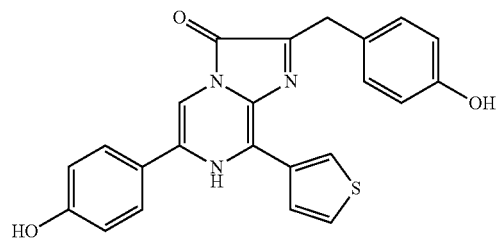
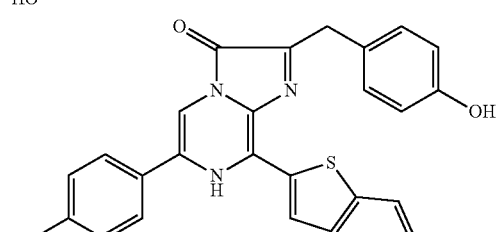
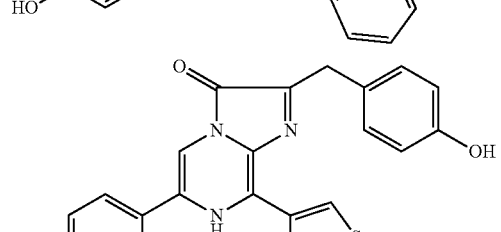
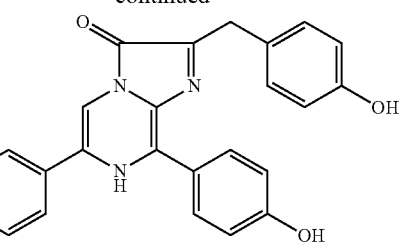
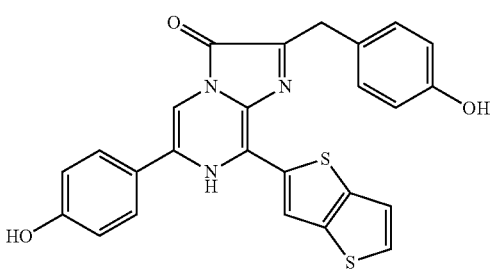
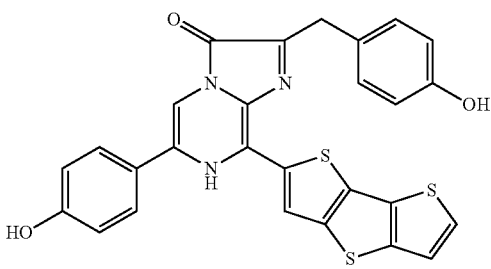
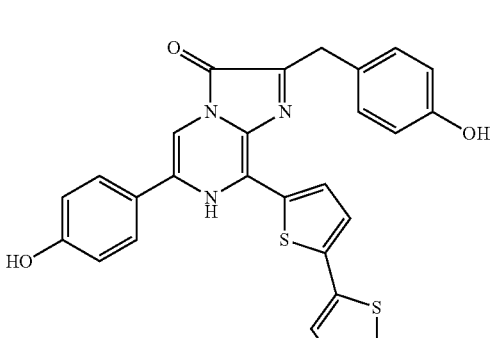
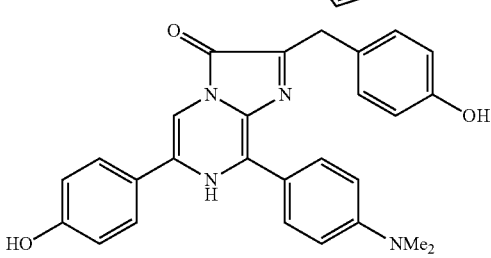
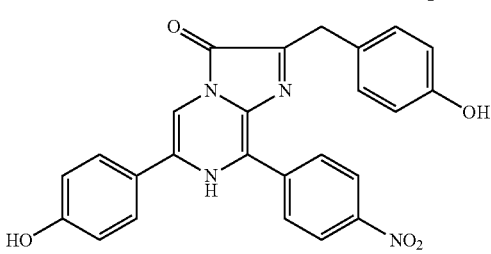

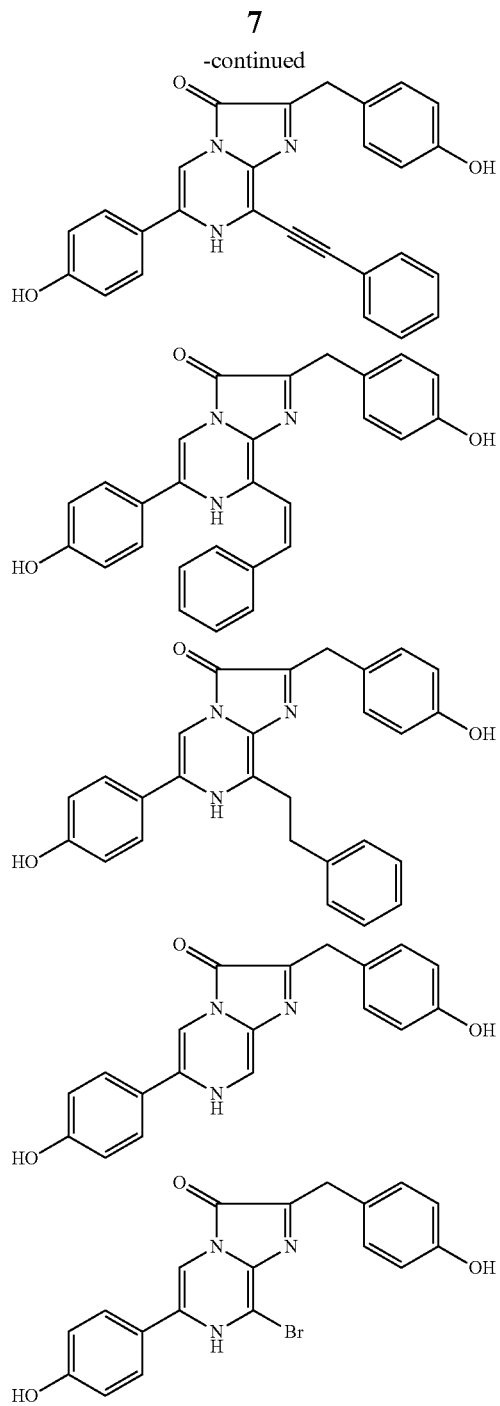
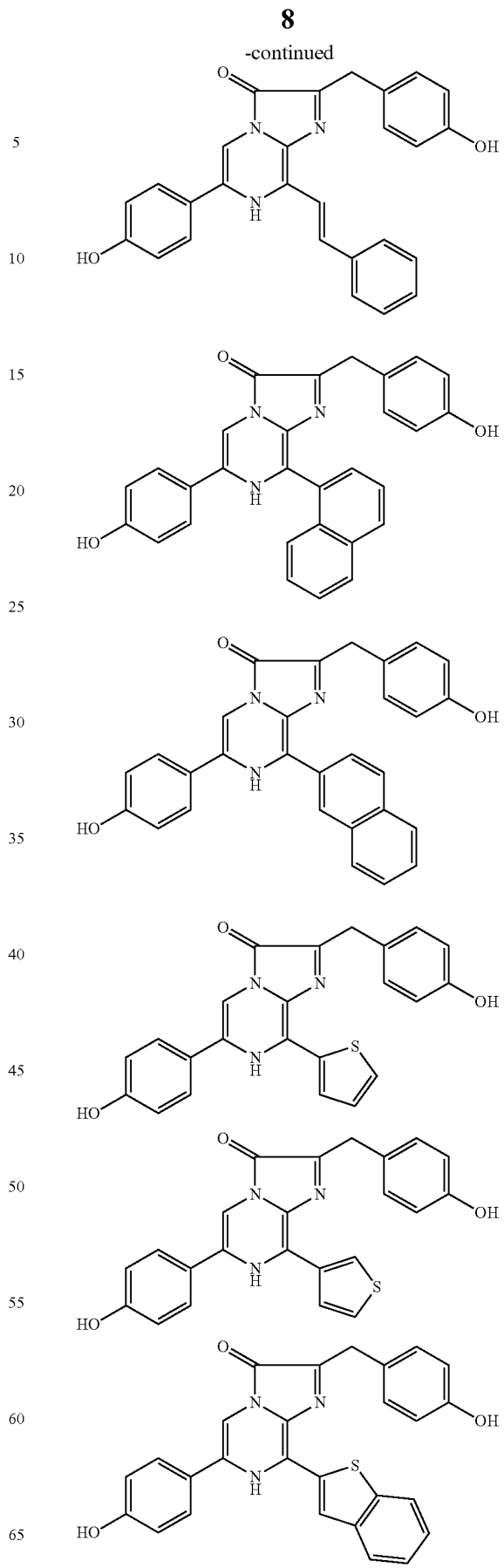
[3] The compound according to [1] above, which is selected from the compounds shown below.
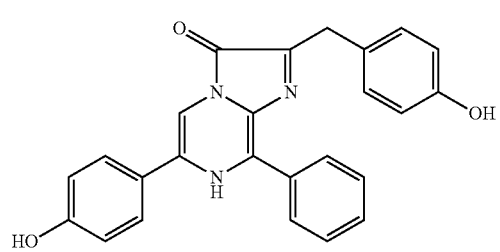
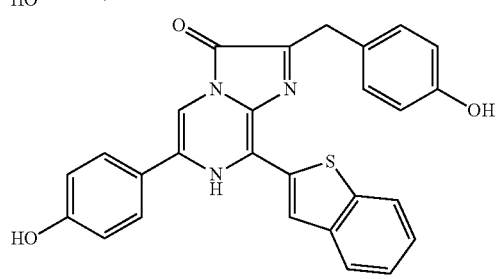

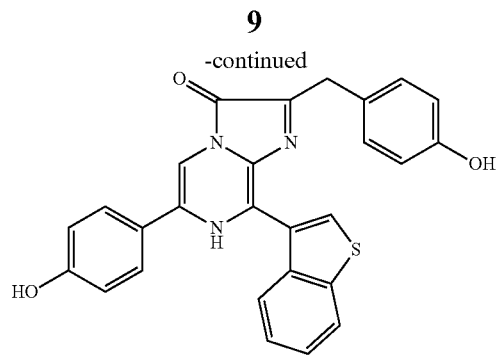

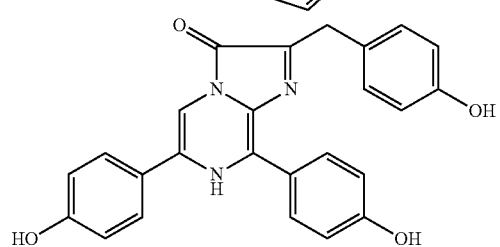

[4] A compound represented by general formula (II) below:

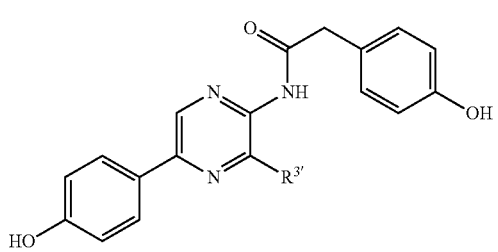

wherein $R^3$ is hydrogen atom, bromine atom and any one selected from the groups represented by formulas below:

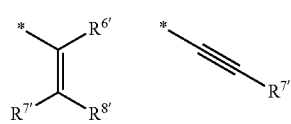

wherein each of $R^{6'}$, $R^{7'}$ and $R^{8'}$ independently represents hydrogen atom, a substituted or unsubstituted alkyl having 1 to 6 carbon atoms, a substituted or unsubstituted aryl, or a substituted or unsubstituted heteroaryl; and $R^{6'}$ and $R^{8'}$ may be combined together to form a substituted or unsubstituted aryl or substituted or unsubstituted heteroaryl with the carbon atom bound to each of $R^{6'}$ and $R^{8'}$.

[5] The compound according to [4] above, which is selected from the compounds shown below.

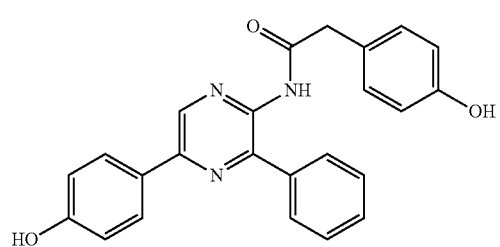

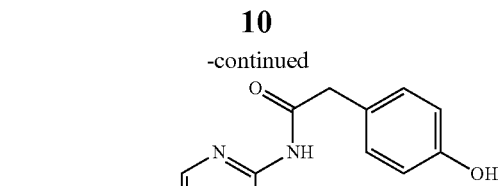

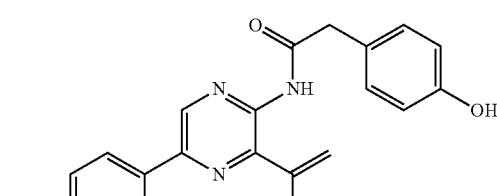

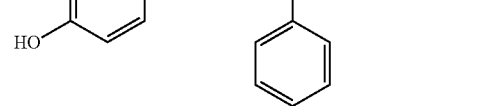

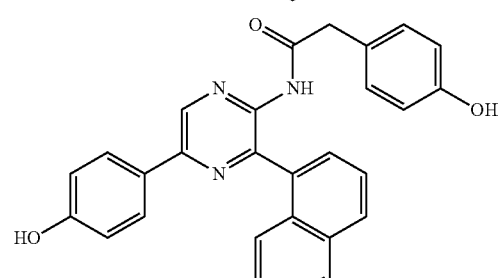

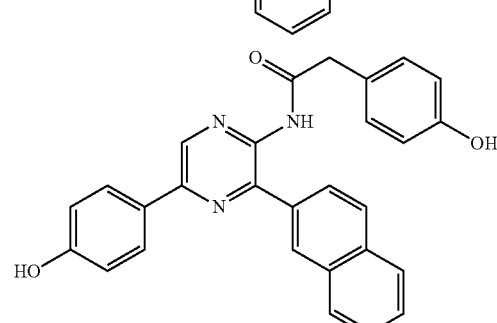

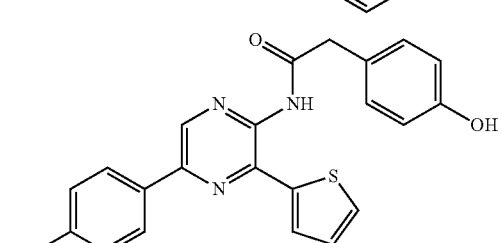

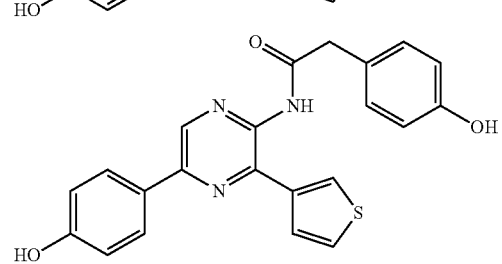

| 11 -continued | 12 -continued |
|---|---|
| 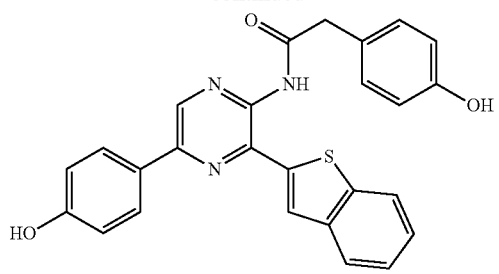 | 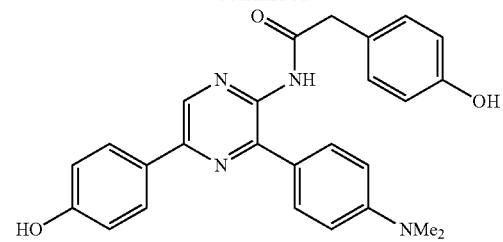 |
| 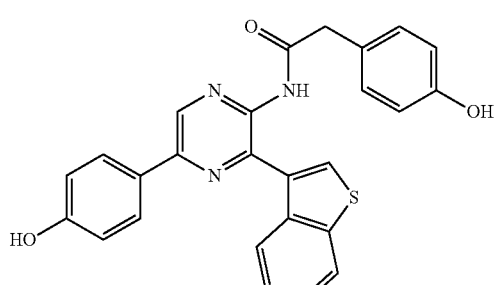 | 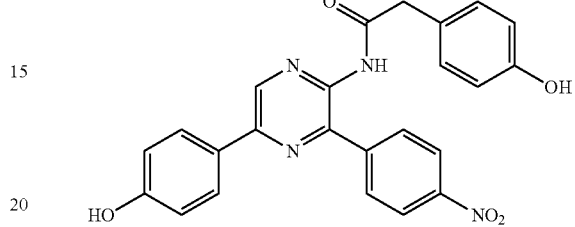 |
| 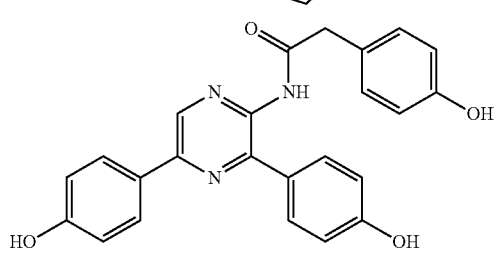 | 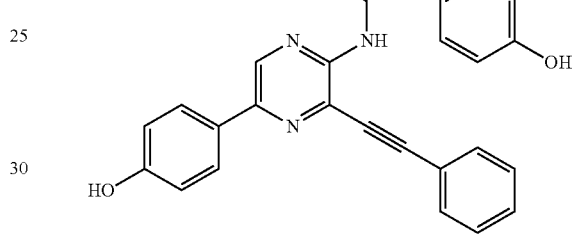 |
| 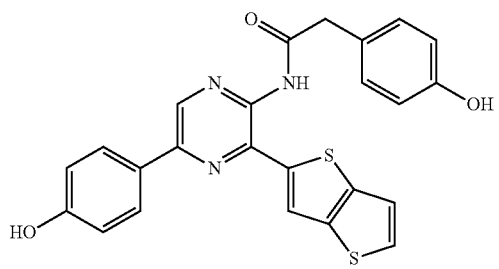 | 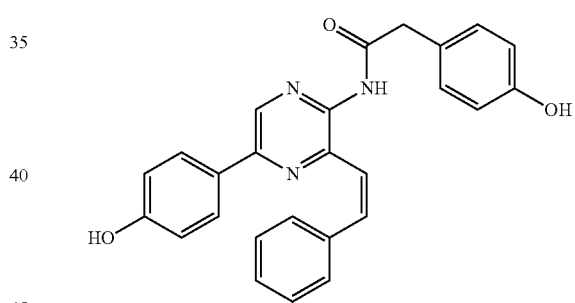 |
| 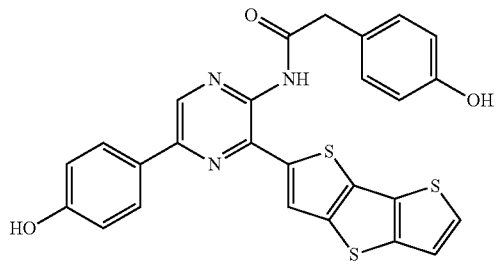 | 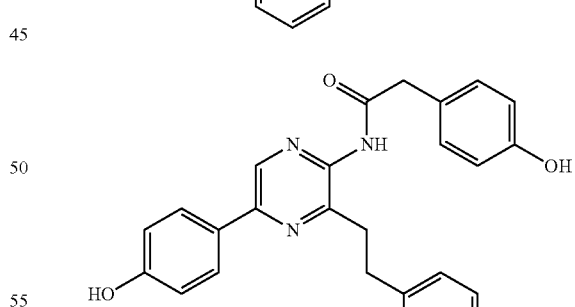 |
| 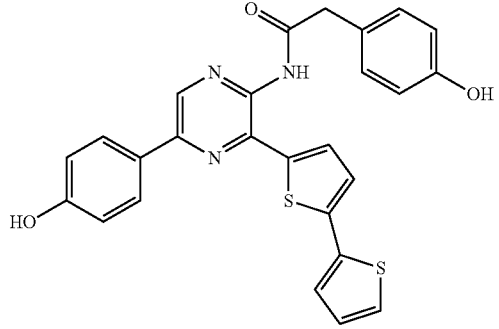 | 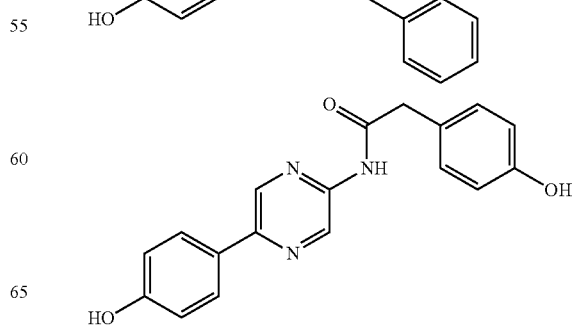 |

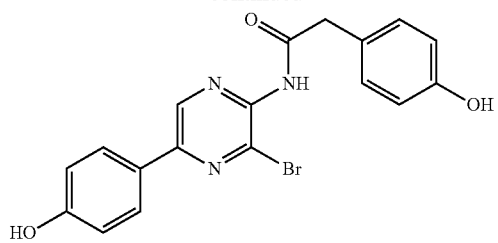

[6] A compound represented by general formula (III) below:

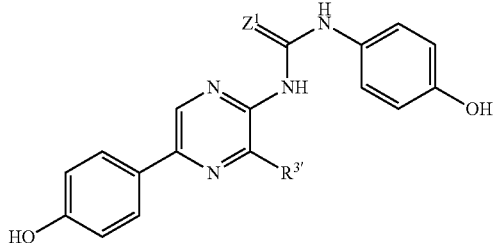

wherein $Z^1$ is O or S; and $R^{3''}$ is hydrogen atom, bromine atom, a substituted or unsubstituted aryl, a substituted or unsubstituted arylalkyl, a substituted or unsubstituted arylalkenyl, a substituted or unsubstituted arylalkynyl, an alkyl which may optionally be substituted with an alicyclic group, an alkenyl which may optionally be substituted with an alicyclic group, an alkynyl which may optionally be substituted with an alicyclic group, an alicyclic group, or a heterocyclic group.

[7] A compound represented by general formula (IV) below:

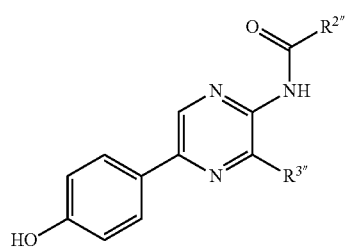

wherein $R^{2'''}$ is a group selected from the groups shown below:

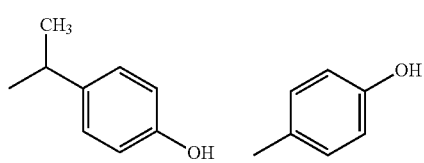

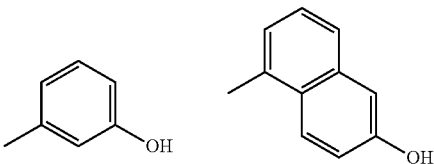

and $R^{3'''}$ is hydrogen atom, bromine atom, a substituted or unsubstituted aryl, a substituted or unsubstituted arylalkyl, a substituted or unsubstituted arylalkenyl, a substituted or unsubstituted arylalkynyl, an alkyl which may optionally be substituted with an alicyclic group, an alkenyl which may optionally be substituted with an alicyclic group, an alkynyl which may optionally be substituted with an alicyclic group, an alicyclic group, or a heterocyclic group.

[8] The compound according to [6] or [7] above, which is selected from the compounds shown below.

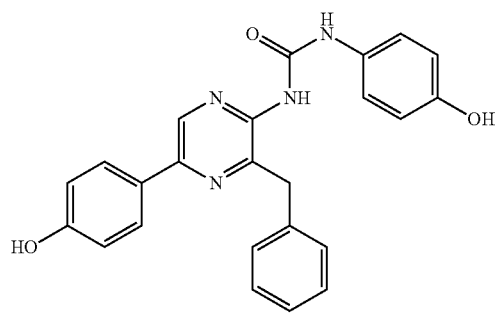

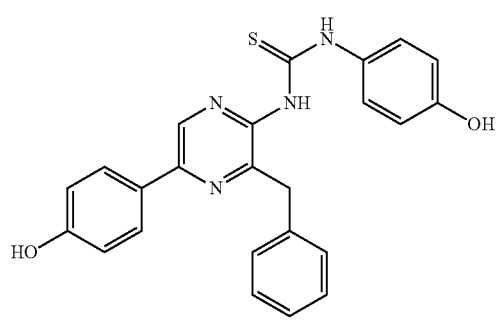

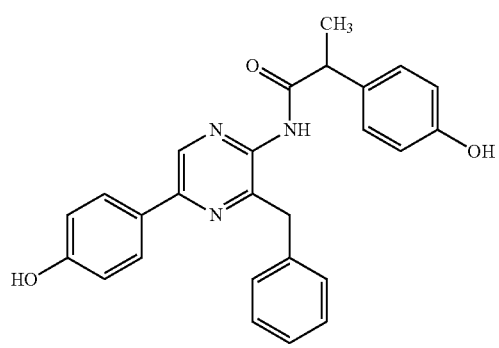

-continued

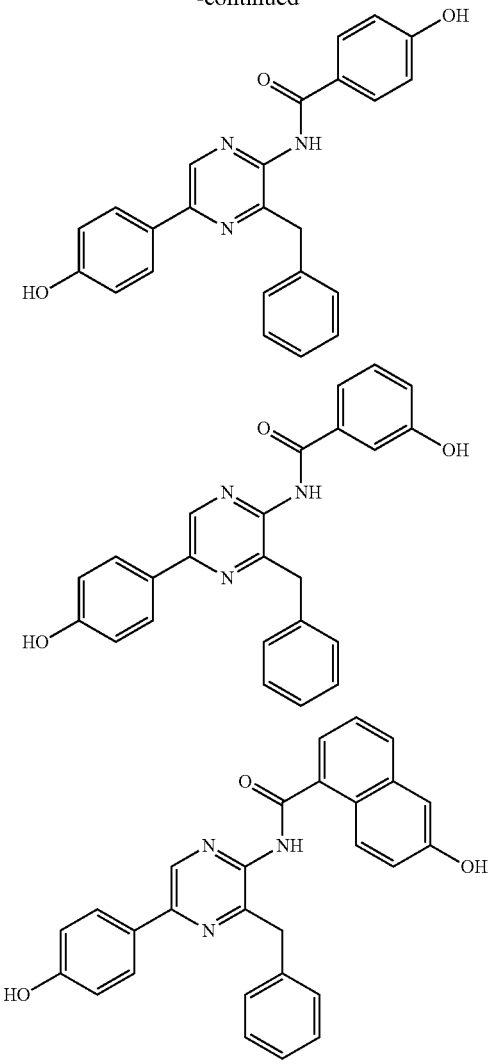

[9] A calcium-binding photoprotein comprising a peroxide of the compound according to any one of [1] to [3] above and an apoprotein of a calcium-binding photoprotein.

[10] A process for producing a calcium-binding photoprotein, which comprises contacting the compound according to any one of [1] to [3] above with an apoprotein of a calcium-binding photoprotein to obtain the calcium-binding photoprotein.

[11] A method for detecting or quantifying calcium ions, which comprises using the calcium-binding photoprotein according to [9] above.

[12] A method for analyzing a physiological function or enzyme activity, which comprises performing the bioluminescence resonance energy transfer (BRET) method using the calcium-binding photoprotein according to [9] above as a donor protein.

[13] A fluorescent protein comprising the compound according to any one of [4] to [8] above, an apoprotein of a calcium-binding photoprotein and calcium ions or divalent or trivalent ions replaceable for the calcium ions.

[14] A method for producing a fluorescent protein, which comprises contacting the calcium-binding photoprotein according to [9] above with calcium ions or divalent or trivalent ions replaceable for the calcium ions to obtain the fluorescent protein.

[15] A method for producing a fluorescent protein, which comprises contacting the compound according to any one of [4] to [8] above with an apoprotein of a calcium-binding photoprotein in the presence of calcium ions or divalent or trivalent ions replaceable for the calcium ions to obtain the fluorescent protein.

[16] The method according to [14] or [15] above, wherein the contact is carried out in the presence of a reducing agent.

[17] A fluorescent protein comprising the compound according to any one of [4] to [8] above and an apoprotein of a calcium-binding photoprotein.

[18] A method for producing a fluorescent protein, which comprises contacting the compound according to any one of [4] to [8] above with an apoprotein of a calcium-binding photoprotein in the presence of a chelating agent for removing calcium ions or divalent or trivalent ions replaceable for the calcium ions to obtain the fluorescent protein.

[19] A method for producing a fluorescent protein, which comprises treating the fluorescent protein according to [13] above with a chelating agent for removing calcium ions or divalent or trivalent ions replaceable for the calcium ions.

[20] The method according to [18] or [19] above, wherein the contact is carried out in the presence of a reducing agent.

[21] A method for analyzing a physiological function or enzyme activity, which comprises performing the fluorescence resonance energy transfer (FRET) method using the fluorescent protein according to [13] or [17] above as an acceptor or a donor.

According to the present invention, a novel coelenterazine analog is provided. Coelenterazine analogs in some embodiments of the present invention show different luminescence properties from those of known coelenterazine.

According to the present invention, a novel coelenteramide analog is provided. Coelenteramide analogs in some embodiments of the present invention show different fluorescence properties from those of known coelenteramide.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
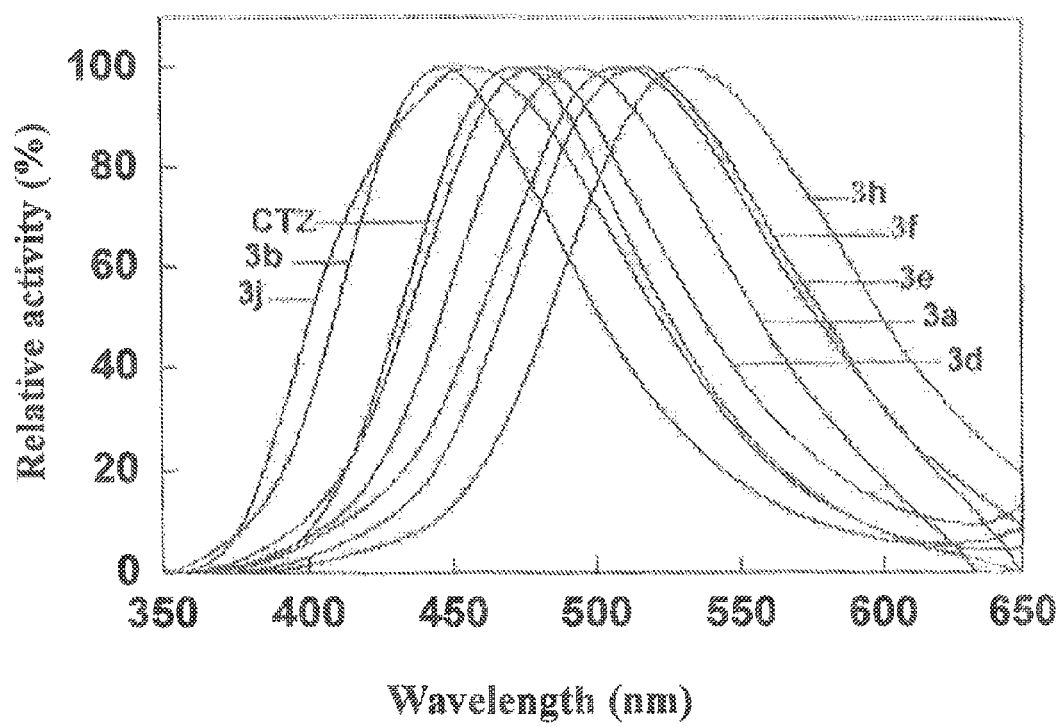
FIG. 1 shows the luminescence spectra of semi-synthetic aequorins prepared from coelenterazine analogs by addition of calcium.

Hereinafter, the present invention is described in detail. 1. Coelenterazine Analogues of the Invention The present invention provides the compounds represented by general formula (1) (sometimes referred to as the "coelenterazine analogs of the present invention"). Coelenterazine analogs are modified at the C-8 position of coelenterazine.

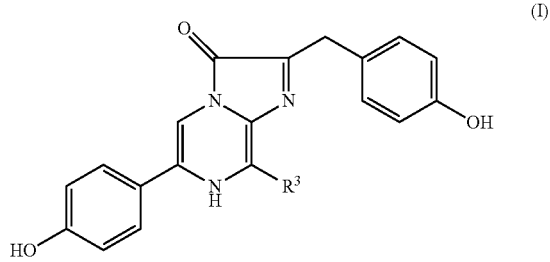

(wherein $R^3$ is hydrogen atom, bromine atom and any one selected from the groups represented by formulas below:

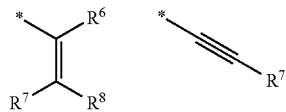

wherein each of $R^6$, $R^7$ and $R^8$ independently represents hydrogen atom, a substituted or unsubstituted alkyl having 1 to 6 carbon atoms, a substituted or unsubstituted aryl, or a substituted or unsubstituted heteroaryl; and $R^6$ and $R^8$ may be combined together to form a substituted or unsubstituted aryl or substituted or unsubstituted heteroaryl with the carbon atom bound to each of $R^6$ and $R^8$).

As used herein, the "substituted or unsubstituted alkyl having 1 to 6 carbon atoms" shown by $R^6$, $R^7$ and $R^8$ is, for example, an alkyl having 1 to 6 carbon atoms and carrying 1 to 5 substituents which may be the same or different, or an unsubstituted alkyl. Examples of the substituent include at least one selected from the group consisting of a halogen (fluorine, chlorine, bromine or iodine), hydroxy group, nitro, cyano, amino, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isopropoxy, sec-butoxy, t-butoxy, pentoxy, isopentoxy, neopentoxy, t-pentoxy, hexyloxy, isohexyloxy), a dialkylamino having 1 to 6 carbon atoms (e.g., dimethylamino, diethylamino, ethylmethylamino, diisopropylamino, 1-piperidinyl, 1-pyrrolidinyl), and the like. The "substituted or unsubstituted alkyl having 1 to 6 carbon atoms" is methyl, ethyl, propyl, isopropyl, butyl, isobutyl, sec-butyl, t-butyl, pentyl, isopentyl, neopentyl, t-pentyl, hexyl, isohexyl, fluoromethyl, a perfluoroalkyl (e.g., trifluoromethyl, perfluorohexyl), or the like.

The "substituted or unsubstituted aryl" shown by $R^6$, $R^7$ and $R^8$ or the "substituted or unsubstituted aryl" formed by combining $R^6$ and $R^8$ together with the carbon atom bound to each of $R^6$ and $R^8$ is, for example, an aryl having 1 to 5 substituents, which are the same or different, or an unsubstituted aryl. The substituent includes, for example, at least one selected from the group consisting of a halogen (fluorine, chlorine, bromine or iodine), hydroxy group, nitro, cyano, amino, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isobutoxy, sec-butoxy, t-butoxy, pentoxy, isopentoxy, neopentoxy, t-pentoxy, hexyloxy, isohexyloxy), a dialkylamino having 1 to 6 carbon atoms (e.g., dimethylamino, diethylamino, ethylmethylamino, diisopropylamino, 1-piperidinyl, 1-pyrrolidinyl), and the like. In some embodiments of the present invention, the substituent includes hydroxy group, nitro or dimethylamino. The "substituted or unsubstituted aryl" specifically includes phenyl, a naphthyl(1-naphthyl, 2-naphthyl), a hydroxyphenyl(2-hydroxyphenyl, 3-hydroxyphenyl, 4-hydroxyphenyl), an aminophenyl (e.g., 4-dimethylaminophenyl), a nitrophenyl (e.g., 4-nitrophenyl), a fluorophenyl (e.g., 4-fluorophenyl), a trifluoromethylphenyl (e.g., 4-trifluoromethylphenyl), and the like.

The "substituted or unsubstituted heteroaryl" shown by $R^6$, $R^7$ and $R^8$ or the "substituted or unsubstituted heteroaryl" formed by combining $R^6$ and $R^8$ together with the carbon atom bound to each of $R^6$ and $R^8$ is, for example, a heteroaryl having 1 to 5 substituents, which are the same or different, or an unsubstituted heteroaryl. The substituent includes, for example, at least one selected from the group consisting of a halogen (fluorine, chlorine, bromine or iodine), hydroxy group, nitro, cyano, amino, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isobutoxy, sec-butoxy, t-butoxy, pentoxy, isopentoxy, neopentoxy, t-pentoxy, hexyloxy, isohexyloxy), a dialkylamino having 1 to 6 carbon atoms (e.g., dimethylamino, diethylamino, ethylmethylamino, diisopropylamino, 1-piperidinyl and 1-pyrrolidinyl, preferably, dimethylamino, diethylamino, ethylmethylamino and diisopropylamino), an aryl (e.g., phenyl, naphthyl, anthranyl), a heteroaryl (e.g., a thienyl(2-thienyl, 3-thienyl), a furyl(2-furyl, 3-furyl), a pyrrolyl(2-pyrrolyl, 3-pyrrolyl), a pyridyl(2-pyridyl, 3-pyridyl, 4-pyridyl), imidazoyl, pyrazoyl, oxazoyl, thiazoyl, isoxazoyl, pyrimidyl, pyrazyl, pyridazoyl), and the like. Specifically, the "substituted or unsubstituted heteroaryl" is a thienyl(2-thienyl, 3-thienyl), a benzothienyl (e.g., benzo[b]thiophen-2-yl, benzo[b]thiophen-3-yl), a thienothienyl (e.g., thieno[2,3-b]thienyl, thieno[3,2-b]thienyl, thieno[3,2-b:2,3-d]thienyl), a bithiophenyl (e.g., 2,2-bithiophen-5-yl), benzofuranyl, indoyl, indazoyl, benzimidazoyl, benzoxazoyl, benzisoxazoyl, quinolinyl, isoquinolinyl, quinoxalinyl, quinazolinyl, acridinyl, or the like.

In a preferred embodiment of the present invention, coelenterazine analog includes the following compounds.

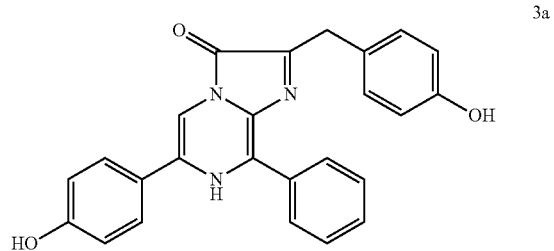

3a

-continued
3b
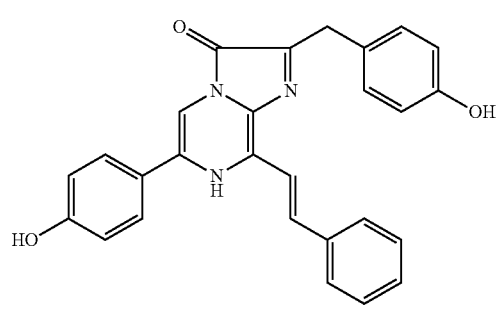
3c
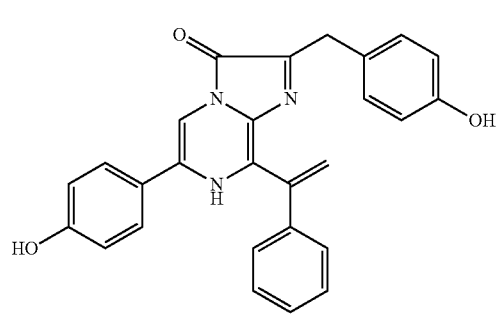
3d
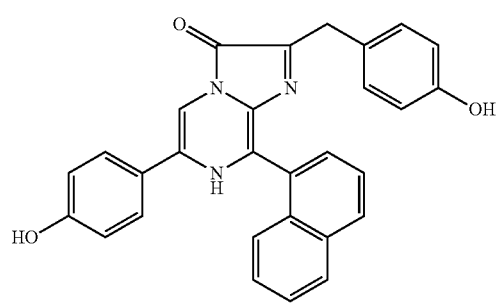
3e
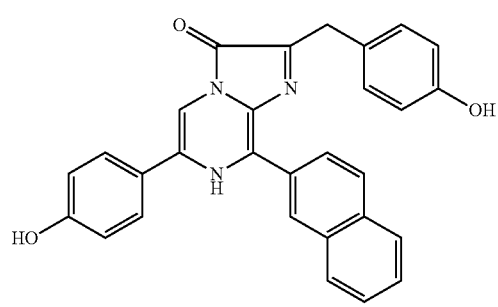
3f
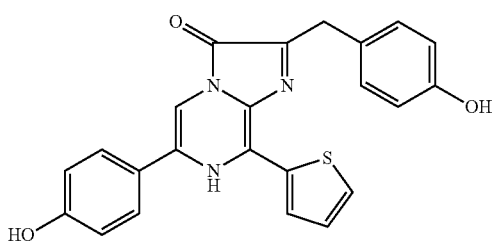
-continued
3g
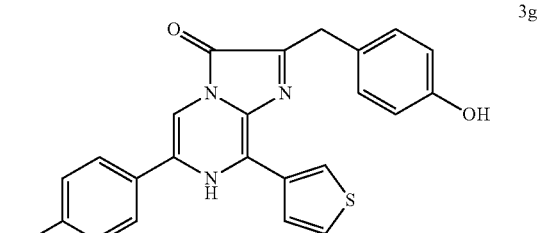
3h
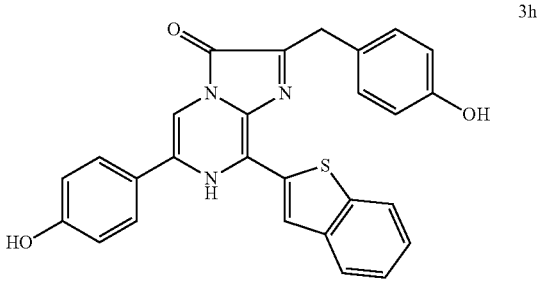
3i
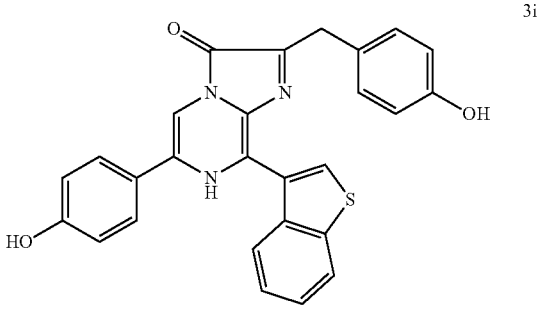
3j
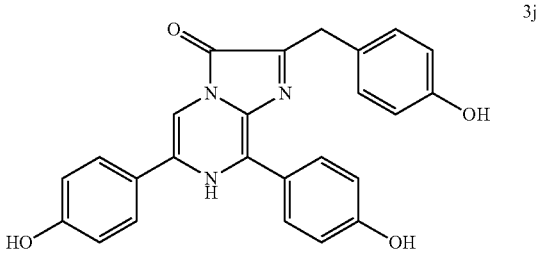
3k
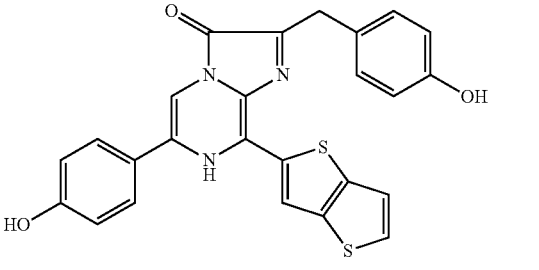
3l
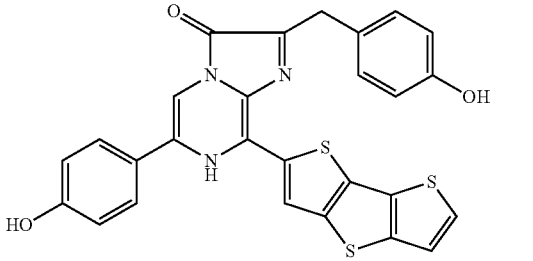

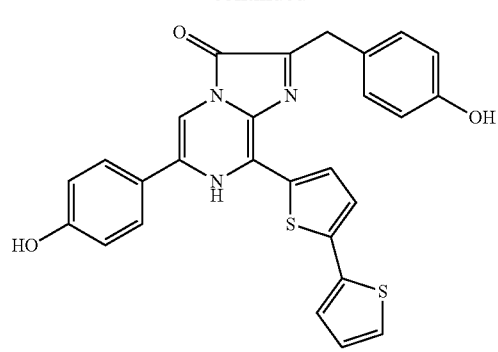
3m
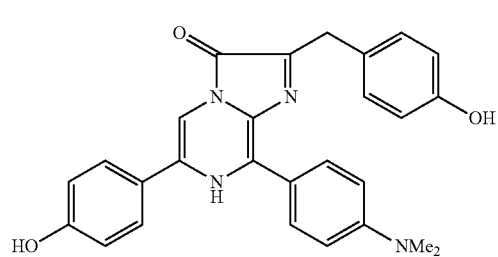
3n
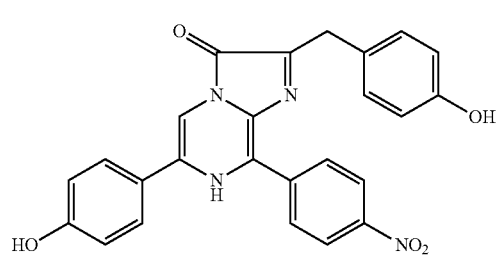
3o
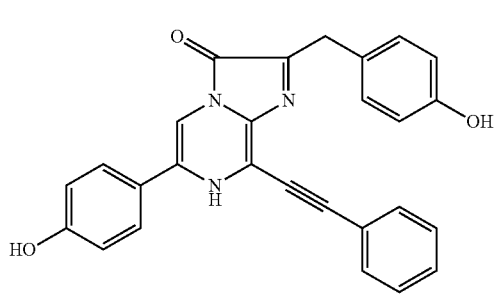
3p
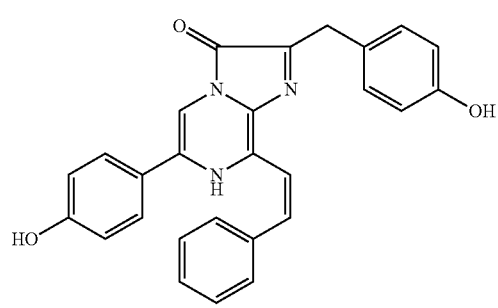
3q
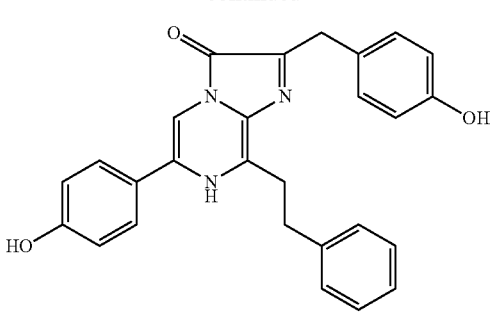
3r
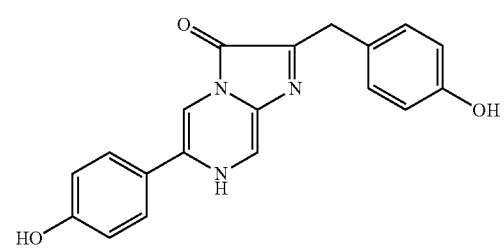
3s
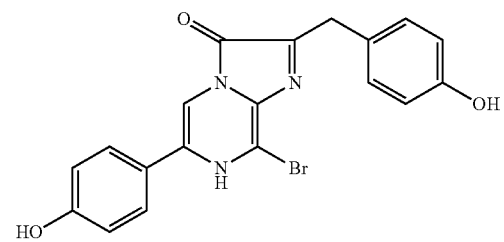
3t
In a more preferred embodiment of the present invention, coelenterazine analog includes the following compounds.
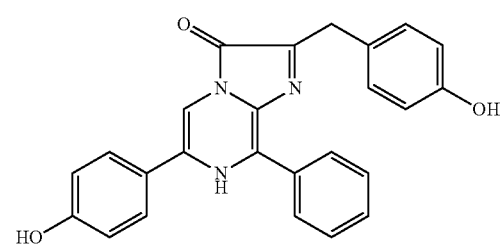
3a (TMD-296)
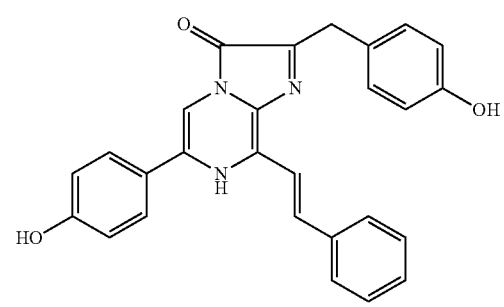
3b (TMD-282)

3d (TMD-276)

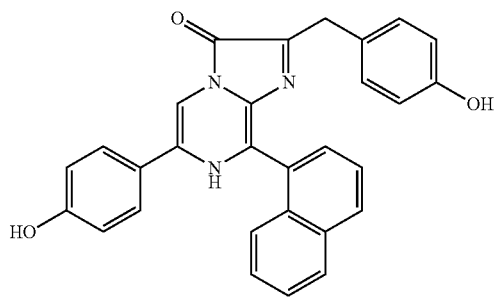

3e (TMD-277)

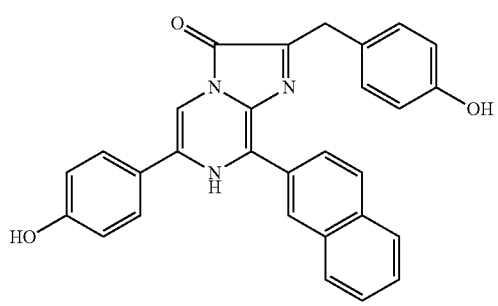

3f (TMD-278)

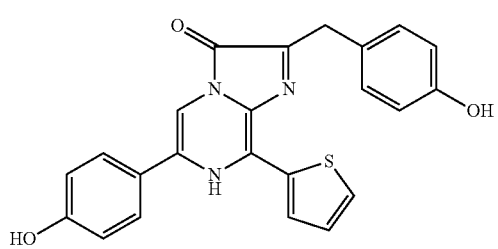

3g (tmd-336)

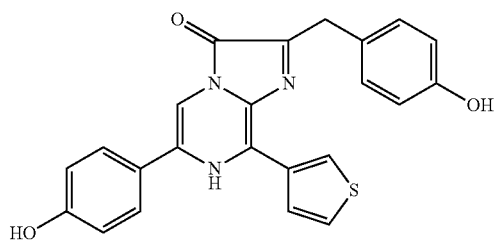

3h (TMD-281)

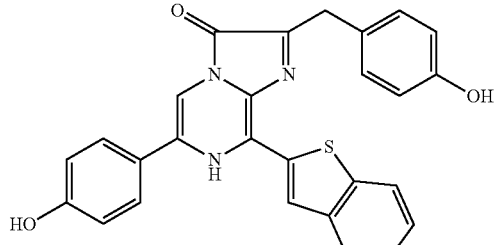

3i (TMD-337)

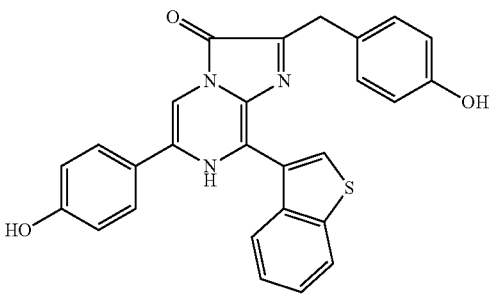

3j (TMD-280)

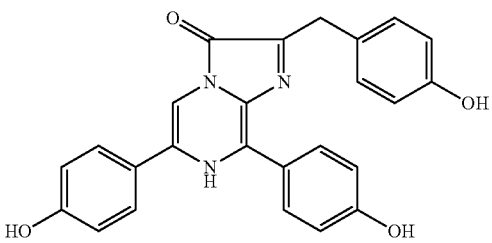

The calcium-binding photoprotein which contains some coelenterazine analogs of the present invention as a light emitting substrate provides a longer half decay time of luminescence, which is a time period in which the luminescence becomes half of the maximum luminescence intensity, when compared to a photoprotein containing coelenterazine as a light emitting substrate. For example, the half decay time is longer by 1.1 times or more, 1.2 times or more, 1.3 times or more, 1.4 times or more, 1.5 times or more, 2.0 times or more, 3.0 times or more, 4.0 times or more, 5.0 times or more, 10 times or more, 15 times or more, 20 times or more, 30 times or more, 40 times or more, 50 times or more, 60 times or more, or 70 times or more. More specifically, coelenterazine analogs, which can provide a longer half decay time of luminescence than that of coelenterazine, are 3a, 3b, 3d, 3e, 3f, 3h and 3j, preferably 3a, 3e, 3f and 3j and more preferably 3f, in coelenterazine analogs (3a to 3t).

The calcium-binding photoprotein which contains some more coelenterazine analogs of the present invention as a light emitting substrate gives different luminescence spectra, unlike fluorescence spectra of the corresponding fluorescent protein prepared by generating luminescence of the calcium-binding photoprotein by addition of calcium. For example, the maximum emission wavelength between the luminescence and the fluorescence is different by ±20 nm or more, ±25 nm or more, ±30 nm or more, ±35 nm or more, ±40 nm or more, ±45 nm or more, ±50 nm or more, ±60 nm or more, ±70 nm or more, ±80 nm or more, ±90 nm or more, ±100 nm or more, ±110 nm or more, ±120 nm or more, or ±130 nm. More specifically, coelenterazine analogs, which can provide different luminescence spectra and fluorescence spectra, are 3a, 3b, 3e, 3f, 3h and 3j, preferably 3a, 3e and 3j and more preferably 3b and 3j, in coelenterazine analogs (3a to 3t). 2. Method for producing coelenterazine analog of the invention Coelenterazine analog of the present invention described above, i.e., coelenterazine analog represented by general formula (1) below:

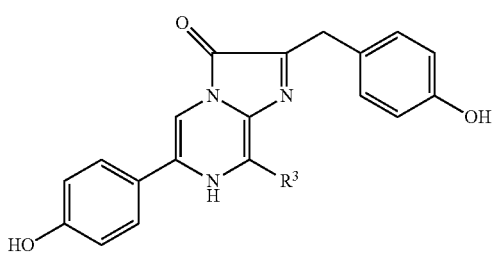

(wherein R³ is the same as defined above) can be produced as follows. That is, coelenterazine analog represented by general formula (1) can be obtained by reacting a compound represented by general formula (I-1) below:

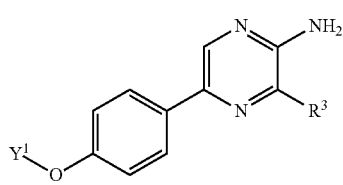

(wherein R³ is the same as defined above and Y¹ is hydrogen atom or a protecting group) with a compound represented by general formula (I-2) below:

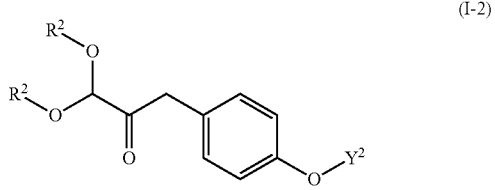

(wherein Y² is hydrogen atom or a protecting group, R² is independently methyl, ethyl, propyl, butyl or isopropyl, and two R² may be combined together to form an alkylene having 2 to 4 carbon atoms). Thus, the compound represented by general formula (1) can be obtained.

As used herein, the protecting groups shown by Y¹ and Y² independently represent, e.g., tert-butyldimethylsilyl (TBDMS), tert-butyldiphenylsilyl (TBDPS), trimethylsilyl (TMS), triethylsilyl (TES), triisopropylsilyl (TIPS), methoxymethyl (MOM), 2-methoxethoxyymethyl (MEM), 2-tetrahydropyranyl (THP), etc., particularly preferably TBDMS, MOM or THP.

The alkylene having 2 to 4 carbon atoms, which are formed by combining two R² together, includes ethylene, propylene, butylene, etc.

The compound represented by general formula (I-1) can be produced by known methods. For example, the compound represented by general formula (I-1) can be produced by, for example, the methods described in Y. Kishi et al., *Tetrahedron Lett.*, 13, 2747-2748 (1972), M. Adamczyk et al., *Org. Prep. Proced. Int.*, 33, 477-485 (2001) or F. D. Wael et al., *Bioorg. Med. Chem.*, 17, 4336-4344 (2009), or modifications of these methods. More specifically, the compound represented by general formula (I-1) can be produced as follows. First, cyclization of a substituted phenylglyoxal aldoxime and a glycinonitrile derivative is carried out to form the pyrazine oxide. Subsequently, the pyrazine oxide is subjected to catalytic hydrogenation using Raney Ni, etc. as a catalyst to produce the compound. Alternatively, the compound can be produced either by the Suzuki-Miyaura coupling reaction of a 2-amino-5-bromopyrazine derivative having a suitable substituent at the 3-position and a substituted phenyl borate or a substituted pinacol borate ester, or by the Suzuki-Miyaura coupling reaction of a 2-amino-5-bromopyrazine derivative and a suitable boric acid derivative or a pinacol borate ester.

The compound represented by general formula (I-2) can be produced by known methods. For example, the compound represented by general formula (I-2) can be produced by, for example, the methods described in M. Adamczyk, M. et al., *Synth. Commun.*, 32, 3199-3205 (2002) or H. Baganz & H.-J. May, *Chem. Ber.*, 99, 3766-3770 (1966) and H. Baganz & H.-J. May, *Angew. Chem. Int. Ed. Eng.*, 5, 420 (1966), or modifications of these methods. More specifically, the compound represented by general formula (I-2) can be produced by reacting a substituted benzyl Grignard reagent with ethyl diethoxyacetate at a low temperature (−78° C.), or by reacting an α-diazo-α-substituted phenyl ketone with tert-butyl hypochlorite in ethanol.

As used herein, the reagent used in the method for producing the compound of the present invention represented by general formula (I) is an acid catalyst such as hydrochloric acid, hydrobromic acid, hydroiodic acid, hydrofluoric acid, perchloric acid, sulfuric acid, phosphoric acid, nitric acid, acetic acid, etc. These reagents may be used alone or as a mixture thereof; hydrochloric acid is particularly preferred.

The solvent used in the method for producing the compound of the present invention represented by general formula (1) is not particularly limited, but various solvents can be used. Examples of the solvent are dioxane, tetrahydrofuran, ether, methanol, ethanol, water, etc., which can be used alone or as a mixture thereof.

In the method for producing the compound of the present invention represented by general formula (I), the reaction temperature and reaction time are not particularly limited but are generally at 0° C. to 200° C. for 1 to 96 hours, at room temperature to 150° C. for 3 to 72 hours, or at 60° C. to 120° C. for 6 to 24 hours.

3. Coelenteramide Analogue of the Invention

The present invention provides the compound represented by general formula (II) or general formula (III) below (hereinafter sometimes referred to as "coelenteramide analog of the present invention"). Coelenteramide analog of the present invention is modified at the C-3 or C-2 position of coelenteramide.

3.1. Coelenteramide Analogue Modified at the C-3 Position

Coelenteramide analog of the present invention, which is modified at the 3-position, includes the following compounds.

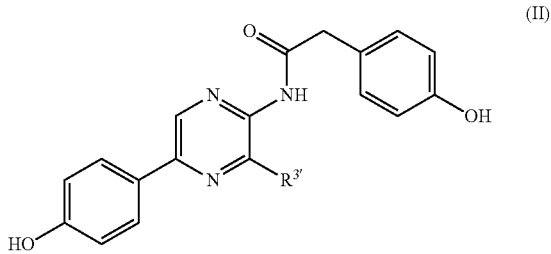

(wherein R³' is hydrogen atom, bromine atom and any one selected from the groups represented by formulas below:

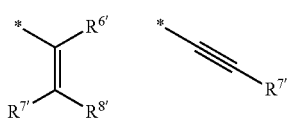

wherein each of R⁶', R⁷' and R⁸' independently represents hydrogen atom, a substituted or unsubstituted alkyl having 1 to 6 carbon atoms, a substituted or unsubstituted aryl, or a substituted or unsubstituted heteroaryl; and R⁶' and R⁸' may be combined together to form a substituted or unsubstituted aryl or substituted or unsubstituted heteroaryl with the carbon atom bound to each of R⁶' and R⁸').

As used herein, the "substituted or unsubstituted alkyl having 1 to 6 carbon atoms" shown by R⁶', R⁷' and R⁸' is, for example, an alkyl having 1 to 6 carbon atoms and carrying 1 to 5 substituents which are the same or different, or an unsubstituted alkyl. Examples of the substituent include at least one selected from the group consisting of a halogen (fluorine, chlorine, bromine or iodine), hydroxy group, nitro, cyano, amino, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isobutoxy, sec-butoxy, t-butoxy, pentoxy, isopentoxy, neopentoxy, t-pentoxy, hexyloxy, isohexyloxy), a dialkylamino having 1 to 6 carbon atoms (e.g., dimethylamino, diethylamino, ethylmethylamino, diisopropylamino, 1-piperidinyl, 1-pyrrolidinyl), and the like. The "substituted or unsubstituted alkyl having 1 to 6 carbon atoms" is methyl, ethyl, propyl, isopropyl, butyl, isobutyl, sec-butyl, t-butyl, pentyl, isopentyl, neopentyl, t-pentyl, hexyl, isohexyl, fluoromethyl, a perfluoroalkyl (e.g., trifluoromethyl, perfluorohexyl), or the like.

As used herein, the "substituted or unsubstituted aryl" shown by R⁶', R⁷' and R⁸' or the "substituted or unsubstituted aryl" formed by combining R⁶' and R⁸' together with the carbon atom bound to each of R⁶' and R⁸' is, for example, an aryl having 1 to 5 substituents which are the same or different, or an unsubstituted aryl. Examples of the substituent include at least one selected from the group consisting of a halogen (fluorine, chlorine, bromine or iodine), hydroxy group, nitro, cyano, amino, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isobutoxy, sec-butoxy, t-butoxy, pentoxy, isopentoxy, neopentoxy, t-pentoxy, hexyloxy, isohexyloxy), a dialkylamino having 1 to 6 carbon atoms (e.g., dimethylamino, diethylamino, ethylmethylamino, diisopropylamino, 1-piperidinyl, 1-pyrrolidinyl) and the like. In some embodiments of the present invention, the substituent is hydroxy group, nitro or dimethylamino. Specifically, the "substituted or unsubstituted aryl" includes phenyl, a naphthyl(1-naphthyl, 2-naphthyl), a hydroxyphenyl(2-hydroxyphenyl, 3-hydroxyphenyl, 4-hydroxyphenyl), an aminophenyl (e.g., 4-dimethylaminophenyl), a nitrophenyl (e.g., 4-nitrophenyl), a fluorophenyl (e.g., 4-fluorophenyl), a trifluoromethylphenyl (e.g., 4-trifluoromethylphenyl), etc.

The "substituted or unsubstituted heteroaryl" shown by R⁶', R⁷' and R⁸' or the "substituted or unsubstituted heteroaryl" formed by combining R⁶' and R⁸ together with the carbon atom bound to each of R⁶' and R⁸' is, for example, a heteroaryl having 1 to 5 substituents which are the same or different, or an unsubstituted heteroaryl. Examples of the substituent include at least one selected from the group consisting of a halogen (fluorine, chlorine, bromine or iodine), hydroxy group, nitro, cyano, amino, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isobutoxy, sec-butoxy, t-butoxy, pentoxy, isopentoxy, neopentoxy, t-pentoxy, hexyloxy, isohexyloxy), a dialkylamino having 1 to 6 carbon atoms (e.g., dimethylamino, diethylamino, ethylmethylamino, diisopropylamino, 1-piperidinyl and 1-pyrrolidinyl, preferably, dimethylamino, diethylamino, ethylmethylamino, diisopropylamino), an aryl (e.g., phenyl, naphthyl, anthranyl), a heteroaryl (e.g., a thienyl(2-thienyl, 3-thienyl), a furyl(2-furyl, 3-furyl), a pyrrolyl(2-pyrrolyl, 3-pyrrolyl), a pyridyl(2-pyridyl, 3-pyridyl, 4-pyridyl), imidazoyl, pyrazoyl, oxazoyl, thiazoyl, isoxazoyl, pyrimidyl, pyrazyl, pyridazoyl) and the like. Specifically, the "substituted or unsubstituted heteroaryl" is a thienyl(2-thienyl, 3-thienyl), a benzothienyl (e.g., benzo[b]thiophen-2-yl, benzo[b]thiophen-3-yl), a thienothienyl (e.g., thieno[2,3-b]thienyl, thieno[3,2-b]thienyl, thieno[3,2-b:2,3-d]thienyl), a bithiophenyl (e.g., 2,2-bithiophen-5-yl), benzofuranyl, indoyl, indazoyl, benzimidazoyl, benzoxazoyl, benzisoxazoyl, quinolinyl, isoquinolinyl, quinoxalinyl, quinazolinyl, acridinyl, etc.

In a preferred embodiment of the present invention, coelenteramide analog modified at the C-3 position includes the following compounds.

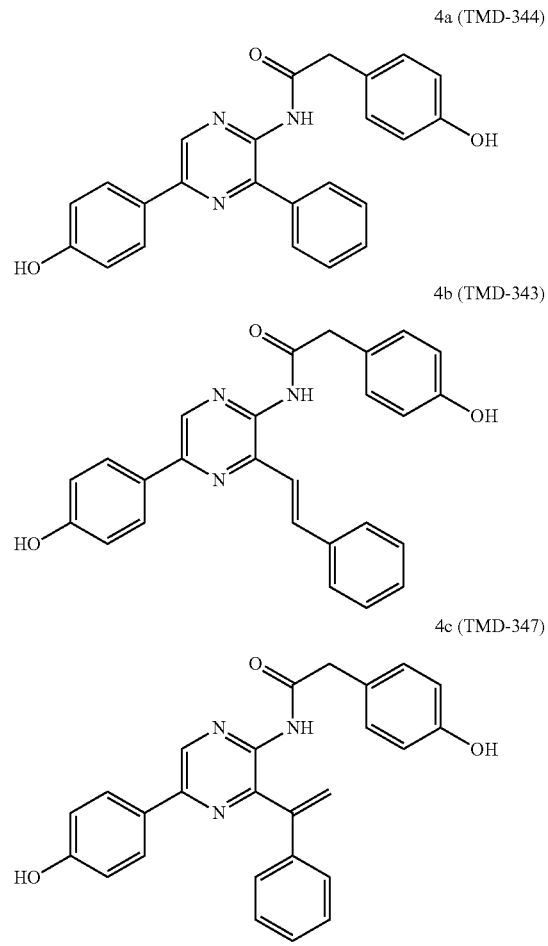

4a (TMD-344)

4b (TMD-343)

4c (TMD-347)

4d (TMD-336)
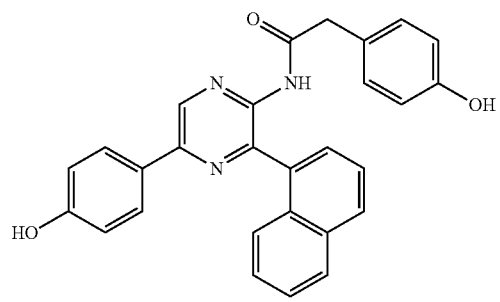
4e (TMD-339)
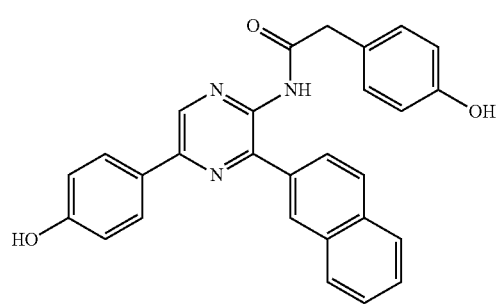
4f (TMD-340)
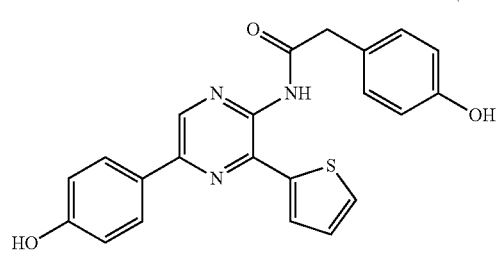
4g (TMD-345)
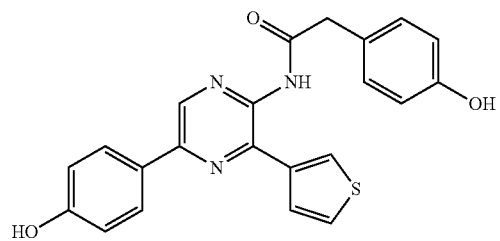
4h (TMD-342)
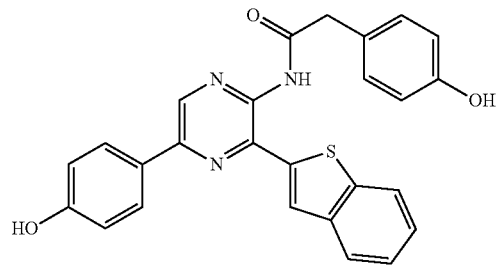
4i (TMD-346)
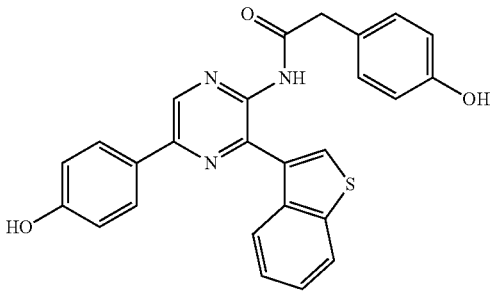
4j (TMD-341)
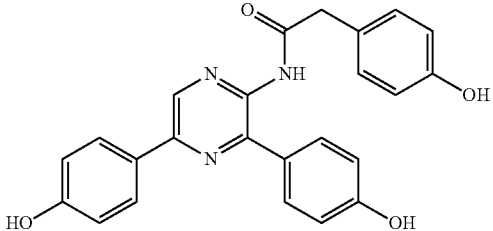
4k (TMD-373)
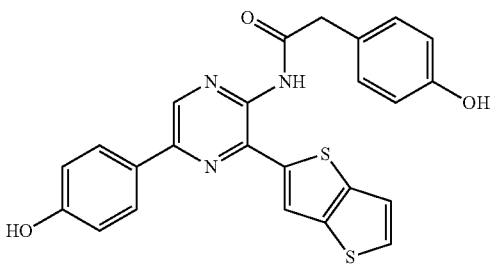
4l (TMD-374)
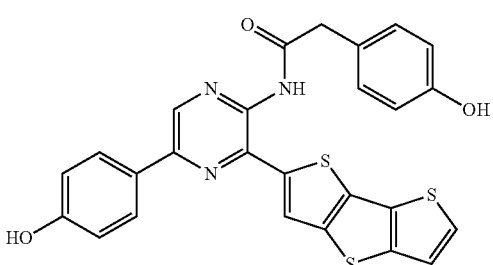
4m (TMD-375)
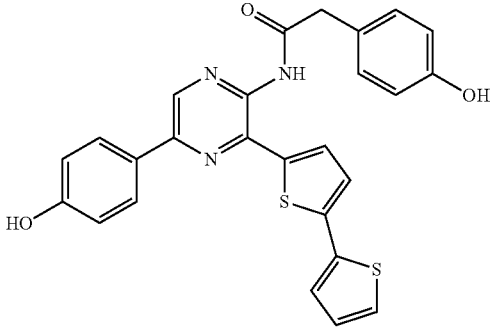

4n (TMD-376)

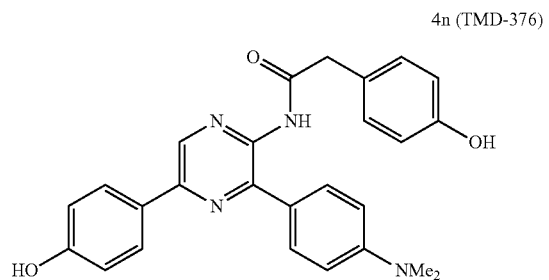

4o (TMD-377)

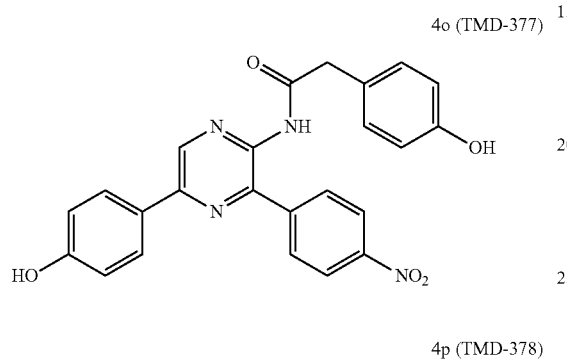

4p (TMD-378)

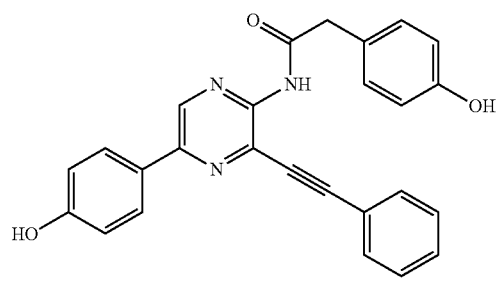

4q

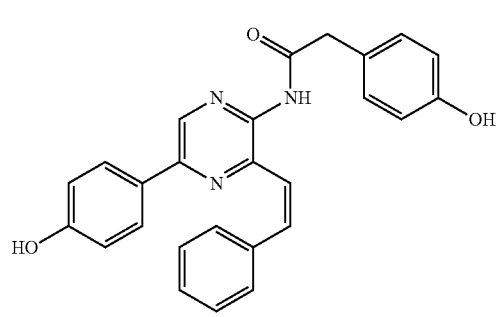

4r (TMD-379)

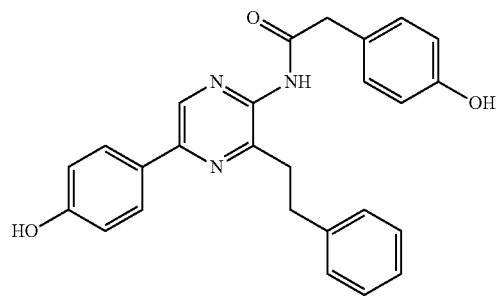

4s (TMD-348)

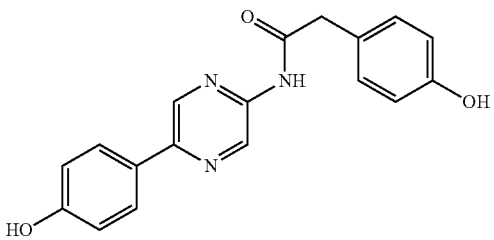

4t (TMD-349)

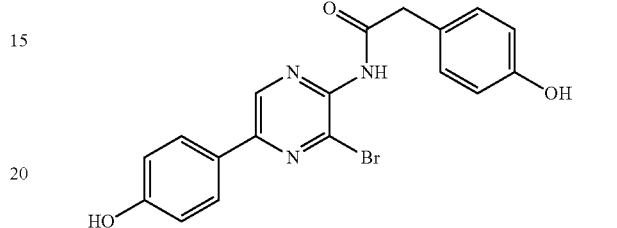

3.2. Coelenteramide Analogue Modified at the C-2 Position

Coelenteramide analog in some embodiments of the present invention, which is modified at the C-2-position, includes the following compounds.

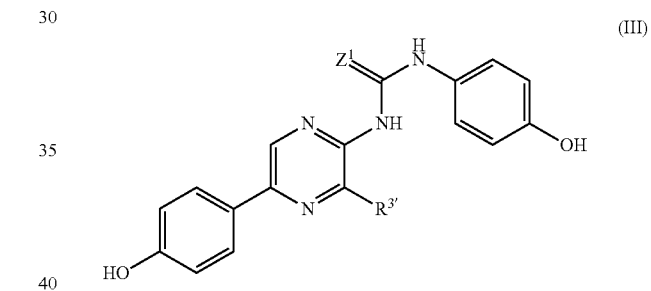

(III)

(wherein $Z^1$ is O or S; and $R^{3''}$ is hydrogen atom, bromine atom, a substituted or unsubstituted aryl, a substituted or unsubstituted arylalkyl, a substituted or unsubstituted arylalkenyl, a substituted or unsubstituted arylalkynyl, an alkyl which may optionally be substituted with an alicyclic group, an alkenyl which may optionally be substituted with an alicyclic group, an alkynyl which may optionally be substituted with an alicyclic group, an alicyclic group, or a heterocyclic group.)

As used herein, the "substituted or unsubstituted aryl" shown by $R^{3''}$ is, for example, an aryl having 1 to 5 substituents, or an unsubstituted aryl. For example, the substituted or unsubstituted aryl is at least one selected from the group consisting of a halogen (fluorine, chlorine, bromine or iodine), hydroxy group, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isobutoxy, sec-butoxy, t-butoxy, pentoxy, isopentoxy, neopentoxy, t-pentoxy, hexyloxy, isohexyloxy), amino, a dialkylamino having 1 to 6 carbon atoms (e.g., dimethylamino, diethylamino, ethylmethylamino, diisopropylamino, 1-piperidinyl, 1-pyrrolidinyl), and the like. In some embodiments of the present invention, the substituent is hydroxy group. Specifically, the "substituted or unsubstituted aryl" is phenyl, p-hydroxyphenyl, p-aminophenyl, p-dimethylaminophenyl, or the like, preferably phenyl, p-hydroxyphenyl, etc. In some embodiments of the present invention, the "substituted or unsubstituted aryl" is an unsubstituted aryl, e.g., phenyl, etc.

The "substituted or unsubstituted arylalkyl" shown by $R^{3''}$ is, for example, an arylalkyl having 7 to 10 carbon atoms and carrying 1 to 5 substituents, or an unsubstituted arylalkyl having 7 to 10 carbon atoms. Examples of the substituents include a halogen (fluorine, chlorine, bromine or iodine), hydroxy group, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isobutoxy, sec-butoxy, t-butoxy, pentoxy, isopentoxy, neopentoxy, t-pentoxy, hexyloxy, isohexyloxy), amino, a dialkylamino having 1 to 6 carbon atoms (e.g., dimethylamino, diethylamino, ethylmethylamino, diisopropylamino, 1-piperidinyl, 1-pyrrolidinyl), and the like. The "substituted or unsubstituted arylalkyl" includes, for example, benzyl, α-hydroxybenzyl, phenylethyl, p-hydroxybenzyl, p-dimethylaminobenzyl, etc., preferably benzyl, α-hydroxybenzyl, phenylethyl, etc. In some embodiments of the present invention, the "substituted or unsubstituted arylalkyl" is benzyl.

The "substituted or unsubstituted arylalkenyl" shown by $R^{3''}$ is, for example, an arylalkenyl having 8 to 10 carbon atoms and carrying 1 to 5 substituents, or an unsubstituted arylalkenyl having 8 to 10 carbon atoms. Examples of the substituents include a halogen (fluorine, chlorine, bromine or iodine), hydroxy group, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isobutoxy, sec-butoxy, t-butoxy, pentoxy, isopentoxy, neopentoxy, t-pentoxy, hexyloxy, isohexyloxy), amino, a dialkylamino having 1 to 6 carbon atoms (e.g., dimethylamino, diethylamino, ethylmethylamino, diisopropylamino, 1-piperidinyl, 1-pyrrolidinyl), and the like. For example, the "substituted or unsubstituted arylalkenyl" is phenylvinyl, p-hydroxyphenylvinyl, or p-dimethylaminophenylvinyl. In some embodiments of the present invention, the "substituted or unsubstituted arylalkenyl" is an unsubstituted arylalkenyl, e.g., phenylvinyl.

The "substituted or unsubstituted arylalknyl" shown by $R^{3''}$ is, for example, an arylalknyl having 8 to 10 carbon atoms and carrying 1 to 5 substituents, or an unsubstituted arylalknyl having 8 to 10 carbon atoms. Examples of the substituents include a halogen (fluorine, chlorine, bromine or iodine), hydroxy group, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isobutoxy, sec-butoxy, t-butoxy, pentoxy, isopentoxy, neopentoxy, t-pentoxy, hexyloxy, isohexyloxy), amino, a dialkylamino having 1 to 6 carbon atoms (e.g., dimethylamino, diethylamino, ethylmethylamino, diisopropylamino, 1-piperidinyl, 1-pyrrolidinyl), and the like. Examples of the "substituted or unsubstituted arylalknyl" are phenylethynyl, naphthylethynyl, 4-fluorophenylethynyl, 4-trifluoromethylphenylethynyl, 4-methoxyphenylethynyl, 4-nitrophenylethynyl, etc., preferably, phenylethynyl, etc.

The "alkyl which may optionally be substituted with an alicyclic group" shown by $R^{3''}$ is, for example, an unsubstituted straight or branched alkyl having 1 to 4 carbon atoms, or a straight or branched alkyl having 1 to 4 carbon atoms, which is substituted with an alicyclic group having, e.g., 1 to 10 carbon atoms. Examples of the alicyclic group include cyclohexyl, cyclopentyl, adamantyl, cyclobutyl, cyclopropyl, and the like. Preferably, the alicyclic group is cyclohexyl, cyclopentyl or adamantyl. Examples of the "alkyl which may optionally be substituted with an alicyclic group" are methyl, ethyl, propyl, 2-methylpropyl, adamantylmethyl, cyclopentylmethyl, cyclohexylmethyl, cyclohexylethyl, cyclobutylmethyl, cyclopropylmethyl, or the like, preferably, methyl, ethyl, propyl, 2-methylpropyl, adamantylmethyl, cyclopentylmethyl, cyclohexylmethyl, cyclohexylethyl, etc. In some embodiments of the present invention, the "alkyl which may optionally be substituted with an alicyclic group" is a straight alkyl which may optionally be substituted with an alicyclic group, for example, methyl, ethyl, propyl, adamantylmethyl, cyclopentylmethyl, cyclohexylmethyl, cyclohexylethyl, etc.

The "alkenyl which may optionally be substituted with an alicyclic group" shown by $R^{3''}$ is, for example, an unsubstituted straight or branched alkenyl having 2 to 6 carbon atoms, or a straight or branched alkenyl having 2 to 6 carbon atoms, which is substituted with an alicyclic group having, e.g., 1 to 10 carbon atoms. Examples of the alicyclic group include cyclohexyl, cyclopentyl, adamantyl, cyclobutyl, cyclopropyl, etc. Preferably, the alicyclic group is cyclohexyl, cyclopentyl, adamantly, or the like. The "alkenyl which may optionally be substituted with an alicyclic group" includes, for example, vinyl, I-propenyl, 2-propenyl, 1-butenyl, 2-butenyl, 3-butenyl, 2-methylpropenyl, etc., preferably, 2-methylpropenyl, etc.

The "alkynyl which may optionally be substituted with an alicyclic group" shown by $R^{3''}$ is, for example, an unsubstituted straight or branched alkynyl having 2 to 6 carbon atoms, or a straight or branched alkynyl having 2 to 6 carbon atoms, which is substituted with an alicyclic group having, e.g., 1 to 10 carbon atoms. Examples of the alicyclic group include cyclohexyl, cyclopentyl, adamantyl, cyclobutyl, cyclopropyl, and the like. Preferably, the alicyclic group is cyclohexyl, cyclopentyl, adamantly, etc. Examples of the "alkynyl which may optionally be substituted with an alicyclic group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like, preferably, 1-propynyl, etc.

The "aliphatic group" shown by $R^{3''}$ includes, for example, cyclohexyl, cyclopentyl, adamantyl, cyclobutyl, cyclopropyl, and the like, preferably, cyclohexyl, etc.

The "heterocyclic group" shown by $R^3$ is, for example, a group formed by a 5- to 7-membered ring containing 1 to 3 atoms selected from the group consisting of N, O and S as the atoms for forming the ring, in addition to carbons and bound through carbon, a group formed by condensing at least two such rings and bound through carbon, or a group formed by condensing such rings with a benzene ring and bound through carbon. Examples of the "heterocyclic group" are thiophen-2-yl, 2-furanyl, 4-pyridyl, etc. In some embodiments of the present invention, the "heterocyclic group" is a heterocyclic group containing sulfur, e.g., thiophen-2-yl.

In a preferred embodiment of the present invention, $R^{3''}$ is phenyl, p-hydroxyphenyl, benzyl, t-hydroxybenzyl, phenylethyl, phenylvinyl, cyclohexyl, cyclohexylmethyl, cyclohexylethyl, methyl, ethyl, propyl, 2-methylpropyl, 2-methylpropenyl, adamantylmethyl, cyclopentylmethyl or thiophen-2-yl. In a more preferred embodiment of the present invention, $R^3$ is benzyl.

In a still preferred embodiment of the present invention, $R^{3''}$ is hydrogen atom, bromine atom or any one selected from the groups shown below:

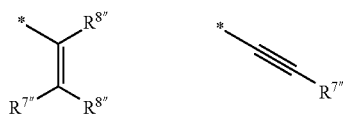

(wherein each of R[6″], R[7″] and R[8″] independently represents hydrogen atom, a substituted or unsubstituted alkyl having 1 to 6 carbon atoms, a substituted or unsubstituted aryl, or a substituted or unsubstituted heteroaryl, and R[6″] and R[8″] may be combined together with the carbon atom bound to each of R[6″] and R[8″] to form a substituted or unsubstituted aryl or a substituted or unsubstituted heteroaryl).

As used herein, the "substituted or unsubstituted alkyl having 1 to 6 carbon atoms" shown by R[6″], R[7″] and R[8″] is, for example, an alkyl having 1 to 6 carbon atoms and carrying 1 to 5 substituents which are the same or different, or an unsubstituted alkyl. The substituent is, for example, at least one selected from the group consisting of a halogen (fluorine, chlorine, bromine or iodine), hydroxy group, nitro, cyano, amino, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isobutoxy, sec-butoxy, t-butoxy, pentoxy, isopentoxy, neopentoxy, t-pentoxy, hexyloxy, isohexyloxy), a dialkylamino having 1 to 6 carbon atoms (e.g., dimethylamino, diethylamino, ethylmethylamino, diisopropylamino, 1-piperidinyl, 1-pyrrolidinyl), etc. Specifically, the "substituted or unsubstituted alkyl having 1 to 6 carbon atoms" is methyl, ethyl, propyl, isopropyl, butyl, isobutyl, sec-butyl, t-butyl, pentyl, isopentyl, neopentyl, t-pentyl, hexyl, isohexyl, fluoromethyl, a perfluoroalkyl (e.g., trifluoromethyl, perfluorohexyl), etc.

The "substituted or unsubstituted aryl" shown by R[6″], R[7″] and R[8″] or the "substituted or unsubstituted aryl" formed by combining R[6″] and R[8″] together with the carbon atom bound to each of R[6″] and R[8″] is, for example, an aryl having 1 to 5 substituents which are the same or different, or an unsubstituted aryl. Examples of the substituent include at least one selected from the group consisting of a halogen (fluorine, chlorine, bromine or iodine), hydroxy group, nitro, cyano, amino, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isobutoxy, sec-butoxy, t-butoxy, pentoxy, isopentoxy, neopentoxy, t-pentoxy, hexyloxy, isohexyloxy), a dialkylamino having 1 to 6 carbon atoms (e.g., dimethylamino, diethylamino, ethylmethylamino, diisopropylamino, 1-piperidinyl, 1-pyrrolidinyl), etc. In some embodiments of the present invention, the substituent is hydroxy group, nitro or dimethylamino. Specific examples are phenyl, a naphthyl(1-naphthyl, 2-naphthyl), a hydroxyphenyl(2-hydroxyphenyl, 3-hydroxyphenyl, 4-hydroxyphenyl), an aminophenyl (e.g., 4-dimethylaminophenyl), a nitrophenyl (e.g., 4-nitrophenyl), a fluorophenyl (e.g., 4-fluorophenyl), a trifluoromethylphenyl (e.g., 4-trifluoromethylphenyl), etc.

The "substituted or unsubstituted heteroaryl" shown by R[6″], R[7″] and R[8″] or the "substituted or unsubstituted heteroaryl" formed by combining R[6″] and R[8″] together with the carbon atom bound to each of R[6″] and R[8″] is, for example, a heteroaryl having 1 to 5 substituents which are the same or different, or an unsubstituted heteroaryl. Examples of the substituent include at least one selected from the group consisting of a halogen (fluorine, chlorine, bromine or iodine), hydroxy group, nitro, cyano, amino, an alkyl having 1 to 6 carbon atoms (e.g., methyl, ethyl, propyl, isopropyl, butyl, isobutyl, sec-butyl, t-butyl, pentyl, isopentyl, neopentyl, t-pentyl, hexyl, isohexyl), an alkoxyl having 1 to 6 carbon atoms (e.g., methoxy, ethoxy, propoxy, isopropoxy, butoxy, isobutoxy, sec-butoxy, t-butoxy, pentoxy, isopentoxy, neopentoxy, t-pentoxy, hexyloxy, isohexyloxy), a dialkylamino having 1 to 6 carbon atoms (e.g., dimethylamino, diethylamino, ethylmethylamino, diisopropylamino, 1-piperidinyl and 1-pyrrolidinyl, preferably, dimethylamino, diethylamino, ethylmethylamino, diisopropylamino), an aryl (e.g., phenyl, naphthyl, anthranyl), a heteroaryl (e.g., a thienyl(2-thienyl, 3-thienyl), a furyl(2-furyl, 3-furyl), a pyrrolyl(2-pyrrolyl, 3-pyrrolyl), a pyridyl(2-pyridyl, 3-pyridyl, 4-pyridyl), imidazoyl, pyrazoyl, oxazoyl, thiazoyl, isoxazoyl, pyrimidyl, pyrazyl, pyridazoyl), etc. Specifically, the "substituted or unsubstituted heteroaryl" is a thienyl(2-thienyl, 3-thienyl), a benzothienyl (e.g., benzo[b]thiophen-2-yl, benzo[b]thiophen-3-yl), a thienothienyl (e.g., thieno[2,3-b]thienyl, thieno[3,2-b]thienyl, thieno[3,2-b:2,3-d]thienyl), a bithiophenyl (e.g., 2,2-bithiophen-5-yl), benzofuranyl, indoyl, indazoyl, benzimidazoyl, benzoxazoyl, benzisoxazoyl, quinolinyl, isoquinolinyl, quinoxalinyl, quinazolinyl, acridinyl, etc.

In some other embodiments of the present invention, coelenteramide analog modified at the C-2-position includes the following compounds.

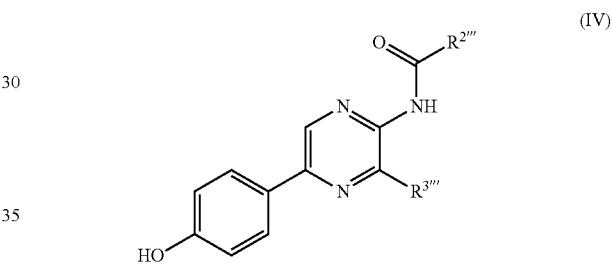

wherein R[2‴] is a group selected from the groups shown below:

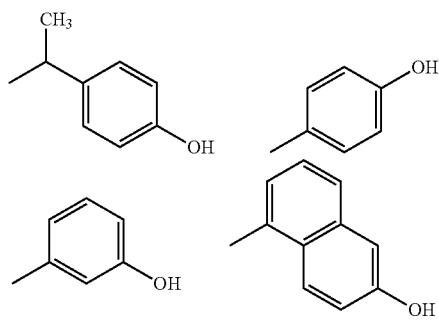

and R[3‴] is hydrogen atom, bromine atom, a substituted or unsubstituted aryl, a substituted or unsubstituted arylalkyl, a substituted or unsubstituted arylalkenyl, a substituted or unsubstituted arylalkynyl, an alkyl which may optionally be substituted with an alicyclic group, an alkenyl which may optionally be substituted with an alicyclic group, an alkynyl which may optionally be substituted with an alicyclic group, an alicyclic group, or a heterocyclic group.

As used herein, the "substituted or unsubstituted aryl," "substituted or unsubstituted arylalkyl," "substituted or unsubstituted arylalkenyl," "substituted or unsubstituted arylalkynyl," "alkyl which may optionally be substituted with an alicyclic group," "an alkenyl which may optionally be substituted with an alicyclic group," "alkynyl which may optionally be substituted with an alicyclic group," "alicyclic group" and "heterocyclic group" shown by $R^{3'''}$ are the same as those defined for $R^{3'''}$.

In a preferred embodiment of the present invention, coelenteramide analog includes the following compounds.

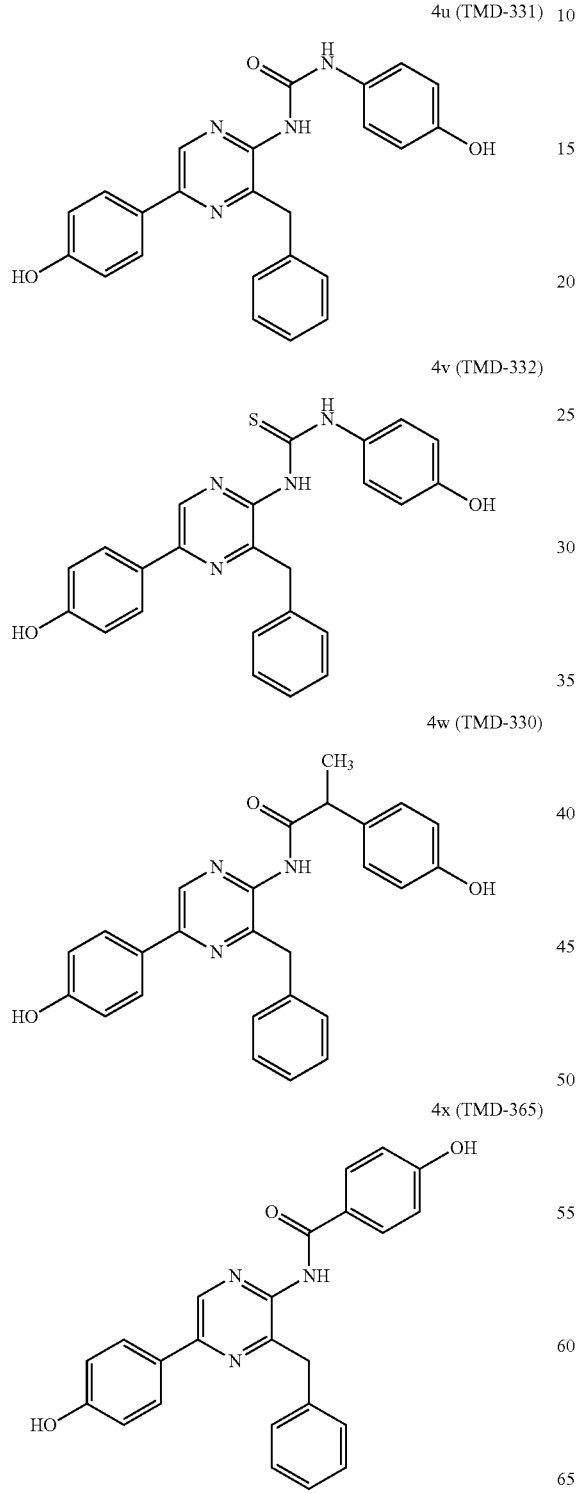

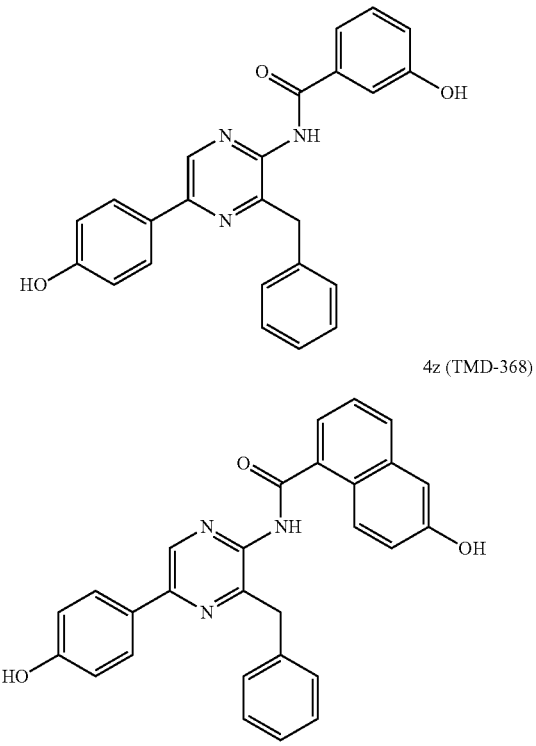

The fluorescent protein containing coelenteramide analog in some embodiments of the present invention has the maximum fluorescence wavelength of 485 nm or more, for example, 485 nm or more, 486 nm or more, 487 nm or more, 488 nm or more, 489 nm or more, 490 nm or more, 491 nm or more, 492 nm or more, 493 nm or more, 494 nm or more, 495 nm or more, 496 nm or more, 497 nm or more, 498 nm or more, 499 nm or more, 500 nm or more, 510 nm or more, 515 nm or more, 520 nm or more, 525 nm or more, 530 nm or more, 535 nm or more, 540 nm or more, and 545 nm or more. More specifically, in coelenteramide analogs (4a to 4z) described above, coelenteramide analog which can shift the maximum fluorescence wavelength to 485 nm or more includes 4a to 4l, 4n to 4p and 4u to 4z, preferably, 4a to 4d, 4f to 4l, 4p, 4n, 4v and 4x to 4z, more preferably, 4a, 4b, 4d, 4f to 4i, 4k, 4l and 4p, much more preferably, 4b, 4f, 4h, 4k and 4p, and most preferably, 4b, 4h and 4p.

The fluorescent protein containing coelenteramide analog in some embodiments of the present invention shows a stronger fluorescence intensity than that of the corresponding coelenteramide analog alone, for example, stronger by 1.5 times or more, 1.6 times or more, 1.7 times or more, 1.8 times or more, 1.9 times or more, 2.0 times or more, 2.1 times or more, 2.2 times or more, 2.3 times or more, 2.4 times or more, 2.5 times or more, 3.0 times or more, 4.0 times or more, 5.0 times or more, 10 times or more, 15 times or more, 20 times or more, 30 times or more, 40 times or more, 50 times or more, 60 times or more, 70 times or more, 80 times or more, 90 times or more, 100 times or more, 110 times or more, 120 times or more and 130 times or more. More specifically, among coelenteramide analogs (4a to 4z) described above, coelenteramide analog in the form of fluorescent protein which can provide a stronger fluorescence intensity than that of the corresponding coelenteramide analog alone includes 4a to 4p and 4r to 4z, preferably, 4a to 4g, 4i to 4p and 4r to 4z, more preferably, 4a, 4f, 4g and 4w, and most preferably, 4a, 4f and 4w.

The fluorescent protein containing coelenteramide analog in some embodiments of the present invention provides different fluorescence spectra from those of the corresponding coelenteramide analog alone. The maximum fluorescence wavelengths in the two cases are different by ±5 nm or more, ±10 nm or more, ±15 nm or more, ±20 nm or more, ±25 nm or more, ±30 nm or more, ±35 nm or more, ±40 nm or more, ±45 nm or more, ±50 nm or more, ±55 nm or more, ±60 nm or more, ±65 nm or more, ±70 nm or more, ±75 nm or more, ±80 nm or more, ±85 nm or more, ±90 nm or more, ±95 nm or more, or ±100 nm or more. More specifically, coelenteramide analog which can change the maximum fluorescence intensity between the fluorescent protein and the corresponding coelenteramide alone includes 4a to 4n, 4p, 4r, 4s and 4u to 4z, preferably, 4a to 4e, 4f, 4h, 4i, 4k, 4m, 4n, 4p, 4u and 4w to 4z, among coelenteramide analogs (4a to 4z) described above.

4. Method for Producing Coelenteramide Analogue of the Present Invention 4.1. Coelenteramide Analogue Modified at the C-3 Position In coelenteramide analog of the present invention, coelenteramide analog modified at the C-3 position represented by general formula (II) below:

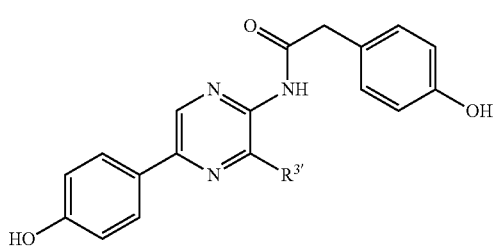

(II)

(wherein $R^3$ is the same as defined above) can be produced as follows.

That is, coelenteramide analog represented by general formula (II) can be produced by reacting a compound represented by general formula (II-1) shown below:

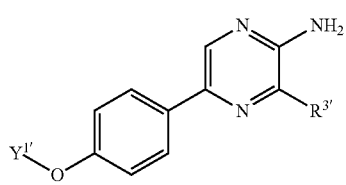

(II-1)

(wherein $R^{3'}$ is the same as defined above and $Y^{1'}$ is hydrogen atom or a protecting group) with a compound represented by general formula (II-2) shown below:

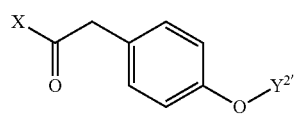

(II-2)

(wherein X is a splitting-off group and $Y^{2'}$ is hydrogen atom or a protecting group) to give a compound represented by general formula (II-3) shown below:

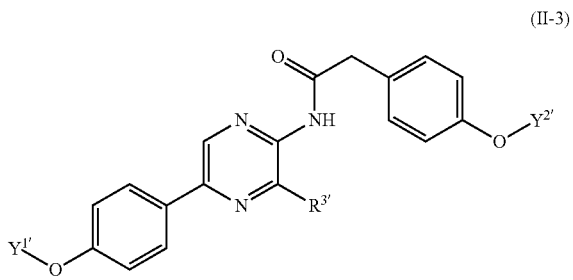

(II-3)

(wherein $R^{3'}$, $Y^{1'}$ and $Y^{2'}$ are the same as defined above), or the like.

As used herein, the protecting groups shown by $Y^{1'}$ and $Y^{2'}$ independently represent, e.g., tert-butyldimethylsilyl (TBDMS), tert-butyldiphenylsilyl (TBDPS), trimethylsilyl (TMS), triethylsilyl (TES), triisopropylsilyl (TIPS), methoxymethyl (MOM), 2-methoxethoxyymethyl (MEM), 2-tetrahydropyranyl (THP), methyl (Me), tert-butyl (t-Bu), benzyl (Bn), p-methoxybenzyl (PMB), acetyl (Ac) or benzoyl (Bz); particularly preferred is TBDMS, Me, Bn or Ac.

The splitting-off group shown by X includes, for example, a halogen (e.g., chlorine, fluorine, bromine or iodine), a reactive residue of a sulfonic acid (e.g., methanesulfonyloxy, benzenesulfonyloxy or toluenesulfonyloxy), and an acyloxy for forming an acid anhydride (e.g., (4-$Y^{2'}$O)$C_6H_4CH_2COO$— (wherein $Y^{2'}$ is the same as defined above)). Among them, a halogen is preferred and chlorine is more preferred.

The compound represented by general formula (II-1) can be produced by known production methods, for example, the methods described in Kishi et al. (1972) *Tetrahedron Lett.* 13, 2747-2748, Adamczyk et al. (2001) *Org. Prep. Proced. Int.* 33, 477-485 or Wael, F. D. et al. (2009) *Bioorg. Med. Chem.* 17, 4336-4344, or modifications of these methods.

The compound represented by general formula (II-2) can be produced by known production methods. Specifically, any compound can be produced either by reacting the corresponding carboxylic acid with an excess of thionyl chloride while heating to reflux followed by concentration under reduced pressure, or by reacting the corresponding carboxylic acid with oxalyl dichloride in a dichloromethane solvent in the presence of a catalytic amount of N,N-dimethylformamide (DMF) followed by concentration under reduced pressure. Alternatively, the compound may also be commercially available.

The compound represented by general formula (II-3) can be produced by known production methods. Specifically, any compound can be produced by reacting the compound represented by general formula (II-1) with the compound represented by general formula (II-2), e.g., in an organic solvent in the presence of a base or in a basic organic solvent.

In the compound represented by general formula (II-3) thus produced wherein $Y^{1'}$ and $Y^{2'}$ represent protecting groups, coelenteramide analog represented by general formula (II) can be produced by removing the protecting groups from the compound represented by general formula (II-3). More specifically, coelenteramide analog represented by general formula (II) can be produced by the method described in EXAMPLES below or modifications thereof.

Herein, where the protecting groups ($Y^{1'}$ and $Y^{2'}$) are, e.g., TBDMS, the reagents used in the method for producing coelenteramide analog represented by general formula (II) are fluorine reagents such as tetrabutylammonium fluoride (TBAF), potassium fluoride, hydrofluoric acid, etc. or acids such as acetic acid, hydrochloric acid, hydrobromic acid, hydroiodic acid, hydrofluoric acid, perchloric acid, sulfuric acid, phosphoric acid, nitric acid, etc. These reagents may be used alone or as a mixture thereof. TBAF is particularly preferred.

Where the protecting groups ($Y^{1'}$ and $Y^{2'}$) are, e.g., TBDMS, various solvents can be used as the solvent in the method for producing coelenteramide analog represented by general formula (II), and examples include tetrahydrofuran (THF), dioxane, ether, acetonitrile, ethyl acetate, acetone, N,N-dimethylformamide (DMF), dimethylsulfoxide (DMSO), toluene, dichloromethane, methanol, ethanol, butanol, water, etc. These solvents can be used alone or as a mixture thereof.

In the method for producing coelenteramide analog represented by general formula (II) where the protecting groups ($Y^{1'}$ and $Y^{2'}$) are, e.g., TBDMS, the reaction temperature and reaction time are not particularly limited but are generally at −20° C. to 200° C. for 10 minutes to 24 hours, preferably at 0° C. to 100° C. for 10 minutes to 6 hours, more preferably, at room temperature to 50° C. for 30 minutes to 2 hours.

Further when the protecting groups ($Y^{1'}$ and $Y^{2'}$) are, e.g., Me, various reagents can be used as the reagents in the method for producing coelenteramide analog represented by general formula (II) in accordance with the method described in Inouye & Hosoya (2009) *Biochem. Biophys. Res. Commun.* 386, 617-622 or modifications thereof. For example, boron tribromide or pyridinium chloride can be used, and boron tribromide is particularly preferred.

In the method for producing coelenteramide analog represented by general formula (II), solvents can be used. When the protecting groups ($Y^{1'}$ and $Y^{2'}$) are, e.g., Me, various solvents can be used and examples are dichloromethane, chloroform, tetrahydrofuran (THF), dioxane, ether, acetonitrile, ethyl acetate, acetone, N,N-dimethylformamide (DMF), dimethylsulfoxide (DMSO), toluene, etc. These solvents can be used alone or as a mixture thereof.

In the method for producing coelenteramide analogs represented by general formula (II), where the protecting groups ($Y^{1'}$ and $Y^{2'}$) are, e.g., Me, the reaction temperature and reaction time are not particularly limited but are generally at −78° C. to 200° C. for 10 minutes to 72 hours, preferably, 0° C. to 150° C. for 30 minutes to 36 hours, and more preferably, at room temperature to 60° C. for an hour to 12 hours.

4.2. Coelenteramide Analogue Modified at the C-2 Position 4.2.1. Coelenteramide Analogue Represented by General Formula (III)

In coelenteramide analogs of the present invention, coelenteramide analog modified at the C-2 position, which is represented by general formula (III) shown below:

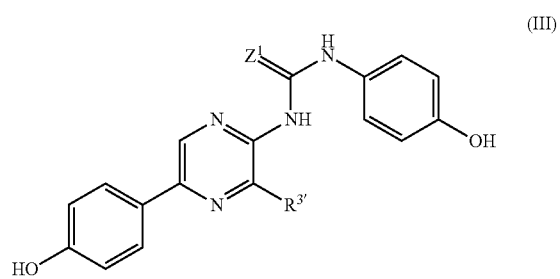

(wherein $Z^1$ and $R^{3'''}$ are the same as defined above) can be produced as follows.

The above compound can be produced by first reacting a compound represented by general formula (III-1) shown below:

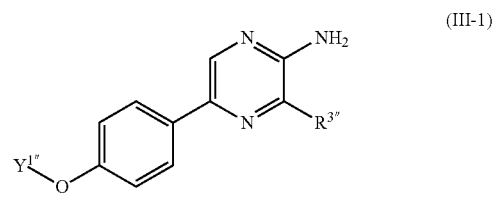

(wherein $R^{3'''}$ is the same as defined above and $Y^{1'''}$ is hydrogen atom or a protecting group) with a compound represented by general formula (III-2) shown below:

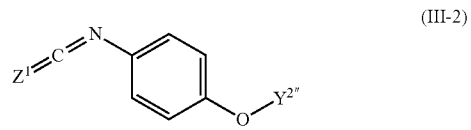

(wherein $Z^1$ is the same as defined above and $Y^{2'''}$ is hydrogen atom or a protecting group) to give a compound represented by general formula (III-3) shown below:

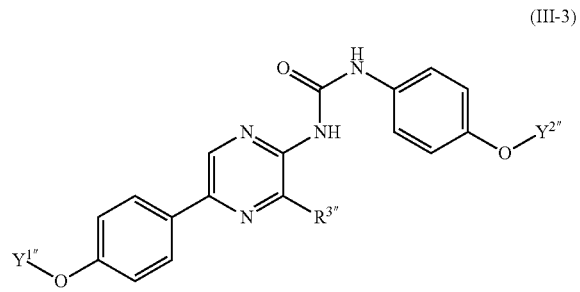

(wherein $R^{3'''}$, $Y^{1'''}$, $Y^{2'''}$ and $Z^1$ are the same as defined above), and so on.

As used herein, the "protecting groups" shown by $Y^{1'''}$ and $Y^{2'''}$ are the same as those described for $Y^{1'''}$ and $Y^{2'}$.

The compound represented by general formula (III-1) can be produced by known production methods, for example, the methods described in Y. Kishi et al., *Tetrahedron Lett.*, 13, 2747-2748 (1972), M. Adamczyk et al., *Org. Prep. Proced. Int.*, 33, 477-485 (2001), or F. D. Wael et al., *Bioorg. Med. Chem.*, 17, 4336-4344 (2009), or modifications of these methods.

The compound represented by general formula (III-2) can be produced by known production methods, for example, the method described in S. Knaggs et al., *Org. Biomol. Chem.*, 3, 4002-4010 (2005) or modifications thereof. Alternatively, the compound is commercially available.

The compound represented by general formula (III-3) can be produced by known production methods. Specifically, any compound can be produced by reacting the compound represented by general formula (III-1) with the compound represented by general formula (III-2), e.g., in an organic solvent in the presence of a base or in a basic organic solvent.

In the compound represented by general formula (III-3) thus produced wherein $Y^{1''}$ and $Y^{2''}$ represent protecting groups, coelenteramide analogs represented by general formula (III) can be produced by removing the protecting groups from the compound represented by general formula (III-3). More specifically, coelenteramide analogs represented by general formula (III) can be produced by the method described in EXAMPLES below or modifications thereof.

Herein, where the protecting groups ($Y^{1''}$ and $Y^{2''}$) are, e.g., TBDMS, the reagents used in the method for producing coelenteramide analogs represented by general formula (III) are fluorine reagents such as tetrabutylammonium fluoride (TBAF), potassium fluoride, hydrofluoric acid, etc. or acids such as acetic acid, hydrochloric acid, hydrobromic acid, hydroiodic acid, hydrofluoric acid, perchloric acid, sulfuric acid, phosphoric acid, nitric acid, etc. These reagents may be used alone or as a mixture thereof. TBAF is particularly preferred.

Where the protecting groups ($Y^{1'}$ and $Y^{2'}$) are, e.g., TBDMS, various solvents can be used as the solvent in the method for producing coelenteramide analogs represented by general formula (II), and examples include tetrahydrofuran (THF), dioxane, ether, acetonitrile, ethyl acetate, acetone, N,N-dimethylformamide (DMF), dimethylsulfoxide (DMSO), toluene, dichloromethane, methanol, ethanol, butanol, water, etc. These solvents can be used alone or as a mixture thereof.

In the method for producing coelenteramide analogs represented by general formula (III), when the protecting groups ($Y^{1''}$ and $Y^{2''}$) are, e.g., TBDMS, the reaction temperature and reaction time are not particularly limited but are generally at −20° C. to 200° C. for 10 minutes to 24 hours, preferably, at 0° C. to 100° C. for 10 minutes to 6 hours, and more preferably, at room temperature to 50° C. for 30 minutes to 2 hours.

Also, when the protecting groups ($Y^{1''}$ and $Y^{2''}$) are, e.g., Me, various reagents can be used as the reagents in the method for producing coelenteramide analogs represented by general formula (III) in accordance with the method described in Inouye & Hosoya, *Biochem. Biophys. Res. Commun.*, 386, 617-622 (2009), or modifications thereof. For example, boron tribromide or pyridinium chloride can be used, and boron tribromide is particularly preferred.

In the method for producing coelenteramide analogs represented by general formula (III), solvents can be used and where the protecting groups ($Y^{1''}$ and $Y^{2''}$) are, e.g., Me, various solvents can be used. Examples are dichloromethane, chloroform, tetrahydrofuran (THF), dioxane, ether, acetonitrile, ethyl acetate, acetone, N,N-dimethylformamide (DMF), dimethylsulfoxide (DMSO), toluene, etc. These solvents can be used alone or as a mixture thereof.

In the method for producing coelenteramide analogs represented by general formula (III) where the protecting groups ($Y^{1''}$ and $Y^{2''}$) are, e.g., Me, the reaction temperature and reaction time are not particularly limited but are generally at −78° C. to 200° C. for 10 minutes to 72 hours, preferably, at 0° C. to 150° C. for 30 minutes to 36 hours, and more preferably, at room temperature to 60° C. for an hour to 12 hours.

4.2.2. Coelenteramide Analogue Represented by General Formula (IV)

In coelenteramide analogs of the present invention, coelenteramide analog represented by general formula (IV) shown below, which is modified at the C-2 position can be prepared as follows:

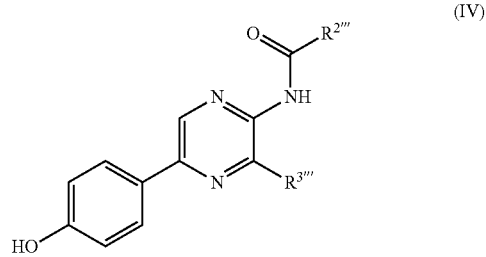

(wherein $R^{2'''}$ and $R^{3'''}$ are the same as defined above).

That is, a compound represented by general formula (IV-1) shown below:

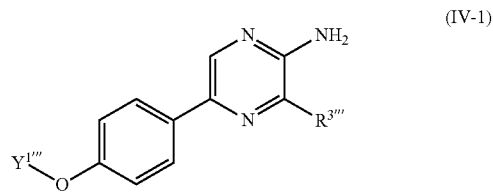

(wherein $R^{3'''}$ is the same as defined above and $Y^{1'''}$ is hydrogen atom or a protecting group) is reacted with a compound represented by general formula (IV-2) shown below:

(wherein X is a splitting-off group and $R^{2'''}$ is a group selected from:

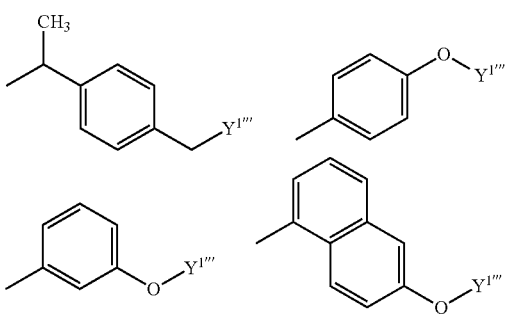

(wherein $Y^{1'''}$ is hydrogen atom or a protecting group) to give a compound represented by general formula (IV-3-1) or (IV-3-2) shown below:

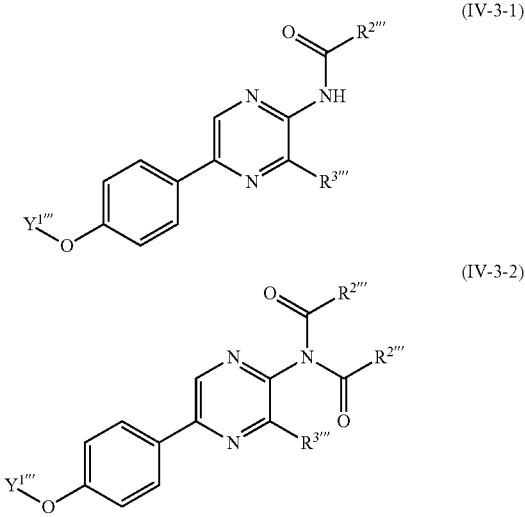

(wherein R$^{2'''}$, R$^{3''''}$ and Y$^{1''''}$ are the same as defined above), and so on.

Herein, the splitting off group shown by X includes, for example, a halogen (e.g., chlorine, fluorine, bromine or iodine), a reactive residue of a sulfonic acid (e.g., methanesulfonyloxy, benzenesulfonyloxy or toluenesulfonyloxy), and an acyloxy for forming an acid anhydride (e.g., (4-Y$^{1'''}$O) C$_6$H$_4$CH$_2$COO— (wherein Y$^{1'''}$ is the same as defined above)). Among them, a halogen is preferred and chlorine is more preferred.

The compound represented by general formula (IV-1) can be produced by known production methods, for example, the methods described in Kishi et al., *Tetrahedron Lett.,* 13, 2747-2748 (1972), Adamczyk et al., *Org. Prep. Proced. hat.,* 33, 477-485 (2001), or modifications of these methods.

The compound represented by general formula (IV-2) can be produced by known production methods. Specifically, any compound can be produced either by reacting the corresponding carboxylic acid with an excess of thionyl chloride while heating to reflux followed by concentration under reduced pressure, or by reacting the corresponding carboxylic acid with oxalyl dichloride in a dichloromethane solvent in the presence of a catalytic amount of N,N-dimethylformamide (DMF) followed by concentration under reduced pressure. Alternatively, the compound may also be commercially available.

The compound represented by general formula (IV-3-1) or general formula (IV-3-2) can be produced by known production methods. Specifically, any compound can be produced by reacting the compound represented by general formula (IV-1) with the compound represented by general formula (IV-2), e.g., in an organic solvent in the presence of a base or in a basic organic solvent.

In the compound represented by general formula (IV-3-1) or general formula (IV-3-2) thus produced wherein Y$^{1'''}$ and Y$^{2'''}$ represent protecting groups, coelenteramide analogs represented by general formula (IV) can be produced by removing the protecting groups from the compound represented by general formula (IV-3-1) or general formula (V-3-2). More specifically, coelenteramide analogs represented by general formula (IV) can be produced by the method described in EXAMPLES below or modifications thereof.

Herein, where the protecting groups (Y$^{1'''}$ and Y$^{2'''}$) are, e.g., TBDMS, the reagents used in the method for producing coelenteramide analogs represented by general formula (IV) are fluorine reagents such as tetrabutylammonium fluoride (TBAF), potassium fluoride, hydrofluoric acid, etc. or acids such as acetic acid, hydrochloric acid, hydrobromic acid, hydroiodic acid, hydrofluoric acid, perchloric acid, sulfuric acid, phosphoric acid, nitric acid, etc. These reagents may be used alone or as a mixture thereof. TBAF is particularly preferred.

Where the protecting groups (Y$^{1'''}$ and Y$^{2'''}$) are, e.g., TBDMS, various solvents can be used as the solvent in the method for producing coelenteramide analogs represented by general formula (IV), and examples include tetrahydrofuran (THF), dioxane, ether, acetonitrile, ethyl acetate, acetone, N,N-dimethylformamide (DMF), dimethylsulfoxide (DMSO), toluene, dichloromethane, methanol, ethanol, butanol, water, etc. These solvents can be used alone or as a mixture thereof.

In the method for producing coelenteramide analog represented by general formula (IV) wherein the protecting groups (Y$^{1'''}$ and Y$^{2'''}$) are, e.g., TBDMS, the reaction temperature and reaction time are not particularly limited but are generally at −20° C. to 200° C. for 10 minutes to 24 hours, preferably, at 0° C. to 100° C. for 10 minutes to 6 hours, and more preferably, at room temperature to 50° C. for 30 minutes to 2 hours.

Further when the protecting groups (Y$^{1'''}$ and Y$^{2'''}$) are, e.g., Me, various reagents can be used as the reagent in the method for producing coelenteramide analog represented by general formula (IV) in accordance with the method described in Inouye & Hosoya (2009) *Biochem. Biophys. Res. Commun.* 386, 617-622 or modifications thereof. For example, boron tribromide or pyridinium chloride can be used, and boron tribromide is particularly preferred.

In the method for producing coelenteramide analog represented by general formula (IV), solvents can be used. When the protecting groups (Y$^{1'''}$ and Y$^{2'''}$) are, e.g., Me, various solvents can be used and examples are dichloromethane, chloroform, tetrahydrofuran (THF), dioxane, ether, acetonitrile, ethyl acetate, acetone, N,N-dimethylformamide (DMF), dimethylsulfoxide (DMSO), toluene, etc. These solvents can be used alone or as a mixture thereof.

In the method for producing coelenteramide analog represented by general formula (IV) where the protecting groups (Y$^{1'''}$ and Y$^{2'''}$) are, e.g., Me, the reaction temperature and reaction time are not particularly limited but are generally at −78° C. to 200° C. for 10 minutes to 72 hours, preferably, at 0° C. to 150° C. for 30 minutes to 36 hours, and more preferably, at room temperature to 60° C. for an hour to 12 hours.

5. Method for Producing the Calcium-Binding Photoprotein
5.1. Production from Coelenterazine Analogue The calcium-binding photoprotein of the present invention can be produced or regenerated by contacting coelenterazine analog of the present invention described above with an apoprotein of the calcium-binding photoprotein thereby to obtain the calcium-binding photoprotein.

As used herein, the term "contact" means that coelenterazine analog of the present invention and an apoprotein of the calcium-binding photoprotein are allowed to be present in the same reaction system, and includes, for example, states that an apoprotein of the calcium-binding photoprotein is added to a container charged with coelenterazine analog of the present invention, coelenterazine analog of the present invention is added to a container charged with an apoprotein of the calcium-binding photoprotein, coelenterazine analog of the present invention is mixed with an apoprotein of the calcium-binding photoprotein, and the like.

In some embodiments of the present invention, the contact is effected at a low temperature in the presence of a reducing agent (e.g., mercaptoethanol, dithiothreitol, etc.) and oxygen. More specifically, the calcium-binding photoprotein of the present invention can be produced or regenerated by the methods described in, e.g., Shimomura, O. et al. Biochem. J. 251, 405-410 (1988), Shimomura, O. et al. Biochem. J. 261, 913-920 (1989), etc. The calcium-binding photoprotein of the present invention exists as a complex which, in the presence of oxygen, generates from a peroxide of coelenterazine analog produced from coelenterazine analog of the invention and molecular oxygen, and an apoprotein. When calcium ions bind to the complex described above, the complex emits a transient light to generate coelenteramide analog as the oxide of coelenterazine analog and carbon dioxide. The complex described above is sometimes referred to as the "photoprotein of the present invention."

Examples of the apoprotein used to produce the photoprotein of the present invention include apoaequorin, apoclytin-I, apoclytin-II, apobelin, apomitrocomin, apomineopsin, apobervoin, and the like. In some embodiments of the present invention, the apoprotein is apoaequorin, apobelin, apoclytin-1, apoclytin-II, mitrocomin, etc., e.g., apoaequorin. These apoproteins may be obtained from natural sources or genetically engineered. Furthermore, the amino acid sequence may also be mutated from the native sequence by gene recombination technology, as long as the apoproteins are capable of producing the calcium-binding photoprotein.

The nucleotide sequences and amino acid sequences of the apoproteins of photoproteins obtained from the nature (native apoproteins) are as follows. The nucleotide sequence and amino acid sequence of native apoaequorin are shown by SEQ ID NO: 1 and SEQ ID NO: 2, respectively. The nucleotide sequence and amino acid sequence of native apoclytin-I are shown by SEQ ID NO: 3 and SEQ ID NO: 4, respectively. The nucleotide sequence and amino acid sequence of native apoclytin-II are shown by SEQ ID NO: 5 and SEQ ID NO: 6, respectively. The nucleotide sequence and amino acid sequence of native apomitrocomin are shown by SEQ ID NO: 7 and SEQ ID NO: 8, respectively. The nucleotide sequence and amino acid sequence of native apobelin are shown by SEQ ID NO: 9 and SEQ ID NO: 10, respectively. The nucleotide sequence and amino acid sequence of native apobervoin are shown by SEQ ID NO: 11 and SEQ ID NO: 12, respectively.

The apoprotein mutated by recombinant technology is a protein selected from the group consisting of (a) to (c) below:

(a) a protein comprising the amino acid sequence of native apoprotein in which 1 or more amino acids are deleted, substituted, inserted and/or added, and having the activity or function of the apoprotein of the calcium-binding photoprotein;

(b) a protein comprising an amino acid sequence which has 90% or more homology to the amino acid sequence of native apoprotein, and having the activity or function of the apoprotein of the calcium-binding photoprotein; and, (c) a protein comprising an amino acid sequence encoded by a polynucleotide that hybridizes under stringent conditions to a polynucleotide comprising a nucleotide sequence complementary to the nucleotide sequence of native apoprotein, and having the activity or function of the apoprotein of the calcium-binding photoprotein.

Examples of the "native apoprotein" described above are apoaequorin, apoclytin-I, apoclytin-II, apobelin, apomitrocomin, apomineopsin, apobervoin, etc. In an embodiment of the present invention, the apoprotein is apoaequorin, apoclytin-I, apoclytin-II, apobelin, apomitrocomin, etc., preferably apoaequorin. The amino acid sequences and nucleotide sequences of these native apoproteins are the same as described above.

The "activity or function of the apoprotein of the calcium-binding photoprotein" means the activity or function of the apoprotein which binds to a peroxide of coelenterazine or a peroxide of coelenterazine analog to produce the calcium-binding photoprotein. Specifically, "the protein binds to a peroxide of coelenterazine or a peroxide of coelenterazine analog to produce the calcium-binding photoprotein" means not only (1) that the apoprotein binds to the peroxide of coelenterazine or the peroxide of coelenterazine analog to produce the photoprotein, but also (2) that the apoprotein is brought in contact with coelenterazine or its analogs in the presence of oxygen to produce the photoprotein (complex) containing the apoprotein and the peroxide of coelenterazine or the peroxide of coelenterazine analog. As used herein, the term "contact" means that the apoprotein and coelenterazine or its analog are allowed to be present in the same reaction system, and includes, for example, addition of the apoprotein to a container charged with coelenterazine or its analog, addition of coelenterazine or its analog to a container charged with the apoprotein, mixing of the apoprotein with coelenterazine or its analog, and the like. "Coelenterazine analog" refers to a compound capable of constituting as the apoprotein the calcium-binding photoprotein such as aequorin, etc. as in coelenterazine. Examples of coelenterazine or its analog are, in addition to coelenterazine analog of the present invention, coelenterazine, h-coelenterazine, f-coelenterazine, cl-coelenterazine, n-coelenterazine, cp-coelenterazine, ch-coelenterazine, hch-coelenterazine, fch-coelenterazine, e-coelenterazine, ef-coelenterazine, ech-coelenterazine, hcp-coelenterazine, and the like. These coelenterazine and analogs of the present invention can be produced, e.g., by the method described in EXAMPLES below or its modifications. The other coelenterazine and analogs thereof can be produced by the methods described in, e.g., Shimomura et al. (1988) Biochem. J. 251, 405-410, Shimomura et al. (1989) Biochem. J. 261, 913-920 and Shimomura et al. (1990) Biochem. J. 270, 309-312, or modifications thereof. Alternatively, these compounds are commercially available from Chisso Corp., Wako Pure Chemicals, Promega Inc., etc. and such commercial products may also be used.

The range of "1 or more" in "the amino acid sequence in which 1 or more amino acids are deleted, substituted, inserted and/or added" is, for example, 1 to 20, 1 to 15, 1 to 10, 1 to 9, 1 to 8, 1 to 7, 1 to 6 (1 to several), 1 to 5, 1 to 4, 1 to 3, 1 to 2, and 1. In general, the less the number of amino acids deleted, substituted, inserted or added, the more preferable. In the deletion, substitution, insertion and addition of the amino acid residues described above, two or more may occur concurrently. Such regions can be acquired by using site-directed mutagenesis described in Sambrook J. et al., Molecular Cloning: A Laboratory Manual, Third Edition, Cold Spring Harbor Laboratory Press (2001); Ausbel F. M. et al., Current Protocols in Molecular Biology, Supplement 1-38, John Wiley and Sons (1987-1997); Nuc. Acids. Res., 10, 6487 (1982); Proc. Natl. Acad. Sci. USA, 79, 6409 (1982); Gene, 34, 315 (1985); Nuc. Acids. Res., 13, 4431 (1985); Proc. Natl. Acad. Sci. USA, 82, 488 (1985); etc.

The range of "90% or more" in the "amino acid sequence which has 90% or more homology" is, for example, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. It is generally preferable for the numerical value indicating the degree of homology to be higher. The homology between amino acid sequences or nucleotide sequences can be determined using a sequencing program such as BLAST (see, e.g., Altzchul, S. F. et al., J. Mol. Biol., 215, 403 (1990), etc.) or the like. When BLAST is used, the defaul parameters for the respective programs are used.

The "polynucleotide that hybridizes under stringent conditions" described above refers to a polynucleotide (e.g., DNA) which is obtained by, for example, colony hybridization, plaque hybridization, Southern hybridization, etc., using as a probe all or part of a polynucleotide comprising a nucleotide sequence complementary to the nucleotide sequence of native apoprotein or a polynucleotide encoding the amino acid sequence of native apoprotein. Specific examples include a polynucleotide which can be identified by performing hybridization at 65° C. in the presence of 0.7 to 1.0 mol/L NaCl using a filter on which the polynucleotide from a colony or plaque is immobilized, then washing the filter at 65° C. with an SSC (saline-sodium citrate) solution having a concentration of 0.1 to 2 times (a 1×SSC solution is composed of 150 mmol/L of sodium chloride and 15 mmol/L of sodium citrate).

Hybridization may be performed in accordance with modifications of the methods described in textbooks of experiment, e.g., Sambrook, J. et al.: Molecular Cloning: A Laboratory Manual, Third Edition, Cold Spring Harbor Laboratory Press (2001), Ausbel F. M. et al., Current Protocols in Molecular Biology, Supplement 1-38, John Wiley and Sons (1987-1997), Glover D. M. and Hames B. D., DNA Cloning 1: Core Techniques, A practical Approach, Second Edition, Oxford University Press (1995), etc., or their modifications.

As used herein, "stringent conditions" may refer to less stringent conditions, moderately stringent conditions and highly stringent conditions. The "less stringent conditions" are, for example, the conditions under 5×SSC, 5×Denhardt's solution, 0.5% (w/v) SDS and 50% (v/v) formamide at 32° C. The "moderately stringent conditions" are, for example, the conditions under 5×SSC, 5×Denhardt's solution, 0.5% (w/v) SDS and 50% (v/v) formamide at 42° C. The "highly stringent conditions" are, for example, the conditions under 5×SSC, 5×Denhardt's solution, 0.5% (w/v) SDS and 50% (v/v) formamide at 50° C. The more stringent the conditions are, the higher the complementarity required for double strand formation. Specifically, for example, under these conditions, a polynucleotide (e.g., DNA) of higher homology is expected to be obtained efficiently at higher temperatures, although multiple factors are involved in hybridization stringency, including temperature, probe concentration, probe length, ionic strength, time and base concentration; one skilled in the art may appropriately select these factors to realize a similar stringency.

When a commercially available kit is used for the hybridization, for example, AlkPhos Direct Labeling Reagents (manufactured by Amersham Pharmacia) can be used. According to the protocol bound to the kit in this case, incubation with a labeled probe is performed overnight, the membrane is then washed with a primary wash buffer containing 0.1% (w/v) SDS at 55° C., and finally the hybridized DNA can be detected.

Other hybridizable polynucleotides include, as calculated by a sequencing program such as BLAST or the like using the default parameters, DNAs having homology of 60% or more, 65% or more, 70% or more, 75% or more, 80% or more, 85% or more, 88% or more, 90% or more, 92% or more, 95% or more, 97% or more, 98% or more, 99% or more, 99.3% or more, 99.5% or more, 99.7% or more, 99.8% or more, or 99.9% or more, to the polynucleotide encoding the amino acid sequence of the apoprotein. The homology of an amino acid sequence or a nucleotide sequence can be determined using the method described hereinabove.

Examples of the recombinant apoprotein which can be used in the present invention include recombinant aequorin described in Shimomura, O. and Inouye, S. Protein Express. Purif. (1999) 16: 91-95, recombinant clytin-I described in Inouye, S. and Sahara, Y. Protein Express. Purif. (2007) 53: 384-389, recombinant clytin-II described in Inouye, S. J. Biochem. (2008) 143: 711-717, and the like.

The calcium-binding photoprotein thus produced may be further purified. Purification of the calcium-binding photoprotein can be performed in a conventional manner of separation/purification. The separation/purification includes, for example, precipitation with ammonium sulfate, gel filtration chromatography, ion exchange chromatography, affinity chromatography, reversed phase high performance liquid chromatography, dialysis, ultrafiltration, etc., alone or in an appropriate combination of these techniques.

The photoprotein in some embodiments of the present invention exhibits different luminescence properties from those of known photoproteins. The photoprotein in a preferred embodiment of the present invention provides a longer half decay time of luminescence, which is a time period in which the luminescence becomes half of the maximum luminescence intensity, when compared to a photoprotein containing coelenterazine as a light emitting substrate. Furthermore, the photoprotein in a more preferred embodiment of the present invention provides different luminescence spectra from luminescence spectra of the corresponding fluorescent protein prepared by causing luminescence of the photoprotein in the presence of calcium.

5.2. Production from Green Fluorescent Protein (gFP)-Like Protein

Figure 8:
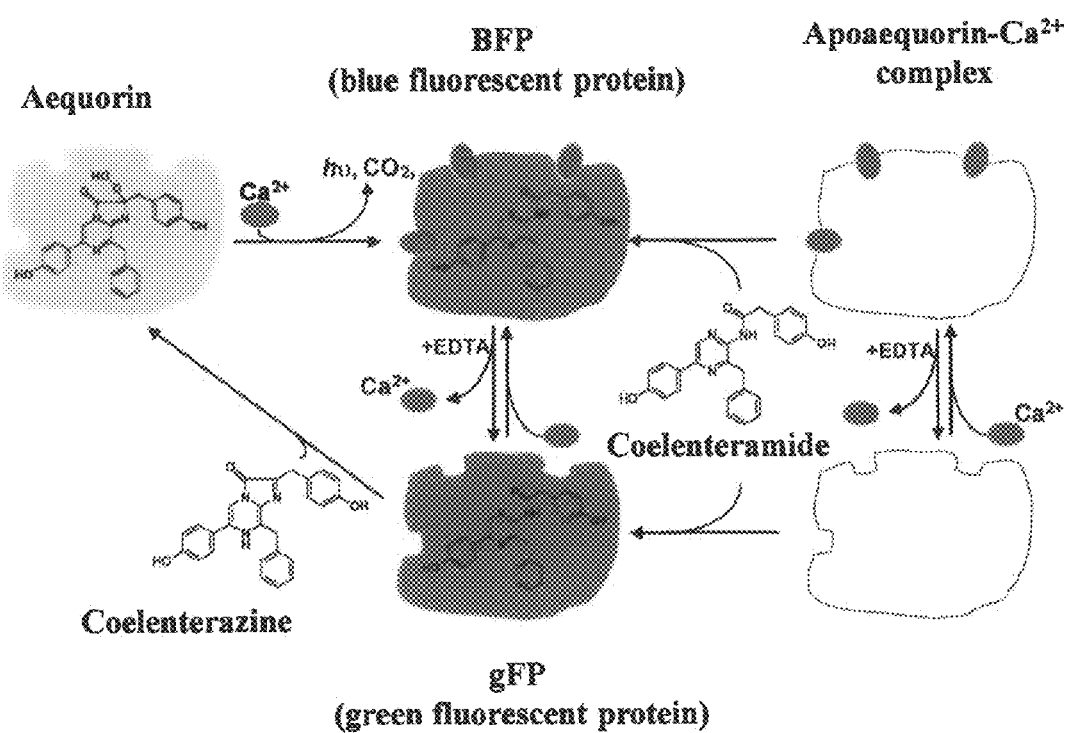
FIG. 8 shows the scheme for preparing BFP, gFP, aequorin, etc. from coelenteramide.

As illustrated in FIG. 8, the calcium-binding photoprotein such as aequorin, etc. can be produced by contacting coelenterazine or its analogs with the gFP-like protein of the present invention in the presence of a chelating agent such as EDTA, etc., for sequestering calcium ions or divalent or trivalent ions replaceable for the calcium ions thereby to obtain the calcium-binding photoprotein. The term "contact" means that the gFP-like protein of the present invention and coelenterazine or its analog are allowed to be present in the same reaction system, and includes, for example, addition of the gFP-like protein of the present invention to a container charged with coelenterazine or its analog, addition of coelenterazine or its analog of the present invention to a container charged with the gFP-like protein of the present invention, mixing of the gFP-like protein of the present invention with coelenterazine or its analog, and the like.

The gFP-like protein of the present invention used to produce the calcium-binding photoprotein of the present invention is described hereinbelow.

Examples of coelenterazine or its analog used to produce the calcium-binding photoprotein of the present invention include, in addition to coelenterazine analog of the present invention, coelenterazine, h-coelenterazine, f-coelenterazine, cl-coelenterazine, n-coelenterazine, cp-coelenterazine, ch-coelenterazine, hch-coelenterazine, fch-coelenterazine, e-coelenterazine, ef-coelenterazine, ech-coelenterazine, hcp-coelenterazine, and the like, preferably coelenterazine, h-coelenterazine and e-coelenterazine. These coelenterazine and analogs thereof are available as described above.

The amount of coelenterazine or its analog used to produce the calcium-binding photoprotein is not particularly limited, and is, e.g., 1.2 mol or more per mol of the gFP-like protein.

In the method for producing the calcium-binding photoprotein, the reaction temperature and reaction time are not particularly limited and are, for example, at 0° C. to 42° C. for 0.1 to 2 hours, at 4° C. to 37° C. for 0.1 to 2 hours, or at 4° C. to 15° C. for 0.1 to 24 hours.

It is preferred to carry out the reaction of the gFP-like protein of the present invention with coelenterazine or its analog in the presence of the chelating agent for sequestering calcium ions or divalent or trivalent ions replaceable for the calcium ions. The chelating agent used to produce the gFP-like protein in the present invention is the same as described above, and may be any agent but is not particularly limited, so long as it strongly binds to calcium ions or divalent or trivalent ions replaceable for the calcium ions. Examples of the chelating agent include ethylenediaminetetraacetic acid (EDTA), ethylene glycol-bis(β-aminoethyl ether)-N,N,N',N'-tetraacetic acid (EGTA), trans-1,2-diaminocyclohexane-N,N,N',N'-tetraacetic acid (CyDTA), N-(2-hydroxyethyl)iminodiacetic acid (HIDA) and the like. As used herein, the calcium ions or divalent or trivalent ions replaceable for the calcium ions are the same as those described above.

The amount of the chelating agent used to produce the gFP-like protein is not particularly limited unless its concentration affects regeneration of the gFP-like protein. Since it is demonstrated that 3 mols of calcium ions bind to 1 mol of ion apoaequorin, e.g., 3 mols or more are preferred.

In a more preferred embodiment of the present invention, the fluorescent protein is reacted with coelenterazine or its analog in the presence of a reducing agent. Examples of the reducing agent used herein include dithiothreitol (DTT), mercaptoethanol, etc. The amount of the reducing agent used to produce the calcium-binding photoprotein is not particularly limited, so long as the amount does not affect the regeneration, but the concentration is preferably sufficient to prevent the S—S bonds formed by the presence of cysteine residues at the three positions of apoaequorin. The concentration is, for example, 1 mM dithiothreitol or 0.1% (v/v) mercaptoethanol in a final concentration.

6. Use of the Photoprotein of the Invention (1) Detection or Quantitative Determination of Calcium Ions The photoprotein of the present invention obtained as described above is a non-covalent complex of an apoprotein and a peroxide of coelenterazine analog formed from coelenterazine analog and molecular oxygen and is a photoprotein (holoprotein) that emits light by the action of calcium ions. Therefore, the photoprotein of the invention can be used for the detection or quantitative determination of calcium ions.

The detection or quantitative determination of calcium ions can be performed, for example, by adding a sample solution directly to a solution of the photoprotein and measuring the luminescence generated. Alternatively, calcium ions can also be detected or quantified by adding a solution of the photoprotein to a sample solution and measuring the luminescence generated. Also, the photoprotein above may be formed by previously contacting an aqueous apoprotein solution with coelenterazine analog of the present invention prior to its addition to the assay system for the detection or quantitative determination of calcium ions and the resulting photoprotein may be provided for use. The photoprotein comprising an apoprotein and a peroxide of coelenterazine analog may also be formed in the assay system by contacting the apoprotein with coelenterazine analog. The photoprotein formed is a complex (photoprotein) of the apoprotein and the peroxide of coelenterazine analog of the invention. The complex (i.e., the photoprotein of the present invention) emits light dependently on the calcium ion concentration.

The detection or quantitative determination of calcium ions can be performed by measuring the luminescence of the photoprotein of the invention through the action of calcium ions, using a luminometer. Luminometers which may be used include commercially available instruments, such as a Centro LB 960 (manufactured by Berthold, Inc.), etc. The calcium ion concentration can be quantitatively determined by preparing a luminescence standard curve for known calcium ion concentrations using the photoprotein.

Coelenterazine analog of the present invention may also be used for the detection of changes in the intracellular calcium ion concentration under the physiological conditions by preparing the photoprotein comprising an apoprotein and a peroxide of coelenterazine analog and injecting the photoprotein directly into cells by means of microinjection, etc.

Coelenterazine analog of the present invention may also be used to produce the photoprotein, which is performed, in addition to the injection using techniques such as microinjection, by intracellularly expressing a gene for the apoprotein (a polynucleotide encoding the apoprotein) to produce the protein in the cells and adding coelenterazine analog of the present invention to the resulting apoprotein from the external cells.

Using the photoprotein of the present invention thus introduced into cells or produced in cells, changes in the intracellular calcium ion concentration caused by external stimulation (e.g., stimulation with receptor-associated drugs, etc.) can also be determined.

(2) Use as a Reporter Protein, Etc. Utilizing Luminescence

The photoprotein of the present invention can also be used as a reporter protein to determine the transcription activity of a promoter, etc. A polynucleotide encoding an apoprotein is fused to a target promoter or other expression control sequence (e.g., an enhancer, etc.) to construct a vector. The vector described above is transfected to a host cell, and coelenterazine analog of the present invention is brought in contact with the host cell. By detecting the luminescence from the photoprotein of the present invention, the activity of the target promoter or other expression control sequence can be determined. As used herein, the term "contact" means that a host cell and coelenterazine analog of the present invention are allowed to be present in the same culture/reaction system, and includes, for example, addition of coelenterazine analog of the present invention to a culture container charged with a host cell, mixing of a host cell with coelenterazine analog of the present invention, culture of a host cell in the presence of coelenterazine analog of the present invention, and the like.

The present invention further provides a kit used for the measurement of transcription activity of a promoter, etc. In some embodiments of the present invention, the kit comprises coelenterazine analog of the present invention, cells containing a polynucleotide (e.g., DNA) encoding the apoprotein of the calcium-binding photoprotein, etc. Reagent such as coelenterazine analog of the present invention, etc. may be dissolved in a suitable solvent and prepared to be suitable for storage. The solvent which may be used is at least one selected from the group consisting of water, ethanol, various buffer solutions, and the like. The kit may additionally comprise, if necessary, at least one selected from the group consisting of a container designed therefor, other necessary accessories and an instruction manual, and the like.

(3) Use as a Detection Marker Utilizing Luminescence

The photoprotein of the present invention can be used as a marker for detection by luminescence. The detection marker of the present invention can be used to detect a target substance in, e.g., immunoassay, hybridization assay, etc. The photoprotein of the present invention can be used in the form bound to a target substance (protein, nucleic acid, etc.) in a conventional manner including chemical modification. Detection methods using the detection marker can be performed in a conventional manner. The detection marker of the present invention can also be used to determine the distribution of a target substance by expressing the marker, e.g., as a fusion protein of the apoprotein and the target substance, then inserting the fusion protein into cells by means of microinjection or the like and contacting them with coelenterazine analog of the present invention thereby to produce the photoprotein of the present invention. As used herein, the term "contact" means that cells and coelenterazine analog of the present invention are allowed to be present in the same culture/reaction system, and includes, for example, addition of coelenterazine analog of the present invention to a culture container charged with cells, mixing of cells with coelenterazine analog of the present invention, culture of host cells in the presence of coelenterazine analog of the present invention, and the like.

The distribution of such a target protein, etc. can be determined by a method for detection such as luminescence imaging. The apoprotein can also be used after expression in cells, in addition to the insertion into cells by means of microinjection, etc.

The present invention further provides a kit used for the detection of a target substance in an immunoassay, hybridization assay, etc. The kit in some embodiments of the present invention comprises the photoprotein of the present invention. The kit in another embodiment of the present invention comprises coelenterazine analog of the present invention, a cell containing a polynucleotide (e.g., DNA) encoding the apoprotein of the calcium-binding photoprotein, etc. Reagent such as coelenterazine analog, etc. may be dissolved in a suitable solvent and prepared to be suitable for storage. The solvent which may be used is at least one selected from the group consisting of water, ethanol, various buffer solutions, and the like. The kit may additionally comprise, if necessary, at least one selected from the group consisting of a container designed therefor, other necessary accessories and an instruction manual, and the like.

(4) Material for Amusement Supplies

The complex (photoprotein of the present invention) comprising the apoprotein and a peroxide of coelenterazine analog of the present invention emits light only by binding to a trace of calcium ions. The photoprotein of the present invention can be preferably used as a luminescence material for amusement supplies. Examples of such amusement supplies are luminescent soap bubbles, luminescent ice, luminescent candies, luminescent color paints, etc. The amusement supplies of the present invention can be prepared in a conventional manner.

(5) Bioluminescence Resonance Energy Transfer (BRET) Method

The photoprotein of the present invention can be used for analyses including an analysis of biological functions, an assay for enzyme activities, etc., based on the principle of intermolecular interaction by the bioluminescence resonance energy transfer (BRET) method.

For example, using the photoprotein of the invention as a donor protein and an organic compound or a fluorescent protein as an acceptor protein, the interaction between the proteins can be detected by generating bioluminescence resonance energy transfer (BRET) between them. In some embodiments of the present invention, the organic compound used as an acceptor protein is Hoechist 3342, Indo-1, DAPJ, etc. In another embodiment of the present invention, the fluorescent protein used as an acceptor protein is a green fluorescent protein (GFP), a blue fluorescent protein (BFP), a mutant GFP fluorescent protein, phycobilin, etc. In a preferred embodiment of the present invention, the physiological functions to be analyzed include an orphan receptor (in particular, G-protein conjugated receptor), apoptosis, transcription regulation by gene expression, etc. Still in a preferred embodiment of the present invention, the enzyme to be analyzed is protease, esterase, kinase, etc.

Analysis of the physiological functions by the BRET method may be performed by known methods, for example, by modifications of the methods described in Biochem. J. 2005, 385, 625-637, Expert Opin. Ther. Targets, 2007 11: 541-556, etc. Assay for the enzyme activity may also be performed by known methods, for example, by modifications of the methods described in Nat. Methods 2006, 3:165-174, Biotechnol. J. 2008, 3: 311-324, etc.

The present invention further provides a kit used for the analysis method described above. The kit comprises the photoprotein of the present invention and the organic compound and/or the fluorescent protein. Reagent such as the photoprotein of the present invention, organic compounds, fluorescent proteins, etc. may be dissolved in a suitable solvent and prepared to be suitable for storage. The solvent which may be used is at least one selected from the group consisting of water, ethanol, various buffer solutions, and the like. The kit may additionally comprise, if necessary, at least one selected from the group consisting of a container designed therefor, other necessary accessories and an instruction manual, and the like.

7. Fluorescent Protein

As illustrated in FIG. 8, the blue fluorescent protein (BFP)-like fluorescent protein can be produced by contacting coelenteramide or its analogs with an apoprotein such as apoaequorin, etc. Alternatively, the BFP-like fluorescent protein can also be produced by generating luminescence through contact of the calcium-binding photoprotein such as acquorin, etc. with calcium ions or bivalent or trivalent ions replaceable for the calcium ions to obtain the BFP-like protein.

On the other hand, the green fluorescent protein (gFP)-like fluorescent protein can be produced by contacting coelenteramide or its analogs with an apoprotein such as apoaequorin, etc. in the presence of a chelating agent for sequestering calcium ions or bivalent or trivalent ions replaceable for the calcium ions thereby to obtain the gFP-like fluorescent protein. Alternatively, the gFP-like fluorescent protein can also be produced by treating the BFP-like fluorescent protein with a chelating agent such as EDTA, etc., for sequestering calcium ions or bivalent or trivalent ions replaceable for the calcium ions.

7.1. Blue Fluorescent Protein (BFP)-Like Fluorescent Protein 7.1.1. Production of Blue Fluorescent Protein (BFP)-Like Fluorescent Protein The blue fluorescent protein (BFP)-like fluorescent protein of the present invention is a complex of the calcium-binding photoprotein and coelenteramide analog of the present invention which is coordinated to the apoprotein of the photoprotein. That is, the BFP-like fluorescent protein of the present invention comprises coelenteramide analog of the present invention, the apoprotein of the calcium-binding photoprotein and calcium ions or bivalent or trivalent ions replaceable for the calcium ions. The BFP-like fluorescent protein can emit fluorescence upon excitation of light and can also generate luminescence upon contact of the BFP-like fluorescent protein with coelenterazine or its analog.

According to the present invention, the BFP-like fluorescent protein is prepared from coelenteramide analog of the present invention as follows. That is, coelenteramide analog of the present invention is brought in contact with the apoprotein of the calcium-binding photoprotein in the presence of calcium ions or divalent or trivalent ions replaceable for the calcium ions thereby to obtain the BFP-like fluorescent protein. As used herein, the term "contact" means that the apoprotein and coelenteramide analog are allowed to be present in the same reaction system, and includes, for example, addition of the apoprotein to a container charged with coelenteramide analog, addition of coelenteramide analog to a container charged with the apoprotein, mixing of the apoprotein with coelenteramide analog, and the like.

In the present invention, coelenteramide analog of the present invention used to produce the BFP-like fluorescent protein is the same as described above. Examples of coelenteramide analog of the present invention include compounds prepared in EXAMPLES below or by methods modified therefrom.

The divalent or trivalent ions replaceable for the calcium ions which are used in the present invention to produce the BFP-like fluorescent protein are divalent or trivalent ions which trigger the luminescence reaction when they react with the calcium-binding photoprotein, in place of calcium ions. In other words, they refer to ions that exert the function similar to calcium ions on the calcium-binding photoprotein. Examples of the calcium ions or divalent or trivalent ions replaceable for the calcium ions include calcium ions ($Ca^{2+}$), magnesium ions ($Mg^{2+}$), strontium ions ($Sr^{2+}$), barium ions ($Ba^{2+}$), lead ions ($Pb^{2+}$), cobalt ions ($Co^{2+}$), nickel ions ($Ni^{2+}$), cadmium ions ($Cd^{2+}$), yttrium ions ($Y^{3+}$), lanthanum ions ($La^{3+}$), samarium ions ($Sm^{3+}$), europium ions ($Eu^{3+}$), dysprosium ions ($Dy^{3+}$), thulium ions ($Tm^{3+}$), ytterbium ions ($Yb^{3+}$), and the like. Among these ions, the divalent metal ions are preferred, more preferably the divalent metal ions other than transition metals, e.g., $Ca^{2+}$, $Sr^{2+}$, $Pb^{2+}$, etc.

In the present invention, the apoprotein of the calcium-binding photoprotein used to produce the BFP-like fluorescent protein is the same as described above.

The amount of coelenteramide analog of the present invention used to produce the BFP-like fluorescent protein is not particularly limited and is in a range of, e.g., 1 mol to 5 mol, preferably 1 mol to 2 mol, more preferably 1 mol to 1.2 mol, based on 1 mol of apoprotein.

In the production of the BFP-like fluorescent protein, preferably coelenteramide analog of the present invention is reacted with the apoprotein and calcium ions or divalent or trivalent ions replaceable for the calcium ions in the presence of a reducing agent. Examples of the reducing agent used herein include dithiothreitol (DTT), mercaptoethanol, etc. The amount of the reducing agent used to produce the BFP-like fluorescent protein is not particularly limited so long as the amount does not affect the regeneration of the BFP-like fluorescent protein, and the concentration is preferably sufficient to prevent the S—S bonds formed by the presence of cysteine residues at the three positions of apoaequorin. Such a concentration is, for example, 1 mM dithiothreitol or 0.1% (v/v) mercaptoethanol in a final concentration.

In the method for producing the BFP-like fluorescent protein, the reaction temperature and reaction time are not particularly limited but are generally at 0° C. to 42° C. for 0.1 to 2 hours, at 4° C. to 37° C. for 0.1 to 2 hours, or at 4° C. to 15° C. for 0.1 to 24 hours.

The BFP-like fluorescent protein thus produced may be further purified. Purification of the BFP-like fluorescent protein can be performed in a conventional manner of separation/purification. The separation/purification includes, for example, precipitation with ammonium sulfate, gel filtration chromatography, ion exchange chromatography, affinity chromatography, reversed phase high performance liquid chromatography, dialysis, ultrafiltration, etc., alone or in an appropriate combination of these techniques.

7.1.2. Use of Blue Fluorescent Protein (BFP)-Like Fluorescent Protein (1) Use as a Luminescent Catalyst The BFP-like fluorescent protein of the present invention acts on a luminescence substrate to emit light from the substrate and can be used as a luminescent catalyst. Therefore, the present invention provides a method for emitting light, which comprises contacting the BFP-like fluorescent protein of the present invention with coelenterazine or its analogs. As used herein, the term "contact" means that the BFP-like fluorescent protein and coelenterazine or its analog are allowed to be present in the same reaction system, and includes, for example, addition of the BFP-like fluorescent protein to a container charged with coelenterazine or its analog, addition of coelenterazine or its analog to a container charged with the BFP-like fluorescent protein, mixing of the BFP-like fluorescent protein with coelenterazine or its analog, and the like.

The luminescent substrate used in the method for light emission according to the present invention is, for example, coelenterazine or its analog. The analog of coelenterazine includes the same as described above.

These coelenterazine and analogs thereof are brought in contact with the BFP-like fluorescent protein. By the catalytic action of the BFP-like fluorescent protein contacted, coelenterazine or its analog is oxidized to the corresponding coelenteramide or its analog, whereby luminescence generates (at this time carbon dioxide is released). The luminescence time is generally 0.5 to 3 hours. However, the luminescence time can be further prolonged or more shortened, depending upon conditions chosen.

(2) Use as a Reporter Protein

The BFP-like fluorescent protein of the present invention can also be used as a reporter protein to determine the transcription activity of a promoter, etc. A polynucleotide encoding the apoprotein is fused to a target promoter or other expression control sequence (e.g., an enhancer, etc.) to construct a vector. The vector described above is transfected to a host cell. Coelenteramide analog of the present invention and calcium ions or divalent or trivalent ions replaceable for the calcium ions are brought in contact with the host cell. By detecting the fluorescence from the fluorescent protein of the present invention, the activity of the target promoter or other expression control sequence can be determined. As used herein, the term "contact" means that a host cell and coelenteramide analog as well as the calcium ions or divalent or trivalent ions replaceable for the calcium ions are allowed to be present in the same culture/reaction system, and includes, for example, addition of coelenteramide analog and calcium ions or divalent or trivalent ions replaceable for the calcium ions to a culture container charged with a host cell, mixing of a host cell with coelenteramide analog and calcium ions or divalent or trivalent ions replaceable for the calcium ions, culture of a host cell in the presence of coelenteramide analog and calcium ions or divalent or trivalent ions replaceable for the calcium ions, and the like.

(3) Use as a Detection Marker

The BFP-like fluorescent protein of the present invention can be used as a marker for detection by fluorescence. The detection marker of the present invention can be used to detect a target substance in, e.g., immunoassay, hybridization assay, etc. The BFP-like fluorescent protein of the present invention can be used in the form bound to a target substance (protein, nucleic acid, etc.) in a conventional manner including chemical modification. Detection methods using the detection marker can be performed in a conventional manner.

The detection marker of the present invention can also be used to determine the distribution of a target substance by expressing the marker, e.g., as a fusion protein of the apoprotein and the target substance, then inserting the fusion protein into cells by means of microinjection or the like, and contacting them with coelenteramide analog of the present invention and calcium ions or divalent or trivalent ions replaceable for the calcium ions. As used herein, the term "contact" means that cells and coelenteramide analog as well as calcium ions or divalent or trivalent ions replaceable for the calcium ions are allowed to be present in the same culture/reaction system, and includes, for example, addition of coelenteramide analog and calcium ions or divalent or trivalent ions replaceable for the calcium ions to a culture container charged with cells, mixing of cells with coelenteramide analog and calcium ions or divalent or trivalent ions replaceable for the calcium ions, culture of a host cell in the presence of coelenteramide analog and calcium ions or divalent or trivalent ions replaceable for the calcium ions, and the like.

The distribution of such a target protein, etc. can be determined by a method for detection such as fluorescence imaging. The apoprotein can also be used after expression in cells, in addition to the insertion into cells by means of microinjection, etc.

(4) Material for Amusement Supplies

When excited with light, the BFP-like fluorescent protein of the invention emits fluorescence. Therefore, the BFP-like fluorescent protein of the present invention can be preferably used as a fluorescence material for amusement supplies. Examples of such amusement supplies are fluorescent soap bubbles, fluorescent ice, fluorescent candies, fluorescent color paints, etc. The amusement supplies of the invention can be prepared in a conventional manner.

(5) Fluorescence Resonance Energy Transfer (FRET) Method

The BFP-like fluorescent protein of the present invention can be used for analyses including an analysis of biological functions, an assay (a determination) for enzyme activities, etc., based on the principle of intermolecular interaction by the fluorescence resonance energy transfer (FRET) method.

For example, using the BFP-like fluorescent protein of the invention as a donor or an acceptor and an organic compound or another fluorescent protein as an acceptor or a donor, the interaction between the proteins can be detected by causing fluorescence resonance energy transfer (FRET) between them. In some embodiments of the present invention, the organic compound used as an acceptor or a donor is Hoechst 3342, Indo-1, DAP1, etc. In some other embodiments of the present invention, another fluorescent protein used as an acceptor or a donor is another green fluorescent protein (GFP), another blue fluorescent protein (BFP), another mutant GFP fluorescent protein, phycobilin, etc. In a preferred embodiment of the present invention, the physiological functions to be analyzed include an orphan receptor (in particular, G-protein conjugated receptor), apoptosis, transcription regulation by gene expression, etc. In a preferred embodiment of the present invention, the enzyme to be analyzed is protease, esterase, kinase, etc.

Analysis of the physiological functions by the FRET method may be performed by known methods, for example, by modifications of the methods described in Hoffmann, C. et al *Nat Methods* (2005) 2: 171-176, Paulsson, J. F. et al. *Exp. Diabetes Res.* 2008: 2008, 865850, etc. Assay for the enzyme activity may also be performed by known methods, for example, by modifications of the methods described in Ting, A. Y. et al (2001) *Proc. Natl. Acad. Sci. USA* 98: 15003-15008, Evellin, S. et al (2004) *Methods. Mol. Biol.* 284: 259-270, Palmer A. E. & Tsien, R. Y. (2006) 1:1057-1065, etc.

Still, the present invention provides a kit used for the analysis method described above. The kit comprises the BFP-like fluorescent protein of the present invention and the organic compound and/or the fluorescent protein. Reagent such as the BFP-like fluorescent protein of the present invention, organic compounds, other fluorescent proteins, etc. may be dissolved in a suitable solvent and prepared to be suitable for storage. The solvent which may be used is at least one selected from the group consisting of water, ethanol, various buffer solutions, and the like. The kit may additionally comprise, if necessary, at least one selected from the group consisting of a container designed therefor, other necessary accessories and an instruction manual, and the like.

7.2. Green Fluorescent Protein (gFP)-Like Protein 7.2.1. Production of Green Fluorescent Protein (gFP)-Like Protein The green fluorescent protein (gFP)-like protein of the present invention is a complex of the calcium-binding photoprotein and coelenteramide analog of the present invention which is coordinated to the apoprotein of the photoprotein. That is, the gFP-like protein of the present invention comprises coelenteramide analog of the present invention and the apoprotein of the calcium-binding photoprotein. On the other hand, the gFP-like protein of the present invention does not comprise calcium ions or divalent or trivalent ions replaceable for the calcium ions. The gFP-like protein can emit fluorescence upon excitation of light.

The gFP-like protein of the present invention can be produced by contacting coelenteramide analog of the present invention with the apoprotein of the calcium-binding photoprotein in the presence of a chelating agent for removing calcium ions or divalent or trivalent ions replaceable for the calcium ions thereby to obtain the gFP-like protein.

Alternatively, the gFP-like protein can also be produced by removing calcium ions or divalent or trivalent ions replaceable for the calcium ions from the BFP-like fluorescent protein above to obtain the gFP-like protein. The calcium ions or divalent or trivalent ions replaceable for the calcium ions can be removed from the BFP-like fluorescent protein by treating with a chelating agent for sequestering calcium ions or divalent or trivalent ions replaceable for the calcium ions.

The chelating agent used to produce the gFP-like protein in the present invention may be any agent but is not particularly limited, so long as it strongly binds to calcium ions or divalent or trivalent ions replaceable for the calcium ions. Examples of the chelating agent include ethylenediaminetetraacetic acid (EDTA), ethylene glycol-bis(P-aminoethyl ether)-N,N,N', N'-tetraacetic acid (EGTA), trans-1,2-diaminocyclohexane-N,N,N',N'-tetraacetic acid (CyDTA), N-(2-hydroxyethyl) iminodiacetic acid (HIDA) and the like. As used herein, the calcium ions or divalent or trivalent ions replaceable for the calcium ions are the same as those described above.

The amount of the chelating agent used to produce the gFP-like fluorescent protein is not particularly limited unless its concentration affects regeneration of the gFP-like fluorescent protein. Since it is demonstrated that 3 mols of calcium ions bind to 1 mol of ion apoaequorin, e.g., 3 mols or more are preferred.

In the method for producing the gFP-like protein, the reaction temperature and reaction time are not particularly limited but are generally at 0° C. to 42° C. for 0.1 to 2 hours, at 4° C. to 37° C. for 0.1 to 2 hours, or at 4° C. to 15° C. for 0.1 to 24 hours.

The gFP-like protein thus obtained may be further purified. Purification of the gFP-like protein can be performed in a conventional manner of separation/purification. The separation/purification includes, for example, precipitation with ammonium sulfate, gel filtration chromatography, ion exchange chromatography, affinity chromatography, reversed phase high performance liquid chromatography, dialysis, ultrafiltration, etc., alone or in an appropriate combination of these techniques.

7.2.2. Use of Green Fluorescent Protein (gFP)-Like Protein (1) Use as a Reporter Protein The gFP-like protein of the present invention can also be used as a reporter protein to determine the transcription activity of a promoter, etc. A polynucleotide encoding the apoprotein is fused to a target promoter or other expression control sequence (e.g., an enhancer, etc.) to construct a vector. The vector described above is transfected to a host cell. Coelenteramide analog of the present invention is brought in contact with the host cell to produce the BFP-like protein, which is then brought in contact with the chelating agent for removing calcium ions or divalent or trivalent ions replaceable for the calcium ions, thereby to produce the gFP-like protein. By detecting the fluorescence from the gFP-like protein of the present invention, the activity of the target promoter or other expression control sequence can be determined.

(2) Use as a Detection Marker

The gFP-like protein of the present invention can be used as a detection marker by its fluorescence. The detection marker of the present invention can be used to detect a target substance in, e.g., immunoassay, hybridization assay, etc. The gFP-like protein of the present invention can be used in the form bound to a target substance (protein, nucleic acid, etc.) in a conventional manner, including chemical modification. Detection methods using the detection marker can be performed in a conventional manner. The detection marker of the present invention can also be used to determine the distribution of a target substance by expressing the marker, e.g., as a fusion protein of the apoprotein and the target substance, then inserting the fusion protein into cells by means of microinjection or the like. Coelenteramide analog of the present invention is brought in contact therewith to produce the BFP-like protein, which is then brought in contact with the chelating agent for removing calcium ions or divalent or trivalent ions replaceable for the calcium ions to produce the gFP-like protein, and so on. The marker can thus be used to determine the distribution of the target protein described above. The distribution of such a target protein, etc. can be determined by a method for detection such as fluorescence imaging. The apoprotein can also be used after expression in cells, in addition to the insertion into cells by means of microinjection, etc.

(3) Material for Amusement Supplies

The gFP-like protein of the present invention can be preferably used as a fluorescent material for amusement supplies. Examples of such amusement supplies are fluorescent soap bubbles, fluorescent ice, fluorescent candies, fluorescent color paints, etc. The amusement supplies of the present invention can be prepared in a conventional manner.

(4) Fluorescence Resonance Energy Transfer (FRET) Method

The gFP-like fluorescent protein of the present invention can be used for analyses including an analysis of biological functions, an assay for enzyme activities, etc., based on the principle of intermolecular interaction by the fluorescence resonance energy transfer (FRET) method.

For example, using the gFP-like fluorescent protein of the invention as a donor or an acceptor and an organic compound or another fluorescent protein as an acceptor or a donor, the interaction between the proteins can be detected by causing fluorescence resonance energy transfer (FRET) between them. In some embodiments of the present invention, the organic compound used as an acceptor or a donor is Hoechist 3342, Indo-1, DAP1, etc. In some other embodiments of the present invention, another fluorescent protein used as an acceptor or a donor is another green fluorescent protein (GFP), another blue fluorescent protein (BFP), another mutant GFP fluorescent protein, phycobilin, etc. In a preferred embodiment of the present invention, the physiological functions to be analyzed include an orphan receptor (in particular, G-protein conjugated receptor), apoptosis, transcription regulation by gene expression, etc. In a preferred embodiment of the present invention, the enzyme to be analyzed is protease, esterase, kinase, etc.

Analysis of the physiological functions by the FRET method may be performed by known methods, for example, by modifications of the methods described in Hoffmann, C. et al *Nat. Methods* (2005) 2: 171-176, Paulsson, J. F. et al. *Exp. Diabetes Res.* 2008:2008, 865850, etc. Assay for the enzyme activity may be performed by known methods, for example, by modifications of the methods described in Ting, A. Y. et al (2001) *Proc. Natl. Acad. Sci. USA* 98: 15003-15008, Evellin, S. et al (2004) *Methods. Mol. Biol.* 284: 259-270, Palmer A. E. & Tsien, R. Y. (2006) 1:1057-1065, etc.

The present invention further provides a kit used for the analysis method described above. The kit comprises the gFP-like fluorescent protein of the present invention and the organic compound and/or another fluorescent protein. Reagent such as the gFP-like fluorescent protein of the present invention, organic compounds, other fluorescent proteins, etc. may be dissolved in a suitable solvent and prepared to be suitable for storage. The solvent which may be used is at least one selected from the group consisting of water, ethanol, various buffer solutions, and the like. The kit may additionally comprise, if necessary, at least one selected from the group consisting of a container designed therefor, other necessary accessories and an instruction manual, and the like.

All literatures and publications mentioned in this specification are herein incorporated in their entirety by reference into the specification, irrespective of their purposes. The disclosure of the specification, the claims, abstract and drawings of Japanese Application JP2010-088175 filed on Apr. 6, 2010, based upon which the present application claims the benefit of priority, are entirely incorporated herein by reference.

The objects, characteristics, advantages and of the present invention as well as the idea thereof are apparent to those skilled in the art from the descriptions given herein, and those skilled in the art can easily implement the present invention. It is to be understood that the best mode to carry out the invention and specific examples are to be taken as preferred embodiments of the present invention. These descriptions are only for illustrative and explanatory purposes and are not intended to restrict the invention thereto. It is further apparent to those skilled in the art that various modifications may be made based on the descriptions given herein within the intent and scope of the present invention disclosed herein.

EXAMPLES

Synthesis Examples

Materials and Methods (1) High Performance Liquid Chromatography (HPLC)

The purities of coelenterazine analogs and coelenteramide analogs were determined by a 1100 Series HPLC System manufactured by Agilent. The column used was a Lichrosorb RP-18 (5 μm, 4.0 mm i.d.×125 mm) manufactured by Merck Chemicals. Moving phase: gradient 60-100% methanol/0.1% aqueous TFA for 40 min; flow rate: 0.45 mL/min; detection: UV 225 nm; the amount of injected sample: 0.5 mg/5 mL in methanol/0.1% aqueous TFA=6/4.

(2) Chromatography

Thin layer chromatography (TLC) for analysis was performed on a glass plate (MERCK 5715, silica gel 60 $F_{254}$) previously coated with silica gel. The spots were detected under a UV lamp (254 nm or 365 nm) by adsorbing iodine, dipping in an aqueous anisaldehyde solution and charring on a hot plate. The unsaturated C—C bonds were detected by dipping in an aqueous potassium permanganate solution followed by charring on a hot plate.

For preparative flush column chromatography, silica gels (Kanto Chemical Co., Inc., 37563-85, silica gel 60 N (spherical, neutral), particle size 45-50 μm) and (Kanto Chemical Co., Inc., 37565-85, silica gel 60 N (spherical, neutral), particle size 63-210 μm) were used. For purification of the CTZ analogs, however, silica gels (Kanto Chemical Co., Inc., 37562-79, silica gel 60 N (spherical), particle size 40-50 μm) and (Kanto Chemical Co., Inc., 37558-79, silica gel 60 N (spherical), particle size 100-210 μm) were used.

(3) Nuclear Magnetic Resonance (NMR) Spectra $^1$H Nuclear magnetic resonance (NMR) spectra (400 MHz) were determined on a Unity Plus 400 nuclear magnetic resonance apparatus manufactured by Varian, Inc. Chemical shifts (δ) were expressed as values relative to the peaks from tetramethylsilane (($CH_3)_4$Si) (measured in $CDCl_3$; 0 ppm) or the peaks from non-deuterated solvent for analysis (measured in $CD_3OD$; 3.31 ppm, measured in DMSO-$d_6$; 2.49 ppm) as an internal standard. Abbreviations s, d and m used for the signal splitting patterns represent singlet, doublet and multiplet, respectively.

$^{13}$C Nuclear magnetic resonance spectra (75.5 or 67.8 MHz) were determined by a Mercury 300 nuclear magnetic resonance apparatus manufactured by Varian, Inc., or on JNM-EX270 manufactured by JEOL. Chemical shifts (δ) were expressed as values relative to the peaks from carbon in the solvent for analysis (measured in acetone-d; 29.8 ppm, measured in DMSO-$d_6$; 39.5 ppm) as an internal standard.

(4) Infrared Absorption (IR) Spectra

IR spectra were determined by the diffuse reflection method using a SHIMADZU IR Prestige-21 spectrophotometer equipped with DRS-8000, manufactured by Shimadzu Corporation.

(5) Mass Spectrometry

High resolution mass spectrometry (HRMS) was performed by the electrospray ionization method (ESI$^+$) with a Bruker micrOTOF manufactured by Bruker or by the fast atom bombardment method (FAB$^+$) using JMS-700 manufactured by JEOL.

(6) Elemental Analysis

Elemental analysis (Anal.) was performed using YANACO CHN CORDER MT-5.

(7) Chemical Reagents

The reagents were all commercially available and used without further treatment unless otherwise indicated. The solvents for the reactions, extractions and chromatography were DMF, ethyl acetate, n-hexane, anhydrous THF, toluene, ethanol, DMSO, diethyl ether, methanol, THF, dichloromethane, 1,4-dioxane, anhydrous pyridine, diethylamine, anhydrous dichloromethane, anhydrous 1,2-dichloroethane and anhydrous DMF, all commercially available, and used without further treatment.

Mixing ratios of the solvents are based on volume, unless otherwise indicated.

The reaction reagents below were used. Imidazole (Cat. No. 095-0015), triisopropyl borate (Cat. No. 324-41535), $Na_2CO_3$ (Cat. No. 199-01585), aminopyrazine (Cat. No. 013-12083), N-bromosuccinimide (Cat. No. 025-07235), p-hydroxybenzaldehyde (Cat. No. 081-05925), triethylamine (Cat. No. 202-02646), methanesulfonyl chloride (Cat. No. 131-01583), 1-naphthaleneboronic acid (Cat. No. 322-63393), benzo[b]thiophene-2-boronic acid (Cat. No. 329-64121), p-nitrophenylboronic acid (Cat. No. 327-59813), hydrochloric acid (Cat. No. 080-01066), p-hydroxyphenylacetic acid (Cat. No. 084-04185), oxalyl dichloride (Cat. No. 155-01642), 4-(dimethylamino)pyridine (Cat. No. 042-19212), thionyl chloride (Cat. No. 200-01106) and m-anisoyl chloride (Cat. No. 326-77701), purchased from Wako Pure Chemical Co., Ltd., dichlorobis(triphenylphosphine) palladium (II) (Cat. No. 412740), 2-naphthaleneboronic acid (Cat. No. 480134), 2-(tributylstannyl)thiophene (Cat. No. 414492), thianaphthene-3-boronic acid (Cat. No. 512117), trans-2-phenylvinylboronic acid (Cat. No. 473790), 3-thienylboronic acid (Cat. No. 436844), 1-phenylvinylboronic acid (Cat. No. 571350), 4-(dimethylamino)phenylboronic acid (Cat. No. 483532), copper (1) iodide (Cat. No. 21554), phenylacetylene (Cat. No. 117706) and 1 M tetrabutylammonium fluoride in THF (Cat. No. 216143), purchased from Aldrich, Inc., 4-bromophenol (Cat. No. B0787), tert-butyldimethylsilyl chloride (Cat. No. B0995), 5-bromopyrazin-2-amine (Cat. No. A1683), ethyl diethoxyacetate (Cat. No. D1883), phenylboronic acid (Cat. No. B0857), thieno[3,2-b]thiophen-2-boronic acid (Cat. No. T2621), dithieno[3,2-b:2',3'-d]thiophen-2-boronic acid (Cat. No. D3823), 5-(4,4,5,5-tetramethyl-1,3,2-dioxaborolan-2-yl)-2,2'-bithiophene (Cat. No. 12518), 4-methoxyphenyl isocyanate (Cat. No. 10440), 4-methoxyphenyl isothiocyanate (Cat. No. 10513) and 4-methoxybenzoyl chloride (Cat. No. M0721), purchased from Tokyo Chemical Industry Co., Ltd., 2.64 M n-butyl lithium in n-hexane (Cat. No. 04937-25), sodium borohydride (Cat. No. 37828-35), magnesium, turning (Cat. No. 26000-25), $NH_4Cl$ (Cat. No. 01287-01) and sodium hydride (Cat. No. 37842-35), purchased from Kanto Chemical Co., Inc., and, palladium/charcoal activated (10% Pd) (Cat. 8.07104.0010) purchased from MERCK, Inc., were used without further treatment.

Reference Synthesis Example 1

(4-Bromophenoxy)(tert-butyl)dimethylsilane (36)
(known compound, Reference: P. Jeanjot, et al., *Synthesis*, 513-522 (2003))

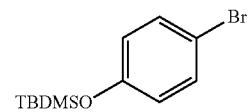

To a solution of 4-bromophenol (35) (20.0 g, 116 mmol) in DMF (200 mL) were successively added imidazole (23.6 g, 347 mmol) and tert-butyldimethylsilyl chloride (24.4 g, 162 mmol) at 0° C., and the mixture was stirred for 3 hours while elevating to room temperature. To the mixture was added water and the product was extracted with ethyl acetate (200 mL×3). The combined organic extract was washed successively with water (300 mL) and brine (200 mL), and dried over anhydrous sodium sulfate. After filtration and concentration under reduced pressure, the residue was purified by column chromatography (silica gel 200 g, n-hexane/ethyl acetate=100/1) to give Compound 36 (32.3 g, crude) as a colorless oil. The product was used in the following reaction without further purification. $R_f$=0.57 (n-hexane/ethyl acetate=49/1); $^1$H NMR (400 MHz, CDCl$_3$) δ 0.18 (s, 6H), 0.97 (s, 9H), 6.68-6.75 (AA'BB', 2H), 7.30-7.35 (AA'BB', 2H).

Reference Synthesis Example 2

4-(tert-Butyldimethylsilyloxy)phenylboronic acid (37) (known compound, Reference: P. Jeanjot, et al., *Synthesis*, 513-522 (2003))

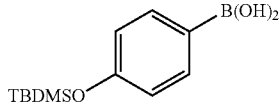 [SMILES: CC(C)(C)[Si](C)(C)Oc1ccc(B(O)O)cc1]

Under an argon atmosphere, to a solution of (4-bromophenoxy)(tert-butyl)dimethylsilane (36) (32.3 g. crude) prepared above in anhydrous THF (300 mL) was added n-butyl lithium (2.64 M n-hexane solution) (46.0 mL, 121 mmol) at −78° C., and the mixture was stirred for an hour. To this was added triisopropyl borate (134 mL, 579 mmol) at the same temperature and the mixture was stirred for 13 hours while elevating to room temperature. To the mixture was added 1 M hydrochloric acid (200 mL) and the product was extracted with ethyl acetate (200 mL×3). The combined organic extract was washed successively with water (300 mL) and brine (200 mL), followed by drying over anhydrous sodium sulfate. After filtration and concentration under reduced pressure, the residue was recrystallized (n-hexane/ethyl acetate) to give Compound 37 (20.9 g, 82.9 mmol, 71.8% (2 steps)) as a colorless solid. $R_f$=0.62 (n-hexane/ethyl acetate=1/1); $^1$H NMR (400 MHz, CDCl$_3$) δ 0.25 (s, 6H), 1.01 (s, 9H), 6.93-6.98 (AA'BB', 2H), 8.09-8.14 (AA'BB', 2H).

Reference Synthesis Example 3

5-[4-(tert-Butyldimethylsilyloxy)phenyl]pyrazin-2-amine (39) (known compound)

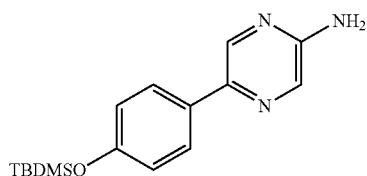 [SMILES: CC(C)(C)[Si](C)(C)Oc1ccc(-c2cnc(N)cn2)cc1]

Under an argon atmosphere, to a solution of 4-(tert-butyldimethylsilyloxy)phenylboronic acid (37) (7.97 g, 31.6 mmol) in toluene (290 mL) and ethanol (10 mL) were successively added 5-bromopyrazin-2-amine (38) (5.00 g, 28.7 mmol), dichlorobis(triphenylphosphine)palladium (II) (1.21 g, 1.72 mmol) and 1 M Na$_2$CO$_3$ aqueous solution (29.0 mL, 29.0 mmol) at room temperature, and the mixture was heated to reflux for 17 hours. After cooling to room temperature, to the mixture was added water and the metal catalyst was removed by filtration. The product was extracted with ethyl acetate (100 mL×3). The combined organic extract was washed successively with water (300 mL) and brine (200 mL), followed by drying over anhydrous sodium sulfate. After filtration and concentration under reduced pressure, the residue was purified by column chromatography (silica gel 200 g, n-hexane/ethyl acetate=2/1) to give Compound 39 (7.82 g, 25.9 mmol, 90.2%) as a colorless solid. $R_f$=0.39 (n-hexane/ethyl acetate=1/1); $^1$H NMR (400 MHz, CDCl$_3$) δ 0.22 (s, 6H), 1.00 (s, 9H), 4.53 (s, 2H), 6.88-6.95 (AA'BB', 2H), 7.71-7.79 (AA'BB', 2H), 8.04 (s, 1H), 8.84 (s, 1H); $^{13}$C NMR (75.5 MHz, DMSO-d$_6$) δ −4.6 (2C), 17.9, 25.5 (3C), 120.0 (2C), 126.1 (2C), 130.7, 131.3, 138.1, 139.2, 154.5, 154.7; IR (KBr, cm$^{-1}$) 417, 478, 513, 544, 567, 629, 644, 658, 683, 750, 781, 806, 841, 912, 1007, 1052, 1080, 1103, 1169, 1207, 1254, 1341, 1379, 1418, 1474, 1506, 1539, 1570, 1605, 1639, 2857, 2893, 2928, 2955, 3163, 3302, 3431.

Reference Synthesis Example 4

3-Bromo-5-[4-(tert-butyldimethylsilyloxy)phenyl]pyrazin-2-amine (5) (known compound, Reference: F. D. Wael, et al., *Bioorg. Med. Chem.*, 17, 4336-4344 (2009))

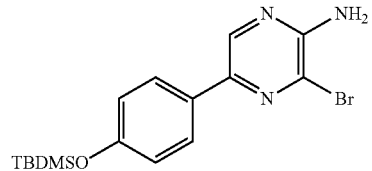 [SMILES: CC(C)(C)[Si](C)(C)Oc1ccc(-c2cnc(N)c(Br)n2)cc1]

To a solution of 5-[4-(tert-butyldimethylsilyloxy)phenyl]pyrazin-2-amine (39) (12.7 g, 42.1 mol) in DMSO (790 mL) and water (19.5 mL) was added N-bromosuccinimide (7.90 g, 44.4 mmol) at room temperature and the mixture was stirred for 17 hours. To the mixture was added water and the product was extracted with diethyl ether (400 mL×8). The combined organic extract was washed successively with water (300 mL×2) and brine (200 mL×2), followed by drying over anhydrous sodium sulfate. After filtration and concentration under reduced pressure, the residue was purified by column chromatography (silica gel 200 g, n-hexane/ethyl acetate=3/1) to give Compound 5 (13.0 g, 34.2 mmol, 80.9%) as a yellow solid. $R_f$=0.32 (n-hexane/ethyl acetate=3/1); $^1$H NMR (400 MHz, CDCl$_3$) δ 0.22 (s, 6H), 0.99 (s, 9H), 4.99 (s, 2H), 6.87-6.94 (AA'BB', 2H), 7.71-7.77 (AA'BB', 2H), 8.34 (s, 1H); $^{13}$C NMR (75.5 MHz, DMSO-d$_6$) −4.6 (2C), 17.9, 25.4 (3C), 120.1 (2C), 124.7, 126.4 (2C), 128.9, 137.4, 140.0, 152.0, 155.2; IR (KBr, cm$^{-1}$) 554, 619, 646, 675, 704, 756, 779, 806, 849, 905, 1036, 1094, 1109, 1169, 1202, 1261, 1337, 1416, 1464, 1501, 1566, 1605, 1630, 2857, 2928, 2955, 3138, 3281, 3460.

Reference Synthesis Example 5

3,5-Dibromopyrazin-2-amine (42) (known compound, Reference: P. Jeanjot, et al., *Synthesis*, 513-522 (2003))

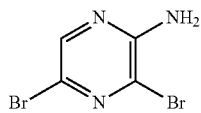

To a solution of aminopyrazine (41) (10.0 g, 105 mmol) in DMSO (200 mL) and water (5 mL) was added N-bromosuccinimide (39.3 g, 221 mmol) at room temperature, and the mixture was stirred for 23 hours. To the mixture was added water and the product was extracted with diethyl ether (300 mL×4). The combined organic extract was washed successively with water (400 mL×2) and brine (500 mL×2), followed by drying over anhydrous sodium sulfate. After filtration and concentration under reduced pressure, the residue was purified by column chromatography (silica gel 280 g, n-hexane/dichloromethane/ethyl acetate=5/4/1). The resulting solid was further purified by recrystallization (n-hexane/ethyl acetate) to give Compound 42 (17.3 g, 68.3 mmol, 64.9%) as a colorless solid. $R_f$=0.48 (n-hexane/dichloromethane/ethyl acetate=5/4/1); $^1$H NMR (400 MHz, CDCl$_3$) δ 5.05 (s, 2H), 8.05 (s, 1H).

Reference Synthesis Example 6

4-(tert-Butyldimethylsilyloxy)benzaldehyde (44) (known compound, Reference: M. Adamczyk, et al., *Tetrahedron*, 59, 8129-8142 (2003))

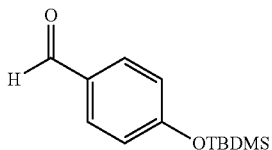 [SMILES: CC(C)(C)[Si](C)(C)Oc1ccc(C=O)cc1]

To a solution of p-hydroxybenzaldehyde (43) (12.0 g, 98.3 mmol) in DMF (25 mL) was successively added imidazole (16.7 g, 245 mmol) and tert-butyldimethylsilyl chloride (17.8 g, 118 mmol) at 0° C., and the mixture was stirred for 3 hours while elevating to room temperature. To the mixture was added water and the product was extracted with ethyl acetate (200 mL×3). The organic layer was washed successively with saturated aqueous solution of K$_2$CO$_3$ (300 mL), water (300 mL) and brine (200 mL), followed by drying over anhydrous sodium sulfate. After filtration and concentration under reduced pressure, the residue was purified by column chromatography (silica gel 200 g, n-hexane/ethyl acetate=19/1) to give Compound 44 (20.5 g, 86.7 mmol, 88.2%) as a colorless oil. $R_f$=0.32 (n-hexane/ethyl acetate=19/1); $^1$H NMR (400 MHz, CDCl$_3$) δ 0.25 (s, 6H), 1.00 (s, 9H), 6.92-6.98 (AA'BB', 2H), 7.76-7.83 (AA'BB', 2H), 9.89 (s, 1H).

Reference Synthesis Example 7

4-(tert-Butyldimethylsilyloxy)benzyl alcohol (45) (known compound, Reference: M. Adamczyk, et al., *Tetrahedron*, 59, 8129-8142 (2003))

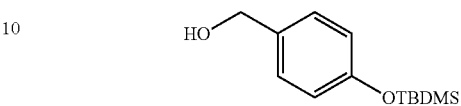

To a solution of 4-(tert-butyldimethylsilyloxy)benzaldehyde (44) (20.5g, 86.7 mmol) in methanol (120 mL) was added sodium borohydride (3.93 g, 104 mmol) at 0° C., and the mixture was stirred for 5 hours while elevating to room temperature. To the mixture was added water and the product was extracted with diethyl ether (300 mL×3). The combined organic extract was washed successively with water (300 mL) and brine (200 mL), followed by drying over anhydrous sodium sulfate. The residue was filtered and concentrated under reduced pressure to give Compound 45 (20.5 g, 104 mmol, 100%) as a colorless oil. The product has a sufficient purity and used in the following reaction without further purification. $R_f$=0.21 (n-hexane/ethyl acetate=19/1); $^1$H NMR (400 MHz, CDCl$_3$) δ 0.19 (s, 6H), 0.98 (s, 9H), 1.59 (br, 1H), 4.61 (s, 2H), 6.80-6.85 (AA'BB', 2H), 7.20-7.26 (AA'BB', 2H).

Reference Synthesis Example 8

4-(tert-Butyldimethylsilyloxy)benzyl chloride (46) (known compound, Reference: M. Adamczyk, et al., *Tetrahedron*, 59, 8129-8142 (2003))

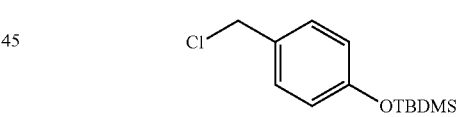

To a solution of 4-(tert-butyldimethylsilyloxy)benzyl alcohol (45) (10.0 g, 42.0 mmol) in DMF (100 mL) were successively added triethylamine (12.0 mL, 86.1 mmol) and methanesulfonyl chloride (4.90 mL, 63.1 mmol) at 0° C., and the mixture was stirred for 20 hours while elevating to room temperature. To the mixture was added water and the product was extracted with ethyl acetate (200 mL×3). The combined organic extract was washed successively with water (300 mL) and brine (200 mL), followed by drying over anhydrous sodium sulfate. After filtration and concentration under reduced pressure, the residue was purified by column chromatography (silica gel 200 g, n-hexane/diethyl ether=10/1) to give Compound 46 (8.07 g, 31.4 mmol, 74.9%) as a colorless oil. $R_f$=0.71 (n-hexane/ethyl acetate=19/1); $^1$H NMR (400

MHz, CDCl$_3$) δ 0.20 (s, 6H), 0.98 (s, 9H), 4.56 (s, 2H), 6.78-6.84 (AA'BB', 2H), 7.22-7.27 (AA'BB', 2H).

Reference Synthesis Example 9

3-[4-(tert-Butyldimethylsilyloxy)phenyl]-1,1-diethoxypropan-2-one (8) (known compound, Reference: M. Adamczyk, et al., *Terahedron*, 59, 8129-8142 (2003))

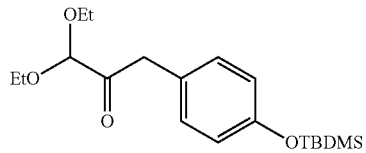 [SMILES: CCOC(OCC)C(=O)Cc1ccc(O[Si](C)(C)C(C)(C)C)cc1]

Magnesium turnings (640 mg, 26.3 mmol) were placed in a reaction flask and dried in vacuo by heating with a heat gun. The flask were then allowed to cool to room temperature and filled with a dry argon atmosphere. To this was added anhydrous THF (28 mL) and to the mixture was added dropwise 4-(tert-butyldimethylsilyloxy)benzyl chloride (46) (6.15 g, 24.0 mmol) at room temperature. The mixture was stirred at room temperature for an hour while the most of the magnesium turnings disappeared affording a THF solution of 4-(tert-butyldimethylsilyloxy)benzyl magnesium chloride, which was used in the following reaction without further treatment.

Under an argon atmosphere, to a solution of ethyl diethoxyacetate (4.30 mL, 24.0 mmol) in anhydrous THF (50 mL) was added the THF solution of 4-(tert-butyldimethylsilyloxy)benzyl magnesium chloride prepared above at −78° C. The mixture was stirred at −78° C. for 2 hours and an aqueous 10% NH$_4$Cl solution (150 mL) was added thereto. The product was extracted with ethyl acetate (200 mL×3). The combined organic extract was washed successively with a 10% NH$_4$Cl aqueous solution (300 mL), water (300 mL) and brine (200 mL), followed by drying over anhydrous sodium sulfate. After filtration and concentration under reduced pressure, the residue was purified by column chromatography (silica gel 200 g, n-hexane/ethyl acetate=40/1) to give Compound 8 (6.19 g, 17.6 mmol, 72.9%) as a colorless oil. R$_f$=0.43 (n-hexane/ethyl acetate=19/1); $^1$H NMR (400 MHz, CDCl$_3$) δ 0.18 (s, 6H), 0.97 (s, 9H), 1.24 (t, 6H, J=7.1 Hz), 3.53 (dq, 2H, J=2.3, 7.1 Hz), 3.68 (dq, 2H, J=2.3, 7.1 Hz), 4.63 (s, 1H), 6.74-6.81 (AA'BB', 2H), 7.03-7.10 (AA'BB', 21-H).

Reference Synthesis Example 10

2-[4-(tert-Butyldimethylsilyloxy)phenyl]acetic acid (9) (known compound, Reference: O. Brummer, et al., *Tetrahedron Lett.*, 42, 2257-2259 (2001))

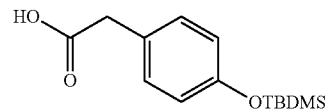 [SMILES: CC(C)(C)[Si](C)(C)Oc1ccc(CC(=O)O)cc1]

To a solution of p-hydroxyphenylacetic acid (48) (10.0 g, 65.7 mmol) in THF (80 mL) were successively added imidazole (22.4 g, 329 mmol) and tert-butyldimethylsilyl chloride (27.7 g, 184 mmol) at 0° C., and the mixture was stirred for an hour while elevating to room temperature. To this was added a solution of saturated Na$_2$CO$_3$ (250 mL) and the mixture was stirred at room temperature for an hour. To the mixture was added 2 M HCl aqueous solution (650 mL) and the product was extracted with ethyl acetate (300 mL×3). The combined organic extract was washed successively with water (400 mL) and brine (300 mL), followed by drying over anhydrous sodium sulfate. After filtration and concentration under reduced pressure, the residue was purified by column chromatography (silica gel 200 g, n-hexane→n-hexane/ethyl acetate/acetic acid=1/1/0.05) to give Compound 9 (10.6 g, 39.9 mmol, 60.7%) as a colorless solid. R$_f$=0.64 (n-hexane/ethyl acetate=1/2); $^1$H NMR (400 MHz, CDCl$_3$) δ 0.20 (s, 6H), 0.99 (s, 9H), 3.58 (s, 2H), 6.76-6.85 (AA'BB', 2H), 7.10-7.17 (AA'BB', 2H).

Synthesis Example 1

Coelenterazine (CTZ) Analogues Modified at the C-8 Position 1-1) TMD-296 (3a)

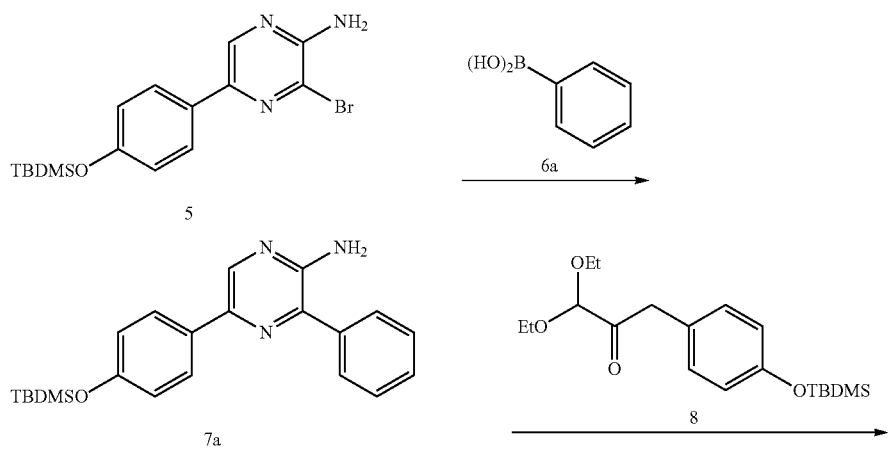

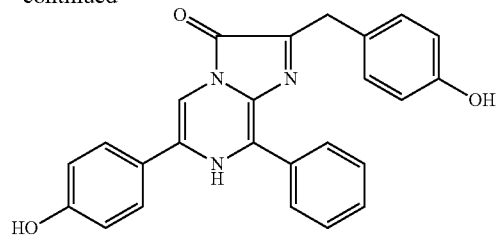

3a (TMD-296)

5-[4-(tert-Butyldimethylsilyloxy)phenyl]-3-phenylpyrazin-2-amine (7a)

Under an argon atmosphere, to a solution of 3-bomo-5-[4-(ter-butyldimethylsilyloxy)phenyl]pyran-2-amine (5) (1.50 g, 3.94 mmol) in toluene (45 mL) and ethanol (1.7 mL) were successively added phenylboronic acid (6a) (577 mg, 4.73 mmol), dichlorobis(triphenylphosphine)palladium (II) (165 mg, 235 µmol) and 1 M $Na_2CO_3$ aqueous solution (4.00 mL, 4.00 mmol) at room temperature, and the mixture was heated to reflux for 17 hours. After cooling to room temperature, to the mixture was added water and the metal catalyst was removed by filtration. The product was extracted with ethyl acetate (200 mL×3). The combined organic extract was washed successively with water (300 mL) and brine (300 mL), followed by drying over anhydrous sodium sulfate. After filtration and concentration under reduced pressure, the residue was purified by column chromatography (silica gel 100 g, n-hexane/ethyl acetate=3/1) to give Compound 7a (1.46 g, 3.87 mmol, 98.1%) as a brown solid. $R_f$=0.41 (n-hexane/ethyl acetate=1/1); $^1$H NMR (400 MHz, DMSO-$d_6$) δ 0.21 (s, 6H), 0.96 (s, 9H), 6.20 (s, 2H), 6.89-6.94 (AA'BB', 2H), 7.42-7.55 (m, 3H), 7.76-7.82 (m, 2H), 7.85-7.91 (AA'BB', 2H), 8.48 (s, 1H); $^{13}$C NMR (75.5 MHz, DMSO-$d_6$) 8-4.6 (2C), 17.9, 25.5 (3C), 120.0 (2C), 126.4 (2C), 128.2 (2C), 128.4, 128.6 (2C), 130.5, 137.2, 137.68, 137.72, 139.9, 151.6, 155.0; IR (KBr, cm$^{-1}$) 523, 637, 677, 700, 720, 752, 779, 808, 841, 914, 1018, 1070, 1092, 1105, 1167, 1204, 1263, 1319, 1362, 1381, 1435, 1460, 1510, 1605, 2857, 2886, 2928, 2955, 3059, 3159, 3291, 3428; HRMS (ESI$^+$) m/z 378.1990 ([M+H]$^+$, $C_{22}H_{28}N_3OSi^+$ requires 378.1996).

2-(4-Hydroxybenzyl)-6-(4-hydroxyphenyl)-8-phenylimidazo[1,2-a]pyrazin-3(7H)-one (3a, TMD-296)

Under an argon atmosphere, to a mixture of 5-[4-(tert-butyldimethylsilyloxy)phenyl]-3-phenylpyrazin-2-amine (7a) (272 mg, 720 mol) and 3-[4-(tert-butyldimethylsilyloxy)phenyl]-1,1-diethoxypropan-2-one (8) (381 mg, 1.08 mmol) dissolved in 1,4-dioxane (2 mL) was added 4 M hydrochloric acid (780 µL) at 0° C., and the mixture was heated to reflux for 17 hours. After cooling to room temperature, the mixture was concentrated under reduced pressure and the residue was purified by column chromatography in an argon flow (acidic silica gel 20 g, n-hexane/ethyl acetate=1/2→ethyl acetate→ethyl acetate/methanol=20/1). To the suspension obtained during the concentration under reduced pressure was added n-hexane. The precipitates were collected by filtration and dried in vacuo to give Compound 3a (TMD-296) (158 mg, 386 µmol, 53.6%) as an orange solid. $R_f$=0.59 (ethyl acetate); HPLC retention time 8.0 min; $^1$H NMR (400 MHz, CD$_3$OD) δ 4.16 (s, 2H), 6.69-6.76 (AA'BB', 2H), 6.91-6.97 (AA'BB', 2H), 7.09-7.16 (AA'BB', 2H), 7.56-7.68 (m, 3H), 7.84-7.91 (AA'BB', 2H), 7.98-8.03 (m, 2H), 8.39 (s, 1H); IR (KBr, cm$^{-1}$) 523, 656, 696, 779, 843, 891, 1173, 1265, 1342, 1443, 1512, 1591, 1609, 1655, 2814, 3154; HRMS (ESI$^+$) m/z 410.1497 ([M+H]$^+$, $C_{25}H_{20}N_3O_3^+$ requires 410.1499).

1-2) TMD-282 (3b)

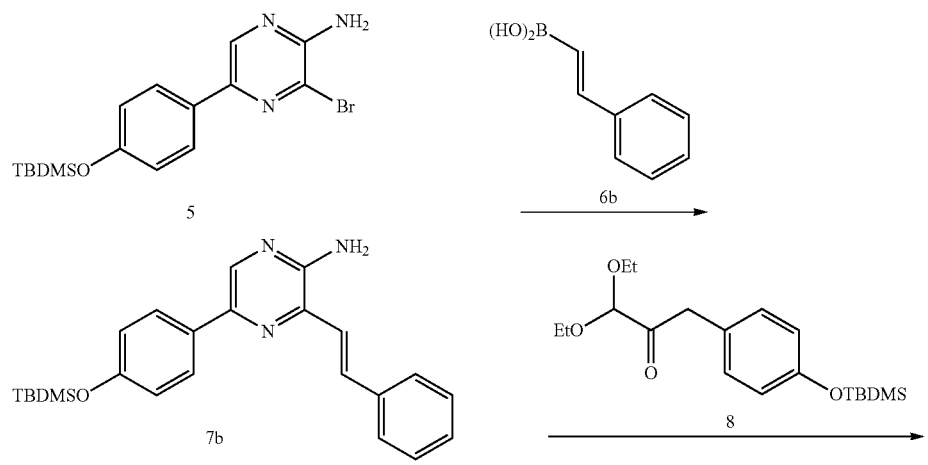

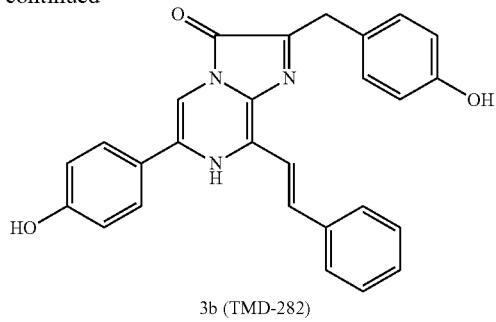

3b (TMD-282)

(E)-5-[4-(tert-Butyldimethylsilyloxy)phenyl]-3-styrylpyrazin-2-amine (7b)

Under an argon atmosphere, to a solution of 3-bromo-5-[4-(tert-butyldimethylsilyloxy)phenyl]pyrazin-2-amine (5) (1.00 g, 2.63 mmol) in toluene (30 mL) and ethanol (1.2 mL) were successively added trans-2-phenylvinylboronic acid (6b) (543 mg, 3.16 mmol), dichlorobis(triphenylphosphine)palladium (11) (111 mg, 158 μmol) and 1 M $Na_2CO_3$ aqueous solution (2.70 mL, 2.70 mmol) at room temperature, and the mixture was heated to reflux for 18 hours. After cooling to room temperature, to the mixture was added water, and the metal catalyst was removed by filtration. The product was extracted with ethyl acetate (200 mL×3). The combined organic extract was washed successively with water (300 mL) and brine (300 mL), followed by drying over anhydrous sodium sulfate. After filtration and concentration under reduced pressure, the residue was purified by column chromatography (silica gel 100 g, n-hexane/ethyl acetate=3/1) to give Compound 7b (997 mg, 2.47 mmol, 94.0%) as a yellow solid. $R_f$=0.19 (n-hexane/ethyl acetate=3/1); $^1$H NMR (400 MHz, DMSO-$d_6$) δ 0.19 (s, 6H), 0.94 (s, 9H), 6.60 (s, 2H), 6.84-6.91 (AA'BB', 2H), 7.22-7.31 (m, 1H), 7.31-7.44 (m, 2H), 7.55 (d, 1H, J=16 Hz), 7.65-7.77 (m, 3H), 7.87-7.93 (AA'BB', 2H), 9.39 (s, 1H); $^{13}$C NMR (75.5 MHz, DMSO-$d_6$) δ −4.6 (2C), 17.9, 25.5 (3C), 120.1 (2C), 122.1, 126.5 (2C), 127.3 (2C), 128.2, 128.7 (2C), 130.8, 132.8, 133.8, 136.9, 137.7, 139.4, 152.0, 155.0; IR (KBr, $cm^{-1}$) 444, 463, 507, 534, 633, 691, 745, 781, 806, 841, 914, 964, 1011, 1072, 1088, 1103, 1153, 1213, 1263, 1379, 1420, 1454, 1512, 1566, 1605, 1634, 2856, 2886, 2930, 2955, 3057, 3196, 3329; HRMS (ESI) m/z 404.2161 ([M+H]$^+$, $C_{24}H_{30}N_3OSi^+$ requires 404.2153).

(E)-2-(4-Hydroxybenzyl)-6-(4-hydroxyphenyl)-8-styrylimidazo[1,2-α]pyrazin-3(7H)-one (3b, TMD-282)

Under an argon atmosphere, to a mixture of (E)-5-[4-(tert-butyldimethylsilyloxy)phenyl]-3-styrylpyrazin-2-amine (7b) (290 mg, 719 μmol) and 3-[4-(tert-butyldimethylsilyloxy)phenyl]-1,1-diethoxypropan-2-one (8) (380 mg, 1.08 mmol) dissolved in 1,4-dioxane (2 mL) was added 4 M hydrochloric acid (600 μL) at, 0° C. and the mixture was heated to reflux for 15 hours. After cooling to room temperature, the mixture was concentrated under reduced pressure and the residue was purified by column chromatography in an argon flow (acidic silica gel 20 g, n-hexane/ethyl acetate=1/2→ethyl acetate→ethyl acetate/methanol=20/1). To the suspension obtained during the concentration under reduced pressure was added n-hexane. The precipitates were collected by filtration and dried in vacuo to give Compound 3b (TMD-282) (74.0 mg, 170 μmol, 23.6%) as a brown solid. $R_f$=0.22 (ethyl acetate); HPLC retention time 14.3 min.

1-3) TMD-276 (3d)

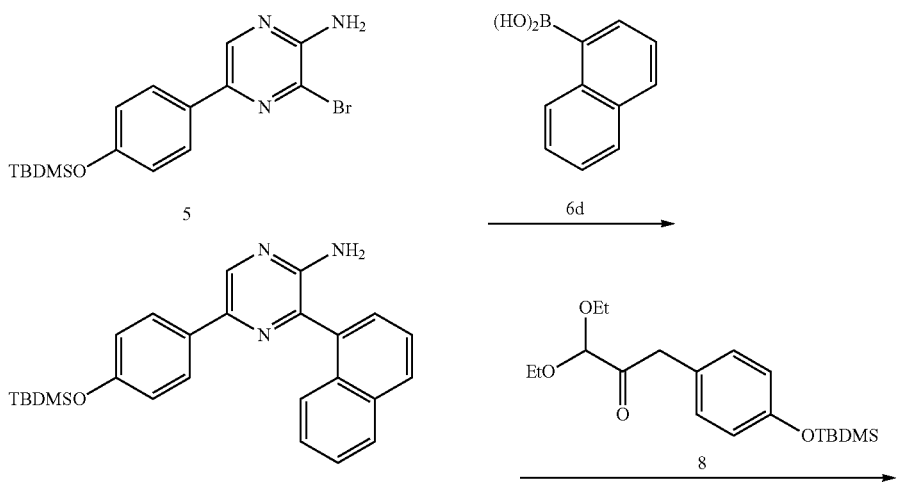

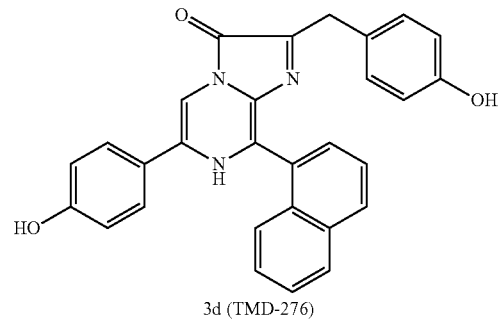

3d (TMD-276)

5-[4-(tert-Butyldimethylsilyloxy)phenyl]-3-(naphthalen-1-yl)pyrazin-2-amine (7d)

Under an argon atmosphere, to a solution of 3-bromo-5-[4-(tert-butyldimethylsilyloxy)phenyl]pyrazin-2-amine (5) (1.48 g, 3.90 mmol) in toluene (45 mL) and ethanol (2 mL) were successively added 1-naphthaleneboronic acid (6d) (805 mg, 4.68 mmol), dichlorobis(triphenylphosphine)palladium (II) (164 mg, 234 μmol) and 1 M $Na_2CO_3$ aqueous solution (4.00 mL, 4.00 mmol) at room temperature, and the mixture was heated to reflux for 18 hours. After cooling to room temperature, to the mixture was added water and the metal catalyst was removed by filtration. The product was extracted with ethyl acetate (200 mL×3). The combined organic extract was washed successively with water (300 mL) and brine (300 mL), followed by drying over anhydrous sodium sulfate. After filtration and concentration under reduced pressure, the residue was purified by column chromatography (silica gel 100 g, n-hexane/ethyl acetate=4/1) to give Compound 7d (1.44 g, 3.37 mmol, 86.5%) as a yellow foamy solid. $R_f$=0.25 (n-hexane/ethyl acetate=4/1); $^1$H NMR (400 MHz, DMSO-$d_6$) δ 0.14 (s, 6H), 0.90 (s, 9H), 5.89 (s, 2H), 6.80-6.87 (AA'BB', 2H), 7.41-7.48 (m, 1H), 7.48-7.64 (m, 4H), 7.74-7.81 (AA'BB', 2H), 7.96-8.04 (m, 2H), 8.55 (s, 1H); $^{13}$C NMR (75.5 MHz, DMSO-$d_6$) 8-4.6 (2C), 17.9, 25.5 (3C), 120.1 (2C), 125.2, 125.8, 126.0, 126.37 (2C), 126.40, 127.2, 128.4, 128.8, 130.6, 130.9, 133.6, 134.7, 137.8, 138.1, 139.5, 152.5, 154.9; IR (KBr, cm$^{-1}$) 517, 544, 579, 631, 675, 706, 739, 777, 806, 841, 910, 980, 1055, 1080, 1103, 1121, 1169, 1179, 1198, 1265, 1337, 1362, 1375, 1423, 1450, 1508, 1570, 1605, 2857, 2886, 2928, 2955, 3051, 3179, 3300, 3383, 3474; HRMS (ESI$^+$) m/z 428.2163 ([M+H]$^+$, $C_{26}H_{30}N_3OSi^+$ requires 428.2153).

2-(4-Hydroxybenzyl)-6-(4-hydroxyphenyl)-8-(naphthalen-1-yl)imidazo[1,2-a]pyrazin-3(7H)-one (3d, TMD-276)

Under an argon atmosphere, to a mixture of 5-[4-(tert-butyldimethylsilyloxy)phenyl]-3-(naphthalen-1-yl)pyrazin-2-amine (7d) (255 mg, 596 μmol) and 3-[4-(tert-butyldimethylsilyloxy)phenyl]-1,1-diethoxypropan-2-one (8) (315 mg, 894 μmol) dissolved in 1,4-dioxane (2 mL) was added, 4 M hydrochloric acid (780 μL) at 0° C. and the mixture was heated to reflux for 15 hours. After cooling to room temperature, the mixture was concentrated under reduced pressure and the residue was purified by column chromatography in an argon flow (acidic silica gel 20 g, n-hexane/ethyl acetate=1/2→ethyl acetate→ethyl acetate/methanol=20/1). To the suspension obtained during the concentration under reduced pressure was added n-hexane. The precipitates were collected by filtration and dried in vacuo to give Compound 3d (TMD-276) (74.3 mg, 162 μmol, 27.1%) as an orange solid. $R_f$=0.54 (ethyl acetate/methanol=20/1); HPLC retention time 9.1 min; $^1$H NMR (400 MHz, CD$_3$OD) δ 4.06 (s, 2H), 6.64-6.70 (AA'BB', 2H), 6.88-6.95 (AA'BB', 2H), 7.00-7.07 (AA'BB', 2H), 7.47-7.55 (m, 1H), 7.55-7.63 (m, 1H), 7.68-7.73 (m, 1H), 7.80-7.92 (m, 4H, includes AA'BB'), 8.00-8.07 (m, 1H), 8.14-8.22 (m, 1H), 8.54 (s, 1H); IR (KBr, cm$^{-1}$) 463, 492, 646, 779, 808, 968, 1015, 1045, 1082, 1109, 1173, 1240, 1325, 1346, 1443, 1508, 1591, 1609, 1653, 2814, 3169; HRMS (ESI$^+$) m/z 460.1656 ([M+H]$^+$, $C_{29}H_{22}N_3O_3^+$ requires 460.1656).

1-4) TMD-277 (3e)

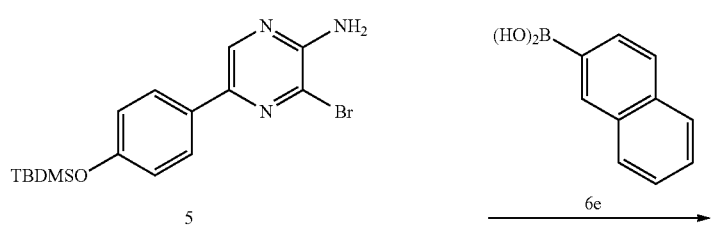

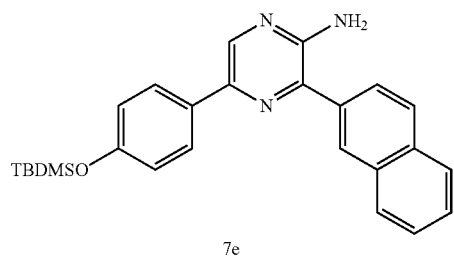

7e

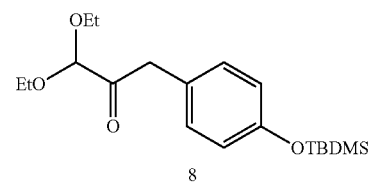

8

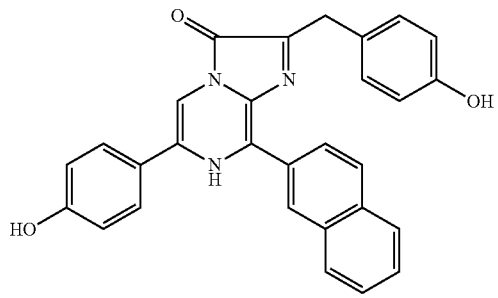

3e (TMD-277)

5-[4-(tert-Butyldimethylsilyloxy)phenyl]-3-(naphthalen-2-yl)pyrazin-2-amine (7e)

Under an argon atmosphere, to a solution of 3-bromo-5-[4-(tert-butyldimethylsilyloxy)phenyl]pyrazin-2-amine (5) (1.00 g, 2.63 mmol) in toluene (30 mL) and ethanol (1.2 mL) were successively added 2-naphthaleneboronic acid (6e) (543 mg, 3.16 mmol), dichlorobis(triphenylphosphine)palladium (11) (110 mg, 157 μmol) and 1 M $Na_2CO_3$ aqueous solution (2.70 mL, 2.70 mmol) at room temperature, and the mixture was heated to reflux for 15 hours. After cooling to room temperature, to the mixture was added water and the metal catalyst was removed by filtration. The product was extracted with ethyl acetate (200 mL×3). The combined organic extract was washed successively with water (300 mL) and brine (300 mL), followed by drying over anhydrous sodium sulfate. After filtration and concentration under reduced pressure, the residue was purified by column chromatography (silica gel 100 g, n-hexane/ethyl acetate=3/1) to give Compound 7e (1.04 g, 2.43 mmol, 92.2%) as a yellow solid. $R_f$=0.33 (n-hexane/diethyl ether=2/3); $^1$H NMR (400 MHz, DMSO-$d_6$) δ 0.17 (s, 6H), 0.92 (s, 9H), 6.32 (s, 2H), 6.85-6.92 (AA'BB', 2H), 7.49-7.57 (m, 2H), 7.84-7.91 (m, 3H, includes AA'BB'), 7.91-7.96 (m, 1H), 7.97-8.03 (m, 2H), 8.31 (s, 1H), 8.47 (s, 1H); IR (KBr, cm$^{-1}$) 419, 438, 530, 648, 669, 698, 743, 779, 814, 841, 918, 939, 1009, 1103, 1126, 1165, 1192, 1219, 1252, 1341, 1362, 1389, 1420, 1431, 1462, 1508, 1530, 1566, 1605, 1636, 2859, 2895, 2930, 2955, 3038, 3057, 3159, 3296, 3416; HRMS (ESI$^+$) m/z 428.2155 ([M+H]$^+$, $C_{26}H_{30}N_3OSi^+$ requires 428.2153).

2-(4-Hydroxybenzyl)-6-(4-hydroxyphenyl)-8-(naphthalen-2-yl)imidazo[1,2-a]pyrazin-3(7H)-one (3e, TMD-277)

Under an argon atmosphere, to a mixture of 5-[4-(tert-butyldimethylsilyloxy)phenyl]-3-(naphthalen-2-yl)pyrazin-2-amine (7e) (308 mg, 720 μmol) and 3-[4-(tert-butyldimethylsilyloxy)phenyl]-1,1-diethoxypropan-2-one (8) (381 mg, 1.08 mmol) dissolved in 1,4-dioxane (2 mL) was added 4 M hydrochloric acid (600 μL) at 0° C., and the mixture was heated to reflux for 14 hours. After cooling to room temperature the mixture was concentrated under reduced pressure and the residue was purified by column chromatography in an argon flow (acidic silica gel 20 g, n-hexane/ethyl acetate=1/2→ethyl acetate→ethyl acetate/methanol=20/1). To the suspension obtained during the concentration under reduced pressure was added n-hexane. The precipitates were collected by filtration and dried in vacuo to give Compound 3e (TMD-277) (89.9 mg, 196 μmol, 27.2%) as an orange solid. $R_f$=0.59 (ethyl acetate/methanol=20/1); HPLC retention time 13.6 min; $^1$H NMR (400 MHz, CD$_3$OD) δ 4.17 (s, 2H), 6.70-6.77 (AA'BB', 2H), 6.91-6.98 (AA'BB', 2H), 7.11-7.17 (AA'BB', 2H), 7.56-7.68 (m, 2H), 7.88-7.94 (AA'BB', 2H), 7.95-8.00 (m, 1H), 8.01-8.06 (m, 1H), 8.08-8.11 (m, 2H), 8.37 (s, 1H), 8.55 (s, 1H); IR (KBr, cm$^{-1}$) 480, 552, 656, 752, 822, 903, 1111, 1173, 1242, 1269, 1356, 1447, 1513, 1558, 1611, 1653, 2814, 2897, 3165; HRMS (ESI$^+$) m/z 460.1666 ([M+H]$^+$, $C_{29}H_{22}N_3O_3^+$ requires 460.1656).

1-5) TMD-278 (3f)

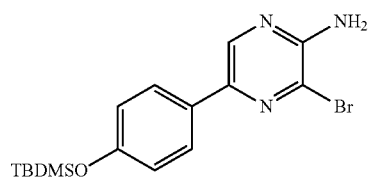

5

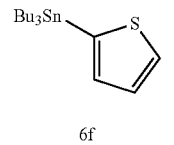

6f

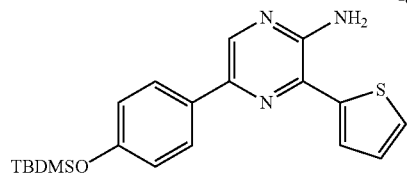

7f

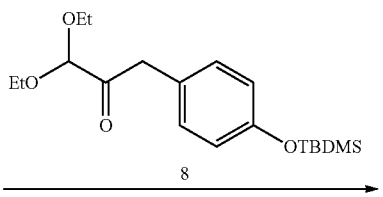

8

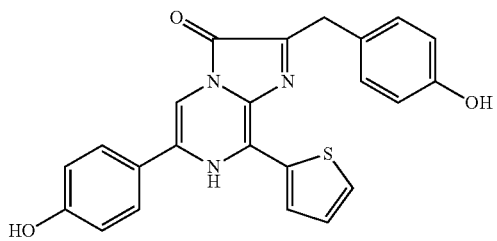

3f (TMD-276)

5-[4-(tert-Butyldimethylsilyloxy)phenyl]-3-(thiophen-2-yl)pyrazin-2-amine (7f)

Under an argon atmosphere, to a solution of 3-bromo-5-[4-(tert-butyldimethylsilyloxy)phenyl]pyrazin-2-amine (5) (1.20 g, 3.15 mmol) in 1,4-dioxane (30 mL) were successively added 2-(tributylstannyl)thiophene (6f) (1.10 mL, 3.46 mmol) and dichlorobis(triphenylphosphine)palladium (11) (111 mg, 158 μmol) at room temperature, and the mixture was heated to reflux for 14 hours. After cooling to room temperature, to the mixture was added saturated KF aqueous solution and the mixture was stirred at room temperature for 30 minutes. The metal catalyst was removed by filtration, and the product was extracted with ethyl acetate (200 mL×3). The combined organic extract was washed successively with saturated KF aqueous solution (300 mL), water (300 mL) and brine (300 mL), followed by drying over anhydrous sodium sulfate. After filtration and concentration under reduced pressure, the residue was purified by column chromatography (silica gel 100 g, n-hexane/ethyl acetate=3/1) to give Compound 7f (1.03 g, 2.68 mmol, 84.9%) as a yellow solid. $R_f$=0.33 (n-hexane/ethyl acetate=3/1); $^1$H NMR (400 MHz, DMSO-$d_6$) δ 0.19 (s, 6H), 0.94 (s, 9H), 6.42 (s, 2H), 6.87-6.94 (AA'BB', 2H), 7.17 (dd, 1H, J=3.8, 5.2 Hz), 7.65 (d, 1H, J=5.2 Hz), 7.74 (d, 1H, J=3.8 Hz), 7.83-7.91 (AA'BB', 2H), 8.46 (s, 1H); $^{13}$C NMR (75.5 MHz, DMSO-$d_6$) δ −4.6 (2C), 17.9, 25.5 (3C), 120.1 (2C), 125.6, 126.4 (2C), 128.2, 128.3, 129.9, 131.8, 136.9, 139.5, 142.6, 149.8, 155.2; IR (KBr, cm$^{-1}$) 471, 509, 536, 581, 623, 646, 669, 716, 741, 779, 804, 822, 839, 912, 1011, 1057, 1082, 1111, 1172, 1202, 1263, 1279, 1360, 1379, 1435, 1454, 1477, 1512, 1564, 1607, 2857, 2895, 2930, 2953, 3335, 3439; HRMS (ESI$^+$) m/z 384.1551 ([M+H]$^+$, $C_{20}H_{26}N_3OSSi^+$ requires 384.1560).

2-(4-Hydroxybenzyl)-6-(4-hydroxyphenyl)-8-(thiophen-2-yl)imidazo[1,2-a]pyrazin-3(7H)-one (3f, TMD-278)

Under an argon atmosphere, to a mixture of 5-[4-(tert-butyldimethylsilyloxy)phenyl]-3-(thiophen-2-yl)pyrazin-2-amine (7f) (276 mg, 720 μmol) and 3-[4-(tert-butyldimethylsilyloxy)phenyl]-1,1-diethoxypropan-2-one (8) (381 mg, 1.08 mmol) dissolved in 1,4-dioxane (2 mL) was added 4 M hydrochloric acid (780 μL) at 0° C. and the mixture was heated to reflux for 16 hours. After cooling to room temperature, the mixture was concentrated under reduced pressure and the residue was purified by column chromatography in an argon flow (acidic silica gel 20 g, n-hexane/ethyl acetate=1/2→ethyl acetate→ethyl acetate/methanol=20/1). To the suspension obtained during the concentration under reduced pressure was added n-hexane. The precipitates were collected by filtration and dried in vacuo to give Compound 3f (TMD-278) (68.2 mg, 164 μmol, 22.8%) as a brown solid. $R_f$=0.67 (ethyl acetate/methanol=20/1); HPLC retention time 9.5 min; $^1$H NMR (400 MHz, CD$_3$OD) δ 4.22 (s, 2H), 6.72-6.78 (AA'BB', 2H), 6.90-6.97 (AA'BB', 2H), 7.11-7.18 (AA'BB', 2H), 7.32 (dd, 1H, J=3.8, 5.2 Hz), 7.87 (dd, 1H, J=1.1, 5.2 Hz), 7.91-7.97 (AA'BB', 2H), 8.12 (dd, 1H, J=1.1, 3.8 Hz), 8.48 (s, 1H); IR (KBr, cm$^{-1}$) 521, 581, 629, 721, 777, 841, 881, 966, 1109, 1172, 1261, 1341, 1429, 1508, 1533, 1609, 1653, 2822, 3107; HRMS (ESI$^+$) m/z 416.1075 ([M+H]$^+$, $C_{23}H_{18}N_3O_3S^+$ requires 416.1063).

1-6) TMD-336 (3g)

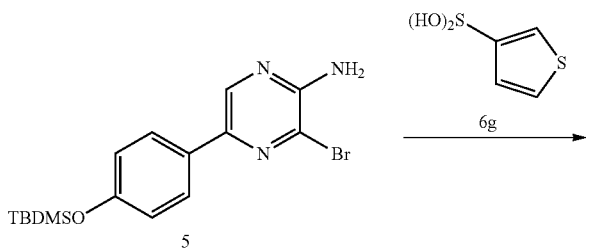 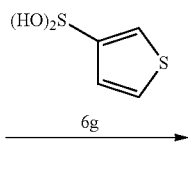

6g

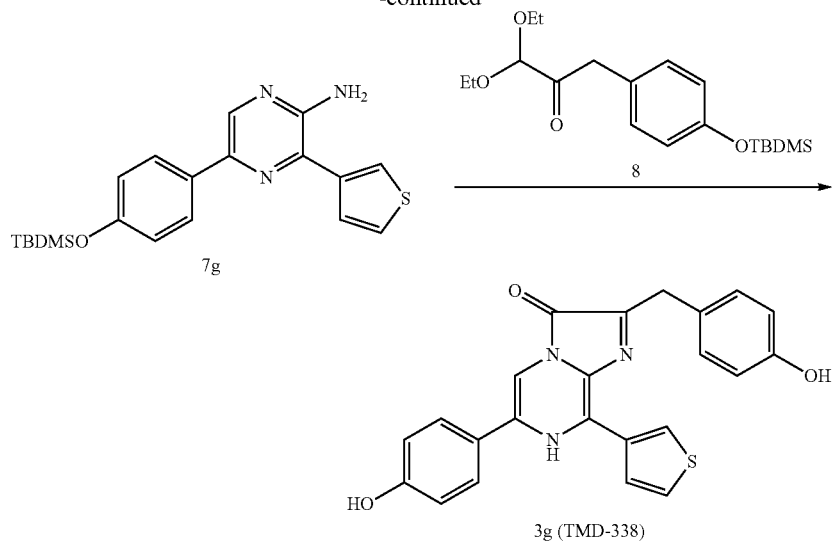

5-[4-(tert-Butyldimethylsilyloxy)phenyl]-3-(thiophen-3-yl)pyrazin-2-amine (7g)

Under an argon atmosphere, to a solution of 3-bromo-5-[4-(tert-butyldimethylsilyloxy)phenyl]pyrazin-2-amine (5) (1.50 g, 3.94 mmol) in toluene (45 mL) and ethanol (1.8 mL) were successively added 3-thienylboronic acid (6 g) (605 mg, 4.73 mmol), dichlorobis(triphenylphosphine)palladium (II) (165 mg, 235 μmol) and 1 M $Na_2CO_3$ aqueous solution (4.00 mL, 4.00 mmol) at room temperature and the mixture was heated to reflux for 15 hours. After cooling to room temperature, to the mixture was added water and the metal catalyst was removed by filtration. The product was extracted with ethyl acetate (200 mL×3). The combined organic extract was washed successively with water (300 mL) and brine (300 mL), followed by drying over anhydrous sodium sulfate. After filtration and concentration under reduced pressure, the residue was purified by column chromatography (silica gel 150 g, n-hexane/ethyl acetate=3/1) to give Compound 7g (1.19 g, 3.11 mmol, 78.9%) as a red solid. $R_f$=0.50 (n-hexane/ethyl acetate=1/1); $^1$H NMR (400 MHz, DMSO-$d_6$) δ 0.21 (s, 6H), 0.96 (s, 9H), 6.29 (s, 2H), 6.88-6.96 (AA'BB', 2H), 7.66-7.73 (m, 2H), 7.88-7.93 (AA'BB', 2H), 8.06-8.09 (m, 1H), 8.47 (s, 1H); $^{13}$C NMR (75.5 MHz, DMSO-$d_6$) δ −4.5 (2C), 17.9, 25.5 (3C), 120.1 (2C), 124.7, 126.1, 126.4 (2C), 128.2, 130.4, 133.5, 136.7, 138.7, 139.6, 151.2, 155.0; IR (KBr, cm$^{-1}$) 511, 534, 551, 635, 662, 694, 719, 737, 754, 779, 808, 843, 916, 1009, 1034, 1086, 1103, 1167, 1182, 1196, 1215, 1260, 1331, 1366, 1389, 1408, 1454, 1510, 1566, 1605, 2857, 2886, 2928, 2953, 3038, 3115, 3175, 3289, 3412; HRMS (ESI$^+$) m/z 384.1560 ([M+H]$^+$, $C_{20}H_{26}N_3OSSi^+$ requires 384.1560).

2-(4-Hydroxybenzyl)-6-(4-hydroxyphenyl)-8-(thiophen-3-yl)imidazo[1,2-a]pyrazin-3(7H)-one (3g, TMD-336)

Under an argon atmosphere, to a mixture of 5-[4-(tert-butyldimethylsilyloxy)phenyl]-3-(thiophen-3-yl)pyrazin-2-amine (7g) (311 mg, 811 μmol) and 3-[4-(tert-butyldimethylsilyloxy)phenyl]-1,1-diethoxypropan-2-one (8) (396 mg, 1.22 mmol) dissolved in 1,4-dioxane (2 mL) was added 4 M hydrochloric acid (780 μL) at 0° C., and the mixture was heated to reflux for 15 hours. After cooling to room temperature, the mixture was concentrated under reduced pressure and the residue was purified by column chromatography in an argon flow (acidic silica gel 20 g, n-hexane/ethyl acetate=1/2→ethyl acetate→ethyl acetate/methanol=20/1). To the suspension obtained during the concentration under reduced pressure was added n-hexane. The precipitates were collected by filtration and dried in vacuo to give Compound 3 g (TMD-336) (179 mg, 431 μmol, 53.2%) as an orange solid. $R_f$=0.70 (ethyl acetate); HPLC retention time 7.9 min; $^1$H NMR (400 MHz, $CD_3OD$) δ 4.18 (s, 2H), 6.70-6.76 (AA'BB', 2H), 6.91-6.99 (AA'BB', 2H), 7.11-7.19 (AA'BB', 2H), 7.70 (dd, 1H, J=2.8, 5.2 Hz), 7.81-7.88 (AA'BB', 2H), 7.95 (dd, 1i, J=1.2, 5.2 Hz), 8.29 (s, 1H), 8.50 (dd, 1H, J=1.2, 2.8 Hz); IR (KBr, cm$^{-1}$) 519, 652, 804, 841, 926, 1173, 1233, 1271, 1341, 1437, 1508, 1609, 1647, 3107; HRMS (ESI$^+$) m/z 416.1065 ([M+H]$^+$, $C_{23}H_{18}N_3O_3S^+$ requires 416.1063).

1-7) TMD-281 (3h)

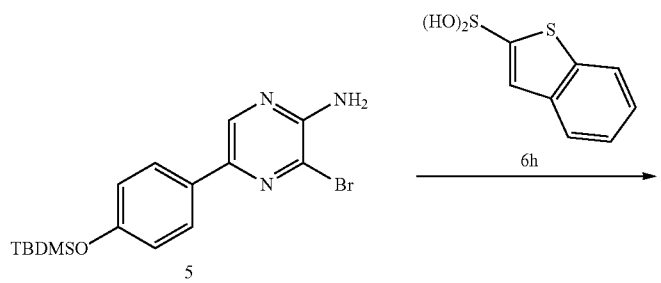

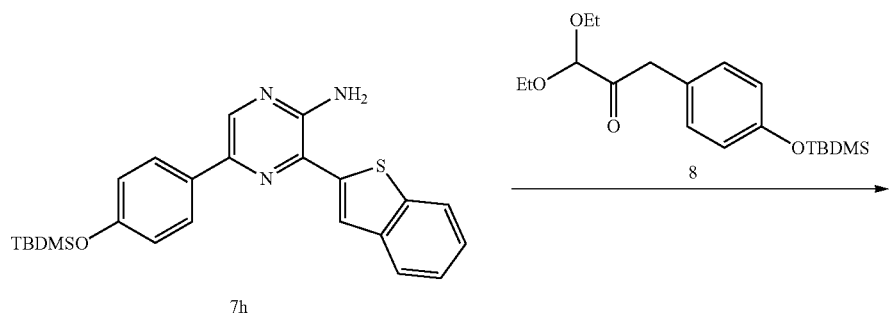

3-(Benzo[b]thiophen-2-yl)-5-[4-(tert-butyldimethylsilyloxy)phenyl]pyrazin-2-amine (7h)

Under an argon atmosphere, to a solution of 3-bromo-5-[4-(tert-butyldimethylsilyloxy)phenyl]pyrazin-2-amine (5) (971 mg, 2.55 mmol) in toluene (27 mL) and ethanol (1.3 mL) were successively added benzo[b]thiophene-2-boronic acid (6h) (500 mg. 2.81 mmol), dichlorobis(triphenylphosphine)palladium (II) (108 mg, 153 μmol) and 1 M $Na_2CO_3$ aqueous solution (2.60 mL, 2.60 mmol) at room temperature and the mixture was heated to reflux for 17 hours. After cooling to room temperature, to the mixture was added water and the metal catalyst was removed by filtration. The product was extracted with ethyl acetate (200 mL×3). The combined organic extract was washed successively with water (300 mL) and brine (300 mL), followed by drying over anhydrous sodium sulfate. After filtration and concentration under reduced pressure, the residue was purified by column chromatography (silica gel 100 g, n-hexane/ethyl acetate=3/1) to give Compound 7h (746 mg, 1.72 mmol, 67.3%) as an orange solid. $R_f$=0.67 (n-hexane/ethyl acetate=1/1); $^1$H NMR (400 MHz, DMSO-$d_6$) δ 0.20 (s, 6H), 0.95 (s, 9H), 6.68 (s, 21H), 6.91-6.98 (AA'BB', 2H), 7.33-7.41 (m, 2H), 7.81-7.88 (m, 1H), 7.91-7.99 (m, 3H, includes AA'BB'), 8.11 (s, 1H), 8.55 (s, 1H); $^{13}$C NMR (75.5 MHz, DMSO-$d_6$) 8-4.6 (2C), 17.9, 25.5 (3C), 120.2 (2C), 122.0, 122.3, 124.37, 124.42, 125.1, 126.5 (2C), 129.8, 131.0, 137.8, 139.4, 139.6, 140.9, 143.1, 150.4, 155.3; IR (KBr, cm$^{-1}$) 527, 552, 584, 642, 675, 708, 723, 741, 779, 808, 835, 918, 974, 1009, 1072, 1101, 1128, 1165, 1221, 1252, 1371, 1418, 1462, 1510, 1533, 1566, 1605, 1636, 1728, 2857, 2895, 2928, 2955, 3161, 3294, 3416; HRMS (ESI$^+$) m/z 434.1713 ([M+H]$^+$, $C_{24}H_{28}N_3OSSi^+$ requires 434.1717).

8-(Benzo[b]thiophen-2-yl)-2-(4-hydroxybenzyl)-6-(4-hydroxyphenyl)imidazo[1,2-a]pyrazin-3(7H)-one (3h, TMD-281)

Under an argon atmosphere, to a mixture of 3-(benzo[b]thiophen-2-yl)-5-[4-(tert-butyldimethylsilyloxy)phenyl]pyrazin-2-amine (7h) (153 mg, 352 μmol) and 3-[4-(tert-butyldimethylsilyloxy)phenyl]-1,1-diethoxypropan-2-one (8) (190 mg, 539 μmol) dissolved in 1,4-dioxane (2 mL) was added 4 M hydrochloric acid (400 μL) at 0° C. and the mixture was heated to reflux for 14 hours. After cooling to room temperature, the mixture was concentrated under reduced pressure and the residue was purified by column chromatography in an argon flow (acidic silica gel 20 g, n-hexane/ethyl acetate=1/2→ethyl acetate→ethyl acetate/methanol=20/1). To the suspension obtained during the concentration under reduced pressure was added n-hexane. The precipitates were collected by filtration and dried in vacuo to give Compound 3h (TMD-281) (31.0 mg, 66.6 μmol, 18.9%) as an orange solid. $R_f$=0.67 (ethyl acetate/methanol=20/1); HPLC retention time 19.9 min; $^1$H NMR (400 MHz, CD$_3$OD) δ 4.12 (s, 2H), 6.75-6.84 (AA'BB', 2H), 6.84-6.94 (AA'BB', 21-1), 7.16-7.24 (AA'BB', 2H), 7.32-7.45 (m, 2H), 7.77-7.84 (m, 2H), 7.85-7.92 (AA'BB', 2H), 8.30 (s, 1H), 8.35 (s, 1H); IR (KBr, cm$^{-1}$) 430, 523, 573, 621, 637, 658, 725, 746, 839, 885, 962, 1107, 1173, 1204, 1233, 1342, 1441, 1519, 1560, 1611, 1655, 3057.

1-8) TMD-337 (3i)

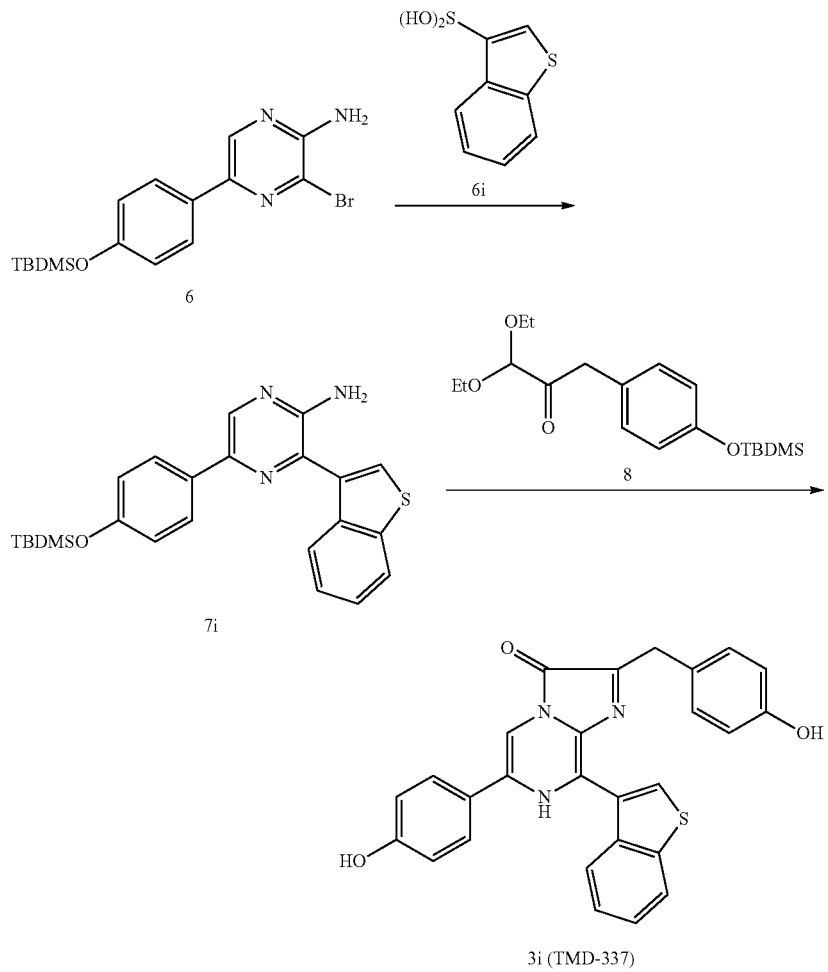

3-(Benzo[b]thiophen-3-yl)-5-[4-(tert-butyldimethylsilyloxy)phenyl]pyrazin-2-amine (7i)

Under an argon atmosphere, to a solution of 3-bromo-5-[4-(tert-butyldimethylsilyloxy)phenyl]pyrazin-2-amine (5) (1.50 g, 3.94 mmol) in toluene (45 mL) and ethanol (1.8 mL) were successively added thianaphthene-3-boronic acid (6i) (842 mg, 4.73 mmol), dichlorobis(triphenylphosphine)palladium (11) (165 mg, 235 µmol) and 1 M $Na_2CO_3$ aqueous solution (4.00 mL, 4.00 mmol) at room temperature, and the mixture was heated to reflux for 15 hours. After cooling to room temperature, to the mixture was added water and the metal catalyst was removed by filtration. The product was extracted with ethyl acetate (200 mL×3). The combined organic extract was washed successively with water (300 mL) and brine (300 mL), followed by drying over anhydrous sodium sulfate. After filtration and concentration under reduced pressure, the residue was purified by column chromatography (silica gel 150 g, n-hexane/ethyl acetate=3/1) to give Compound 7i (1.19 g, 3.11 mmol, 78.9%) as an orange solid. $R_f$=0.30 (n-hexane/diethyl ether=2/3); $^1H$ NMR (400 MHz, DMSO-$d_6$) δ 0.21 (s, 6H), 0.96 (s, 9H), 6.29 (s, 2H), 6.89-6.95 (AA'BB', 2H), 7.41-7.92 (m, 2H), 7.85-7.92 (AA'BB', 2H), 7.95-8.02 (m, 1H), 8.07-8.13 (m, 1H), 8.16 (s, 1H), 8.55 (s, 1H); $^{13}C$ NMR (75.5 MHz, DMSO-$d_6$) 5-4.6 (2C), 17.9, 25.5 (3C), 120.1 (2C), 122.8, 123.6, 124.4, 124.6, 126.3 (2C), 127.7, 130.4, 132.2, 133.7, 137.3, 138.0, 139.3, 139.7, 152.5, 155.0; IR (KBr, $cm^{-1}$) 471, 631, 664, 683, 712, 733, 758, 781, 808, 839, 912, 968, 1011, 1059, 1080, 1103, 1128, 1169, 1188, 1263, 1346, 1362, 1389, 1447, 1508, 1605, 2857, 2886, 2928, 2953, 3065, 3177, 3298, 3368, 3472; HRMS ($ESI^+$) m/z 434.1725 ($[M+H]^+$, $C_{24}H_{28}N_3OSSi^+$ requires 434.1769).

8-(Benzo[b]thiophen-3-yl)-2-(4-hydroxybenzyl)-6-(4-hydroxyphenyl)imidazo[1,2-a]pyrazin-3(7H)-one (3i, TMD-337)

Under an argon atmosphere, to a mixture of 3-(benzo[b]thiophen-3-yl)-5-[4-(tert-butyldimethylsilyloxy)phenyl]pyrazin-2-amine (7i) (336 mg, 775 µmol) and 3-[4-(tert-butyldimethylsilyloxy)phenyl]-1,1-diethoxypropan-2-one (8) (378 mg, 1.16 mmol) in 1,4-dioxane (2 mL) was added 4 M hydrochloric acid (780 µL) at 0*C and the mixture was heated to reflux for 18 hours. After cooling to room temperature, the mixture was concentrated under reduced pressure and the residue was purified by column chromatography in an argon flow (acidic silica gel 20 g, n-hexane/ethyl acetate=1/2→ethyl acetate→ethyl acetate/methanol=20/1). To the suspension obtained during the concentration under reduced pressure was added n-hexane. The precipitates were collected by filtration and dried in vacuo to give Compound 3i (TMD-337) (136 mg, 292 µmol, 37.6%) as an orange solid. $R_f$=0.37 (ethyl acetate); HPLC retention time 11.5 min; $^1H$ NMR (400

MHz, CD$_3$OD) δ 4.16 (s, 2H), 6.68-6.77 (AA'BB', 2H), 6.90-6.96 (AA'BB', 2H), 7.07-7.15 (AA'BB', 2H), 7.43-7.54 (m, 21H), 7.90-7.97 (AA'BB', 2H), 8.00-8.07 (m, 1H), 8.22-8.30 (m, 1H), 8.36 (s, 1H), 8.52 (s, 1H); IR (KBr, cm$^{-1}$) 517, 571, 637, 735, 764, 839, 959, 1049, 1107, 1171, 1231, 1354, 1362, 1437, 1508, 1608, 3101; HRMS (ESI$^+$) m/z 466.1233 ([M+H]$^+$, C$_{27}$H$_{20}$N$_3$O$_3$S$^+$ requires 466.1220).

1-9) TMD-280 (3j)

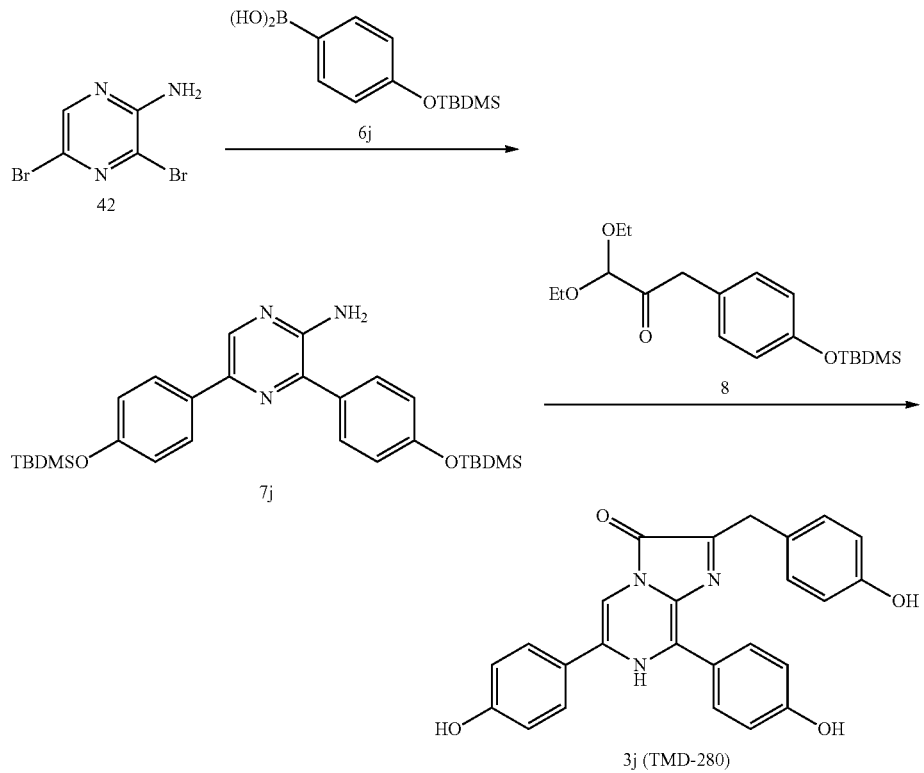

3,5-Bis[4-(tert-butyldimethylsilyloxy)phenyl]pyrazin-2-amine (7j) (known compound, Reference: P. Jeanjot, et al., *Synthesis*, 513-522 (2003))

Under an argon atmosphere, to a solution of 3,5-dibromopyrazin-2-amine (42) (1.00 g, 3.95 mmol) dissolved in toluene (60 mL) and ethanol (4.0 mL) were successively added (4-bromophenoxy)(tert-butyl)dimethylsilane (6j) (2.49 g, 9.89 mmol), dichlorobis(triphenylphosphine)palladium (11) (167 mg, 237 µmol) and 1 M Na$_2$CO$_3$ aqueous solution (8.00 mL, 8.00 mmol) at room temperature, and the mixture was heated to reflux for 17 hours. After cooling to room temperature, to the mixture was added water and the metal catalyst was removed by filtration. The product was extracted with ethyl acetate (200 mL×3). The combined organic extract was washed successively with water (300 mL) and brine (300 mL), followed by drying over anhydrous sodium sulfate. After filtration and concentration under reduced pressure, the residue was purified by column chromatography (silica gel 100 g, n-hexane/ethyl acetate=4/1) to give Compound 7j (1.75 g, 3.45 mmol, 87.4%) as a yellow solid. R$_f$=0.26 (n-hexane/ethyl acetate=4/1); $^1$H NMR (400 MHz, DMSO-d$_6$) δ 0.18 (s, 6H), 0.22 (s, 61H), 0.93 (s, 9H), 0.96 (s, 9H), 6.11 (s, 2H), 6.85-6.91 (AA'BB', 2H), 6.91-6.97 (AA'BB', 2H), 7.65-7.71 (AA'BB', 2H), 7.81-7.87 (AA'BB', 2H), 8.40 (s, 1H); $^{13}$C NMR (75.5 MHz, DMSO-d$_6$) −4.5 (4C), 18.0 (2C), 25.6 (6C), 119.9 (2C), 120.1 (2C), 126.4 (2C), 129.6 (2C), 130.6, 130.8, 136.6, 137.7, 139.8, 151.5, 154.9, 155.5; IR (KBr, cm$^{-1}$) 438, 513, 573, 633, 665, 675, 696, 739, 781, 806, 824, 841, 912, 1009, 1086, 1103, 1167, 1202, 1263, 1362, 1379, 1408, 1422, 1452, 1512, 1566, 1605, 2857, 2885, 2928, 2955, 3061, 3183, 3304, 3377, 3478; HRMS (ESI) m/z 508.2820 ([M+H]J, C$_{28}$H$_{42}$N$_3$O$_2$Si$_2^+$ requires 508.2810).

2-(4-Hydroxybenzyl)-6,8-bis(4-hydroxyphenyl)imidazo[1,2-α]pyrazin-3(7H)-one (3j, TMD-280)

Under an argon atmosphere, to a mixture of 3,5-bis[4-(tert-butyldimethylsilyloxy)phenyl]pyrazin-2-amine (7j) (366 mg, 721 µmol) and 3-[4-(tert-butyldimethylsilyloxy)phenyl]-1,1-diethoxypropan-2-one (8) (380 mg, 1.08 mmol) dissolved in 1,4-dioxane (2 mL) was added 4 M hydrochloric acid (900 µL) at 0° C., and the mixture was heated to reflux for 16 hours. After cooling to room temperature, the mixture was concentrated under reduced pressure, and the residue was purified by column chromatography in an argon flow (acidic silica gel 20 g, n-hexane/ethyl acetate=1/2→ethyl acetate→ethyl acetate/methanol=20/1). To the suspension obtained during the concentration under reduced pressure was added n-hexane. The precipitates were collected by filtration and dried in vacuo to give Compound 3j (TMD-280) (96.4 mg, 227 µmol, 31.4%) as an orange solid. R$_f$=0.22 (ethyl acetate); HPLC retention time 5.2 min; $^1$H NMR (400 MHz, CD$_3$OD) δ 4.12 (s, 2H), 6.65-6.71 (AA'BB', 2H), 6.88-6.94 (AA'BB', 2H), 6.94-7.02 (AA'BB', 2H), 7.06-7.12 (AA'BB', 2H), 7.74-7.84 (AA'BB', 2H), 7.91-7.98 (AA'BB', 2H), 8.24 (s, 1H); IR (KBr, cm$^{-1}$) 554, 841, 891, 1132, 1242, 1273, 1341, 1437, 1458, 1508, 1543, 1558, 1609, 1653, 2812, 2895, 3096; HRMS (ESI$^+$) m/z 426.1458 ([M+H]$^+$, C$_{25}$H$_{20}$N$_3$O$_4^+$ requires 426.1448).

Synthesis Example 2

Coelenteramide (CTMD) Analogues Modified at the C-3 Position

2-1) TMD-344 (4a)

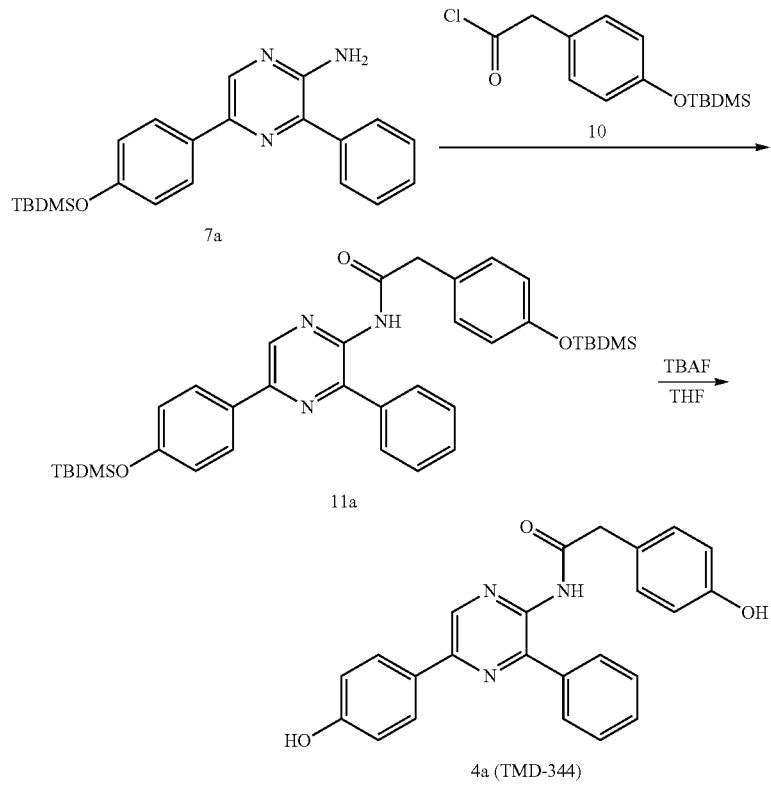

2-[4-(tert-Butyldimethylsilyloxy)phenyl]-N-{5-[4-(tert-butyldimethylsilyloxy)phenyl]-3-phenylpyrazin-2-yl}acetamide (11a)

Under an argon atmosphere, to a solution of 2-[4-(tert-butyldimethylsilyloxy)phenyl]acetic acid (9) (1.07 g, 4.02 mmol) in $CH_2Cl_2$ (10 mL) was added DMF (3 drops) by a Pasteur pipette at room temperature. To this was added oxalyl dichloride (680 µL, 8.04 mmol) at 0° C. and the mixture was stirred for 30 minutes while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 5-[4-(tert-butyldimethylsilyloxy)phenyl]-3-phenylpyrazin-2-amine (7a) (504 mg, 1.33 mmol) and 4-(dimethylamino)pyridine (16.3 mg, 133 µmol) dissolved in anhydrous pyridine (20 mL) was added 2-[4-(tert-butyldimethylsilyloxy)phenyl]acetyl chloride (10) prepared above at 0° C. and the mixture was heated with stirring at 50° C. for 18 hours. After cooling to room temperature, to this was added water and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=4/1) to give Compound 11a (630 mg, 1.01 mmol, 75.4%) as a yellow foamy solid. $R_f$=0.33 (n-hexane/diethyl ether=2/3); $^1H$ NMR (400 MHz, DMSO-$d_6$) δ 0.18 (s, 6H), 0.23 (s, 6H), 0.94 (s, 9H), 0.96 (s, 9H), 3.47 (s, 2H), 6.72-6.79 (AA'BB', 2H), 6.96-7.02 (AA'BB', 2H), 7.03-7.09 (AA'BB', 2H), 7.29-7.39 (m, 3H), 7.66-7.74 (m, 2H), 8.05-8.12 (AA'BB', 2H), 8.98 (s, 1H), 10.54 (s, 1H); $^{13}C$ NMR (75.5 MHz, DMSO-$d_6$) δ −4.6 (4C), 17.9, 18.0, 25.50 (3C), 25.54 (3C), 41.7, 119.5 (2C), 120.3 (2C), 127.8 (2C), 127.9, 128.0 (2C), 128.2 (2C), 128.5, 128.9, 130.3 (2C), 130.5, 137.6, 142.8, 147.6, 148.0, 153.8, 156.7, 169.3; IR (KBr, $cm^{-1}$) 523, 694, 781, 804, 839, 914, 1020, 1070, 1086, 1105, 1169, 1263, 1371, 1416, 1510, 1605, 1672, 2857, 2886, 2930, 2955, 3040, 3059, 3233; HRMS (ESI$^+$) m/z 648.3043 ([M+Na]$^+$, $C_{36}H_{47}N_3NaO_3Si_2^+$ requires 648.3048).

2-(4-Hydroxyphenyl)-N-[5-(4-hydroxyphenyl)-3-phenylpyrazin-2-yl]acetamide (4a, TMD-344)

To a solution of 2-[4-(tert-butyldimethysilyloxy)phenyl]-N-[5-{4-(tert-butyldimethylsilyloxy)phenyl}-3-phenylpyrazin-2-yl]acetamide (11a) (500 mg, 799 µmol) in THF (7 mL) was added tetrabutylammonium fluoride (1.0 M THF solution) (4.00 mL, 4.00 mmol) at 0° C., and the mixture was stirred for 40 minutes while elevating to room temperature. To the mixture was added saturated $NH_4Cl$ aqueous solution (50 mL) and the product was extracted with ethyl acetate (100 mL×3). The combined organic extract was washed successively with saturated $NH_4Cl$ aqueous solution (200 mL), water (200 mL) and brine (200 mL), followed by drying over anhydrous sodium sulfate. After filtration and concentration under reduced pressure, the residue was recrystallized (n-hexane/ethanol) to give Compound 4a (TMD-344) (206 mg, 517 μmol, 64.7%) as a colorless solid. $R_f$=0.41 (dichloromethane/methanol=9/1); HPLC retention time 6.5 min; $^1$H NMR (400 MHz, CD$_3$OD) δ 3.51 (s, 2H), 6.69-6.76 (AA'BB', 2H), 6.87-6.94 (AA'BB', 2H), 7.02-7.08 (AA'BB', 2H), 7.30-7.43 (m, 3H), 7.58-7.65 (m, 2H), 7.96-8.02 (AA'BB', 2H), 8.80 (s, 1H); $^{13}$C NMR (75.5 MHz, DMSO-d$_6$) δ 41.8, 115.2 (2C), 116.0 (2C), 125.3, 126.5, 128.0 (2C), 128.2 (2C), 128.3 (2C), 128.7, 130.4 (2C), 137.4, 137.7, 142.5, 147.8, 148.7, 156.2, 159.3, 169.9; IR (KBr, cm$^{-1}$) 527, 607, 675, 700, 799, 841, 968, 1020, 1165, 1225, 1265, 1323, 1368, 1410, 1443, 1458, 1493, 1518, 1537, 1593, 1609, 1676, 3021, 3256, 3368; HRMS (ESI$^+$) m/z 420.1321 ([M+Na]$^+$, C$_{24}$H$_{19}$N$_3$NaO$_3$$^+$ requires 420.1319).

2-2) TMD-343 (4b)

Under an argon atmosphere, to a mixture of (E)-5-[4-(tert-butyldimethylsilyloxy)phenyl]-3-styrylpyrazin-2-amine (7b) (500 mg, 1.24 mmol) and 4-(dimethylamino)pyridine (15.3 mg, 125 μmol) dissolved in anhydrous pyridine (20 mL) was added 2-[4-(tert-butyldimethylsilyloxy)phenyl]acetyl chloride (10) prepared above at 0° C. and the mixture was heated with stirring at 50° C. for 15 hours. After cooling to room temperature, to this was added water and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=3/1) to give Compound 11b (563 mg, 864 μmol, 69.7%) as a yellow

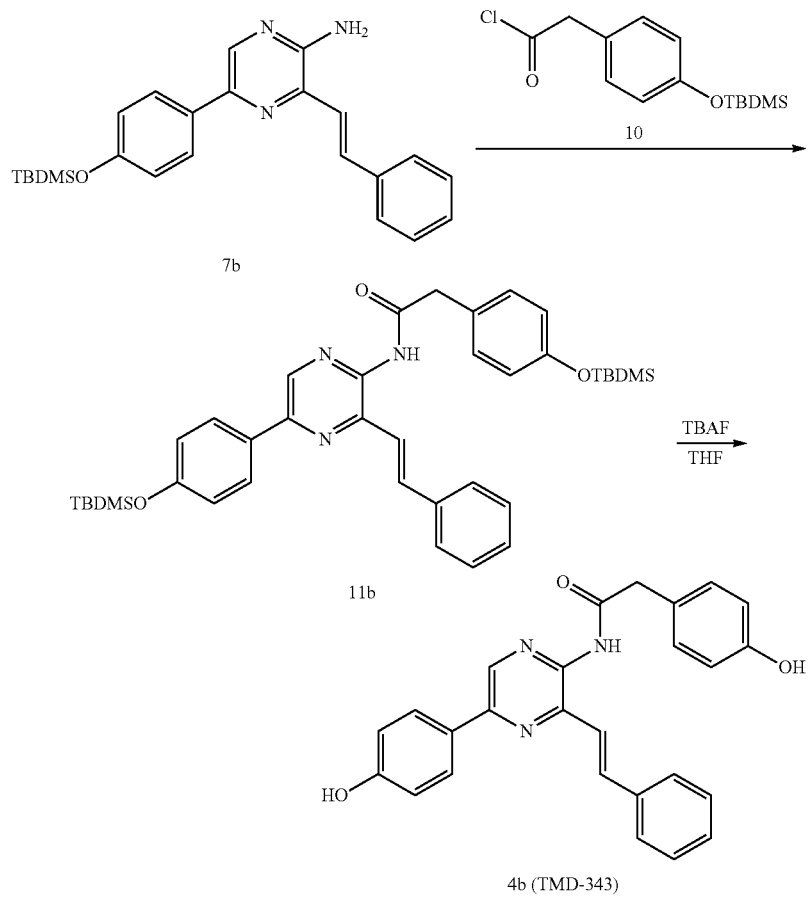

(E)-2-[4-(tert-Butyldimethylsilyloxy)phenyl]-N-[5-{4-(tert-butyldimethylsilyloxy)phenyl}-3-styrylpyrazin-2-yl]acetamide (11 b)

Under an argon atmosphere, to a solution of 2-[4-(tert-butyldimethylsilyloxy)phenyl]acetic acid (9) (1.65 g, 6.19 mmol) in CH$_2$Cl$_2$ (10 mL) was added DMF (3 drops) by a Pasteur pipette at room temperature. To this was added oxalyl dichloride (1.05 mL, 12.4 mmol) at 0° C. and the mixture was stirred for 40 minutes while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

solid. $R_f$=0.29 (n-hexane/ethyl acetate=3/1); $^1$H NMR (400 MHz, DMSO-d$_6$) δ 0.17 (s, 6H), 0.24 (s, 6H), 0.96 (s, 9H), 0.97 (s, 9H), 3.66 (s, 2H), 6.81-6.91 (m, 3H, includes AA'BB'), 6.99-7.04 (AA'BB', 2H), 7.28-7.40 (m, 7H, includes AA'BB'), 7.82 (d, 1H, J=16 Hz), 8.11-8.19 (AA'BB', 2H), 8.91 (s, 1H), 10.66 (s, 1H); $^{13}$C NMR (75.5 MHz, DMSO-d$_6$) δ -4.5 (2C), -4.6 (2C), 17.8, 17.9, 25.5 (6C), 42.0, 119.7 (2C), 120.3 (2C), 122.5, 127.1 (2C), 128.2 (2C), 128.5, 128.7 (2C), 128.9, 129.0, 130.3 (2C), 133.8, 136.0, 137.8, 142.8, 143.9, 148.0, 154.0, 156.7, 170.6; IR (KBr, cm$^{-1}$) 471, 521, 638, 691, 746, 781, 806, 839, 914, 968, 1007, 1080, 1103, 1169, 1263, 1325, 1371, 1391, 1414, 1439, 1472, 1510, 1566, 1605, 1659, 2857, 2886, 2930, 2055, 3028, 3057, 3217; HRMS (ES$^+$) m/z 674.3203 ([M+Na]$^+$, C$_{38}$H$_{49}$N$_3$NaO$_3$Si$_2$$^+$ requires 674.3205).

(E)-2-(4-Hydroxyphenyl)-N-[5-(4-hydroxyphenyl)-3-styrylpyrazin-2-yl]acetamide (4b, TMD-343)

To a solution of (E)-2-[4-(tert-butyldimethylsilyloxy)phenyl]-N-[5-{4-(tert-butyldimethylsilyloxy)phenyl}-3-styrylpyrazin-2-yl]acetamide (1 b) (500 mg, 767 µmol) in THF (5 mL) was added tetrabutylammonium fluoride (1.0 M THF solution) (3.90 mL, 3.90 mmol) at 0° C., and the mixture was stirred for 30 minutes while elevating to room temperature. To the mixture was added saturated NH$_4$Cl aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ethanol) to give Compound 4b (TMD-343) (251 mg, 592 µmol, 77.3%) as a yellow solid. R$_f$=0.50 (dichloromethane/methanol=9/1); HPLC retention time 10.6 min; $^1$H NMR (400 MHz, CD$_3$OD) δ 3.67 (s, 2H), 6.79-6.90 (m, 3H, includes AA'BB'), 6.90-6.96 (AA'BB', 2H), 7.25-7.32 (m, 3H, includes AA'BB'). 7.33-7.39 (m, 4H), 7.88 (d, 1H, J=16 Hz), 8.00-8.07 (AA'BB', 2H), 8.72 (s, 1H); $^{13}$C NMR (75.5 MHz, DMSO-d$_6$) δ 42.2, 115.5 (2C), 116.0 (2C), 122.5, 126.2, 126.6, 127.3 (2C), 128.4 (2C), 128.8, 128.9 (2C), 130.2 (2C), 133.9, 136.1, 137.7, 142.5, 144.1, 148.7, 156.5, 159.3, 171.1; IR (KBr, cm$^{-1}$) 527, 617, 691, 756, 804, 845, 970, 1134, 1175, 1246, 1269, 1327, 1375, 1449, 1497, 1512, 1593, 1609, 1638, 3024, 3159, 3566; HRMS (ESI$^+$) m/z 446.1475 ([M+Na]$^+$, C$_{26}$H$_{21}$N$_3$NaO$_3$$^+$ requires 446.1475).

2-3) TMD-347 (4c)

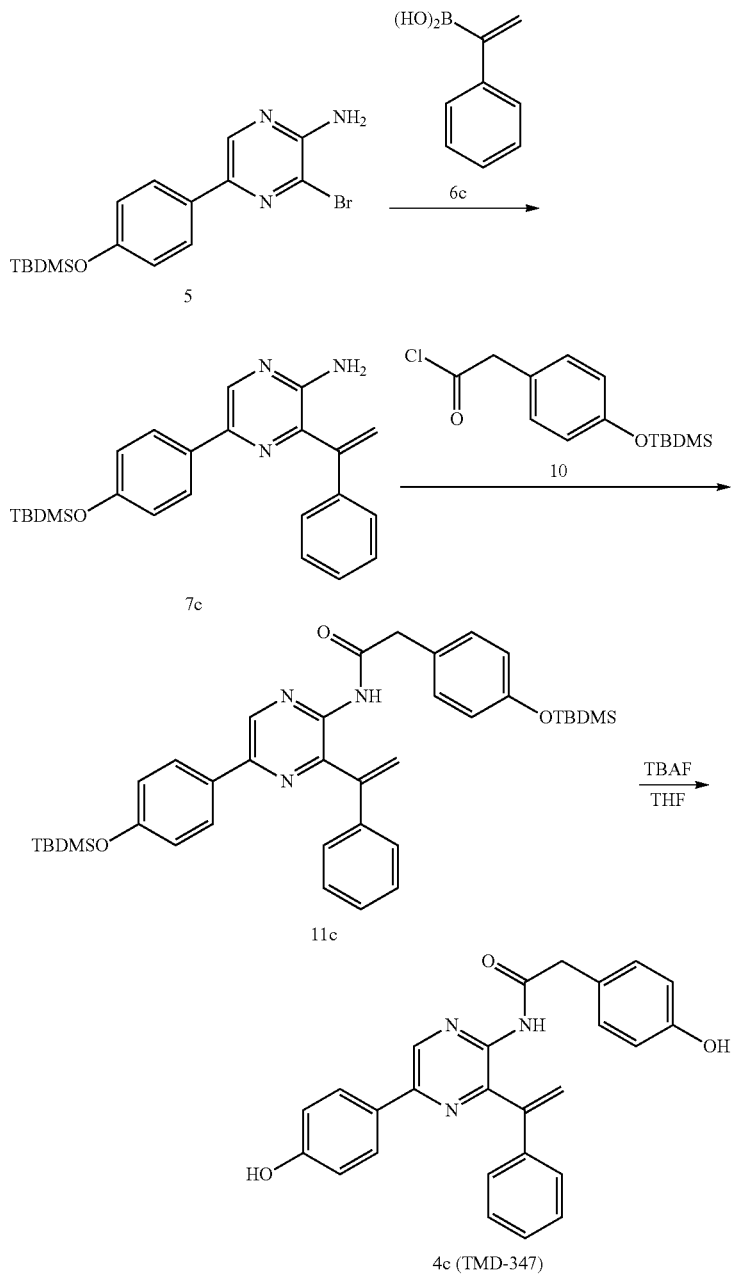

4c (TMD-347)

5-[4-(tert-Butyldimethylsilyloxy)phenyl]-3-(1-phenylvinyl)pyrazin-2-amine (7c)

Under an argon atmosphere, to a solution of 3-bromo-5-[4-(tert-butyldimethylsilyloxy)phenyl]pyrazin-2-amine (5) (1.00 g, 2.63 mmol) in toluene (30 mL) and ethanol (1.2 mL) were successively added 1-phenylvinylboronic acid (6c) (467 mg, 3.16 mmol), dichlorobis(triphenylphosphine)palladium (II) (110 mg, 157 μmol) and 1 M $Na_2CO_3$ aqueous solution (2.70 mL, 2.70 mmol) at room temperature, and the mixture was heated to reflux for 15 hours. After cooling to room temperature, to the mixture was added water and the metal catalyst was removed by filtration. The product was extracted with ethyl acetate (200 mL×3). The combined organic extract was washed successively with water (300 mL) and brine (300 mL), followed by drying over anhydrous sodium sulfate. After filtration and concentration under reduced pressure, the residue was purified by column chromatography (silica gel 100 g, n-hexane/ethyl acetate=3/1) to give Compound 7c (830 mg, 2.06 mmol, 78.2%) as a brown oily substance. $R_f$=0.33 (n-hexane/diethyl ether=2/3); $^1$H NMR (400 MHz, DMSO-$d_6$) δ 0.15 (s, 6H), 0.91 (s, 9H), 5.50 (s, 1H), 5.93 (s, 2H), 5.97 (s, 1H), 6.80-6.87 (AA'BB', 2H), 7.26-7.36 (m, 5H), 7.71-7.77 (AA'BB', 2H), 8.45 (s, 1H); $^{13}$C NMR (75.5 MHz, DMSO-$d_6$) 5-4.6 (2C), 17.9, 25.5 (3C), 117.9, 120.0 (2C), 126.3 (2C), 126.5 (2C), 128.0, 128.4 (2C), 130.5, 137.7, 138.2, 139.0, 139.2, 144.4, 151.8, 154.9; IR (KBr, cm$^{-1}$) 517, 552, 608, 629, 677, 692, 708, 779, 806, 843, 910, 1009, 1026, 1063, 1105, 1148, 1169, 1202, 1263, 1323, 1362, 1389, 1423, 1449, 1510, 1605, 2857, 2886, 2928, 2953, 3034, 3055, 3175, 3298, 3387, 3481.

2-[4-(tert-Butyldimethylsilyloxy)phenyl]-3-(1-phenylvinyl)pyrazin-2-yl}acetamide (11c)

Under an argon atmosphere, to a mixture of 2-[4-(tert-butyldimethylsilyloxy)phenyl]acetic acid (9) (1.80 g, 6.76 mmol) in $CH_2C_2$ (15 mL) was added DMF (4 drops) by a Pasteur pipette at room temperature. To this was added oxalyl dichloride (1.20 mL, 14.2 mmol) at 0° C. and the mixture was stirred for an hour while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 5-[4-(tert-butyldimethylsilyloxy)phenyl]-3-(1-phenylvinyl)pyrazin-2-amine (7c) (543 mg, 1.35 mmol) and 4-(dimethylamino)pyridine (15.0 mg, 123 μmol) dissolved in anhydrous pyridine (20 mL) was added 2-[4-(tert-butyldimethylsilyloxy)phenyl]acetyl chloride (10) prepared above at 0° C., and the mixture was heated with stirring at 50° C. for 16 hours. After cooling to room temperature, to this was added water and the product was extracted with ethyl acetate (200 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=3/1) to give Compound 11c (292 mg, 448 μmol, 33.3%) as a yellow foamy solid. $R_f$=0.26 (n-hexane/diethyl ether=2/3); $^1$H NMR (400 MHz, DMSO-$d_6$) δ 0.13 (s, 6H), 0.18 (s, 6H), 0.91 (s, 9H), 0.92 (s, 9H), 3.22 (s, 2H), 5.51 (s, 1H), 5.65 (s, 1H), 6.67-6.74 (AA'BB', 2H), 6.90-6.97 (AA'BB', 2H), 6.97-7.03 (AA'BB', 2H), 7.19-7.26 (m, 2H), 7.26-7.31 (m, 3H), 7.91-7.98 (AA'BB', 2H), 8.95 (s, 1H), 10.19 (s, 1H); $^{13}$C NMR (75.5 MHz, acetone-$d_6$) −4.3 (4C), 18.6, 18.7, 26.0 (6C), 42.5, 118.8, 120.5 (2C), 121.1 (2C), 127.9 (2C), 128.4, 128.6, 128.78 (2C), 128.84 (2C), 130.1, 131.3 (2C), 138.4, 140.0, 144.2, 146.9, 148.7, 148.9, 155.1, 157.9, 169.7; IR (KBr, cm$^{-1}$) 546, 696, 781, 806, 839, 914, 1007, 1082, 1169, 1261, 1362, 1420, 1435, 1472, 1508, 1605, 1670, 2857, 2886, 2930, 2955, 3030, 3055, 3231; HRMS (ESI$^+$) m/z 652.3390 ([M+H]$^+$, $C_{38}H_{50}N_3O_3Si_2^+$ requires 652.3385).

2-(4-Hydroxyphenyl)-N-[5-(4-hydroxyphenyl)-3-(1-phenylvinyl)pyrazin-2-yl]acetamide (4c, TMD-347)

To a solution of 2-[4-(tert-butyldimethylsilyloxy)phenyl]-N-[S-{4-(tert-butyldimethylsilyloxy)phenyl}-3-(1-phenylvinyl)pyrazin-2-yl]acetamide (11c) (240 mg, 368 μmol) in THF (5 mL) was added tetrabutylammonium fluoride (1.0 M THF solution) (1.90 mL, 1.90 mmol) at 0° C. and the mixture was stirred for an hour while elevating to room temperature. To the mixture was added saturated $NH_4Cl$ aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ethanol) to give Compound 4c (TMD-347) (83.9 mg, 198 μmol, 53.8%) as a brown solid. Rt=0.37 (dichloromethane/methanol=9/1); HPLC retention time 8.0 min; $^1$H NMR (400 MHz, DMSO-$d_6$) δ 3.15 (s, 2H), 5.52 (s, 1H), 5.66 (s, 1H), 6.58-6.64 (AA'BB', 2H), 6.80-6.86 (AA'BB', 2H), 6.86-6.93 (AA'BB', 2H), 7.19-7.25 (m, 2H), 7.25-7.31 (m, 3H), 7.84-7.91 (AA'BB', 2H), 8.89 (s, 1H), 9.20 (s, 1H), 9.83 (s, 1H), 10.54 (s, 11H); $^{13}$C NMR (75.5 MHz, DMSO-$d_6$) δ 41.1, 115.0 (2C), 115.9 (2C), 118.1, 125.4, 126.5, 127.1 (2C), 127.7, 128.15 (2C), 128.20 (2C), 130.3 (2C), 137.8, 139.0, 143.1, 145.5, 148.1, 148.7, 156.1, 159.2, 169.6; IR (KBr, cm$^{-1}$) 519, 546, 606, 698, 779, 837, 916, 1107, 1171, 1231, 1321, 1431, 1481, 1514, 1609, 1670, 3026, 3265; HRMS (ESI) m/z 446.1483 ([M+Na]$^+$, $C_{26}H_{21}N_3NaO_3^+$ requires 446.1475).

2-4) TMD-338 (4d)

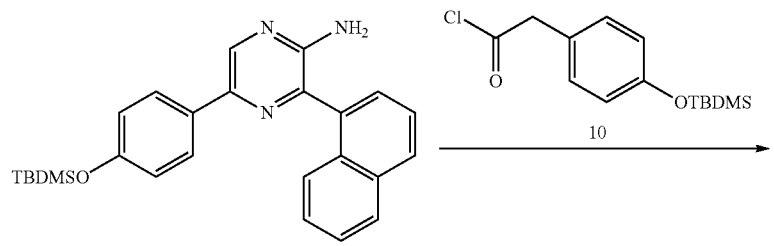

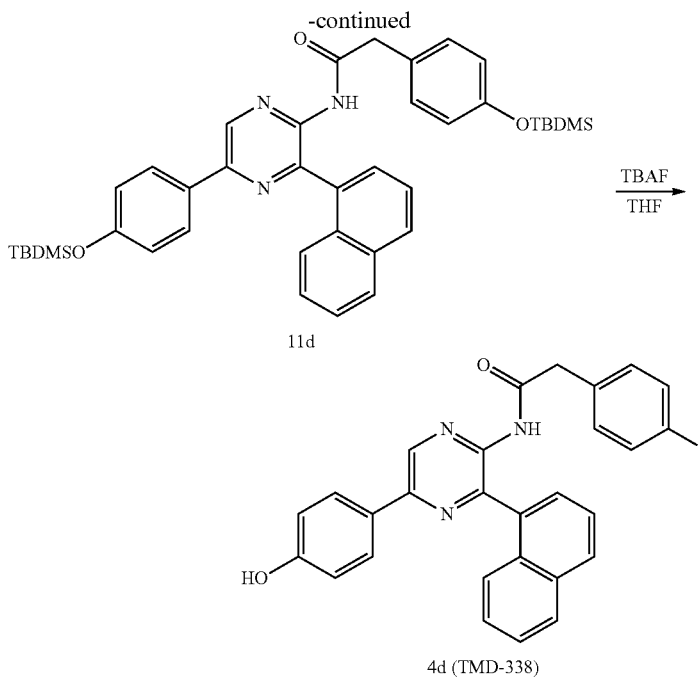

2-[4-(tert-Butyldimethylsilyloxy)phenyl]-N-[5-{4-(tert-butyldimethylsilyloxy)phenyl}-3-(naphthalen-1-yl)pyrazin-2-yl]acetamide (11d)

Under an argon atmosphere, to a solution of 2-[4-(tert-butyldimethylsilyloxy)phenyl]acetic acid (9) (1.55 g, 5.82 mmol) in $CH_2Cl_2$ (10 mL) was added DMF (3 drops) by a Pasteur pipette at room temperature. To this was added oxalyl dichloride (1.00 mL, 11.8 mmol) at 0° C. and the mixture was stirred for 40 minutes while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 5-[4-(tert-butyldimethylsilyloxy)phenyl]-3-(naphthalen-1-yl)pyrazin-2-amine (7d) (500 mg, 1.17 mmol) and 4-(dimethylamino) pyridine (15.3 mg, 125 μmol) dissolved in anhydrous pyridine (20 mL) was added 2-[4-(tert-butyldimethylsilyloxy)phenyl]acetyl chloride (10) at. 0° C. and the mixture was heated with stirring at 50° C. for 16 hours. After cooling to room temperature, to this was added water and the product was extracted with ethyl acetate (200 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=3/1) to give Compound 11d (442 mg, 653 μmol, 55.9%) as a yellow foamy solid. $R_f$=0.26 (n-hexane/diethyl ether=2/3); $^1$H NMR (400 MHz, DMSO-$d_6$) δ 0.13 (s, 6H), 0.19 (s, 6H), 0.91 (s, 9H), 0.92 (s, 9H), 3.24 (s, 2H), 6.54-6.60 (AA'BB', 2H), 6.65-6.72 (AA'BB', 2H), 6.91-6.98 (AA'BB', 2H), 7.36-7.54 (m, 4H), 7.61-7.69 (m, 1H), 7.87-8.08 (m, 4H, includes AA'BB'), 9.09 (s, 1H), 10.27 (s, 1H); $^{13}$C NMR (75.5 MHz, DMSO-$d_6$) δ -4.6 (4C), 17.90, 17.94, 25.48 (3C), 25.55 (3C), 119.4 (2C), 120.4 (2C), 125.0, 125.4, 125.7, 126.2, 126.8, 128.0, 128.15, 128.21 (2C), 128.6, 128.9 (2C), 129.9, 130.7, 133.4, 134.8, 138.2, 144.4, 147.9, 148.3, 153.5, 156.7, 169.3 (one carbon at the benzyl position was unobservable due to overlapping with the septet peak of DMSO); IR (KBr, $cm^{-1}$) 492, 538, 675, 718, 779, 806, 839, 914, 1007, 1080, 1115, 1169, 1260, 1362, 1420, 1441, 1472, 1510, 1605, 1670, 2857, 2886, 2930, 2955, 3046, 3223; HRMS (ESI$^+$) m/z 698.3205 ([M+Na]$^+$, $C_{40}H_{49}N_3NaO_3Si_2^+$ requires 698.3205). 2-(4-Hydroxyphenyl)-N-[5-(4-hydroxyphenyl)-3-(naphthalen-1-yl)pyrazin-2-yl]acetamide (4d, TMD-338)

To a solution of 2-[4-(tert-butyldimethylsilyloxy)phenyl]-N-[5-{4-(tert-butyldimethylsilyloxy)phenyl}-3-(naphthalen-1-yl)pyrazin-2-yl]acetamide (11d) (291 mg, 430 μmol) in THF (5 mL) was added tetrabutylammonium fluoride (1.0 M THF solution) (2.20 mL, 2.20 mmol) at 0° C. and the mixture was stirred for 30 minutes while elevating to room temperature. To the mixture was added saturated $NH_4Cl$ aqueous solution (50 mL) and the product was extracted with ethyl acetate (100 mL×3). The combined organic extract was washed successively with saturated $NH_4Cl$ aqueous solution (200 mL), water (200 mL) and brine (200 mL), followed by drying over anhydrous sodium sulfate. After filtration and concentration under reduced pressure, the residue was recrystallized (n-hexane/ethanol) to give Compound 4d (TMD-338) (181 mg, 404 μmol, 93.8%) as a brown solid. $R_f$=0.56 (dichloromethane/methanol=9/1); HPLC retention time 9.1 min; $^1$H NMR (400 MHz, DMSO-$d_6$) δ 3.17 (s, 2H), 6.45-6.53 (AA'BB', 2H), 6.56-6.64 (AA'BB', 2H), 6.80-6.88 (AA'BB', 2H), 7.35-7.56 (m, 4H), 7.61-7.68 (m, 1H), 7.88-8.04 (m, 4H, includes AA'BB'), 9.03 (s, 1l), 9.15 (s, 1H), 9.85 (s, 1H), 10.14 (s, 1H); $^{13}$C NMR (75.5 MHz, DMSO-$d_6$) δ 41.2, 115.0 (2C), 115.9 (2C), 125.1, 125.3, 125.4, 125.8, 126.3, 126.5, 126.9, 128.25, 128.27 (2C), 128.7, 129.8 (2C), 130.7, 133.4, 134.9, 138.0, 144.0, 148.38, 148.44, 155.9, 159.2, 169.8; IR (KBr, $cm^{-1}$) 492, 540, 623, 777, 802, 839, 982, 1078, 1171, 1231, 1317, 1364, 1447, 1477, 1516, 1609, 1670, 3055, 3246; HRMS (ESI$^+$) m/z 470.1483 ([M+Na]$^+$, $C_{28}H_{21}N_3NaO_3^+$ requires 470.1475).

2-5) TMD-339 (4e)

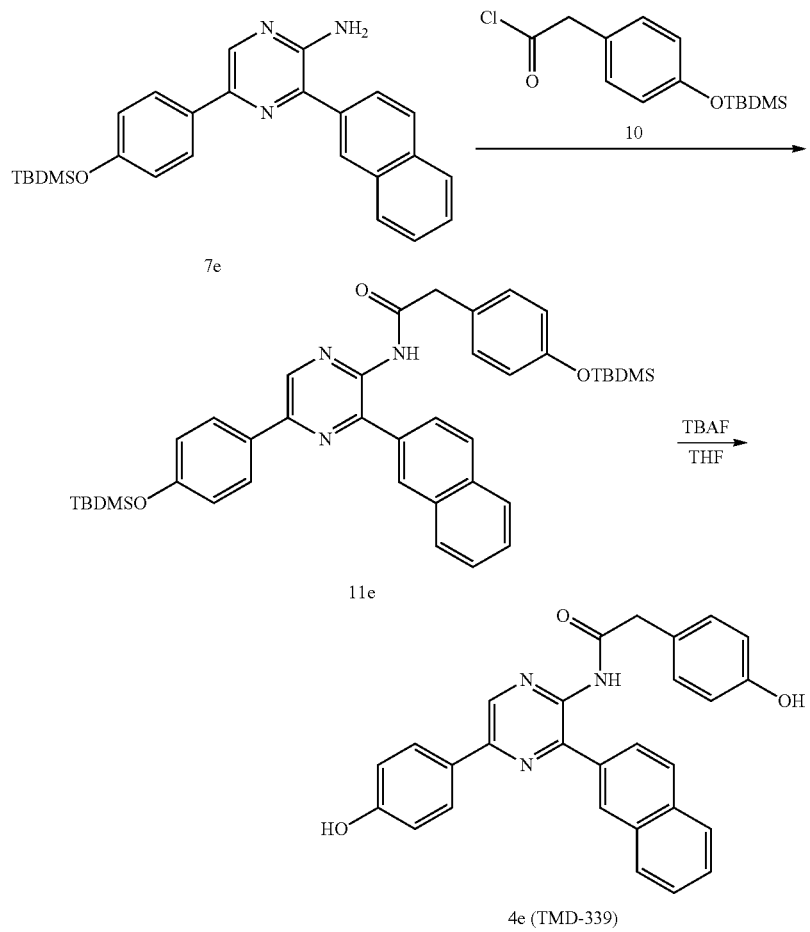

4e (TMD-339)

2-[4-(tert-Butyldimethylsilyloxy)phenyl]-N-[5-{4-(tert-butyldimethylsilyloxy)phenyl}-3-(naphthalen-2-yl)pyrazin-2-yl]acetamide (11e)

Under an argon atmosphere, to a solution of 2-[4-(tert-butyldimethylsilyloxy)phenyl]acetic acid (9) (1.55 g, 5.82 mmol) in $CH_2Cl_2$ (10 mL) was added DMF (3 drops) by a Pasteur pipette at room temperature. To this was added oxalyl dichloride (1.00 mL, 11.8 mmol) at 0° C. and the mixture was stirred for 30 minutes while elevating to room temperature. The mixture was concentrated under reduced pressure to give crude 2-[4-(tert-butyldimethylsilyloxy)phenyl]acetyl chloride (10) as a colorless oil which was used in the following reaction without further purification.

Under an argon atmosphere, to a mixture of 5-[4-(tert-butyldimethylsilyloxy)phenyl]-3-(naphthalen-2-yl)pyrazin-2-amine (7e) (500 mg, 1.17 mmol) and 4-(dimethylamino)pyridine (15.0 mg, 123 μmol) dissolved in anhydrous pyridine (20 mL) was added 2-[4-(tert-butyldimethylsilyloxy)phenyl]acetyl chloride (10) prepared above at 0° C., and the mixture was heated with stirring at 50° C. for 16 hours. After cooling to room temperature, to this was added water and the product was extracted with ethyl acetate (200 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=3/1) to give Compound 11e (460 mg, 681 μmol, 58.2%) as a yellow foamy solid. $R_f$=0.26 (n-hexane/diethyl ether=2/3); $^1$H NMR (400 MHz, DMSO-$d_6$) δ 0.12 (s, 6H), 0.21 (s, 6H), 0.91 (s, 9H), 0.94 (s, 9H), 3.46 (s, 2H), 6.55-6.65 (AA'BB', 2H), 6.91-6.97 (AA'BB', 2H), 6.97-7.03 (AA'BB', 2H), 7.47-7.58 (m, 2H), 7.75-8.00 (m, 4H), 8.08-8.14 (AA'BB', 2H), 8.23 (s, 1H), 9.00 (s, 1H), 10.63 (s, 1H); $^{13}$C NMR (75.5 MHz, DMSO-$d_6$) 8-4.6 (4C), 17.8, 17.9, 25.5 (6C), 119.4 (2C), 120.3 (2C), 125.5, 126.1, 126.6, 127.1, 127.2, 127.3, 127.5, 127.9, 128.2 (2C), 128.5, 130.2 (2C), 132.6, 132.8, 135.3, 137.6, 143.0, 147.5, 148.0, 153.7, 156.7, 169.4 (one carbon at the benzyl position was unobservable due to overlapping with the septet peak of DMSO); IR (KBr, cm$^{-1}$) 478, 527, 687, 718, 746, 781, 804, 839, 914, 1009, 1082, 1103, 1128, 1169, 1261, 1362, 1415, 1445, 1472, 1508, 1605, 1670, 2857, 2886, 2928, 2955, 3057, 3221; HRMS (ESI$^+$) m/z 698.3194 ([M+Na]$^+$, $C_{40}H_{49}N_3NaO_3Si_2^+$ requires 698.3205).

2-(4-Hydroxyphenyl)-N-[5-(4-hydroxyphenyl)-3-(naphthalen-2-yl)pyrazin-2-yl]acetamide (4e, TMD-339)

To a solution of 2-[4-(tert-butyldimethylsilyloxy)phenyl]-N-[5-{4-(tert-butyldimethylsilyloxy)phenyl}]-3-(naphthalen-2-yl)pyrazin-2-yl]acetamide (11e) (300 mg, 444 μmol) in THF (5 mL) was added tetrabutylammonium fluoride (1.0 M THF solution) (2.30 mL, 2.30 mmol) at 0° C., and the mixture was stirred for 30 minutes while elevating to room temperature. To the mixture was added saturated NH$_4$Cl aqueous solution (50 mL) and the product was extracted with ethyl acetate (100 mL×3). The combined organic extract was washed successively with saturated NH$_4$Cl aqueous solution (200 mL), water (200 mL) and brine (200 mL), followed by drying over anhydrous sodium sulfate. After filtration and concentration under reduced pressure, the residue was recrystallized (n-hexane/ethanol) to give Compound 4e (TMD-339) (131 mg, 292 μmol, 65.8%) as a brown solid. R$_f$=0.48 (dichloromethane/methanol=9/1); HPLC retention time 10.9 min; $^1$H NMR (400 MHz, DMSO-d$_6$) δ 3.39 (s, 2H), 6.50-6.58 (AA'BB', 2H), 6.82-6.94 (2AA'BB', 4H), 7.46-7.58 (m, 2H), 7.79-7.91 (m, 4H), 8.02-8.08 (AA'BB', 2H), 8.23 (s, 1H), 8.94 (s, 1H), 9.20 (s, 1H), 9.88 (s, 1H), 10.52 (s, 1HI); $^{13}$C NMR (75.5 MHz, DMSO-d$_6$) δ 41.6, 115.1 (2C), 115.9 (2C), 125.3, 125.6, 126.3, 126.5, 126.8, 127.3, 127.5, 127.6, 128.3 (2C), 128.6, 130.2 (2C), 132.7, 132.9, 135.3, 137.3, 142.7, 147.5, 148.6, 156.1, 159.3, 169.8; IR (KBr, cm$^{-1}$) 529, 635, 669, 752, 826, 968, 1163, 1223, 1356, 1454, 1491, 1516, 1539, 1593, 1611, 1672, 3065, 3246; HRMS (ESI$^+$) m/z 470.1486 ([M+Na]$^+$, C$_{28}$H$_{21}$N$_3$NaO$_3^+$ requires 470.1475).

2-6) TMD-340 (4f)

crude 2-[4-(tert-butyldimethylsilyloxy)phenyl]acetyl chloride (10) as a colorless oil, which was used in the following reaction without further purification.

Under an argon atmosphere, to a mixture of 5-[4-(tert-butyldimethylsilyloxy)phenyl]-3-(thiophen-2-yl)pyrazin-2-amine (7f) (600 mg, 1.59 mmol) and 4-(dimethylamino)pyridine (19.8 mg, 162 μmol) dissolved in anhydrous pyridine (20 mL) was added 2-[4-(tert-butyldimethylsilyloxy)phenyl]acetyl chloride (10) prepared above at 0° C. and the mixture was heated with stirring at 50° C. for 15 hours. After cooling to room temperature, to this was added water and the product was extracted with ethyl acetate (200 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=3/1). The resulting solid was recrystallized (n-hexane/ethyl acetate) to give Compound 1 f (446 mg, 706 μmol, 44.4%) as a colorless solid. R$_f$=0.26 (n-hexane/diethyl ether=2/3); $^1$H NMR (400 MHz, DMSO-d$_6$) δ 0.18 (s, 6H), 0.23 (s, 6H), 0.94 (s, 9H), 0.97 (s, 9H), 3.65 (s, 2H), 0.678-6.86 (AA'BB', 2H), 6.97-7.06 (m, 3H, includes AA'BB'), 7.19-7.27 (AA'BB', 2H), 7.51

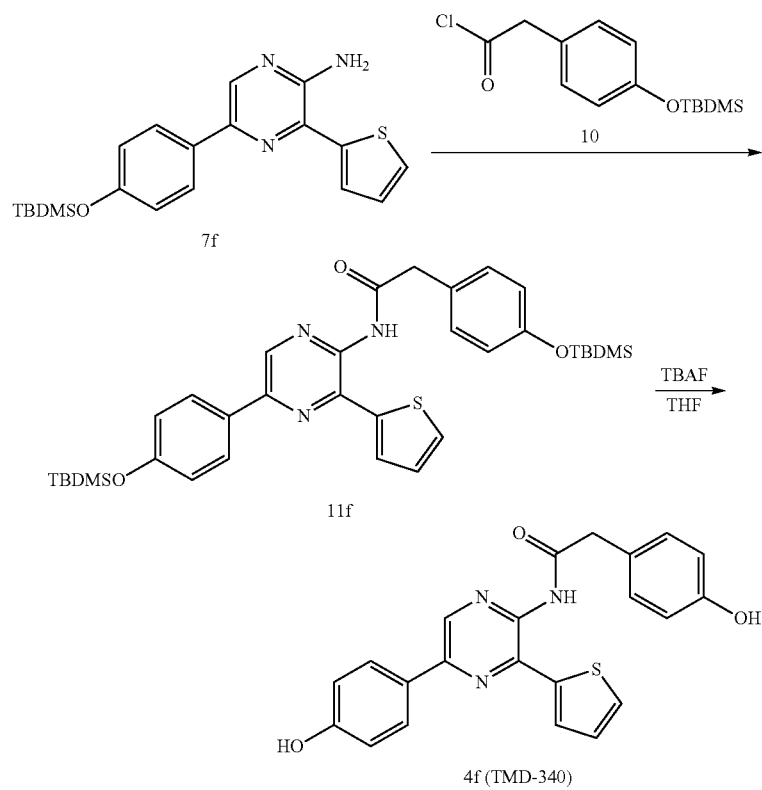

2-[4-(tert-Butyldimethylsilyloxy)phenyl]-N-[5-{4-(tert-butyldimethylsilyloxy)phenyl}-3-(thiophen-2-yl)pyrazin-2-yl]acetamide (11f)

Under an argon atmosphere, to a solution of 2-[4-(tert-butyldimethylsilyloxy)phenyl]acetic acid (9) (2.12 g, 7.96 mmol) in CH$_2$Cl$_2$ (10 mL) was added DMF (3 drops) by a Pasteur pipette at room temperature. To this was added oxalyl dichloride (1.35 mL, 16.0 mmol) at 0° C. and the mixture was stirred for an hour while elevating to room temperature. The mixture was concentrated under reduced pressure to give (dd, 1H, J=0.9, 3.7 Hz), 7.69 (dd, 1H, J=0.9, 5.0 Hz), 8.06-8.14 (AA'BB', 2H), 8.93 (s, 1H), 10.60 (s, 1H); $^{13}$C NMR (75.5 MHz, DMSO-d$_6$) 8-4.6 (4C), 17.9, 18.0, 25.50 (3C), 25.54 (3C), 41.9, 119.6 (2C), 120.4 (2C), 127.8, 127.9, 128.0, 128.2 (2C), 128.4, 129.5, 130.5 (2C), 137.3, 140.5, 140.6, 142.5, 148.0, 153.9, 157.0, 170.3; IR (KBr, cm$^{-1}$) 419, 519, 673, 704, 741, 781, 802, 839, 916, 1169, 1265, 1335, 1362, 1373, 1414, 1439, 1472, 1510, 1605, 1667, 2857, 2887, 2930, 2955, 3221; HRMS (ESI$^+$) m/z 654.2617 ([M+Na]$^+$, C$_{34}$H$_{45}$N$_3$NaO$_3$Si$_2^+$ requires 654.2612).

2-(4-Hydroxyphenyl)-N-[5-(4-hydroxyphenyl)-3-(thiophen-2-yl)pyrazin-2-yl]acetamide (4f, TMD-340)

To a solution of 2-[4-(tert-butyldimethylsilyloxy)phenyl]-N-[5-{4-(tert-butyldimethylsilyloxy)phenyl}-3-(thiophen-2-yl)pyrazin-2-yl]acetamide (11f) (252 mg, 398 µmol) in THF (4 mL) added tetrabutylammonium fluoride (1.0 M THF solution) (2.00 mL, 2.00 mmol) at 0° C., and the mixture was stirred for an hour while elevating to room temperature, To the mixture was added saturated $NH_4Cl$ aqueous solution (50 mL) and the product was extracted with ethyl acetate (100 mL×3). The combined organic extract was washed successively with saturated $NH_4Cl$ aqueous solution (200 mL), water (200 mL) and brine (200 mL), followed by drying over anhydrous sodium sulfate. Filtration and concentration under reduced pressure gave Compound 4f (TMD-340) (160 mg, 397 µmol, 99.6%) as a colorless solid. $R_f$=0.37 (dichloromethane/methanol=9/1); HPLC retention time 6.8 min; $^1$H NMR (400 MHz, DMSO-$d_6$) δ 3.59 (s, 2H), 6.70-6.76 (AA'BB', 2H), 6.90-6.96 (AA'BB', 2H), 6.99 (dd, 1H, J=3.8, 5.0 Hz), 7.12-7.18 (AA'BB', 2H), 7.48 (dd, 1H, J=1.1, 3.8 Hz), 7.69 (dd, 1H, J=1.1, 5.0 Hz), 8.01-8.07 (AA'BB', 2H), 8.89 (s, 1H), 9.32 (s, 1H), 9.97 (s, 1H), 10.50 (s, 1H); $^{13}$C NMR (75.5 MHz, DMSO-$d_6$) δ42.0, 115.2 (2C), 116.0 (2C), 125.2, 126.0, 128.1, 128.25, 128.34 (2C), 129.6, 130.5 (2C), 137.1, 140.1, 140.8, 142.7, 148.6, 156.3, 159.5, 170.8; IR (KBr, cm$^{-1}$) 523, 631, 698, 725, 791, 841, 966, 984, 1074, 1113, 1167, 1227, 1263, 1317, 1375, 1406, 1431, 1450, 1495, 1518, 1535, 1593, 1609, 1674, 3021, 3244, 3372; HRMS (ESI$^+$) m/z 426.0877 ([M+Na]$^+$, $C_{22}H_{17}N_3NaO_3S^+$ requires 426.0883).

2-7) TMD-345 (4g)

2-[4-(tert-Butyldimethylsilyloxy)phenyl]-N-{5-[4-(tert-butyldimethylsilyloxy)phenyl]-3-(thiophen-3-yl)pyrazin-2-yl}acetamide (11g)

Under an argon atmosphere, to a solution of 2-[4-(tert-butyldimethylsilyloxy)phenyl]acetic acid (9) (1.55 g, 5.82 mmol) in $CH_2Cl_2$ (10 mL) was added DMF (3 drops) by a Pasteur pipette at room temperature. To this was added oxalyl dichloride (1.00 mL, 11.8 mmol) at 0° C. and the mixture was stirred for 30 minutes while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 5-[4-(tert-butyldimethylsilyloxy)phenyl]-3-(thiophen-3-yl)pyrazin-2-amine (7g) (450 mg, 1.17 mmol) and 4-(dimethylamino)pyridine (15.5 mg, 127 µmol) dissolved in anhydrous pyridine (20 mL) was added 2-[4-(tert-butyldimethylsilyloxy)phenyl]acetyl chloride (10) prepared above at 0° C. and the mixture was heated with stirring at 50° C. for 15 hours. After cooling to room temperature, to this was added water and the product was extracted with ethyl acetate (200 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=3/1) to give Compound 11 g (512 mg, 809 µmol, 69.0%) as a yellow solid. $R_f$=0.22 (n-hexane/diethyl ether=2/3); $^1$H NMR (400 MI-Hz, DMSO-$d_6$) δ 0.16 (s, 6H), 0.20 (s, 6H), 0.92 (s, 9H), 0.94 (s, 91H), 3.56 (s, 2H), 6.72-6.82 (AA'BB', 2H), 6.93-7.02 (AA'BB', 2H), 7.12-7.22 (AA'BB', 2H), 7.50 (dd,

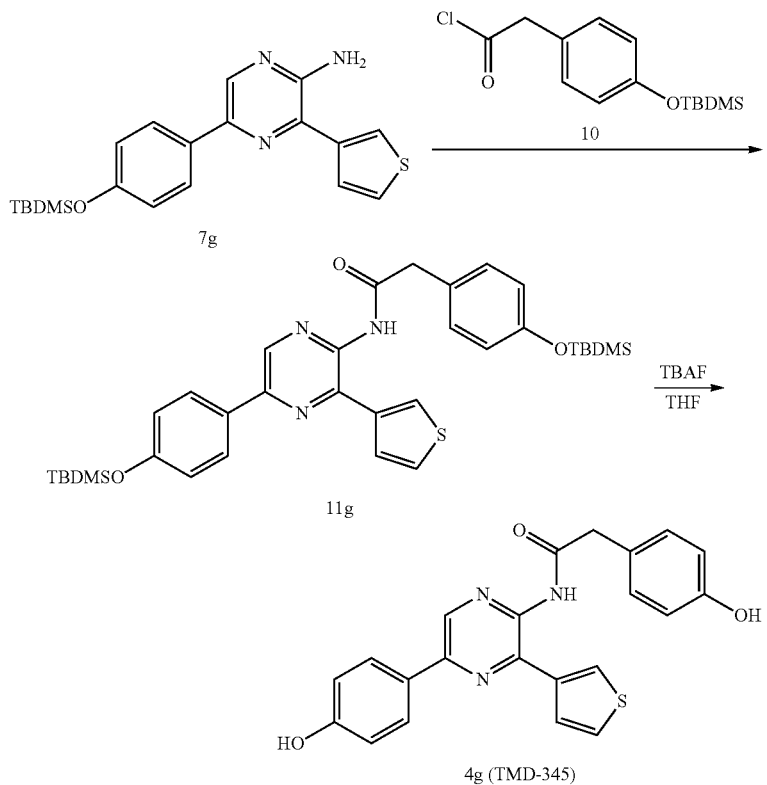

1H, J=2.9, 5.0 Hz), 7.59 (d, 1H, J=5.0 Hz), 7.81 (d, 1H, J=2.9 Hz), 8.04-8.12 (AA'BB', 2H), 8.91 (s, 1H), 10.50 (s, 1H); $^{13}$C NMR (75.5 MHz, DMSO-$d_6$) δ −4.6 (4C), 17.90, 17.95, 25.50 (3C), 25.54 (3C), 41.9, 119.6 (2C), 120.3 (2C), 125.7, 126.0, 127.7, 127.9, 128.2 (2C), 128.8, 130.5 (2C), 137.1, 138.2, 142.0, 143.5, 148.0, 153.9, 156.8, 169.9; IR (KBr, cm$^{-1}$) 517, 669, 712, 741, 781, 806, 839, 914, 1007, 1082, 1105, 1169, 1261, 1341, 1362, 1441, 1472, 1508, 1605, 1665, 2857, 2886, 2930, 2955, 3057, 3227; HRMS (ESI$^+$) m/z 654.2618 ([M+Na]$^+$, $C_{34}H_{45}N_3NaO_3Si_2^+$ requires 654.2612). 2-(4-Hydroxyphenyl)-N-[5-(4-hydroxyphenyl)-3-(thiophen-3-yl)pyrazin-2-yl]acetamide (4g, TMD-345)

To a solution of 2-[4-(tert-butyldimethylsilylyloxy)phenyl]-N-[5-{4-(tert-butyldimethylsilylyloxy)phenyl}-3-(thiophen-3-yl)pyrazin-2-yl]acetamide (11 g) (310 mg, 491 µmol) in THF (5 mL) was added tetrabutylammonium fluoride (1.0 M THF solution) (2.50 mL, 2.50 mmol) at 0° C. and the mixture was stirred for an hour while elevating to room temperature. To the mixture was added saturated NH$_4$Cl aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ethanol) to give Compound 4g (TMD-345) (85.0 mg, 211 µmol, 43.0%) as a yellow solid. R$_f$=0.50 (dichloromethane/methanol=9/1); HPLC retention time 6.2 min; $^1$H NMR (400 MHz, DMSO-$d_6$) δ 3.50 (s, 2H), 6.65-6.72 (AA'BB', 2H), 6.84-6.92 (AA'BB', 2H), 7.03-7.11 (AA'BB', 2H), 7.49 (dd, 1H, J=2.9, 5.0 Hz), 7.58 (dd, 1H, J=1.2, 5.0 Hz), 7.80 (dd, 1H, J=1.2, 2.9 Hz), 7.98-8.06 (AA'BB', 2H), 8.85 (s, 1H), 9.27 (s, 1H), 9.87 (s, 1H), 10.39 (s, 1H); $^{13}$C NMR (75.5 MHz, DMSO-$d_6$) δ 41.9, 115.2 (2C), 115.9 (2C), 125.2, 125.9, 126.2, 126.4, 127.8, 128.3 (2C), 130.4 (2C), 136.9, 138.3, 141.6, 143.7, 148.6, 156.3, 159.3, 170.4; IR (KBr, cm$^{-1}$) 419, 517, 609, 671, 706, 783, 804, 839, 934, 1040, 1082, 1111, 1173, 1227, 1248, 1272, 1312, 1352, 1441, 1516, 1593, 1611, 1674, 2808, 3250; HRMS (ESI$^+$) m/z 426.0878 ([M+Na], $C_{22}H_{17}N_3NaO_3S^+$ requires 426.0883).

2-8) TMD-342 (4h)

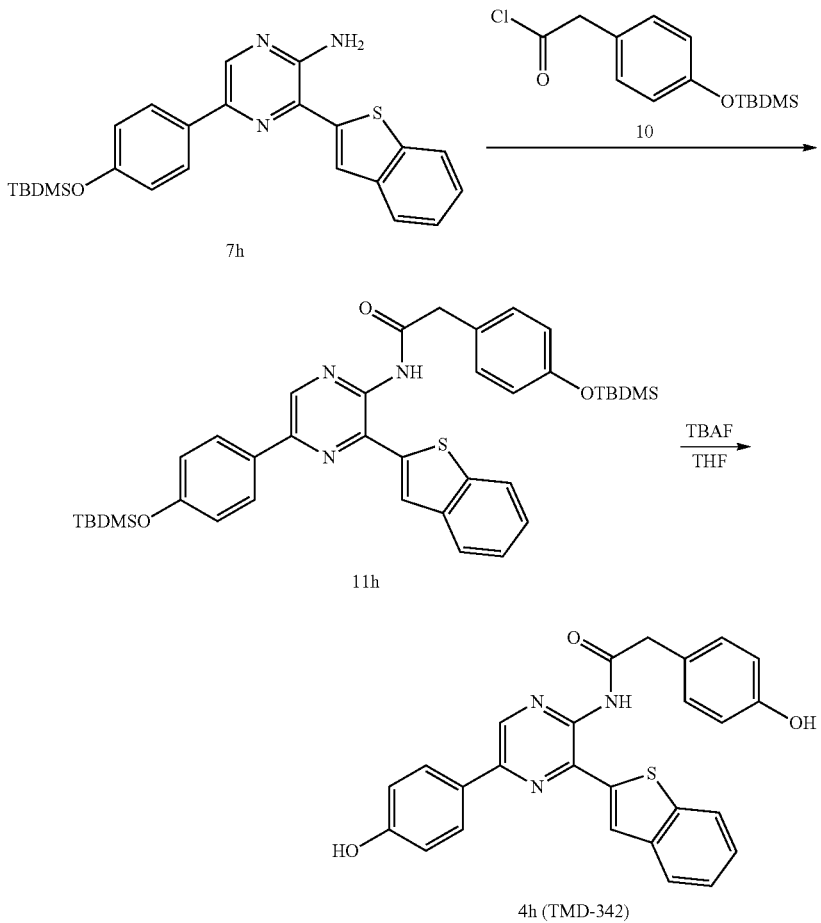

N-[3-(Benzo[b]thiophen-2-yl)-5-{4-(tert-butyldimethylsilyloxy)phenyl}pyrazin-2-yl]-2-[4-(tert-butyldimethylsilyloxy)phenyl]acetamide (11 h)

Under an argon atmosphere, to a solution of 2-[4-(tert-butyldimethylsilyloxy)phenyl]acetic acid (9) (1.55 g, 5.82 mmol) in CH$_2$Cl$_2$ (10 mL) was added DMF (3 drops) by a Pasteur pipette at room temperature. To this was added oxalyl dichloride (985 µL, 11.6 mmol) at 0° C. and the mixture was stirred for 30 minutes while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 3-(benzo[b]thiophen-2-yl)-5-[4-(tert-butyldimethylsilyloxy)phenyl]pyrazin-2-amine (7h) (505 mg, 1.16 mmol) and 4-(dimethylamino)pyridine (15.0 mg, 123 μmol) dissolved in anhydrous pyridine (20 mL) was added 2-[4-(tert-butyl dimethylsilyloxy)phenyl]acetyl chloride (10) prepared above at 0° C. and the mixture was heated with stirring at 50° C. for 15 hours. After cooling to room temperature, to this was added water and the product was extracted with ethyl acetate (200 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=3/1). The resulting solid was recrystallized (n-hexane/ethanol) to give Compound 11h (294 mg, 431 μmol, 37.0%) as a colorless solid. $R_f$=0.19 (n-hexane/diethyl ether=2/3); $^1$H NMR (400 MHz, DMSO-$d_6$) δ 0.19 (s, 6H), 0.25 (s, 6H), 0.96 (s, 9H), 0.97 (s, 9H), 3.71 (s, 2H), 6.82-6.89 (AA'BB', 2H), 7.01-7.08 (AA'BB', 2H), 7.26-7.42 (m, 4H, includes AA'BB'), 7.60-7.65 (m, 2H), 7.96 (d, 1H, J=7.9 Hz), 8.10-8.18 (AA'BB', 2H), 9.02 (s, 1H), 10.82 (s, 1H); IR (KBr, cm$^{-1}$) 525, 677, 692, 710, 727, 743, 779, 797, 808, 835, 922, 972, 1011, 1074, 1171, 1256, 1327, 1362, 1391, 1416, 1445, 1503, 1603, 1657, 859, 2886, 2930, 2957, 3059, 3161, 3211; HRMS (ESI$^+$) m/z 704.2758 ([M+Na]$^+$, $C_{38}H_{47}N_3NaO_3SSi_2^+$ requires 704.2769).

N-[3-(Benzo[b]thiophen-2-yl)-5-(4-hydroxyphenyl)pyrazin-2-yl]-2-(4-hydroxyphenyl) acetamide (4h, TMD-342)

To a solution of N-[3-(benzo[b]thiophen-2-yl)-5-{4-(tert-butyldimethylsilyloxy)phenyl}pyrazin-2-yl]-2-[4-(tert-butyldimethylsilyloxy)phenyl]acetamide (11 h) (186 mg, 273 μmol) in THF (2 mL) was added tetrabutylammonium fluoride (1.0 M THF solution) (1.40 mL, 1.40 mmol) at 0° C. and the mixture was stirred for an hour while elevating to room temperature. To the mixture was added saturated NH$_4$Cl aqueous solution (50 mL) and the product was extracted with ethyl acetate (100 mL×3). The combined organic extract was washed successively with saturated NH$_4$Cl aqueous solution (200 mL), water (200 mL) and brine (200 mL), followed by drying over anhydrous sodium sulfate. Filtration and concentration under reduced pressure gave Compound 4h (TMD-342) (123 mg, 271 μmol, 99.3%) as a colorless solid. $R_f$=0.41 (dichloromethane/methanol=9/1); HPLC retention time 13.1 min; $^1$H NMR (400 MHz, DMSO-$d_6$) δ 3.62 (s, 2H), 6.70-6.78 (AA'BB', 2H), 6.89-6.95 (AA'BB', 2H), 7.17-7.22 (AA'BB', 2H), 7.30-7.39 (m, 2H), 7.51-7.59 (m, 2H), 7.90-7.95 (m, 1H), 8.01-8.09 (AA'BB', 2H), 8.94 (s, 1H), 9.38 (s, 1H), 9.96 (s, 1H), 10.70 (s, 1H); $^{13}$C NMR (75.5 MHz, DMSO-$d_6$) δ 42.3, 115.4 (2C), 116.1 (2C), 122.3, 124.3, 124.60, 124.63, 125.1, 125.6, 125.8, 128.4 (2C), 130.5 (2C), 137.8, 139.9, 140.3, 141.0, 141.5, 142.0, 148.5, 156.5, 159.6, 170.6; IR (KBr, cm$^{-1}$) 525, 554, 579, 623, 654, 681, 727, 804, 827, 847, 972, 1013, 1070, 1128, 1175, 1242, 1314, 1377, 1439, 1497, 1514, 1593, 1676, 3302; HRMS (ESI$^+$) m/z 476.1052 ([M+Na]$^+$, $C_{26}H_{19}N_3NaO_3S^+$ requires 476.1039).

2-9) TMD-346 (4i)

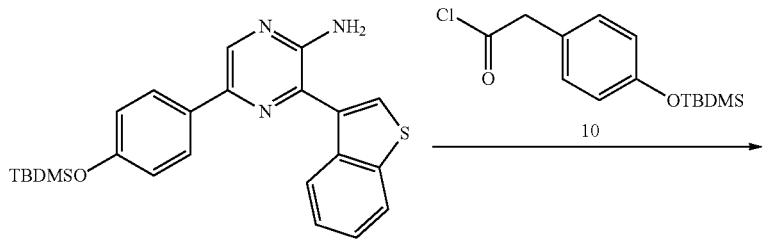

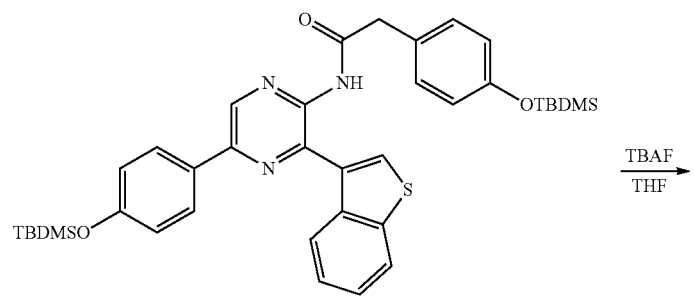

-continued

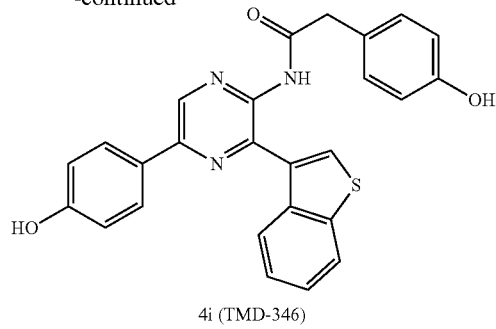

4i (TMD-346)

N-[3-(Benzo[b]thiophen-3-yl)-5-{4-(tert-butyldimethylsilyloxy)phenyl}pyrazin-2-yl]-2-[4-(tert-butyldimethylsilyloxy)phenyl]acetamide (11i)

Under an argon atmosphere, to a solution of 2-[4-(tert-butyldimethylsilyloxy)phenyl]acetic acid (9) (1.55 g, 5.82 mmol) in $CH_2Cl_2$ (10 mL) was added DMF (3 drops) by a Pasteur pipette at room temperature. To this was added oxalyl dichloride (1.00 mL, 11.8 mmol) at 0° C. and the mixture was stirred for an hour while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 3-(benzo[b]thiophen-3-yl)-5-[4-(tert-butyldimethylsilyloxy)phenyl]pyrazin-2-amine (7i) (505 mg, 1.16 mmol) and 4-(dimethylamino)pyridine (15.0 mg, 123 μmol) dissolved in anhydrous pyridine (20 mL) was added 2-[4-(tert-butyl dimethylsilyloxy)phenyl]acetyl chloride (10) prepared above at 0° C. and the mixture was heated with stirring at 50° C. for 15 hours. After cooling to room temperature, to this was added water and the product was extracted with ethyl acetate (200 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=3/1) to give Compound 11i (505 mg, 740 μmol, 63.5%) as a yellow solid. $R_f$=0.19 (n-hexane/diethyl ether=2/3); $^1$H NMR (400 MHz, DMSO-$d_6$) δ 0.15 (s, 6H), 0.20 (s, 6H), 0.91 (s, 9H), 0.93 (s, 9H), 3.41 (s, 2H), 6.65-6.71 (AA'BB', 2H), 6.93-7.00 (2AA'BB', 4H), 7.35-7.42 (m, 2H), 7.80 (s, 1H), 7.95-8.07 (m, 4H, includes AA'BB'), 9.01 (s, 1H), 10.49 (s, 1H); $^{13}$C NMR (75.5 MHz, DMSO-$d_6$) δ −4.5 (4C), 17.89, 17.93, 25.47 (3C), 25.54 (3C), 41.6, 119.5 (2C), 120.4 (2C), 122.6, 123.5, 124.4 (2C), 127.3, 127.9, 128.1 (2C), 128.9, 130.3 (2C), 132.3, 137.5, 137.5, 139.4, 143.7, 143.8, 147.6, 153.8, 156.7, 169.4; IR (KBr, $cm^{-1}$) 683, 700, 735, 758, 781, 804, 839, 914, 1169, 1261, 1331, 1362, 1435, 1472, 1508, 1605, 1670, 2857, 2886, 2930, 2955; HRMS (ESI$^+$) m/z 704.2781 ([M+Na]$^+$, $C_{38}H_{47}N_3NaO_3SSi_2^+$ requires 704.2769).

N-[3-(Benzo[b]thiophen-3-yl)-5-(4-hydroxyphenyl)pyrazin-2-yl]-2-(4-hydroxyphenyl) acetamide (4i, TMD-346)

To a solution of N-[3-(benzo[b]thiophen-3-yl)-5-(4-(tert-butyldimethylsilyloxy)phenyl) pyrazin-2-yl]-2-[4-(tert-butyldimethylsilyloxy)phenyl]acetamide (11i) (300 mg, 440 μmol) in THF (5 mL) was added tetrabutylammonium fluoride (1.0 M THF solution) (2.20 mL, 2.20 mmol) at 0° C. and the mixture was stirred for an hour while elevating to room temperature. To the mixture was added saturated $NH_4Cl$ aqueous solution (50 mL) and the product was extracted with ethyl acetate (100 mL×3). The combined organic extract was washed successively with water (200 mL) and brine (200 mL), and dried over anhydrous sodium sulfate. After filtration and concentration under reduced pressure, the residue was recrystallized (n-hexane/ethanol) to give Compound 4i (TMD-346) (191 mg, 422 μmol, 95.8%) as a brown solid. $R_f$=0.50 (dichloromethane/methanol=9/1); HPLC retention time 9.6 min; $^1$H NMR (400 MHz, DMSO-$d_6$) δ 3.36 (s, 2H), 6.57-6.63 (AA'BB', 2H), 6.84-6.92 (2AA'BB', 4H), 7.36-7.43 (m, 2H), 7.79 (s, 1H), 7.95-8.04 (m, 4H, includes AA'BB'), 8.95 (s, 1H), 9.22 (s, 1H), 9.88 (s, 1H), 10.37 (s, 1H); $^{13}$C NMR (75.5 MHz, DMSO-$d_6$) δ 41.7, 115.1 (2C), 116.0 (2C), 122.8, 123.6, 124.5 (2C), 125.2, 126.5, 127.5, 128.2 (2C), 130.2 (2C), 132.4, 137.2, 137.6, 139.5, 143.3, 144.0, 148.2, 156.1, 159.3, 169.9; IR (KBr, $cm^{-1}$) 419, 473, 525, 611, 735, 760, 837, 970, 1171, 1233, 1329, 1435, 1479, 1514, 1609, 1668, 2957, 3260; HRMS (ESI$^+$) m/z 476.1052 ([M+Na]$^+$, $C_{26}H_{19}N_3O_3S^+$ requires 476.1039).

2-10) TMD-341 (4j)

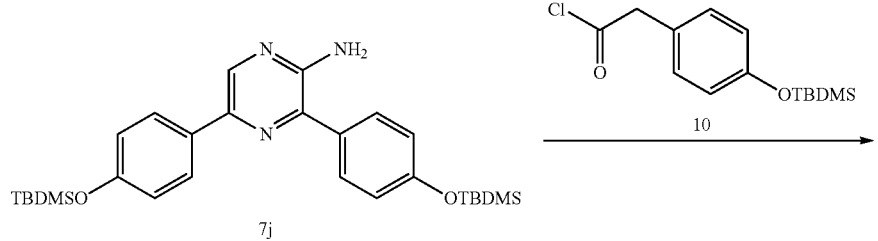

7j

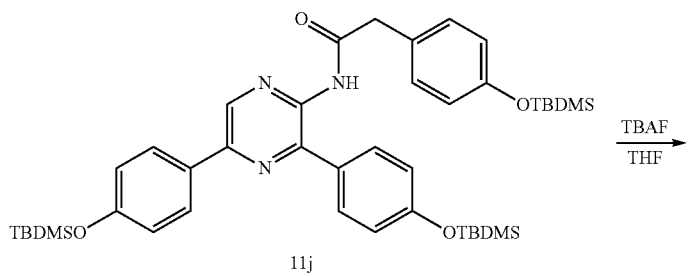

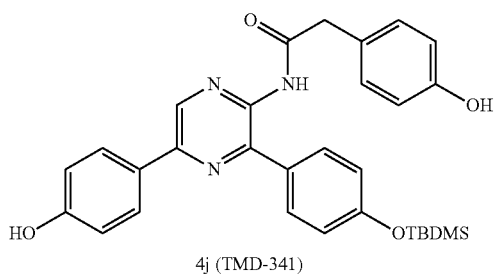

N-[3,5-Bis{4-(tert-butyldimethylsilyloxy) phenyl}pyrazin-2-yl]-2-[4-(tert-butyldimethylsilyloxy)phenyl]acetamide (11j)

Under an argon atmosphere, to a mixture of 2-[4-(tert-butyldimethylsilyloxy)phenyl]acetic acid (9) (1.55 g, 5.82 mmol) in $CH_2Cl_2$ (10 mL) was added DMF (3 drops) by a Pasteur pipette at room temperature. To this was added oxalyl dichloride (985 μL, 11.6 mmol) at 0° C. and the mixture was stirred for 30 minutes while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 3,5-bis[4-(tert-butyldimethylsilyloxy)phenyl]pyrazin-2-amine (7j) (591 mg, 1.16 mmol) and 4-(dimethylamino)pyridine (15.7 mg, 129 μmol) dissolved in anhydrous pyridine (20 mL) was added 2-[4-(tert-butyldimethylsilyloxy)phenyl]acetyl chloride (10) prepared above at 0° C. and the mixture was heated with stirring at 50° C. for 15 hours. After cooling to room temperature, to this was added water and the product was extracted with ethyl acetate (200 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=4/1) to give Compound 11j (714 mg, 945 μmol, 81.1%) as a yellow foamy solid. $R_f$=0.37 (n-hexane/diethyl ether=2/3); $^1H$ NMR (400 MHz, DMSO-$d_6$) δ 0.14 (s, 6H), 0.19 (s, 6H), 0.20 (s, 6H), 0.92 (s, 9H), 0.95 (s, 18H), 3.47 (s, 2H), 6.71-6.78 (2AA'BB', 4H), 6.94-7.02 (AA'BB', 2H), 7.03-7.13 (AA'BB', 2H), 7.57-7.63 (AA'BB', 2H), 8.03-8.10 (AA'BB', 2H), 8.91 (s, 1H), 10.49 (s, 1H); $^{13}C$ NMR (75.5 MHz, DMSO-$d_6$) 8-4.5 (6C), 17.9 (3C), 25.5 (9C), 41.7, 119.3 (2C), 119.5 (2C), 120.3 (2C), 127.9, 128.1 (2C), 128.9, 129.3 (2C), 130.4 (2C), 130.7, 136.9, 142.4, 147.2, 147.8, 153.8, 155.7, 156.7, 169.3; IR (KBr, $cm^{-1}$) 523, 637, 677, 710, 781, 804, 839, 914, 1009, 1078, 1105, 1169, 1258, 1362, 1402, 1416, 1441, 1472, 1510, 1605, 1667, 2857, 2886, 2928, 2955, 3036, 3221; HRMS ($ESI^+$) m/z 778.3853 ([M+Na]$^+$, $C_{42}H_{61}N_3NaO_4Si_3^+$ requires 778.3862).

N-[3,5-Bis(4-hydroxyphenyl)pyrazin-2-yl]-2-(4-hydroxyphenyl)acetamide (4j, TMD-341)

To a solution of N-[3,5-bis{4-(tert-butyldimethylsilyloxy)phenyl}pyrazin-2-yl]-2-[4-(tert-butyldimethylsilyl oxy)phenyl]acetamide (11j) (500 mg, 661 μmol) in THF (5 mL) was added tetrabutylammonium fluoride (1.0 M THF solution) (5.00 mL, 5.00 mmol) at 0° C. and the mixture was stirred for 30 minutes while elevating to room temperature. To the mixture was added saturated $NH_4Cl$ aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ethanol) to give Compound 4j (TMD-341) (263 mg, 637 μmol, 96.3%) as a brown solid. $R_f$=0.43 (dichloromethane/methanol=9/1); HPLC retention time 4.3 min; $^1H$ NMR (400 MHz, DMSO-$d_6$) δ 3.40 (s, 21-), 6.60-6.68 (AA'BB', 2H), 6.68-6.74 (AA'BB', 2H), 6.82-6.90 (AA'BB', 2H), 6.94-7.03 (AA'BB', 2H), 7.54-7.62 (AA'BB', 2H), 7.94-8.02 (AA'BB', 2H), 8.80 (s, 1H), 9.24 (s, 1H), 9.70 (s, 1H), 9.85 (s, 1H), 10.29 (s, 1H); $^{13}C$ NMR (75.5 MHz, DMSO-$d_6$) δ 41.7, 115.1 (4C), 115.9 (2C), 125.4, 126.6, 128.1, 128.2 (2C), 129.6 (2C), 130.3 (2C), 136.3, 141.9, 147.8, 148.4, 156.1, 158.3, 159.2, 170.0; IR (KBr, $cm^{-1}$) 530, 571, 839, 966, 1011, 1080, 1171, 1234, 1321, 1369, 1420, 1481, 1516, 1609, 1670, 3246; HRMS ($ESI^+$) m/z 436.1269 ([M+Na]$^+$, $C_{24}H_{19}N_3NaO_4^+$ requires 436.1268).

2-11) TMD-373 (4k)

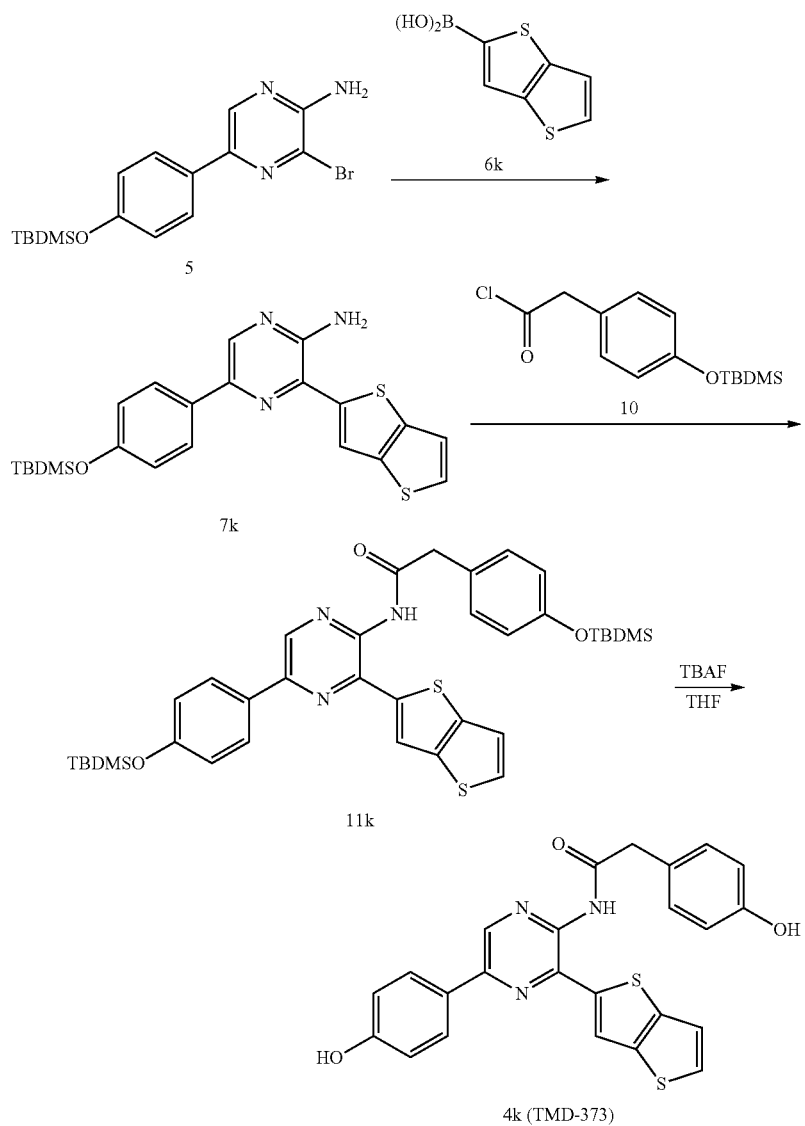

4k (TMD-373)

5-[4-(tert-Butyldimethylsilyloxy)phenyl]-3-(thieno[3,2-b]thiophen-2-yl)pyrazin-2-amine (7k)

Under an argon atmosphere, to a solution of 3-bromo-5-[4-(tert-butyldimethylsilyloxy)phenyl]pyrazin-2-amine (5) (500 mg, 1.31 mmol) in toluene (15 mL) and ethanol (600 μL) were successively added thieno[3,2-b]thiophen-2-boronic acid (6k) (290 mg, 1.58 mmol), dichlorobis(triphenylphosphine)palladium (II) (56.0 mg, 79.8 μmol) and 1 M $Na_2CO_3$ aqueous solution (1.40 mL, 1.40 mmol) at room temperature and the mixture was heated to reflux for 21 hours. After cooling to room temperature, to the mixture was added water and the metal catalyst was removed by filtration. The product was extracted with ethyl acetate (100 mL×3). The combined organic extract was washed successively with water (200 mL) and brine (300 mL), followed by drying over anhydrous sodium sulfate. After filtration and concentration under reduced pressure, the residue was purified by column chromatography (silica gel 50 g, n-hexane/ethyl acetate=3/1) to give Compound 7k (278 mg, 632 μmol, 48.0%) as an orange solid. $R_f$=0.19 (n-hexane/ethyl acetate=3/1); $^1$H NMR (400 MHz, DMSO-$d_6$) δ 0.19 (s, 6H), 0.94 (s, 9H), 6.55 (s, 2H), 6.89-6.96 (AA'BB', 2H), 7.44 (d, 1H, J=5.3 Hz), 7.71 (d, 1H, J=5.3 Hz), 7.86-7.94 (AA'BB', 2H), 8.08 (s, 1H), 8.49 (s, 1H); IR (KBr, $cm^{-1}$) 509, 637, 702, 781, 839, 916, 986, 1103, 1165, 1261, 1344, 1418, 1464, 1510, 1605, 1638, 2857, 2930, 2953, 3156, 3296, 3416.

2-[4-(tert-Butyldimethylsilyloxy)phenyl]-N-[5-(4-(tert-butyldimethylsilyloxy)phenyl}-3-(thieno[3,2-b]thiophen-2-yl)pyrazin-2-yl]acetamide (11k)

Under an argon atmosphere, to a solution of 2-[4-(tert-butyldimethylsilyloxy)phenyl]acetic acid (9) (757 mg, 2.84 mmol) in $CH_2Cl_2$ (8 mL) was added DMF (2 drops) by a Pasteur pipette at room temperature. To this was added oxalyl dichloride (490 μL, 5.79 mmol) at 0° C. and the mixture was stirred for 30 minutes while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 5-[4-(tert-butyldimethylsilyloxy)phenyl]-3-(thieno[3,2-b]thiophen-2-yl)pyrazin-2-amine (7k) (250 mg, 569 μmol) and 4-(dimethylamino)pyridine (12.3 mg, 101 μmol) dissolved in anhydrous pyridine (15 mL) was added 2-[4-(tert-butyldimethylsilyloxy)phenyl]acetyl chloride (10) prepared above at 0° C. and the mixture was heated with stirring at 50° C. for 13 hours. After cooling to room temperature, to this was added water and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was purified by column chromatography (silica gel 30 g, n-hexane/ethyl acetate=3/1) to give Compound 11k (228 mg, 331 μmol, 58.2%) as a yellow solid. $R_f$=0.26 (n-hexane/ethyl acetate=3/1); $^1$H NMR (400 MHz, DMSO-$d_6$) δ 0.17 (s, 6H), 0.22 (s, 6H), 0.93 (s, 9H), 0.95 (s, 9H), 3.67 (s, 2H), 6.78-6.86 (AA'BB', 2H), 6.96-7.04 (AA'BB', 2H), 7.20-7.30 (AA'BB', 2H), 7.41 (d, 1H, J=5.2 Hz), 7.57 (s, 1H), 7.73 (d, 1H, J=5.2 Hz), 8.04-8.13 (AA'BB', 2H), 8.92 (s, 1H), 10.69 (s, 1H); IR (KBr, cm$^{-1}$) 527, 635, 702, 779, 837, 918, 1007, 1074, 1169, 1256, 1362, 1445, 1508, 1603, 1655, 2857, 2886, 2928, 2955, 3211.

2-(4-Hydroxyphenyl)-N-[5-(4-hydroxyphenyl)-3-(thieno[3,2-b]thiophen-2-yl)pyrazin-2-yl]acetamide (4k, TMD-373)

To a solution of 2-[4-(tert-butyldimethylsilyloxy)phenyl]-N-[5-{4-(tert-butyldimethylsilyloxy)phenyl}-3-(thieno[3,2-b]thiophen-2-yl)pyrazin-2-yl]acetamide (11k) (172 mg, 250 μmol) in THF (5 mL) was added tetrabutylammonium fluoride (1.0 M THF solution) (1.30 mL, 1.30 mmol) at 0° C. and the mixture was stirred for 30 minutes while elevating to room temperature. To the mixture was added saturated NH$_4$Cl aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ethyl acetate) to give Compound 4k (TMD-373) (88.4 mg, 192 μmol, 77.1%) as a yellow solid. $R_f$=0.37 (dichloromethane/methanol=9/1); HPLC retention time 10.6 min; $^1$H NMR (400 MHz, DMSO-$d_6$) δ 3.59 (s, 2H), 6.71-6.78 (AA'BB', 2H), 6.85-6.94 (AA'BB', 2H), 7.15-7.23 (AA'BB', 2H), 7.37-7.42 (m, 2H), 7.72 (d, 1H, J=5.2 Hz), 7.99-8.05 (AA'BB', 2-1), 8.87 (s, 1H), 9.38 (s, 1H), 9.95 (s, 1H), 10.61 (s, 1H); $^{13}$C NMR (67.8 MHz, DMSO-$d_6$) δ 42.3, 115.4 (2C), 115.9 (2C), 120.1, 120.5, 125.0, 125.8, 128.3 (2C), 130.4 (2C), 130.5, 137.1, 139.7, 140.0, 141.0, 142.4, 142.9, 148.4, 156.5, 159.5, 170.5; IR (KBr, cm$^{-1}$) 530, 635, 704, 725, 804, 986, 1173, 1242, 1325, 1371, 1439, 1491, 1514, 1609, 1676, 3304.

2-12) TMD-374 (41)

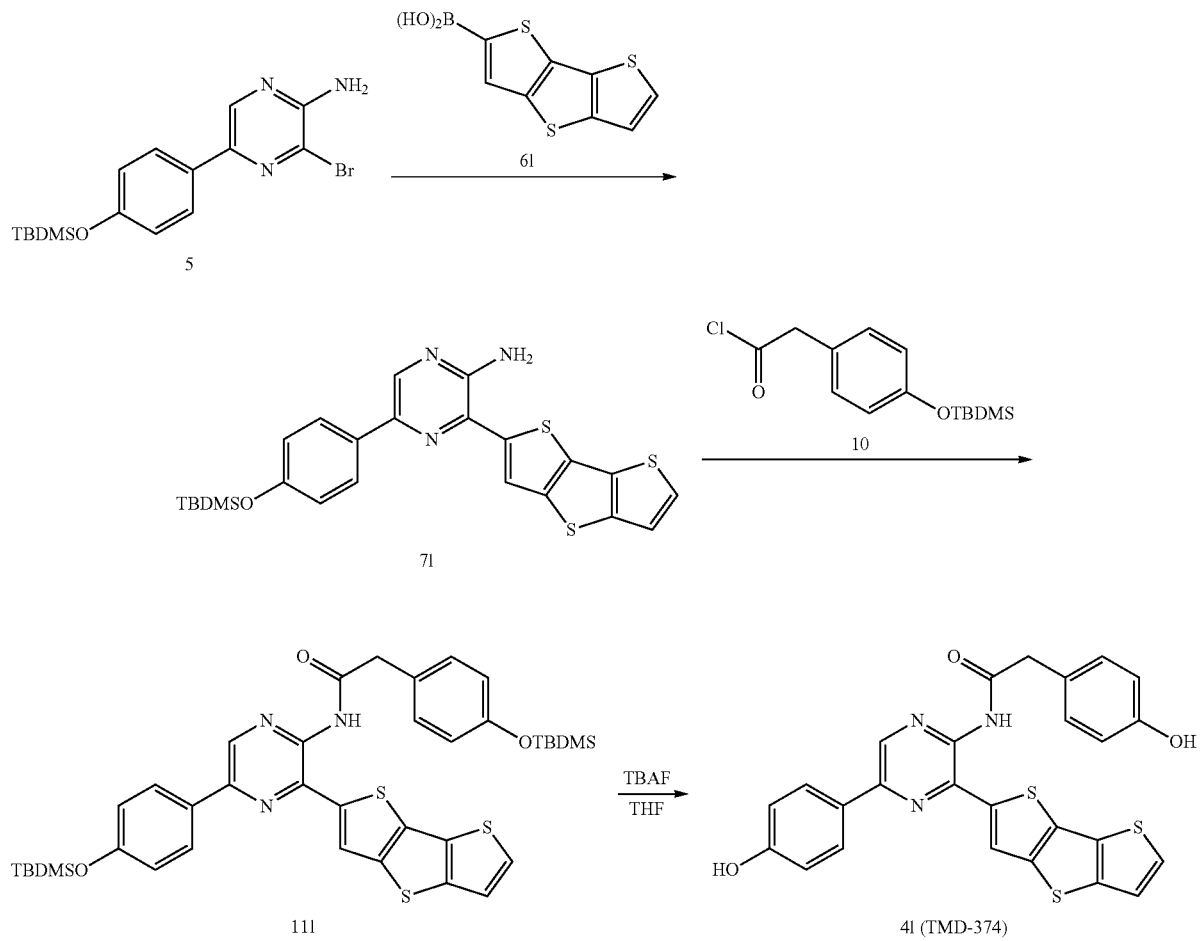

5-[4-(tert-Butyldimethylsilyloxy)phenyl]-3-(dithieno [3,2-b:2',3'-d]thiophen-2-yl)pyrazin-2-amine (71)

Under an argon atmosphere, to a solution of 3-bromo-5-[4-(tert-butyldimethylsilyloxy)phenyl]pyrazin-2-amine (5) (700 mg, 1.84 mmol) in toluene (21 mL) and ethanol (840 μL) were successively added dithieno[3,2-b:2',3'-d]thiophen-2-boronic acid (61) (540 mg, 2.25 mmol), dichlorobis(triphenylphosphine)palladium (11) (78.2 mg, 111 μmol) and 1 M $Na_2CO_3$ aqueous solution (1.90 mL, 1.90 mmol) at room temperature, and the mixture was heated to reflux for 18 hours. After cooling to room temperature, to the mixture was added water and the metal catalyst was removed by filtration. The product was extracted with ethyl acetate (100 mL×3). The combined organic extract was washed successively with water (300 mL) and brine (300 mL), followed by drying over anhydrous sodium sulfate. After filtration and concentration under reduced pressure, the residue was purified by column chromatography (silica gel 100 g, n-hexane/ethyl acetate=3/1) to give Compound 71(477 mg, 963 μmol, 52.3%) as a yellow solid. $R_f$=0.26 (n-hexane/ethyl acetate=3/1); $^1$H NMR (400 MHz, DMSO-$d_6$) δ 0.20 (s, 6H), 0.94 (s, 9H), 6.59 (s, 2H), 6.89-6.97 (AA'BB', 2H), 7.53 (d, 1H, J=5.2 Hz), 7.74 (d, 1H, J=5.2 Hz), 7.88-7.97 (AA'BB', 2H), 8.16 (s, 1H), 8.51 (s, 1H); IR (KBr, cm$^{-1}$) 530, 625, 644, 698, 781, 839, 908, 1072, 1109, 1179, 1225, 1267, 1360, 1393, 1462, 1512, 1605, 2857, 2928, 2957, 3173, 3285, 3424.

2-[4-(tert-Butyldimethylsilyloxy)phenyl]-N-[5-{4-(tert-butyldimethylsilyloxy)phenyl}-3-(dithieno[3,2-b:2',3'-d]thiophen-2-yl)pyrazin-2-yl]acetamide (111)

Under an argon atmosphere, to a solution of 2-[4-(tert-butyldimethylsilyloxy)phenyl]acetic acid (9) (1.00 g, 3.76 mmol) in $CH_2Cl_2$ (10 mL) was added DMF (3 drops) by a Pasteur pipette at room temperature. To this was added oxalyl dichloride (640 μL, 7.56 mmol) at 0° C. and the mixture was stirred for 30 minutes while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 5-[4-(tert-butyldimethylsilyloxy)phenyl]-3-(thieno[3,2-b:2',3'-d] thiophen-2-yl)pyrazin-2-amine (71) (370 mg, 746 μmol) and 4-(dimethylamino)pyridine (14.8 mg, 121 μmol) dissolved in anhydrous pyridine (15 mL) was added 2-[4-(tert-butyldimethylsilyloxy)phenyl]acetyl chloride (10) prepared above at 0° C. and the mixture was heated with stirring at 50° C. for 20 hours. After cooling to room temperature, to this was added water and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=3/1). The resulting solid was recrystallized (n-hexane/ethyl acetate) to give Compound 111 (116 mg, 156 μmol, 20.9%) as a brown solid. $R_f$=0.19 (n-hexane/ethyl acetate=3/1); $^1$H NMR (400 MHz, DMSO-$d_6$) δ 0.16 (s, 6H), 0.21 (s, 6H), 0.93 (s, 9H), 0.94 (s, 9H), 3.68 (s, 2H), 6.78-6.88 (AA'BB', 2H), 6.94-7.06 (AA'BB', 2H), 7.20-7.30 (AA'BB', 2H), 7.47 (d, 1H, J=5.2 Hz), 7.65 (s, 1H), 7.75 (d, 1H, J=5.2 Hz), 8.06-8.14 (AA'BB', 2H), 8.93 (s, 1H), 10.72 (s, 1H); IR (KBr, cm$^{-1}$) 530, 602, 644, 700, 779, 837, 922, 1072, 1171, 1265, 1361, 1447, 1504, 1603, 1657, 2857, 2928, 2955, 3208.

2-(4-Hydroxyphenyl)-N-[5-(4-hydroxyphenyl)-3-(thieno[3,2-b:2',3'-d]thiophen-2-yl)pyrazin-2-yl]acetamide (41, TMD-374)

To a solution of 2-[4-(tert-butyldimethylsilyloxy)phenyl]-N-[5-{4-(tert-butyldimethylsilyloxy)phenyl}-3-(dithieno[3,2-b:2',3'-d]thiophen-2-yl)pyrazin-2-yl]acetamide (111) (82.3 mg, 111 μmol) in THF (5 mL) was added tetrabutylammonium fluoride (1.0 M THF solution) (600 μL, 600 μmol) at 0° C. and the mixture was stirred for 30 minutes while elevating to room temperature. To the mixture was added saturated $NH_4Cl$ aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ ethyl acetate) to give Compound 41 (TMD-374) (50.7 mg, 192 μmol, 88.8%) as a yellow solid. $R_f$=0.37 (dichloromethane/methanol=9/1); HPLC retention time 17.7 min; $^1$H NMR (400 MHz, DMSO-$d_6$) δ 3.61 (s, 2H), 6.70-6.80 (AA'BB', 2H), 6.87-6.94 (AA'BB', 2H), 7.15-7.25 (AA'BB', 2H), 7.44 (s, 1H), 7.52 (d, 1H, J=5.2 Hz), 7.75 (d, 1H, J=5.2 Hz), 8.01-8.09 (AA'BB', 2H), 8.89 (s, 1H), 9.34 (s, 1H), 9.96 (s, 1H), 10.66 (s, 1H); $^{13}$C NMR (67.8 MHz, DMSO-$d_6$) δ 42.3, 115.4 (2C), 115.9 (2C), 121.4, 121.9, 125.0, 125.7, 128.3 (2C), 128.9, 130.3, 130.4 (2C), 132.3, 137.2, 140.0, 141.8, 142.00, 142.02, 142.8, 148.4, 156.5, 159.5, 170.5; IR (KBr, cm$^{-1}$) 534, 598, 644, 706, 793, 835, 893, 972, 1109, 1173, 1190, 1242, 1319, 1389, 1439, 1491, 1611, 1665, 3231. 2-13) TMD-375 (4m)

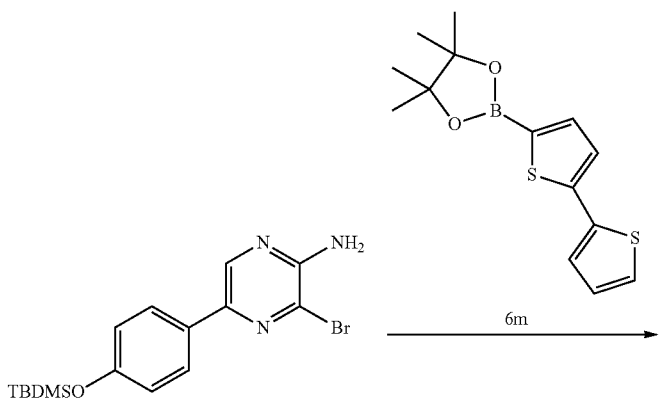

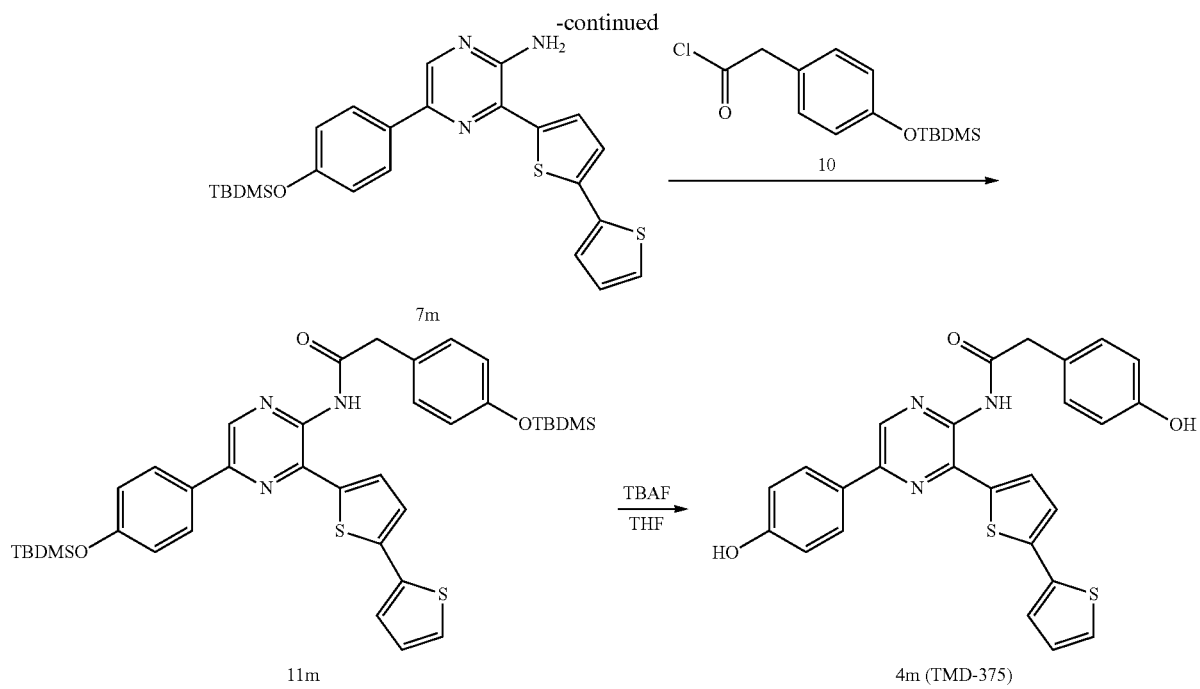

3-(2,2'-Bithiophen-5-yl)-5-[4-(tert-butyldimethylsilyloxy)phenyl]pyrazin-2-amine (7m)

Under an argon atmosphere, to a solution of 3-bromo-5-[4-(tert-butyldimethylsilyloxy)phenyl]pyrazin-2-amine (5) (500 mg, 1.31 mmol) in toluene (15 mL) and ethanol (600 µL) were successively added 5-(4,4,5,5-tetramethyl-1,3,2-dioxaborolan-2-yl)-2,2'-bithiophene (6m) (460 mg, 1.57 mmol), dichlorobis(triphenylphosphine)palladium (II) (56.3 mg, 80.2 µmol) and 1 M Na$_2$CO$_3$ aqueous solution (1.40 mL, 1.40 mmol) at room temperature, followed by heating to reflux for 15 hours. After cooling to room temperature, to the mixture was added water and the metal catalyst was removed by filtration. The product was extracted with ethyl acetate (100 mL×3). The combined organic extract was washed successively with water (200 mL) and brine (300 mL), followed by drying over anhydrous sodium sulfate. After filtration and concentration under reduced pressure, the residue was purified by column chromatography (silica gel 50 g, n-hexane/ethyl acetate=3/1) to give Compound 7m (574 mg, 1.23 mmol, 93.7%) as a yellow solid. R$_f$=0.19 (n-hexane/ethyl acetate=3/1); $^1$H NMR (400 MHz, DMSO-d$_6$) δ 0.19 (s, 6H), 0.94 (s, 9H), 6.49 (s, 2H), 6.88-6.97 (AA'BB', 2H), 7.10 (dd, 1H, J=3.7, 3.7 Hz), 7.34 (d, 1H, J=3.7 Hz), 7.41 (d, 1H, J=3.7 Hz), 7.53 (d, 1H, J=4.0 Hz), 7.70 (d, 1H, J=4.0 Hz), 7.84-7.92 (AA'BB', 2H), 8.47 (s, 1H); $^{13}$C NMR (67.8 MHz, DMSO-d$_6$) δ −4.5 (2C), 18.0, 25.5 (3C), 120.2 (2C), 124.5, 124.9, 125.9, 126.5 (2C), 126.6, 128.5, 129.8, 131.2, 136.4, 137.1, 138.1, 139.5, 141.6, 149.8, 155.3; IR (KBr, cm$^{-1}$) 505, 544, 694, 781, 806, 839, 914, 980, 1011, 1084, 1169, 1209, 1258, 1375, 1418, 1454, 1512, 1605, 2857, 2928, 2953, 3177, 3296, 3453.

N-[3-(2,2'-Bithiophen-5-yl)-5-(4-(tert-butyldimethylsilyloxy)phenyl) pyrazin-2-yl]-2-[4-(tert-butyldimethylsilyloxy)phenyl]acetamide (11m)

Under an argon atmosphere, to a solution of 2-[4-(tert-butyldimethylsilyloxy)phenyl]acetic acid (9) (1.00 g, 3.76 mmol) in CH$_2$Cl$_2$ (10 mL) was added DMF (3 drops) by a Pasteur pipette at room temperature. To this was added oxalyl dichloride (640 µL, 7.56 mmol) at 0° C. and the mixture was stirred for 30 minutes while elevating to room temperature. The mixture was concentrated wider reduced pressure to give crude 2-[4-(tert-butyldimethylsilyloxy)phenyl]acetyl chloride (10) as a colorless oil, which was used in the following reaction without further purification.

Under an argon atmosphere, to a mixture of 3-(2,2'-bithiophen-5-yl)-5-[4-(tert-butyldimethylsilyloxy)phenyl]pyrazin-2-amine (7m) (350 mg, 752 µmol) and 4-(dimethylamino)pyridine (15.0 mg, 123 µmol) dissolved in anhydrous pyridine (15 mL) was added 2-[4-(tert-butyl dimethylsilyloxy)phenyl]acetyl chloride (10) prepared above at 0° C. and the mixture was heated with stirring at 50° C. for 20 hours. After cooling to room temperature, to this was added water and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=3/1) to give Compound 11m (298 mg, crude) as a brown oily substance. R$_f$=0.26 (n-hexane/ethyl acetate=3/1); $^1$H NMR (400 MHz, DMSO-d$_6$) δ 0.16 (s, 6H), 0.22 (s, 6H), 0.92 (s, 9H), 0.94 (s, 9H), 3.64 (s, 2H), 6.76-6.85 (AA'BB', 2H), 6.98-7.05 (AA'BB', 2H), 7.06-7.13 (m, 2H), 7.19-7.27 (AA'BB', 2H), 7.33 (d, 1H, J=3.6 Hz), 7.36 (d, 1H, J=3.6 Hz), 7.54-7.59 (m, 1H), 8.05-8.11 (AA'BB', 2H), 8.91 (s, 1H), 10.65 (s, 1H).

N-[3-(2,2'-Bithiophen-5-yl)-5-(4-hydroxyphenyl)pyrazin-2-yl]-2-(4-hydroxyphenyl)acetamide (4m, TMD-375)

To a solution of N-[3-(2,2'-bithiophen-5-yl)-5-{4-(tert-butyldimethylsilyloxy)phenyl}pyrazin-2-yl]-2-[4-(ter t-butyldimethylsilyloxy)phenyl]acetamide (1 m) (168 mg, crude)

in THF (5 mL) was added tetrabutylammonium fluoride (1.0 M THF solution) (1.20 mL, 1.20 mmol) at 0° C. and the mixture was stirred for 30 minutes while elevating to room temperature. To the mixture was added saturated NH$_4$Cl aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ethyl acetate) to give Compound 4m (TMD-375) (102 mg, 210 μmol, 49.5% (2 steps)) as a yellow solid. R$_f$=0.44 (dichloromethane/methanol=9/1); HPLC retention time 15.3 min; $^1$H NMR (400 MHz, DMSO-d$_6$) δ 3.57 (s, 2H), 6.66-6.75 (AA'BB', 21-1), 6.85-6.95 (AA'BB', 2H), 7.06-7.17 (m, 4H, includes AA'BB'), 7.34-7.40 (m, 2H), 7.53-7.58 (m, 1H), 7.98-8.05 (AA'BB', 2H), 8.85 (s, 1H), 9.30 (s, 1H), 9.95 (s, 1H), 10.53 (s, 1H); $^{13}$C NMR (67.8 MHz, DMSO-d$_6$) δ 42.0, 115.2 (2C), 115.9 (2C), 124.6, 124.9, 125.1, 125.8, 126.3, 128.3 (2C), 128.6, 129.0, 130.4 (2C), 136.1, 137.1, 139.4, 139.5, 140.1, 142.1, 148.5, 156.3, 159.5, 170.7; IR (KBr, cm$^{-1}$) 532, 602, 692, 837, 966, 1105, 1165, 1223, 1265, 1369, 1450, 1491, 1516, 1609, 1676, 3246, 3385.

2-14) TMD-376 (4n)

aqueous solution (1.40 mL, 1.40 mmol) at room temperature, followed by heating to reflux for 24 hours. After cooling to room temperature, to the mixture was added water and the metal catalyst was removed by filtration. The product was extracted with ethyl acetate (100 mL×3). The combined organic extract was washed successively with water (200 mL) and brine (300 mL), followed by drying over anhydrous sodium sulfate. After filtration and concentration under reduced pressure, the residue was purified by column chromatography (silica gel 50 g, n-hexane/ethyl acetate=2/1) to give Compound 7n (488 mg, 1.16 mmol, 88.3%) as a yellow solid. R$_f$=0.19 (n-hexane/ethyl acetate=3/1); $^1$H NMR (400 MHz, DMSO-d$_6$) δ 0.17 (s, 6H), 0.92 (s, 9H), 2.94 (s, 6H), 6.02 (s, 2H), 6.75-6.83 (AA'BB', 2H), 6.83-6.92 (AA'BB', 2H), 7.60-7.70 (AA'BB', 2H), 7.77-7.88 (AA'BB', 2H), 8.32 (s, 1H); $^{13}$C NMR (67.8 MHz, DMSO-d$_6$) 8-4.5 (2C), 17.9, 25.5 (3C), 39.9 (2C), 111.9 (2C), 120.0 (2C), 125.0, 126.3 (2C), 128.9 (2C), 130.7, 135.5, 138.5, 139.7, 150.4, 151.3, 154.8; IR (KBr, cm$^1$) 432, 511, 633, 698, 808, 824, 912, 1009, 1063, 1103, 1167, 1254, 1360, 1422, 1454, 1510, 1607, 2803, 2857, 2886, 2928, 2953, 3179, 3300, 3476.

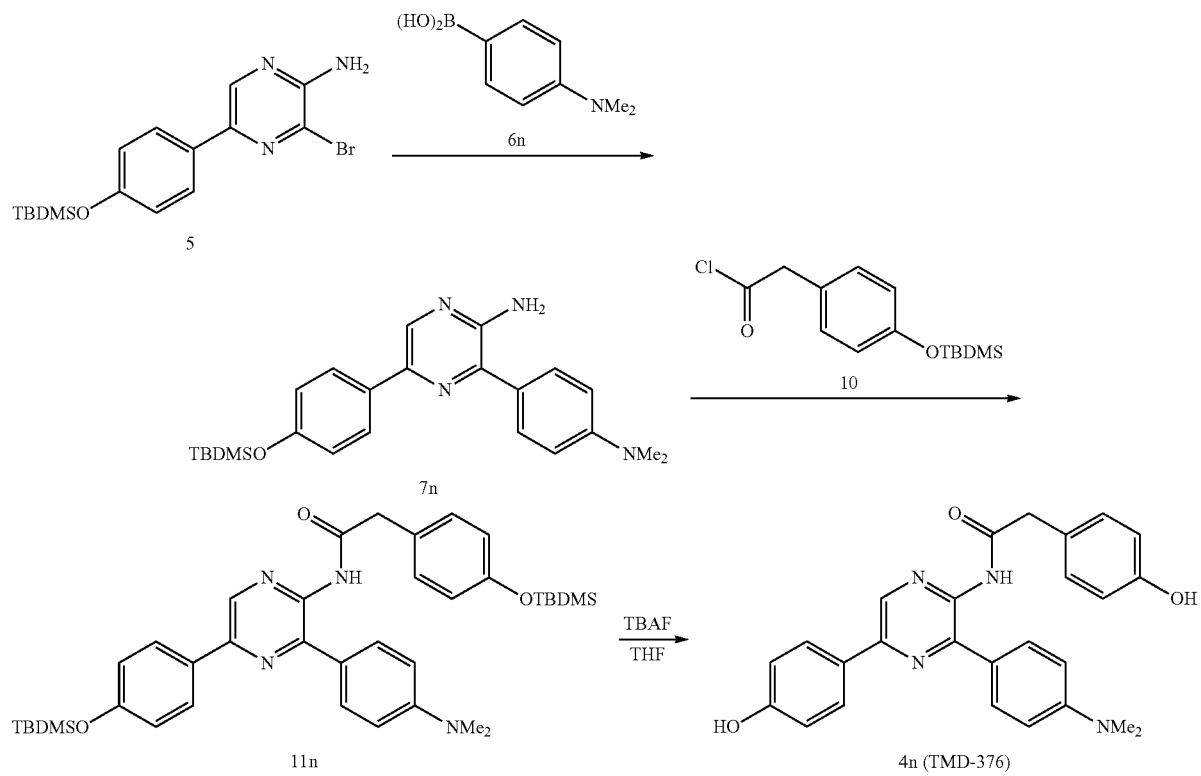

5-[4-(tert-Butyldimethylsilyloxy)phenyl]-3-[4-(dimethylamino)phenyl]pyrazin-2-amine (7n)

Under an argon atmosphere, to a solution of 3-bromo-5-[4-(tert-butyldimethylsilyloxy)phenyl]pyrazin-2-amine (5) (500 mg, 1.31 mmol) in toluene (15 mL) and ethanol (600 μL) were successively added 4-(dimethylamino)phenylboronic acid (6n) (260 mg, 1.58 mmol), dichlorobis(triphenylphosphine)palladium (II) (56.1 mg, 79.9 μmol) and 1 M Na$_2$CO$_3$ 2-[4-(tert-Butyldimethylsilyloxy)phenyl]-N-[5-{4-(tert-butyldimethylsilyloxy)phenyl}-3-{4-(dimethylamino)phenyl}pyrazin-2-yl]acetamide (1 In)

Under an argon atmosphere, to a solution of 2-[4-(tert-butyldimethylsilyloxy)phenyl]acetic acid (9) (1.00 g, 3.76 mmol) in CH$_2$Cl$_2$ (10 mL) was added DMF (3 drops) by a Pasteur pipette at room temperature. To this was added oxalyl dichloride (640 μL, 7.56 mmol) at 0° C. and the mixture was stirred for 30 minutes while elevating to room temperature.

The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 5-[4-(tert-butyldimethylsilyloxy)phenyl]-3-[4-(dimethylamino)phenyl]pyrazin-2-amine (7n) (315 mg, 749 μmol) and 4-(dimethylamino)pyridine (14.8 mg, 121 mol) dissolved in anhydrous pyridine (15 mL) was added 2-[4-(tert-butyl dimethylsilyloxy)phenyl]acetyl chloride (10) prepared above at 0° C. and the mixture was heated with stirring at 50° C. for 20 hours. After cooling to room temperature, to this was added water and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=2/1) to give Compound 11n (200 mg, 300 μmol, 40.0%) as a yellow solid. $R_f$=0.26 (n-hexane/ethyl acetate=2/1); $^1$H NMR (400 MHz, DMSO-$d_6$) δ 0.17 (s, 6H), 0.23 (s, 6H), 0.95 (s, 9H), 0.97 (s, 9H), 2.95 (s, 6H), 3.50 (s, 2H), 6.52-6.65 (AA'BB', 2H), 6.75-6.85 (AA'BB', 2H), 6.95-7.05 (AA'BB', 2H), 7.10-7.20 (AA'BB', 2H), 7.56-7.66 (AA'BB', 2H), 8.04-8.10 (AA'BB', 2H), 8.82 (s, 1H), 10.41 (s, 1H); $^{13}$C NMR (67.8 MHz, DMSO-$d_6$) 8-4.5 (2C), −4.6 (2C), 17.9, 18.0, 25.5 (6C), 39.8 (2C), 41.8, 111.3 (2C), 119.5 (2C), 120.3 (2C), 124.4, 128.05, 128.07 (2C), 128.9 (2C), 129.2, 130.4 (2C), 135.8, 142.0, 147.78, 147.84, 150.5, 153.8, 156.6, 169.3; IR (KBr, cm$^{-1}$) 527, 685, 781, 839, 914, 1080, 1167, 1256, 1371, 1441, 1508, 1607, 1668, 2857, 2928, 2955, 3233.

N-[3-{4-(Dimethylamino)phenyl}-5-(4-hydroxyphenyl)pyrazin-2-yl]-2-(4-hydroxyphenyl)acetamide (4n, TMD-376)

To a solution of 2-[4-(tert-butyldimethylsilyloxy)phenyl]-N-[5-{4-(tert-butyldimethylsilyloxy)phenyl}-3-{4-(dimethylamino)phenyl}pyrazin-2-yl]acetamide (11n) (148 mg, 220 μmol) in THF (5 mL) was added tetrabutylammonium fluoride (1.0 M THF solution) (1.10 mL, 1.10 mmol) at 0° C. and the mixture was stirred for 30 minutes while elevating to room temperature. To the mixture was added saturated NH$_4$Cl aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ethyl acetate) to give Compound 4n (TMD-376) (85.3 mg, 194 μmol, 87.8%) as a yellow solid. $R_f$=0.37 (dichloromethane/methanol=9/1); HPLC retention time 4.5 min; $^1$H NMR (400 MHz, DMSO-$d_6$) δ 2.91 (s, 6H), 3.41 (s, 2H), 6.51-6.59 (AA'BB', 2H), 6.62-6.70 (AA'BB', 2H), 6.82-6.90 (AA'BB', 2H), 6.98-7.08 (AA'BB', 2H), 7.53-7.62 (AA'BB', 2H), 7.94-8.01 (AA'BB', 2H), 8.74 (s, 1H), 9.25 (s, 1H), 9.83 (s, 1H), 10.28 (s, 1H); $^{13}$C NMR (67.8 MHz, DMSO-$d_6$) δ 39.8 (2C), 41.9, 111.4 (2C), 115.0 (2C), 115.8 (2C), 124.4, 125.3, 126.7, 128.1 (2C), 128.9 (2C), 130.3 (2C), 135.5, 141.6, 147.8, 148.3, 150.6, 156.2, 159.1, 169.8; IR (KBr, cm$^{-1}$) 538, 691, 816, 949, 1101, 1169, 1250, 1321, 1375, 1437, 1514, 1533, 1609, 1647, 2810, 3005, 3167, 3348.

2-15) TMD-377 (4o)

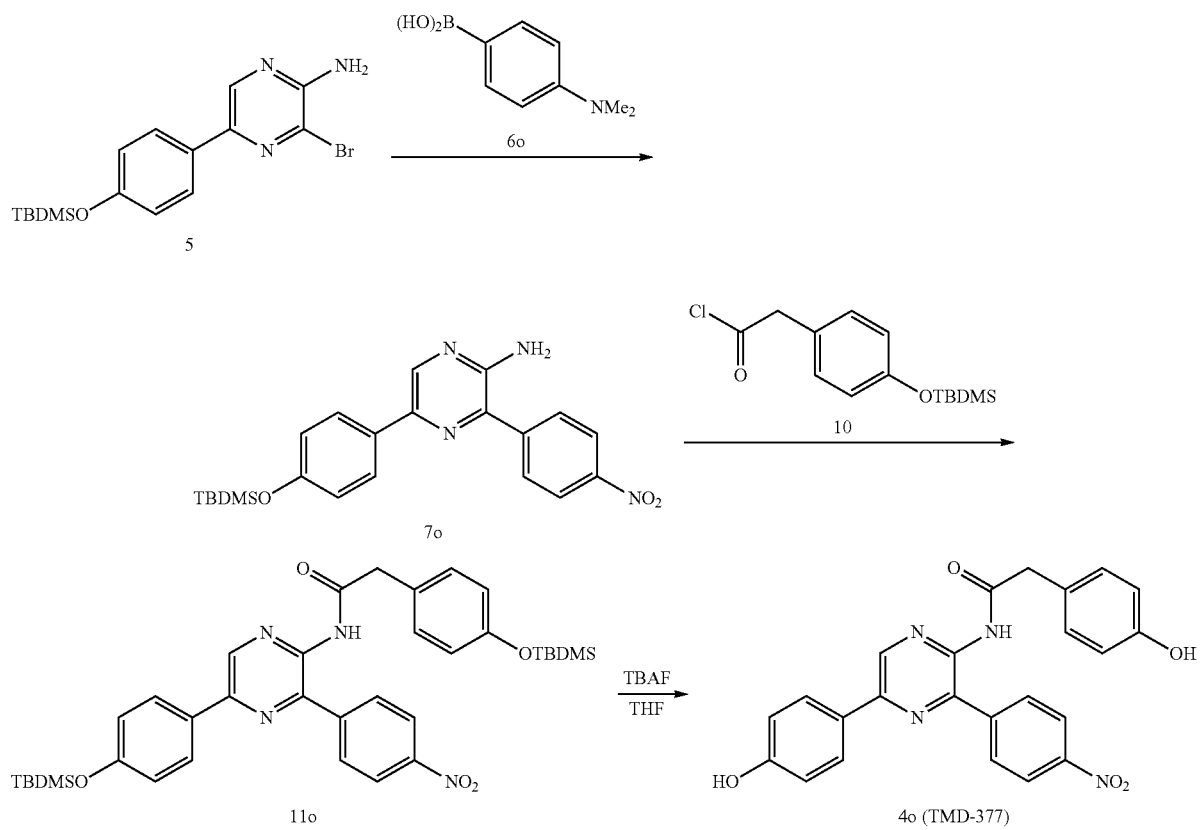

5-[4-(tert-Butyldimethylsilyloxy)phenyl]-3-(4-nitrophenyl)pyrazin-2-amine (7o)

Under an argon atmosphere, to a solution of 3-bromo-5-[4-(tert-butyldimethylsilyloxy)phenyl]pyrazin-2-amine (5) (500 mg, 1.31 mmol) in toluene (15 mL) and ethanol (600 μL) were successively added p-nitrophenylboronic acid (6o) (263 mg, 1.58 mmol), dichlorobis(triphenylphosphine)palladium (II) (56.1 mg, 79.9 μmol) and 1 M $Na_2CO_3$ aqueous solution (1.40 mL, 1.40 mmol) at room temperature, followed by heating to reflux for 22 hours. After cooling to room temperature, to the mixture was added water and the metal catalyst was removed by filtration. The product was extracted with ethyl acetate (100 mL×3). The combined organic extract was washed successively with water (200 mL) and brine (300 mL), followed by drying over anhydrous sodium sulfate. After filtration and concentration under reduced pressure, the residue was purified by column chromatography (silica gel 50 g, n-hexane/ethyl acetate=3/1) to give Compound 7o (451 mg, 1.07 mmol, 81.2%) as a yellow solid. $R_f$=0.19 (n-hexane/ethyl acetate=3/1); $^1$H NMR (400 MHz, DMSO-$d_6$) δ 0.17 (s, 6H), 0.92 (s, 9H), 6.48 (s, 2H), 6.85-6.92 (AA'BB', 2H), 7.82-7.92 (AA'BB', 21H), 8.02-8.10 (AA'BB', 2H), 8.26-8.36 (AA'BB', 2H), 8.55 (s, 1H); $^{13}$C NMR (67.8 MHz, DMSO-$d_6$) δ -4.5 (2C), 18.0, 25.6 (3C), 120.1 (2C), 123.8 (2C), 126.5 (2C), 129.5 (2C), 130.0, 134.8, 138.8, 140.1, 144.3, 146.9, 151.8, 155.2; IR (KBr, cm$^{-1}$) 476, 511, 635, 700, 727, 806, 839, 913, 1026, 1084, 1169, 1213, 1279, 1348, 1402, 1464, 1516, 1603, 1643, 2859, 2951, 3142, 3300, 3372.

2-[4-(tert-Butyldimethylsilyloxy)phenyl]-N-[5-{4-(tert-butyldimethylsilyloxy)phenyl}-3-(4-nitrophenyl)pyrazin-2-yl]acetamide (11o)

Under an argon atmosphere, to a solution of 2-[4-(tert-butyldimethylsilyloxy)phenyl]acetic acid (9) (1.00 g, 3.76 mmol) in $CH_2Cl_2$ (10 mL) was added DMF (3 drops) by a Pasteur pipette at room temperature. To this was added oxalyl dichloride (640 μL, 7.56 mmol) at 0° C. and the mixture was stirred for 30 minutes while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 5-[4-(tert-butyldimethylsilyloxy)phenyl]-3-(4-nitrophenyl)pyrazin-2-amine (7o) (317 mg, 751 μmol) and 4-(dimethylamino)pyridine (15.3 mg, 125 μmol) dissolved in anhydrous pyridine (15 mL) was added 2-[4-(tert-butyldimethylsilyl oxy)phenyl]acetyl chloride (10) prepared above at 0° C. and the mixture was heated with stirring at 50° C. for 20 hours. After cooling to room temperature, to this was added water and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=2/1) to give Compound 11o (242 mg, 361 mol, 48.1%) as a yellow solid. $R_f$=0.30 (n-hexane/ethyl acetate=2/1); $^1$H NMR (400 MHz, DMSO-$d_6$) δ 0.15 (s, 6H), 0.20 (s, 6H), 0.92 (s, 9H), 0.93 (s, 9H), 3.44 (s, 2H), 6.67-6.74 (AA'BB', 2H), 6.94-7.07 (2AA'BB', 411), 7.80-7.86 (AA'BB', 2H), 8.01-8.12 (2AA'BB', 4H), 9.05 (s, 1H), 10.85 (s, 1H); $^{13}$C NMR (67.8 MHz, DMSO-$d_6$) δ -4.5 (2C), -4.6 (2C), 17.9, 18.0, 25.50 (3C), 25.51 (3C), 41.6, 119.4 (2C), 120.4 (2C), 123.2 (2C), 127.4, 128.2, 128.52 (2C), 128.54 (2C), 130.4 (2C), 138.7, 143.0, 144.5, 145.0, 146.9, 147.9, 153.9, 156.9, 168.9; IR (KBr, cm$^{-1}$) 700, 741, 781, 839, 914, 1169, 1265, 1348, 1443, 1508, 1603, 1670, 2857, 2930, 2955.

2-(4-Hydroxyphenyl)-N-[5-(4-hydroxyphenyl)-3-(4-nitrophenyl)pyrazin-2-yl]acetamide (4o, TMD-377)

To a solution of 2-[4-(tert-butyldimethylsilyloxy)phenyl]-N-[5-{4-(tert-butyldimethylsilyloxy)phenyl}-3-(4-nitrophenyl)pyrazin-2-yl]acetamide (11o) (179 mg, 267 μmol) in THF (5 mL) was added tetrabutylammonium fluoride (1.0 M TI-IF solution) (1.40 mL, 1.40 mmol) at 0° C. and the mixture was stirred for 30 minutes while elevating to room temperature. To the mixture was added saturated $NH_4Cl$ aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ethyl acetate) to give Compound 4o (TMD-377) (98.0 mg, 222 mol, 83.0%) as an orange solid. $R_f$=0.48 (dichloromethane/methanol=9/1); HPLC retention time 7.4 min; $^1$H NMR (400 MHz, DMSO-$d_6$) δ 3.40 (s, 2H), 6.60-6.69 (AA'BB', 2H), 6.86-6.93 (AA'BB', 2H), 6.93-7.03 (AA'BB', 2H), 7.81-7.89 (AA'BB', 2H), 8.00-8.10 (2AA'BB', 4H), 9.02 (s, 1H), 9.30 (s, 1H), 9.93 (s, 1H), 10.77 (s, 1H); $^{13}$C NMR (67.8 MHz, DMSO-$d_6$) δ 41.7, 115.0 (2C), 115.9 (2C), 123.2 (2C), 124.7, 126.1, 128.2 (2C), 128.6 (2C), 130.2 (2C), 138.4, 142.7, 144.5, 145.0, 146.9, 148.4, 156.3, 159.3, 169.2; IR (KBr, cm$^{-1}$) 534, 640, 696, 756, 799, 843, 1013, 1080, 1107, 1171, 1236, 1346, 1437, 1516, 1609, 1670, 3250.

2-16) TMD-378 (4p)

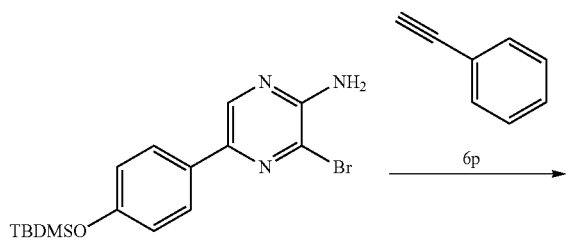

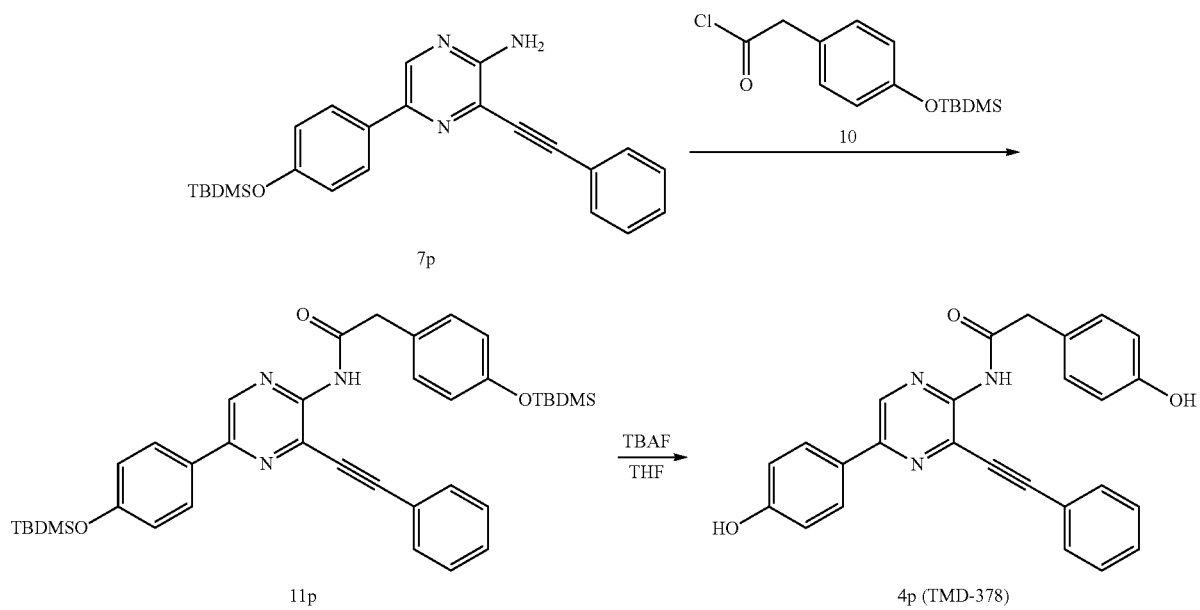

5-[4-(tert-Butyldimethylsilyloxy)phenyl]-3-(phenylethynyl)pyrazin-2-amine (7p)

Under an argon atmosphere, to a solution of 3-bromo-5-[4-(tert-butyldimethylsilyloxy)phenyl]pyrazin-2-amine (5) (1.50 g, 3.94 mmol) in diethylamine (20 mL) were successively added copper (1) iodide (450 mg, 2.36 mmol), phenylacetylene (6p) (900 μL, 8.19 mmol) and dichlorobis(triphenylphosphine)palladium (II) (139 mg, 198 μmol) at room temperature and the mixture was stirred for 4 hours. To this was added water and the metal catalyst was removed by filtration. The product was extracted with ethyl acetate (200 mL×3). The combined organic extract was washed successively with water (300 mL) and brine (300 mL), followed by drying over anhydrous sodium sulfate. After filtration and concentration under reduced pressure, the residue was purified by column chromatography (silica gel 100 g, n-hexane/ethyl acetate=3/1) to give Compound 7p (1.56 g, 3.89 mmol, 98.6%) as a brown solid. $R_f$=0.52 (n-hexane/ethyl acetate=3/1); $^1$H NMR (400 MHz, DMSO-$d_6$) δ 0.17 (s, 6H), 0.92 (s, 9H), 6.75 (s, 2H), 6.85-6.92 (AA'BB', 2H), 7.38-7.46 (m, 3H), 7.69-7.76 (m, 2H), 7.76-7.83 (AA'BB', 2H), 8.50 (s, 1H); $^{13}$C NMR (67.8 MHz, DMSO-$d_6$) δ −4.5 (2C), 17.9, 25.5 (3C), 85.4, 94.2, 120.1 (2C), 121.6, 121.8, 126.5 (2C), 128.6 (2C), 129.3, 129.9, 131.9 (2C), 138.8, 140.0, 154.8, 155.2; IR (KBr, cm$^{-1}$) 529, 638, 689, 754, 781, 806, 824, 912, 1009, 1049, 1070, 1144, 1169, 1258, 1323, 1362, 1420, 1454, 1510, 1562, 1605, 2212, 2857, 2928, 2955, 3057, 3173, 3296, 3474.

2-[4-(tert-Butyldimethylsilyloxy)phenyl]-N-[5-{4-(tert-butyldimethylsilyloxy)phenyl}-3-(phenylethynyl)pyrazin-2-yl]acetamide (11p)

Under an argon atmosphere, to a solution of 2-[4-(tert-butyldimethylsilyloxy)phenyl]acetic acid (9) (1.00 g, 3.76 mmol) in CH$_2$Cl$_2$ (10 mL) was added DMF (3 drops) by a Pasteur pipette at room temperature. To this was added oxalyl dichloride (640 μL, 7.56 mmol) at 0° C. and the mixture was stirred for 30 minutes while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 5-[4-(tert-butyldimethylsilyloxy)phenyl]-3-(phenylethynyl)pyrazin-2-amine (7p) (300 mg, 747 μmol) and 4-(dimethylamino)pyridine (13.8 mg, 113 μmol) dissolved in anhydrous pyridine (15 mL) was added 2-[4-(tert-butyldimethylsilyl oxy)phenyl]acetyl chloride (10) prepared above at 0° C. and the mixture was heated with stirring at 50° C. for 20 hours. After cooling to room temperature, to this was added water and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=3/1) to give Compound 11p (291 mg, 448 μmol, 60.0%) as a brown solid. $R_f$=0.19 (n-hexane/ethyl acetate=3/1); $^1$H NMR (400 MHz, DMSO-$d_6$) δ 0.10 (s, 6H), 0.20 (s, 6H), 0.90 (s, 9H), 0.93 (s, 9H), 3.65 (s, 2H), 6.63-6.73 (AA'BB', 2H), 6.92-7.02 (AA'BB', 2H), 7.17-7.27 (AA'BB', 2H), 7.33-7.48 (m, 5H), 7.96-8.05 (AA'BB', 2H), 8.99 (s, 1H), 10.69 (s, 1H); $^{13}$C NMR (67.8 MHz, DMSO-$d_6$) 8-4.60 (2C), −4.61 (2C), 17.8, 17.9, 25.5 (6C), 41.7, 85.8, 94.5, 119.5 (2C), 120.4 (2C), 121.2, 128.2, 128.28 (2C), 128.34, 128.6 (2C), 129.5, 130.3 (2C), 131.8 (2C), 133.1, 138.5, 146.6, 148.0, 153.8, 156.9, 169.4; IR (KBr, cm$^{-1}$) 530, 689, 756, 781, 839, 914, 1007, 1125, 1169, 1258, 1379, 1433, 1510, 1605, 1672, 2214, 2857, 2930, 2955, 3235.

2-(4-Hydroxyphenyl)-N-[5-(4-hydroxyphenyl)-3-(phenylethynyl)pyrazin-2-yl]acetamide (4p, TMD-378)

To a solution of 2-[4-(tert-butyldimethylsilyloxy)phenyl]-N-[5-{4-(tert-butyldimethylsilyloxy)phenyl}-3-(phenylethynyl)pyrazin-2-yl]acetamide (11p) (198 mg, 305 µmol) in THF (5 mL) was added tetrabutylammonium fluoride (1.0 M THF solution) (1.60 mL, 1.60 mmol) at 0° C., and the mixture was stirred for 30 minutes while elevating to room temperature. To the mixture was added saturated NH$_4$Cl aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ethyl acetate) to give Compound 4p (TMD-378) (93.8 mg, 223 µmol, 73.1%) as a yellow solid. R$_f$=0.48 (dichloromethane/methanol=9/1); HPLC retention time 10.0 min; $^1$H NMR (400 MHz, DMSO-d$_6$) δ 3.58 (s, 2H), 6.60-6.70 (AA'BB', 2H), 6.83-6.93 (AA'BB', 2H), 7.10-7.19 (AA'BB', 2H), 7.24-7.33 (m, 3H), 7.33-7.49 (m, 2H), 7.91-7.98 (AA'BB', 2H), 8.94 (s, 1H), 9.27 (s, 1H), 9.92 (s, 1H), 10.60 (s, 1H); $^{13}$C NMR (67.8 MHz, DMSO-d$_6$) δ 41.8, 86.0, 94.4, 115.2 (2C), 115.9 (2C), 121.2, 125.6, 125.9, 128.3 (2C), 128.7 (2C), 129.7, 130.3 (2C), 131.9 (2C), 133.2, 138.3, 146.3, 148.6, 156.2, 1159.4, 169.7; IR (KBr, cm$^{-1}$) 530, 615, 687, 758, 793, 839, 962, 1125, 1157, 1177, 1219, 1267, 1327, 1389, 1456, 1489, 1582, 1684, 2212, 3231, 3391.

2-17) Compound 4q

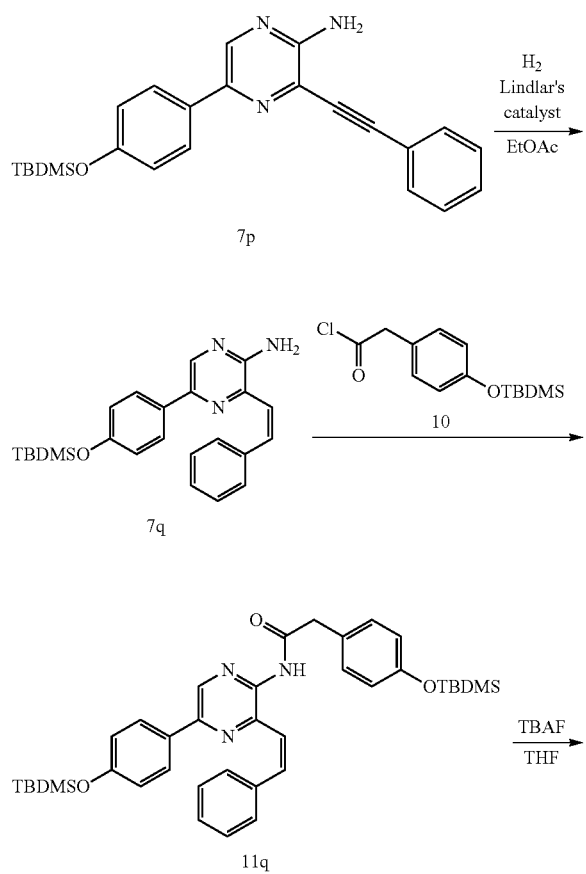

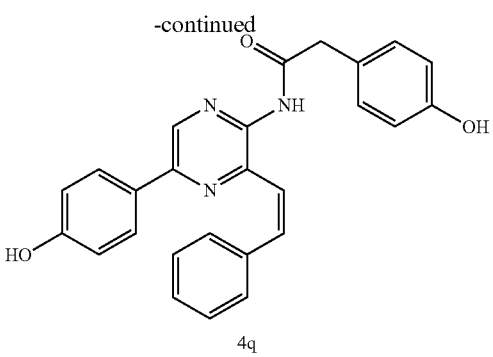

(Z)-5-[4-(tert-Butyldimethylsilyloxy)phenyl]-3-styrylpyrazin-2-amine (7q)

Under an argon atmosphere, to a solution of 5-[4-(tert-butyldimethylsilyloxy)phenyl]-3-(phenylethynyl)pyrazin-2-amine (7p) (100 mg, 249 µmol) in ethyl acetate (5 mL) was added Lindlar's catalyst (10% Pd) (40.0 mg) at room temperature. The atmosphere in the reaction flask was replaced with hydrogen gas and the mixture was stirred at room temperature for 30 hours. After replacing the atmosphere of the reaction system again with argon, to the mixture was added dichloromethane (15 mL) and stirred at room temperature for an hour. After removing the catalyst by filtration, the filtrate was washed successively with water (100 mL) and brine (200 mL), followed by drying over anhydrous sodium sulfate. After filtration and concentration under reduced pressure, the residue was purified by column chromatography (silica gel 10 g, n-hexane/ethyl acetate=3/1) to give the mixture of Compounds 7q, 7p and 7r (98.2 mg) as a brown oil.

(Z)-2-[4-(tert-Butyldimethylsilyloxy)phenyl]-N-{5-[4-(tert-butyldimethylsilyloxy)phenyl]-3-styrylpyrazin-2-yl}acetamide (11q)

Under an argon atmosphere, to a solution of 2-[4-(tert-butyldimethylsilyloxy)phenyl]acetic acid (9) (170 mg, 638 µmol) in CH$_2$Ch (5 mL) was added DMF (1 drop) by a Pasteur pipette at room temperature. To this was added oxalyl dichloride (110 µL, 1.30 mmol) at 0° C. and the mixture was stirred for 30 minutes while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to the mixture (50.3 mg) of 7q, 7p and 7r and 4-(dimethylamino)pyridine (3.0 mg, 25 µmol) dissolved in anhydrous pyridine (5 mL) was added 2-[4-(tert-butyldimethylsilyloxy)phenyl]acetyl chloride (10) prepared above at 0° C. and the mixture was heated with stirring at 50° C. for 20 hours. After cooling to room temperature, to this was added water and the product was extracted with ethyl acetate (30 mL×3). The combined organic extract was washed successively with water (50 mL) and brine (100 mL), followed by drying over anhydrous sodium sulfate. After filtration and concentration under reduced pressure, the residue was purified by column chromatography (silica gel 10 g, n-hexane/ethyl acetate=3/1) to give the mixture (60.0 mg) of Compounds 11q, 11p and 11r as a yellow oily substance. R$_f$=0.20 (n-hexane/ethyl acetate=3/1).

Compound 4q can be prepared by deprotecting the TBDMS group from Compound 11q described above according to modifications of the process described in SYNTHESIS EXAMPLES of the other CTMD analogs.

2-18) TMD-379 (4r)

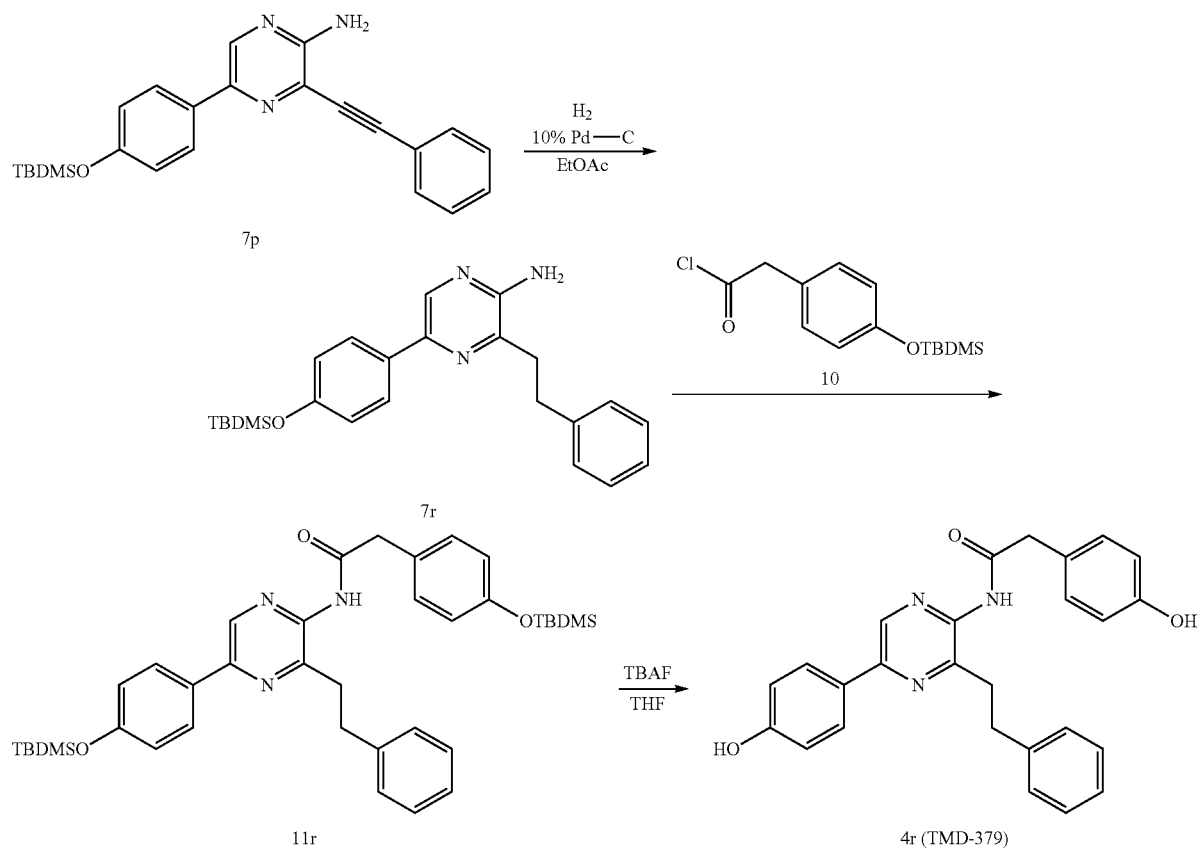

5-[4-(tert-Butyldimethylsilyloxy)phenyl]-3-phenethylpyrazin-2-amine (7r)

Under an argon atmosphere, to a solution of 5-[4-(tert-butyldimethylsilyloxy)phenyl]-3-(phenylethynyl)pyrazin-2-amine (7p) (400 mg, 996 μmol) in ethyl acetate (20 mL) was added Palladium/charcoal activated (10% Pd) (80.0 mg) at room temperature. The atmosphere in the reaction flask was replaced with hydrogen gas and the mixture was stirred at room temperature for 3 hours. After replacing the atmosphere of the reaction system again with argon, to the mixture was added dichloromethane (15 mL) and stirred at room temperature for an hour. The catalyst was removed by filtration. After concentration under reduced pressure, the residue was purified by column chromatography (silica gel 40 g, n-hexane/ethyl acetate=2/1) to give Compound 7r (403 mg, 994 μmol, 99.8%) as a brown oily substance. $R_f$=0.48 (n-hexane/ethyl acetate=2/1); $^1$H NMR (400 MHz, DMSO-d$_6$) δ 0.18 (s, 6H), 0.93 (s, 9H), 2.92 (t, 3H, J=8.0 Hz), 3.05 (t, 3H, J=8.0 Hz), 6.25 (s, 2H), 6.81-6.90 (AA'BB', 2H), 7.10-7.18 (m, 1H), 7.18-7.35 (m, 4H), 7.75-7.85 (AA'BB', 2H), 8.27 (s, 1H); $^{13}$C NMR (67.8 MHz, DMSO-d$_6$) δ −4.5 (2C), 18.0, 25.6 (3C), 31.7, 34.0, 120.0 (2C), 125.7, 126.1 (2C), 128.2 (2C), 128.5 (2C), 130.9, 135.6, 138.5, 140.1, 141.9, 152.3, 154.6; IR (KBr, cm$^{-1}$) 507, 635, 677, 698, 750, 781, 841, 914, 1009, 1103, 1146, 1167, 1213, 1254, 1389, 1420, 1454, 1512, 1605, 2857, 2928, 2955, 3061, 3318.

2-[4-(tert-Butyldimethylsilyloxy)phenyl]-N-[5-{4-(tert-butyldimethylsilyloxy)phenyl}-3-phenethylpyrazin-2-yl]acetamide (11r)

Under an argon atmosphere, to a solution of 2-[4-(tert-butyldimethylsilyloxy)phenyl]acetic acid (9) (1.40 g, 5.26 mmol) in CH$_2$Cl$_2$ (10 mL) was added DMF (3 drops) by a Pasteur pipette at room temperature. To this was added oxalyl dichloride (890 μL, 10.5 mmol) at 0° C. and the mixture was heated with stirring for 30 minutes while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 5-[4-(tert-butyldimethylsilyloxy)phenyl]-3-phenethylpyrazin-2-amine (7r) (403 mg, 994 μmol) and 4-(dimethylamino)pyridine (19.6 mg, 160 μmol) dissolved in anhydrous pyridine (15 mL) was added 2-[4-(tert-butyldimethylsilyloxy)phenyl]acetyl chloride (10) prepared above at 0° C. and the mixture was heated with stirring at 50° C. for 20 hours. After cooling to room temperature, to this was added water and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=3/1) to give Compound 11r (298 mg, 455 μmol, 45.8%) as a yellow oily substance. $R_f$=0.44 (n-hexane/ethyl acetate=2/1); $^1$H NMR (400 MHz, DMSO-d$_6$) 0.12 (s, 6H), 0.20 (s, 6H), 0.91 (s, 9H), 0.93 (s, 9H), 2.83 (t, 1H, J=8.4 Hz), 2.94 (t, 1H, J=8.4 Hz), 3.59 (s, 2H), 6.72-6.79 (AA'BB', 2H), 6.92-7.00 (AA'BB', 2H), 7.01-7.07 (AA'BB', 2H), 7.07-7.15 (m, 1H), 7.16-7.24 (m, 4H), 7.97-8.05 (AA'BB', 2H), 8.81 (s, 1H), 10.44 (s, 1H); 13C NMR (67.8 MHz, DMSO-d$_6$) 8-4.5 (2C), −4.6 (2C), 17.9, 18.0, 25.6 (6C), 32.8, 34.7, 41.7, 119.6 (2C), 120.3 (2C), 125.7, 128.1 (2C), 128.2 (4C), 128.5, 129.1, 130.2 (2C), 130.3, 136.6, 141.4, 143.8, 147.9, 150.6, 153.8, 156.6, 170.3; IR (KBr, cm$^{-1}$) 525, 698, 781, 839, 914, 1007, 1169, 1258, 1362, 1416, 1443, 1510, 1605, 1661, 2857, 2930, 2955, 3225.

2-(4-Hydroxyphenyl)-N-[5-(4-hydroxyphenyl)-3-phenethylpyrazin-2-yl]acetamide (4r, TMD-379)

To a solution of 2-[4-(tert-butyldimethylsilyloxy)phenyl]-N-[5-{4-(tert-butyldimethylsilyloxy)phenyl}-3-phenethylpyrazin-2-yl]acetamide (11r) (197 mg, 301 µmol) in THF (5 mL) was added tetrabutylammonium fluoride (1.0 M THF solution) (1.50 mL, 1.50 mmol) at 0° C. and the mixture was stirred for 30 minutes while elevating to room temperature. To the mixture was added saturated NH$_4$Cl aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ethyl acetate) to give Compound 4r (TMD-379) (100 mg, 236 µmol, 78.3%) as a yellow solid. R$_f$=0.44 (dichloromethane/methanol=9/1); HPLC retention time 9.5 min; 1H NMR (400 MHz, DMSO-d$_6$) δ 2.81 (t, I H, J=8.0 Hz), 2.92 (t, 1H, J=8.0 Hz), 3.52 (s, 2H), 6.62-6.72 (AA'BB', 2H), 6.80-6.90 (AA'BB', 2H), 6.98-7.05 (AA'BB', 2H), 7.07-7.16 (m, 3H), 7.16-7.24 (m, 2H), 7.90-7.98 (AA'BB', 2H), 8.76 (s, 1H), 9.27 (s, 1H), 9.83 (s, 1H), 10.35 (s, 1H); $^{13}$C NMR (67.8 MHz, DMSO-d$_6$) δ 33.0, 34.8, 41.7, 115.2 (2C), 115.8 (2C), 125.8, 126.6, 128.1 (2C), 128.26 (2C), 128.29 (2C), 128.6, 130.1 (2C), 136.4, 141.5, 143.4, 148.5, 150.7, 156.2, 159.0, 170.6; IR (KBr, cm$^{-1}$) 519, 606, 692, 839, 966, 1157, 1223, 1265, 1373, 1452, 1516, 1595, 1674, 3273.

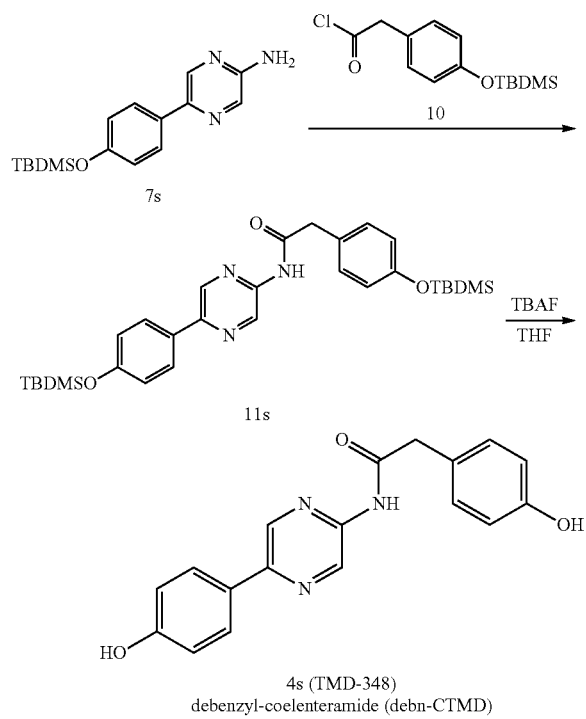

2-[4-(tert-Butyldimethylsilyloxy)phenyl]-N-[5-{4-(tert-butyldimethylsilyloxy)phenyl}pyrazin-2-yl] acetamide (11s)

Under an argon atmosphere, to a solution of 2-[4-(tert-butyldimethylsilyloxy)phenyl]acetic acid (9) (1.55 g, 5.82 mmol) in CH$_2$Cl$_2$ (10 mL) was added DMF (3 drops) by a Pasteur pipette at room temperature. To this was added oxalyl dichloride (1.00 mL, 11.8 mmol) at 0° C. and the mixture was stirred for an hour while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to a mixture of 5-[4-(tert-butyldimethylsilyloxy)phenyl]pyrazin-2-amine (7s) (350 mg, 1.16 mmol) and 4-(dimethylamino)pyridine (15.0 mg, 123 µmol) dissolved in anhydrous pyridine (20 mL) was added 2-[4-(tert-butyldimethylsilyloxy)phenyl]acetyl chloride (10) prepared above at 0° C. and the mixture was heated with stirring at 50° C. for 20 hours. After cooling to room temperature, to this was added water and the product was extracted with ethyl acetate (200 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=7/1) to give Compound 11s (478 mg, 869 µmol, 74.8%) as a yellow foamy solid. R$_f$=0.19 (n-hexane/ethyl acetate=6/1); $^1$H NMR (400 MHz, DMSO-d$_6$) δ 0.14 (s, 6H), 0.19 (s, 6H), 0.91 (s, 9H), 0.94 (s, 9H), 3.66 (s, 2H), 6.75-6.82 (AA'BB', 2H), 6.91-6.97 (AA'BB', 2H), 7.17-7.24 (AA'BB', 2H), 7.93-8.00 (AA'BB', 2H), 8.90 (d, 1H, J=1.4 Hz), 9.28 (d, 1H, J=1.4 Hz), 10.99 (s, 1H); $^{13}$C NMR (75.5 MHz, DMSO-d$_6$) δ −4.6 (4C), 17.8, 17.9, 25.46 (3C), 25.47 (3C), 41.8, 119.6 (2C), 120.2 (2C), 127.5 (2C), 128.2, 129.2, 130.4 (2C), 134.9, 138.7, 146.3, 147.0, 153.8, 156.2, 170.3; IR (KBr, cm$^{-1}$) 417, 517, 575, 638, 681, 708, 781, 806, 839, 914, 1009, 1051, 1103, 1167, 1260, 1354, 1416, 1468, 1508, 1545, 1605, 1670, 2857, 2886, 2930, 2955, 3034, 3063; HRMS (ESI$^+$) m/z 550.2930 ([M+H]$^+$, C$_{30}$H$_{44}$N$_3$O$_3$Si$_2$$^+$ requires 550.2916).

2-(4-Hydroxyphenyl)-N-[5-(4-hydroxyphenyl) pyrazin-2-yl]acetamide (4s, TMD-348)

To a solution of 2-[4-(tert-butyldimethylsilyloxy)phenyl]-N-[5-(4-(tert-butyldimethylsilyloxy)phenyl) pyrazin-2-yl] acetamide (11s) (300 mg, 546 µmol) in THF (5 mL) was added tetrabutylammonium fluoride (1.0 M THF solution) (2.80 mL, 2.80 mmol) at 0° C. and the mixture was stirred for an hour while elevating to room temperature. To the mixture was added saturated NH$_4$Cl aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ethanol) to give Compound 4s (TMD-348) (191 mg, 422 µmol, 95.8%) as a brown solid. R$_f$=0.51 (dichloromethane/methanol=9/1); HPLC retention time 4.9 min; $^1$H NMR (400 MHz, DMSO-d$_6$) δ 3.57 (s, 1H), 6.62-6.70 (AA'BB', 2H), 6.79-6.84 (AA'BB', 2H), 7.06-7.12 (AA'BB', 2H), 7.83-7.92 (AA'BB', 2H), 8.82 (d, 1H, J=1.4 Hz), 9.22 (d, 11, J=1.4 Hz), 9.23 (s, 1H), 9.75 (s, 1H), 10.86 (s, 1H); $^{13}$C NMR (75.5 MHz, DMSO-d$_6$) δ 41.9, 115.2 (2C), 115.8 (2C), 125.7, 126.8, 127.7 (2C), 130.3 (2C), 134.9, 138.4, 146.7, 146.9, 156.3, 158.7, 170.7; IR (KBr, cm$^{-1}$) 419, 519, 613, 681, 804, 837, 910, 1020, 1051, 1107, 1171, 1252, 1356, 1443, 1508, 1541, 1611, 1676, 3026, 3354; HRMS (FAB$^+$/glycerol) m/z 322.1187 ([M+H]+, $C_{18}H_{16}N_3O_3^+$ requires 322.1192).

2-20) TMD-349 (4t)

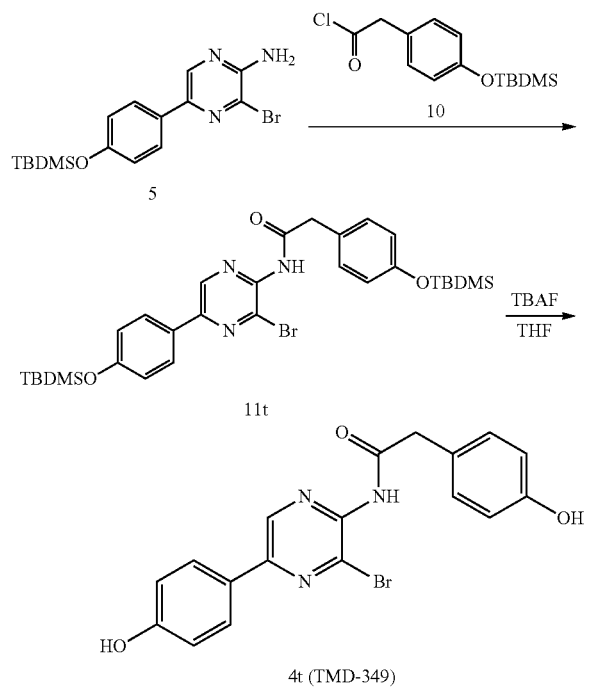

N-[3-Bromo-5-{4-(tert-butyldimethylsilyloxy)phenyl}pyrazin-2-yl]-2-[4-(tert-butyldimethylsilyloxy)phenyl]acetamide (11t)

Under an argon atmosphere, to a solution of 2-[4-(tert-butyldimethylsilyloxy)phenyl]acetic acid (9) (1.55 g, 5.82 mmol) in $CH_2Cl_2$ (10 mL) was added DMF (3 drops) by a Pasteur pipette at room temperature. To this was added oxalyl dichloride (1.00 mL, 11.8 mmol) at 0° C. and the mixture was stirred for an hour while elevating to room temperature. The mixture was concentrated under reduced pressure to give crude 2-[4-(tert-butyldimethylsilyloxy)phenyl]acetyl chloride (10) as a colorless oil, which was used in the following reaction without further purification.

Under an argon atmosphere, to the mixture of 3-bromo-5-[4-(tert-butyldimethylsilyloxy)phenyl]pyrazin-2-amine (5) (443 mg, 1.16 mmol) and 4-(dimethylamino)pyridine (15.2 mg, 124 μmol) dissolved in anhydrous pyridine (20 mL) was added 2-[4-(tert-butyldimethylsilyloxy)phenyl]acetyl chloride (10) prepared above at 0° C. and the mixture was heated with stirring at 50° C. for 19 hours. After cooling to room temperature, to this was added water and the product was extracted with ethyl acetate (200 mL×3). The combined organic extract was washed successively with water (200 mL) and brine (200 mL), followed by drying over anhydrous sodium sulfate. After filtration and concentration under reduced pressure, the residue was purified by column chromatography (silica gel 50 g, n-hexane/ethyl acetate=4/1) to give Compound 1 It (431 mg, 685 I mol, 58.9%) as a yellow foamy solid. R$_f$=0.22 (n-hexane/diethyl ether=1/1); $^1$H NMR (400 MHz, DMSO-d$_6$) δ 0.15 (s, 6H), 0.21 (s, 611), 0.91 (s, 9H), 0.94 (s, 9H), 3.61 (s, 2H), 6.74-6.82 (AA'BB', 2H), 6.94-7.01 (AA'BB', 21-1), 7.16-7.23 (AA'BB', 2H), 7.94-8.01 (AA'BB', 2H), 9.03 (s, 1H), 10.54 (s, 1H); $^{13}$C NMR (75.5 MHz, DMSO-d$_6$) 8-4.6 (4C), 17.89, 17.93, 25.46 (3C), 25.52 (3C), 41.5, 119.6 (2C), 120.5 (2C), 127.3, 128.1, 128.4 (2C), 130.4 (2C), 136.3, 138.0, 144.6, 149.1, 153.8, 157.2, 169.8; IR (KBr, cm$^{-1}$) 467, 521, 623, 685, 716, 781, 802, 839, 914, 1007, 1047, 1078, 1107, 1169, 1256, 1333, 1362, 1412, 1441, 1474, 1508, 1566, 1605, 1672, 2857, 2886, 2930, 2955, 3032, 3057, 3231; HRMS (ESI$^+$) m/z 650.1839 ([M+Na]$^+$, $C_{30}H_{42}BrN_3NaO_3Si_2^+$ requires 650.1840).

N-[3-Bromo-5-(4-hydroxyphenyl)pyrazin-2-yl]-2-(4-hydroxyphenyl)acetamide (4t, TMD-349)

To a solution of N-[3-bromo-5-{4-(tert-butyldimethylsilyloxy)phenyl}pyrazin-2-yl]-2-[4-(tert-butyldimethylsilyloxy)phenyl]acetamide (11 t) (290 mg, 461 μmol) in THE (5 mL) was added tetrabutylammonium fluoride (1.0 M THF solution) (2.30 mL, 2.30 mmol) at 0° C., and the mixture was stirred for an hour while elevating to room temperature. To the mixture was added saturated NH$_4$Cl aqueous solution (50 mL) and the product was extracted with ethyl acetate (100 mL×3). The combined organic extract was washed successively with water (200 mL) and brine (200 mL), followed by drying over anhydrous sodium sulfate. After filtration and concentration under reduced pressure, the residue was recrystallized (n-hexane/ethanol) to give Compound 4t (TMD-349) (147 mg, 367 μmol, 79.5%) as a brown solid. R$_f$=0.50 (dichloromethane/methanol=9/1); HPLC retention time 5.5 min; $^1$H NMR (400 MHz, DMSO-d$_6$) δ 3.54 (s, 2H), 6.65-6.71 (AA'BB', 2H), 6.83-6.89 (AA'BB', 2H), 7.08-7.14 (AA'BB', 2H), 7.87-7.95 (AA'BB', 2H), 8.97 (s, 1H), 9.25 (s, 1H), 10.00 (s, 1H), 10.45 (s, 1H); 13C NMR (75.5 MHz, DMSO-d$_6$) G 41.5, 115.2 (2C), 116.0 (2C), 124.8, 125.4, 128.5 (2C), 130.3 (2C), 136.6, 137.7, 144.2, 149.8, 156.2, 159.8, 170.2; IR (KBr, cm$^{-1}$) 519, 623, 795, 839, 1047, 1080, 1173, 1229, 1271, 1339, 1449, 1483, 1516, 1609, 1676, 3275; HRMS (ESI$^+$) m/z 422.0119 ([M+Na]$^+$, $C_{18}H_{14}BrN_3NaO_3^+$ requires 422.0111).

Synthesis Example 3

Coelenteramide (CTMD) Analogues Modified at the C-2 Position 3-1) TMD-331 (4u)

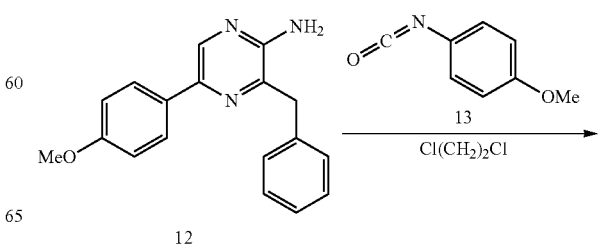

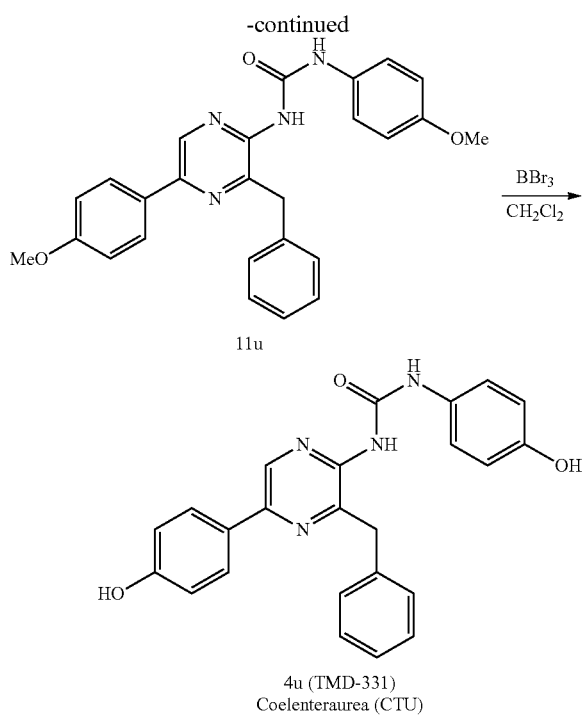

1-[3-Benzyl-5-(4-methoxyphenyl)pyrazin-2-yl]-3-(4-methoxyphenyl)urea (11u)

Under an argon atmosphere, to a solution of 3-benzyl-5-(4-methoxyphenyl)pyrazin-2-amine (12) (synthesized by the process of M. Adamczyk, et al., Org. Prep. Proced Int., 33, 477-485 (2001)) (306 mg, 1.05 mmol) in anhydrous 1,2-dichloroethane (10 mL) was added 4-methoxyphenyl isocyanate (13) (191 L, 1.00 mmol) at room temperature, and the mixture was heated with stirring at 80° C. for 19 hours. After cooling to room temperature, the solid precipitated was collected by filtration and dried in vacuo to give the crude product (293 mg, <664 µmol, <63.2%) as a colorless solid. An aliquot (93.0 mg, <211 µmol) was recrystallized from methanol to give Compound 11u (54.9 mg, 125 µmol, 59.2%) as a colorless solid. $R_f$=0.50 (n-hexane/ethyl acetate=1/1); $^1$H NMR (400 MHz, DMSO-$d_6$) δ 3.73 (s, 3H), 3.81 (s, 3H), 4.36 (s, 2H), 6.98-6.93 (AA'BB', 2H), 7.02-7.08 (AA'BB', 2H), 7.17-7.25 (m, 1H), 7.28-7.32 (m, 4H), 7.43-7.48 (AA'BB', 2H), 7.95-8.01 (AA'BB', 2H), 8.79 (s, 1H), 9.04 (s, 1H), 10.58 (s, 1H); $^{13}$C NMR (67.8 MHz, DMSO-$d_6$) δ 38.5, 55.18, 55.24, 114.0 (2C), 114.4 (2C), 121.1 (2C), 126.3, 127.2 (2C), 128.2, 128.3 (2C), 129.0 (2C), 131.7, 134.5, 137.9, 144.4, 145.0, 145.4, 152.2, 155.1, 160.1; IR (KBr, cm$^{-1}$) 704, 746, 824, 1038, 1173, 1242, 1329, 1369, 1416, 1481, 1510, 1570, 1607, 1668, 2833, 3030, 3261; Anal. Calcd. For $C_{26}H_{24}N_4O_3$: C, 70.89; H, 5.49; N, 12.72. Found: C, 70.66; H, 5.49; N, 12.61.

1-[3-Benzyl-5-(4-hydroxyphenyl)pyrazin-2-yl]-3-(4-hydroxyphenyl)urea (4u, TMD-331)

Under an argon atmosphere, to a solution of 1-[3-benzyl-5-(4-methoxyphenyl)pyrazin-2-yl]-3-(4-methoxy phenyl)urea (11u) (200 mg. 454 µmol) in anhydrous dichloromethane (10 mL) was added boron tribromide (1.0 M dichloromethane solution, 2.27 mL, 2.27 mmol) at room temperature, and the mixture was heated to reflux for 24 hours. After cooling to room temperature, to this was added saturated aqueous sodium bicarbonate solution and the mixture was concentrated under reduced pressure using a rotary evaporator to remove dichloromethane. The solid was collected by filtration and dried in vacuo to give the crude product (180 mg) as a colorless solid. The solid was recrystallized from ethyl acetate/methanol to give Compound 4u (TMD-331) (98.2 mg, 238 µmol, 52.4%) as a colorless solid. $R_f$=0.66 (n-hexane/ethyl acetate=1/2); $^1$H NMR (400 MHz, DMSO-$d_6$) δ 4.35 (s, 2H), 6.69-6.74 (AA'BB', 2H), 6.84-6.88 (AA'BB', 2H), 7.17-7.24 (m, 1H), 7.27-7.33 (m, 51H), 7.84-7.89 (AA'BB', 2H), 8.72 (s. 1H), 8.95 (s, 1H), 9.19 (s, 1H), 9.79 (s, 1H), 10.49 (s, 1H); $^{13}$C NMR (67.8 MHz, DMSO-$d_6$) δ 38.5, 115.3 (2C), 115.7 (2C), 121.5 (2C), 126.3, 126.7, 127.4 (2C), 128.4 (2C), 128.9 (2C), 130.1, 134.2, 138.0, 144.8, 145.2, 152.3, 153.3, 158.5; IR (KBr, cm$^{-1}$) 519, 637, 702, 750, 835, 1105, 1171, 1223, 1246, 1369, 1445, 1481, 1508, 1578, 1609, 1681, 3035, 3256; Anal. Calcd. For $C_{24}H_{20}N_4O_3$: C, 69.89; H, 4.89; N, 13.58. Found: C, 69.58; H, 5.05; N, 13.37.

3-2) TMD-332 (4v)

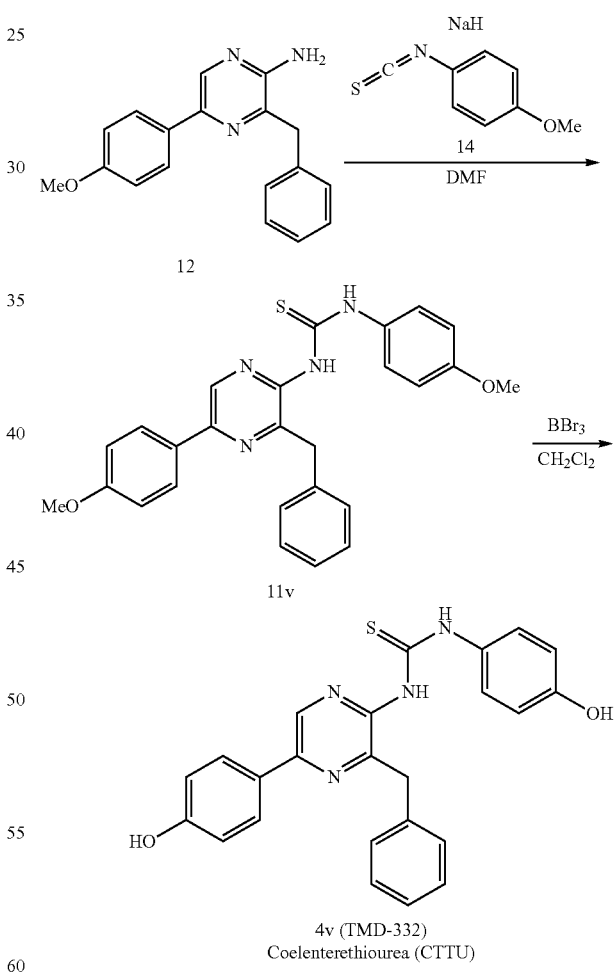

1-[3-Benzyl-5-(4-methoxyphenyl)pyrazin-2-yl]-3-(4-methoxyphenyl)thiourea (11v)

Under an argon atmosphere, to a solution of 3-benzyl-5-(4-methoxyphenyl)pyrazin-2-amine (12) (synthesized by the process of M. Adamczyk, et al., *Org. Prep. Proced. Int.*, 33, 477-485 (2001)) (291 mg, 1.00 mmol) in anhydrous DMF (5 mL) was added sodium hydride (43.6 mg, 1.00 mmol) at room temperature. To the mixture was added a solution of 4-methoxyphenyl isothiocyanate (14) (182 mg, 1.10 mmol) dissolved in anhydrous DMF (2 mL) at 0° C. and stirred for 5.5 hours at room temperature. To this was added aqueous 2 M HCl solution and the resulting solid was collected by filtration. The crude product was purified by column chromatography (silica gel 30 g, n-hexane/ethyl acetate/dichloromethane=57/3/40) to give the product as a yellow solid containing some impurities (327 mg, <716 μmol). The product was recrystallized from ethyl acetate to give Compound 11v (255 mg, 559 μmol, 55.9%) as a yellow solid. $R_f$=0.24 (n-hexane/ethyl acetate=4/1); $^1$H NMR (400 MHz, DMSO-$d_6$) δ 3.75 (s, 3H), 3.82 (s, 3H), 4.42 (s, 2H), 6.90-6.96 (AA'BB', 2H), 7.03-7.09 (AA'BB', 2H), 7.20-7.26 (m, 1H), 7.30-7.36 (m, 4H), 7.38-7.45 (AA'BB', 2H), 7.99-8.05 (AA'BB', 2H), 8.83 (s, 1H), 9.65 (s, 1H), 11.76 (br s, 1H); $^{13}$C NMR (67.8 MHz, DMSO-$d_6$) δ 38.9, 55.2 (2C), 113.7 (2C), 114.4 (2C), 126.2 (2C), 126.5, 127.5 (2C), 128.0, 128.5 (2C), 129.0 (3C), 131.6, 134.7, 137.5, 144.9, 145.7, 157.1, 160.4, 179.0; IR (KBr, cm$^{-1}$) 581, 700, 741, 799, 833, 897, 1022, 1070, 1146, 1248, 1283, 1333, 2037, 2351, 2835, 2988, 3395; Anal. Calcd. For $C_{26}H_{24}N_4O_2S$: C, 68.40; H, 5.30; N, 12.27. Found: C, 68.47; H, 5.20; N, 12.26.

1-[3-Benzyl-5-(4-hydroxyphenyl)pyrazin-2-yl]-3-(4-hydroxyphenyl)thiourea (4v, TMD-332)

Under an argon atmosphere, to a solution of 1-[3-benzyl-5-(4-methoxyphenyl)pyrazin-2-yl]-3-(4-methoxy phenyl)thiourea (11v) (136 mg, 299 μmol) in anhydrous dichloromethane (7 mL) was added boron tribromide (1.0 M dichloromethane solution, 1.50 mL, 1.50 mmol) at room temperature, and the mixture was heated to reflux for 18 hours. After cooling to room temperature, to this was added saturated aqueous sodium bicarbonate solution and the mixture was concentrated under reduced pressure using a rotary evaporator to remove dichloromethane. The solid was collected by filtration and dried in vacuo to give the crude product (126 mg) as an orange solid. The solid was recrystallized from ethyl acetate to give Compound 4v (TMD-332) (80.6 mg, 188 μmol, 62.9%) as an orange solid. $R_f$=0.48 (n-hexane/ethyl acetate 1/2); $^1$H NMR (400 MHz, DMSO-ds) δ 4.40 (s, 2H), 6.70-6.76 (AA'BB', 2H), 6.84-6.90 (AA'BB', 2H), 7.20-7.35 (m, 7H), 7.88-7.94 (AA'BB', 2H), 8.76 (s, 1H), 9.47 (s, 1H), 9.53 (s, 1H), 9.85 (s, 1H), 11.71 (br s, 1H); IR (KBr, cm$^{-1}$) 542, 584, 700, 741, 837, 1157, 1215, 1263, 1342, 1395, 1449, 1510, 1578, 1609, 2941, 3032, 3273, 3406; HRMS (ESI$^+$) m/z 429.1382 ([M+H]$^+$, $C_{24}H_{21}N_4O_2S^+$ requires 429.1380).

3-3) TMD-330 (4w)

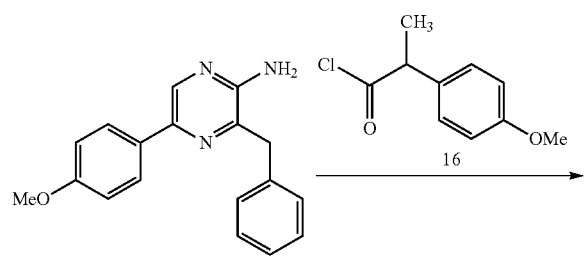

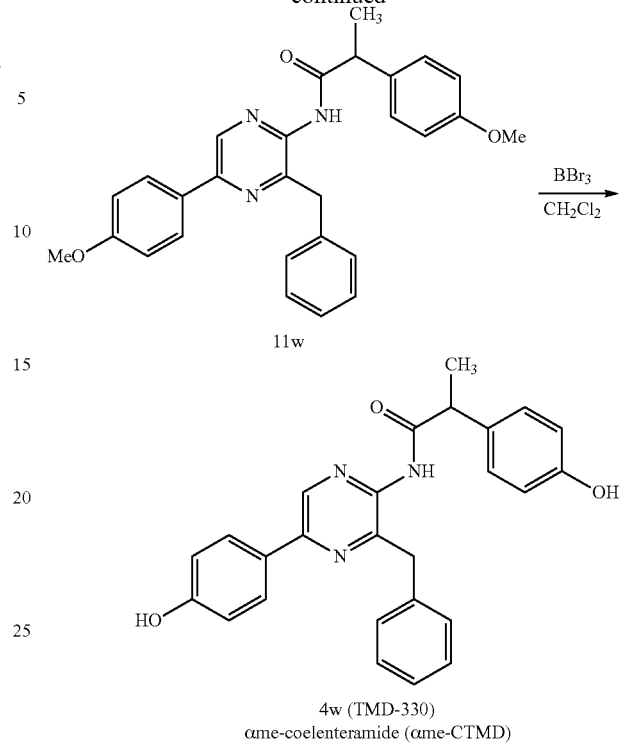

4w (TMD-330)
αme-coelenteramide (αme-CTMD)

N-[3-Benzyl-5-(4-methoxyphenyl)pyrazin-2-yl]-2-(4-methoxyphenyl)propanamide (11 w)

Under an argon atmosphere, 2-(4-methoxyphenyl)propanoic acid (synthesized by the process of I. Shiina, et al., *Eur J. Org. Chem.*, 5887-5890 (2008)) (1.20 g, 6.66 mmol) was dissolved in thionyl chloride (6.00 mL, 82.6 mmol) and the solution was heated to reflux for 27 hours. After cooling to room temperature, the mixture was concentrated under reduced pressure to give the crude product of 2-(4-methoxyphenyl)propanoyl chloride (16) as a colorless oil. The product was used in the following reaction without further purification.

Under an argon atmosphere, to a solution of 3-benzyl-5-(4-methoxyphenyl)pyrazin-2-amine (12) (synthesized by the process of M. Adamczyk, et al., *Org. Prep. Proced. Int.*, 33, 477-485 (2001)) (500 mg, 1.72 mmol) in pyridine (8 mL) were successively added 4-(dimethylamino)pyridine (21.0 mg, 172 μmol) and 2-(4-methoxyphenyl)propanoyl chloride (16) prepared above at room temperature, and the mixture was heated with stirring at 55° C. for 14 hours. After cooling to room temperature, to the mixture was added water and the product was extracted with dichloromethane (×3). The combined organic extract was dried over anhydrous sodium sulfate, filtered and concentrated under reduced pressure. The residual pyridine was azeotropically removed with toluene (×3). The residue was purified twice by column chromatography (silica gel 50 g, dichloromethane/ethyl acetate=9/1, and silica gel 50 g, n-hexane/ethyl acetate=9/1→6/1) to give Compound 11w (942 mg, <quant.) as a colorless foamy solid containing some impurities.

N-[3-Benzyl-5-(4-hydroxyphenyl)pyrazin-2-yl]-2-(4-hydroxyphenyl)propanamide (4w, TMD-330)

Under an argon atmosphere, to a solution of the crude product of N-[3-benzyl-5-(4-methoxyphenyl)pyrazin-2-yl]-2-(4-methoxyphenyl)propanamide (11w) (500 mg, <1.10 mmol) in anhydrous dichloromethane (20 mL) was added boron tribromide (1.0 M dichloromethane solution, 5.50 mL, 5.50 mmol) at room temperature, and the mixture was heated to reflux for 21 hours. After cooling to room temperature, to this was added saturated aqueous sodium bicarbonate solution and the mixture was concentrated under reduced pressure using a rotary evaporator to remove dichloromethane. The solid was collected by filtration and dried in vacuo to give the crude product (330 mg) as a brown solid. The solid was recrystallized from methanol to give Compound 4w (TMD-330) (112 mg, 263 μmol, <23.9% (2 steps)) as a colorless solid. $R_f$=0.26 (n-hexane/ethyl acetate=1/1); $^1$H NMR (400 MHz, DMSO-$d_6$) δ 1.37 (d, 3H, J=7.0 Hz), 3.81 (q, 1H, J=7.0 Hz), 3.84-4.00 (m, 2H), 6.72-6.79 (AA'BB', 2H), 6.85-6.96 (m, 4H), 7.09-7.19 (m, 3H), 7.21-7.27 (AA'BB', 2H), 7.90-7.98 (AA'BB', 2H), 8.79 (s, 1H), 9.31 (s, 1H), 9.87 (s, 1H), 10.30 (s, 1H); $^{13}$C NMR (67.8 MHz, DMSO-$d_6$) δ 18.3, 44.3, 115.2 (2C), 115.7 (2C), 126.1, 126.5, 128.0 (2C), 128.1 (2C), 128.4 (2C), 128.9 (2C), 131.6, 136.8, 138.3, 143.3, 148.6, 150.6, 156.3, 159.1, 173.4 (one carbon at the benzyl position was unobservable due to overlapping with the septet peak of DMSO); IR (KBr, cm$^{-1}$) 530, 596, 700, 725, 837, 924, 1171, 1225, 1267, 1319, 1375, 1450, 1487, 1545, 1611, 1670, 2976, 3310; HRMS (ESI$^+$) m/z 448.1644 ([M+Na]$^+$, $C_{26}H_{23}N_3NaO_3^+$ requires 448.1632).

3-4) TMD-365 (4x)

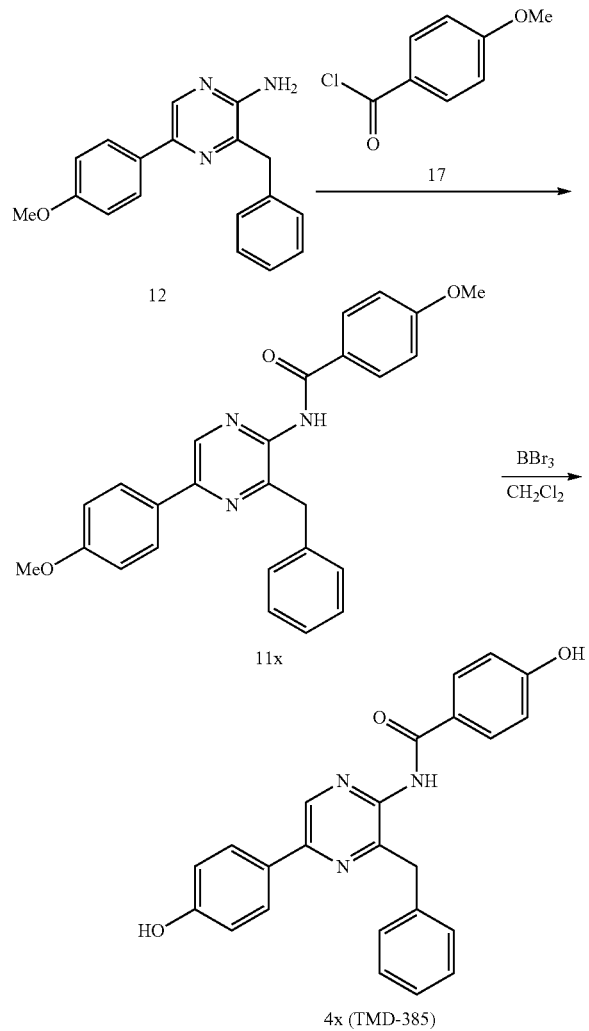

N-[3-Benzyl-5-(4-methoxyphenyl)pyrazin-2-yl]-4-methoxybenzamide (11x)

To a solution of 3-benzyl-5-(4-methoxyphenyl)pyrazin-2-amine (12) (synthesized by the process of M. Adamczyk, et al., Org. Prep. Proced. Int., 33, 477-485 (2001)) (500 mg, 1.72 mmol) in pyridine (5 mL) were successively added 4-(dimethylamino)pyridine (21.0 mg, 172 μmol) and 4-methoxybenzoyl chloride (17) (587 mg, 3.44 mmol) at room temperature, and the mixture was heated with stirring at 50° C. for 17 hours. After cooling to room temperature, to the mixture was added water and the product was extracted with dichloromethane (×3). The combined organic extract was dried over anhydrous sodium sulfate, filtered and concentrated under reduced pressure. The residual pyridine was azeotropically removed with toluene (×3). The residue was purified by column chromatography (silica gel 50 g, dichloromethane/ethyl acetate=9/1). The residue was further recrystallized from ethyl acetate to give Compound 11x (592 mg, 1.39 mmol, 80.8%) as a colorless solid. $R_f$=0.63 (dichloromethane/ethyl acetate=9/1); $^1$H NMR (400 MHz, DMSO-$d_6$) δ 3.83 (s, 3H), 3.85 (s, 3H), 4.17 (s, 2H), 7.04-7.11 (m, 4H), 7.14-7.26 (m, 5H), 7.93-7.98 (AA'BB', 2H), 8.05-8.11 (AA'BB', 2H), 8.96 (s, 1H), 10.63 (s, 1H); $^{13}$C NMR (67.8 MHz, DMSO+CDCl$_3$) 40.3, 54.7, 54.8, 112.9 (2C), 113.7 (2C), 125.4, 125.7, 127.4 (2C), 127.7 (2C), 128.0, 128.5 (2C), 129.4 (2C), 136.2, 137.6, 143.6, 148.2, 150.4, 160.1, 162.0, 165.5; IR (KBr, cm$^{-1}$) 700, 743, 843, 1030, 1159, 1177, 1258, 1290, 1452, 1485, 1514, 1535, 1580, 1609, 1643, 3242; Anal. Calcd. For $C_{26}H_{23}N_3O_3$: C, 73.39; H, 5.45; N, 9.88. Found: C, 73.48; H, 5.40; N, 9.94.

N-[3-Benzyl-5-(4-hydroxyphenyl)pyrazin-2-yl]-4-hydroxybenzamide (4x, TMD-365)

Under an argon atmosphere, to a solution of N-[3-benzyl-5-(4-methoxyphenyl)pyrazin-2-yl]-4-methoxybenzamide (11x) (300 mg, 705 μmol) in anhydrous dichloromethane (15 mL) was added boron tribromide (1.0 M dichloromethane solution, 3.53 mL, 3.53 mmol) at room temperature, and the mixture was was heated to reflux for 17 hours. After cooling to room temperature, to this was added saturated aqueous sodium bicarbonate solution and the mixture was concentrated under reduced pressure using a rotary evaporator to remove dichloromethane. The solid was collected by filtration and dried in vacuo to give the crude product (288 mg) as a brown solid. The solid was purified by column chromatography (silica gel 30 g, n-hexane/ethyl acetate=2/3). The product was further recrystallized from ethyl acetate to give Compound 4x (TMD-365) (119 mg, 300 rμmol, 42.6%) as a yellow solid. $R_f$=0.46 (dichloromethane/methanol=9/1); $^1$H NMR (400 MHz, DMSO-$d_6$) δ 4.14 (s, 2H), 6.83-6.92 (m, 4H), 7.12-7.27 (m, 5H), 7.81-7.88 (AA'BB', 2H), 7.93-7.99 (AA'BB', 2H), 8.88 (s, 1H), 9.89 (br s, 1H), 10.19 (br s, 1H), 10.49 (s, 1H); $^{13}$C NMR (67.8 MHz, DMSO-$d_6$) δ 40.0, 115.0 (2C), 115.8 (2C), 124.1, 126.2, 126.5, 128.1 (2C), 128.2 (2C), 129.0 (2C), 130.1 (2C), 136.9, 138.4, 144.1, 148.6, 151.3, 159.1, 161.0, 165.9; IR (KBr, cm$^{-1}$) 621, 708, 754, 835, 1172, 1215, 1248, 1284, 1368, 1394, 1439, 1485, 1601, 1655, 3030, 3298.

3-5) TMD-366 (4y)

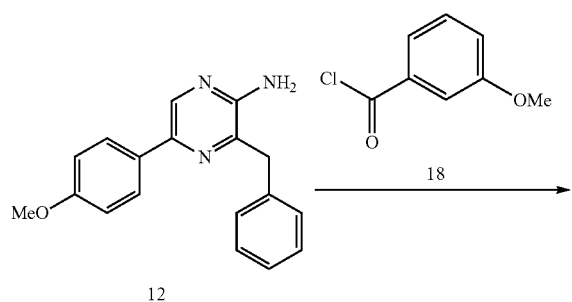

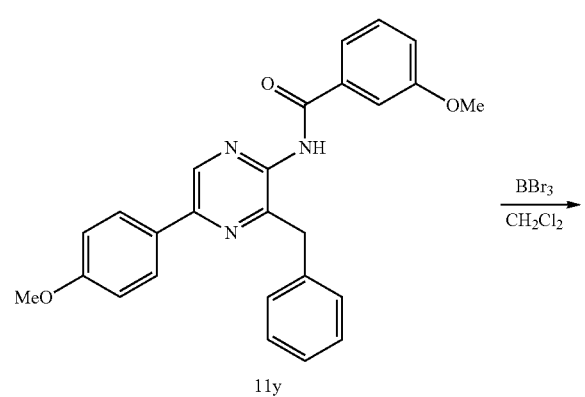

11y

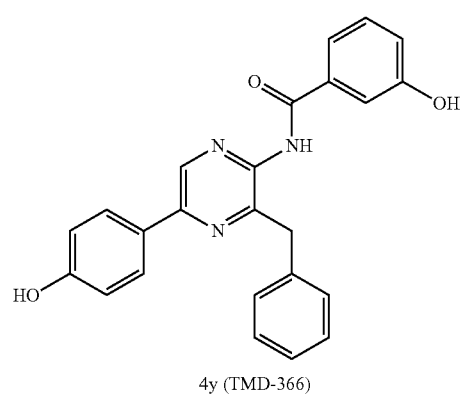

4y (TMD-366)

N-[3-Benzyl-5-(4-methoxyphenyl)pyrazin-2-yl]-3-methoxybenzamide (11y)

To a solution of 3-benzyl-5-(4-methoxyphenyl)pyrazin-2-amine (12) (synthesized by the process of M. Adamczyk, et al., *Org. Prep. Proced. Int.*, 33, 477-485 (2001)) (800 mg, 2.75 mmol) in pyridine (10 mL) were successively added 4-(dimethylamino)pyridine (33.6 mg, 275 μmol) and m-anisoyl chloride (18) (773 μL, 5.50 mmol) at room temperature, and the mixture was heated with stirring at 50° C. for 22 hours. After cooling to room temperature, to the mixture was added water and the product was extracted with dichloromethane (×3). The combined organic extract was dried over anhydrous sodium sulfate. After filtration and concentration under reduced pressure, the residual pyridine was azeotropically removed with toluene (×3). The residue was purified by column chromatography (silica gel 100 g, dichloromethane/ethyl acetate=9/1). The residue was recrystallized from ethyl acetate to give Compound 11y (967 mg, 2.27 mmol, 82.5%) as a colorless solid. $R_f$=0.63 (dichloromethane/ethyl acetate=9/1); $^1$H NMR (400 MHz, DMSO-$d_6$) δ 3.83 (s, 6H), 4.19 (s, 2H), 7.05-7.12 (AA'BB', 2H), 7.14-7.28 (m, 6H), 7.42-7.49 (m, 2H), 7.53 (d, 1H, J=7.5 Hz), 8.06-8.12 (AA'BB', 2H), 8.98 (s, 1H), 10.77 (s, 1H); $^{13}$C NMR (67.8 MHz, CDCl$_3$) δ 41.5, 55.3, 55.4, 112.5, 114.3 (2C), 118.6, 119.3, 126.7 (2C), 128.1, 128.55, 128.61 (2C), 128.5 (2C), 129.6, 135.0, 136.8, 137.7, 143.3, 149.2, 149.9, 159.8, 160.9, 165.7; IR (KBr, cm$^{-1}$) 700, 746, 833, 1022, 1040, 1117, 1179, 1254, 1300, 1325, 1373, 1416, 1441, 1501, 1607, 1655, 2936, 3265; Anal. Calcd. For $C_{26}H_{23}N_3O_3$: C, 73.39; H, 5.45; N, 9.88. Found: C, 73.55; H, 5.36; N, 9.86.

N-[3-Benzyl-5-(4-hydroxyphenyl)pyrazin-2-yl]-3-hydroxybenzamide (4y, TMD-366)

Under an argon atmosphere, to a solution of N-(3-benzyl-5-(4-methoxyphenyl)pyrazin-2-yl)-3-methoxybenzamide (11y) (300 mg, 705 μmol) in anhydrous dichloromethane (15 mL) was added boron tribromide (1.0 M dichloromethane solution, 3.53 mL, 3.53 mmol) at room temperature, and the mixture was heated to reflux for 19 hours. After cooling to room temperature, to this was added saturated aqueous sodium bicarbonate solution and the mixture was concentrated under reduced pressure using a rotary evaporator to remove dichloromethane. The solid was collected by filtration and dried in vacuo to give the crude product (343 mg) as an orange solid. The solid was purified by column chromatography (silica gel 50 g, n-hexane/ethyl acetate=2/3). The product was further recrystallized from ethyl acetate to give Compound 4y (TMD-366) (193 mg, 486 μmol, 68.9%) as a pale yellow solid. $R_f$=0.32 (n-hexane/ethyl acetate=1/2); $^1$H NMR (400 MHz, DMSO-$d_6$) δ 4.16 (s, 2H), 6.86-6.92 (AA'BB', 2H), 6.98-7.03 (m, 1H), 7.14-7.27 (m, 5H), 7.29-7.40 (m, 3H), 7.94-8.00 (AA'BB', 2H), 8.90 (s, 1H), 9.78 (br s, 1H), 9.90 (br s, 1H), 10.65 (s, 1H); $^{13}$C NMR (67.8 MHz, DMSO-$d_6$) δ 114.8, 115.8 (2C), 118.4, 119.0, 126.2, 126.4, 128.1 (2C), 128.3 (2C), 129.0 (2C), 129.5, 135.0, 137.0, 138.3, 143.8, 148.9, 151.3, 157.4, 159.1, 166.3 (one carbon at the benzyl position was unobservable due to overlapping with the septet peak of DMSO); IR (KBr, cm$^{-1}$) 596, 683, 708, 748, 843, 1165, 1209, 1250, 1269, 1304, 1371, 1443, 1503, 1520, 1595, 1649, 3254.

3-6) TMD-368 (4z)

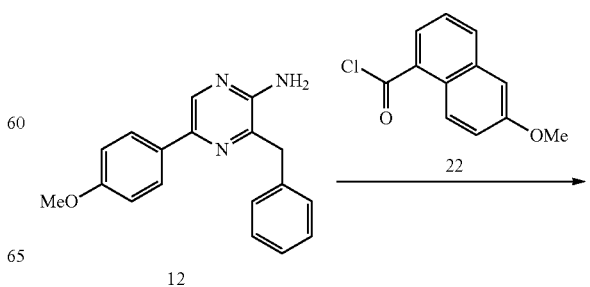

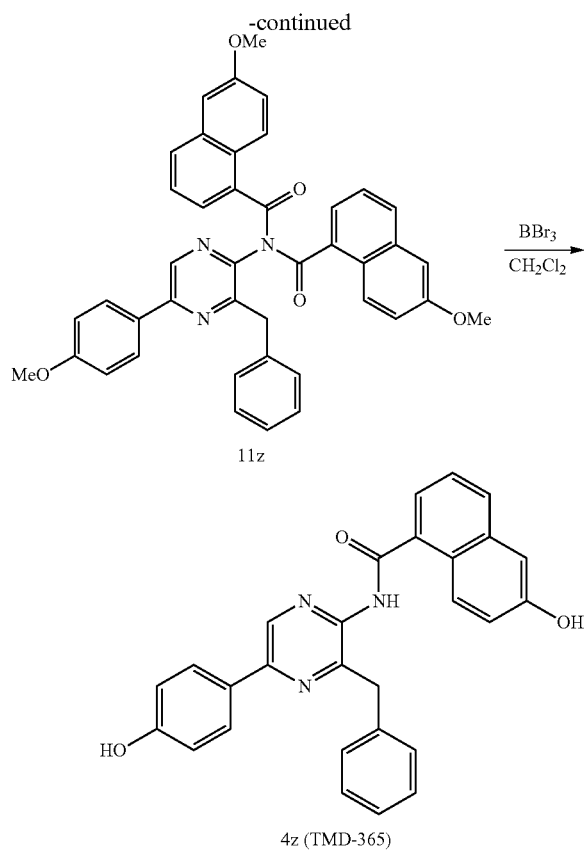

N-[3-Benzyl-5-(4-methoxyphenyl)pyrazin-2-yl]-6-methoxy-N-(6-methoxy-1-naphthoyl)-1-naphthamide (11z)

Under an argon atmosphere, 6-methoxy-1-naphthoic acid (synthesized by the process of J. D. Moseley and J. P. Gilday, Tetrahedron, 62, 4690-4697 (2006)) (1.20 g, 5.93 mmol) was dissolved in thionyl chloride (5.00 mL, 68.8 mmol) and the solution was heated to reflux for 3 hours. After cooling to room temperature, the mixture was concentrated under reduced pressure to give the crude product of 6-methoxy-1-naphthoyl chloride (22) as a colorless oil. The product was used in the following reaction without further purification.

Under an argon atmosphere, to a solution of 3-benzyl-5-(4-methoxyphenyl)pyrazin-2-amine (12) (synthesized by the process of M. Adamczyk, et al., Org. Prep. Proced. Int., 33, 477-485 (2001)) (500 mg, 1.72 mmol) in pyridine (5 mL) were successively added 4-(dimethylamino)pyridine (21.0 mg, 172 μmol) and 6-methoxy-1-naphthoyl chloride (22) prepared above at room temperature, and the mixture was heated with stirring at 50° C. 18 hours. After cooling to room temperature, to the mixture was added water and the product was extracted with dichloromethane (×3). The combined organic extract was dried over anhydrous sodium sulfate, filtered and concentrated under reduced pressure. The residual pyridine was azeotropically removed with toluene (×3). The residue was successively purified twice by column chromatography (silica gel 50 g, dichloromethane/ethyl acetate=9/1, and silica gel 50 g, n-hexane/ethyl acetate=2/1) to give Compound 11z (775 mg, 1.17 mmol, <68.3%) as a brown foamy solid containing some impurities. $R_f$=0.21 (n-hexane/ethyl acetate=2/1); $^1$H NMR (400 MHz, DMSO-$d_6$) δ 3.82 (s, 3H), 3.83 (s, 6H), 4.39 (s, 2H), 7.04-7.09 (AA'BB', 2H), 7.15-7.23 (m, 6H), 7.26-7.31 (m, 1H), 7.34-7.41 (m, 4I), 7.63-7.69 (m, 2H), 7.75-7.80 (AA'BB', 2H), 8.02-8.08 (m, 4H), 9.07 (s, 1H).

N-[3-Benzyl-5-(4-hydroxyphenyl)pyrazin-2-yl]-6-hydroxy-1-naphthamide (4z, TMD-368)

Under an argon atmosphere, to a solution of the crude product of N-[3-benzyl-5-(4-methoxyphenyl)pyrazin-2-yl]-6-methoxy-N-(6-methoxy-N-naphthoyl)-1-n aphthamide (11z) (500 mg, <758 μmol) in anhydrous dichloromethane (15 mL) was added boron tribromide (1.0 M dichloromethane solution, 3.15 mL, 3.15 mmol) at room temperature, and the mixture was heated to reflux for 18 hours. After cooling to room temperature, to this was added saturated aqueous sodium bicarbonate solution. The solid in the suspension obtained during concentration under reduced pressure was collected by filtration and dried to give the crude product (294 mg, 657 μmol, <86.7%) as a brown solid. The product was recrystallized twice from ethyl acetate to give Compound 4z (TMD-368) (10.0 mg, 22.3 μmol, 2.9%) as a pale yellow solid. $R_f$=0.46 (n-hexane/ethyl acetate=1/2); $^1$H NMR (400 MHz, DMSO-$d_6$) δ 4.32 (s, 2H), 6.85-6.94 (AA'BB', 2H), 7.10-7.16 (m, 1H), 7.17-7.33 (m, 6H), 7.34-7.40 (m, 1H), 7.41-7.47 (m, 1H), 7.82-7.88 (m, 1H), 7.94-8.02 (AA'BB', 21H), 8.04-8.09 (m, 1H), 8.92 (s, 1H), 9.91 (s, 2H), 10.83 (s, 1H).

Hereinafter, Compounds 3a, 3b and 3d to 3j in SYNTHESIS EXAMPLES described above are sometimes simply referred to as "coelenterazine analogs" and Compounds 4a to 4z as "coelenteramide analogs."

Example 1

Preparation of Semi-synthetic Aequorins for Substrate Specificity Analysis and Determination of Luminescence Activity In preparing the following semi-synthetic aequorin, recombinant apoaequorin manufactured by Chisso Corporation was used. This recombinant apoaequorin was expressed and purified according to the method described in Inouye, S. and Hosoya. T. Biochem. Biophys. Res. Commun (2009) 386: 612-622.

(1) Preparation of Semi-Synthetic Aequorins

To 1 ml of 30 mM Tris-HCl (pH 7.6) containing 10 mM EDTA, 1μ of 2-mercaptoethanol and 1.31 μg of the recombinant apoaequorin solution (manufactured by Chisso Corporation) were added and mixed. Subsequently, 1 μl of coelenterazine or its analogs dissolved in ethanol was added to the mixture. The mixture was allowed to stand at 4° C. for 18 hours to convert into semi-synthetic aequorins.

(2) Assay for Luminescence Activity

Specifically, the luminescence activity described above was assayed as follows. To 2 μl of a solution of semi-synthetic aequorin in each regeneration process was added 100 μl of 50 mM Tris-HCl (pH 7.6) containing 50 mM calcium chloride solution, whereby the luminescence reaction was triggered. The luminescence activity was measured for 10 seconds on a luminometer luminescencer-PSN AB2200 (manufactured by Atto Co., Ltd.) to obtain the maximum intensity ($I_{max}$) of luminescence activity. Also, the luminescence capacity of semi-synthetic aequorins was obtained by intergrating for 10 seconds.

The results are summarized in TABLE 1 below. Semi-synthetic aequorins including coelenterazine analogs had sufficient luminescence intensities to detect the luminescence activity, though the maximum luminescence intensity was low.

Example 2

Measurement of Luminescence Patterns of Semi-Synthetic Aequorins and Determination of Half Decay Time A solution of the regenerated semi-synthetic aequorin was diluted to 10-fold with 20 mM Tris-HCl (pH 7.6) containing 0.1% BSA (manufactured by Sigma, Inc.), 0.01 mM EDTA and 150 mM NaCl. The dilution was dispensed into a 96-well microplate (Nunc #236108) at 5 µl/well. The luminescence reaction was triggered by injecting 50 mM Tris-HCl (pH 7.6) containing 50 mM calcium chloride solution at 100 µl/well. The luminescence patterns for 60 seconds were measured to determine half decay time of the luminescence (a time period in which the luminescence becomes half of the maximum luminescence intensity).

The results are summarized in TABLE 1. The results reveal that semi-synthetic aequorins prepared from coelenterazine analogs had a longer half-decay time as compared to the half-decay time (0.81 second) of native acquorin prepared from coelenterazine; in particular, the half-decay time of semi-synthetic aequorins prepared from coelenterazine analogs 3a, 3e, 3f and 3j was markedly prolonged.

Example 3

Measurements of Luminescence Spectra of Semi-Synthetic Aequorins

In a quartz cell with light path length of 10 mm, I ml of 50 mM Tris-HCl (pH 7.6) containing 1 mM EDTA and 100 µl (100 µg protein) of a solution of the regenerated semi-synthetic aequorin were charged. Next, 100 µl of 50 mM Tris-HCl (pH 7.6) containing 0.1 ml of 10 mM calcium chloride solution was added thereto to start the luminescence reaction. The spectra were measured on a spectrofluorimeter (FP-6500, manufactured by Jasco Co., Ltd.) with the excitation light source turned off. The measurement conditions were bandwidth: 20 nm, response: 0.5 second, scan speed: 2000 nm/min and 22 to 25° C. The luminescence spectra measured were corrected.

The results are summarized in TABLE 1. The results reveal that the maximum emission peaks of semi-synthetic aequorins prepared from coelenterazine analogs 3a, 3e, 3f and 3h were shifted toward the longer wavelength by about 20 nm to 60 nm, by compared with the maximum emission peak at 472.5 nm from native aequorin prepared with coelenterazine. On the other hand, it became clear that the maximum emission peaks of semi-synthetic aequorins prepared from coelenterazine analogs 3b and 3j were shifted toward the shorter wavelength by about 15 nm to 25.5 nm.

Furthermore, as shown in FIG. 1, it became clear that semi-synthetic aequorins prepared from coelenterazine analogs had wider spectra.

TABLE 1

Luminescence Properties of Semi-Synthetic Aequorins by Addition of Calcium Ions

| Coelenterazine analogue (abbreviation) | Luminescence activity $I_{max}$ (%) | Luminescence capacity 10 sec. (%) | Half decay time (sec) | Maximum luminescence wavelength $\lambda_{max}$ (nm) |
|---|---|---|---|---|
| Coelenterazine (CTZ) | 100.0 | 100.0 | 0.81 | 472.5 |
| 3a (TMD-296) | 2.1 | 32.1 | 15.7 | 494.0 |
| 3b (TMD-282) | 5.9 | 8.5 | 0.96 | 447.0 |
| 3d (TMD-276) | 18.7 | 26.4 | 1.10 | 480.0 |
| 3e (TMD-277) | 0.9 | 5.4 | 3.42 | 507.0 |
| 3f (TMD-278) | 0.1 | 2.5 | >60 | 515.0 |
| 3g (TMD-336) | 0.02 | 0.15 | — | — |
| 3h (TMD-281) | 2.1 | 6.5 | 1.71 | 532.5 |
| 3i (TMD-337) | 0.3 | 1.3 | — | — |
| 3j (TMD-280) | 4.2 | 67.0 | 16.8 | 457.5 |

(—) not measured (the activity is too low)

Example 4

Measurements of Fluorescence Spectra of Novel Fluorescent Proteins Formed from Semi-Synthetic Aequorins The fluorescence spectra of novel fluorescent proteins formed by the $Ca^{2+}$-triggered reaction from semi-synthetic aequorins in EXAMPLE 3 were measured at 25° C. in a quartz cell (10 mm light path length) using a Jasco FP-6500 spectrofluorometer (excitation wavelength: 330 nm, emission/excitation bandwidth: 3 nm; response: 0.5 sec, scan speed, 1000 nm/min). The fluorescence spectra measured were corrected.

Figure 2:
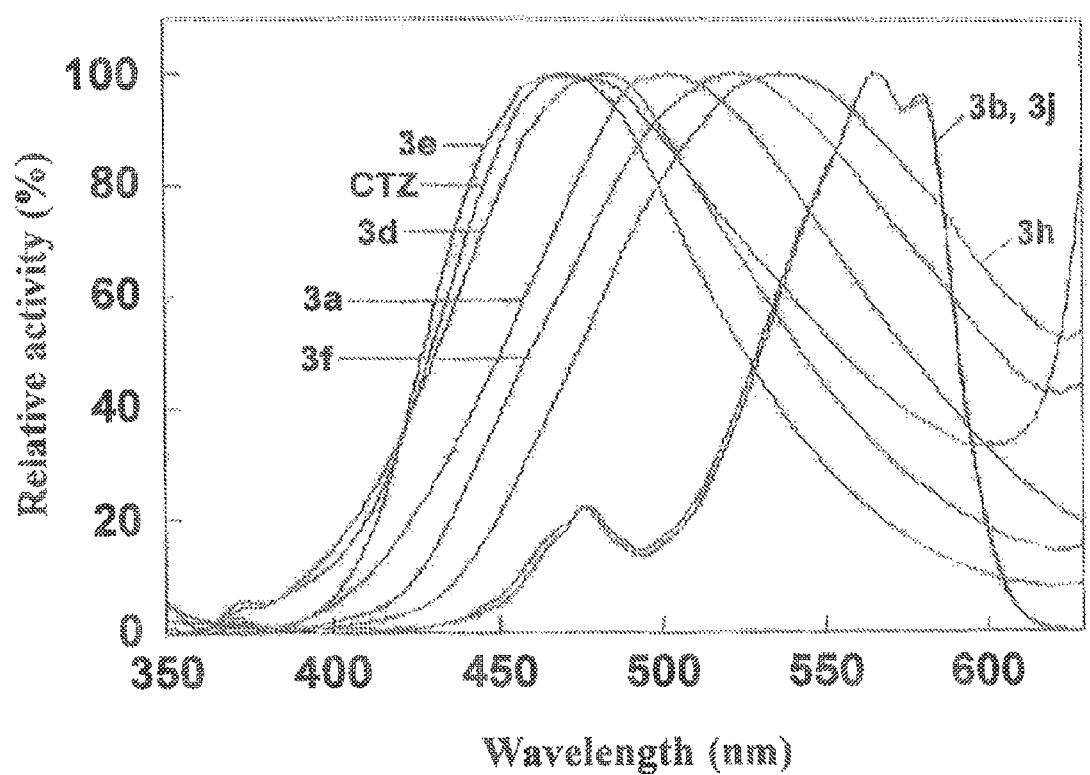
FIG. 2 shows the fluorescence spectra of fluorescent proteins obtained by adding calcium inos to semi-synthetic aequorins prepared from coelenterazine analogs.

The results are summarized in TABLE 2. It was revealed that all samples measured showed flourescnece intensity. The fluorescence spectra are shown in FIG. 2. The fluorescence spectra of fluorescent proteins obtained from coelenterazine analogs 3a, 3b, 3e, 3f, 3h and 3j were different from the emission spectra of semi-synthetic aequorins. Especially with coelenterazine analogs 3b, 3e and 3j, the emission spectra of semi-synthetic aequorins were markedly different from the fluorescence spectra of fluorescent proteins generated by the addition of calcium ions. This is the first example showing that the emission spectra are different from the fluorescence spectra, in spite of semi-synthetic aequorins and fluorescent proteins from the same coelenterazine analogs.

TABLE 2

Fluorescence spectra of fluorescent proteins Generated by Addition of Calcium Ions to Semi-Synthetic Aequorins

| Coelenterazine analogue (abbreviation) | Relative fluorescence intensity (rlu) | Maximum fluorescence wavelength $\lambda_{max}$ (nm) |
|---|---|---|
| Coelenterazine (CTZ) | 63.3 | 473.0 |
| 3a (TMD-296) | 118.1 | 501.5 |
| 3b (TMD-282) | 10.3 | 580.0 |
| 3d (TMD-276) | 61.8 | 482.5 |
| 3e (TMD-277) | 28.0 | 468.5 |
| 3f (TMD-278) | 38.5 | 525.0 |
| 3g (TMD-336) | — | — |
| 3h (TMD-281) | 58.7 | 537.0 |
| 3i (TMD-337) | — | — |
| 3j (TMD-280) | 13.3 | 580.0 |

Example 5

Preparation of Calcium Standard Solution

In 9 ml of 50 mM Tris-HCl (pH 7.6), 1 ml of 1 g/L calcium carbonate standard solution (manufactured by Wako Pure Chemicals) was diluted to prepare $10^{-3}$ M calcium carbonate solution. One milliliter of the resulting $10^{-3}$ M calcium carbonate solution was taken and added to 9 ml of 50 mM Tris-HCl (pH 7.6) to prepare $10^{-4}$ M calcium carbonate solution. Next, 3 ml of the resulting $10^{-4}$ M calcium carbonate solution was taken and added to 6 ml of 50 mM Tris-HCl (pH 7.6) to prepare $3 \times 10^{-4}$ M calcium carbonate solution. One milliliter from the $10^{-4}$ M calcium carbonate solution obtained was added to 9 ml of 50 mM Tris-HCl (pH 7.6) to prepare $10^{-5}$ M calcium carbonate solution. Then, 3 ml of the resulting $10^{-5}$ M calcium carbonate solution was taken and added to 6 ml of 50 mM Tris-HCl (pH 7.6) to prepare $3 \times 10^{-5}$ M calcium carbonate solution. A dilution series was prepared by successively repeating the procedures described above to give the $10^{-3}$ M to $10^{-8}$ M calcium standard solutions.

Example 6

Preparation of Semi-Synthetic Aequorins for the Detection of Calcium Concentration In 5 ml of 50 mM Tris-HCl (pH 7.6) containing 10 mM DTT and 30 mM EDTA, 5 mg of recombinant apoaequorin (manufactured by Chisso Corporation) was dissolved and 100 μg of coelenterazine analog dissolved in ethanol in an amount of 1.2-fold equivalent was added to the solution. The mixture was allowed to stand at 4° C. overnight to convert into semi-synthetic aequorin. The resulting semi-synthetic aequorin was concentrated using Amicon Ultra-4 (manufactured by Millipore, Inc., molecular weight cut-off: 10,000) to remove an excessive of coelenterazine analog. The mixture was then washed 3 times with 3 ml of 30 mM Tris-HCl (pH 7.6) containing 0.05 mM EDTA to give the solution of semi-synthetic aequorin containing 0.05 mM EDTA. This semi-synthetic aequorin solution (2.5 mg/ml) was diluted with 20 mM Tris-HCl (pH 7.6) containing 0.1% BSA (manufactured by Sigma), 0.01 mM EDTA and 150 mM NaCl.

Example 7

Preparation of Calcium Standard Curve

The calcium standard solution prepared as above was dispensed into a 96-well microplate (Nunc #236108) at 50 μl/well and 10 μl of the diluted semi-synthetic aequorin solution was injected into 50 μl of various concentration of calcium standard solution. The luminescence intensity was measured for 60 seconds on a luminescence plate reader Centro LB960 (manufactured by Berthold) and expressed in terms of the maximum intensity ($I_{max}$) of luminescence. The luminescence intensity was measured on each semi-synthetic aequorin in the same procedures. Semi-synthetic aequorins for practically use were chosen by the maximum intensity ($I_{max}$) of luminescence and the calcium standard curve of semi-synthetic aequorin was prepared.

Figure 3:
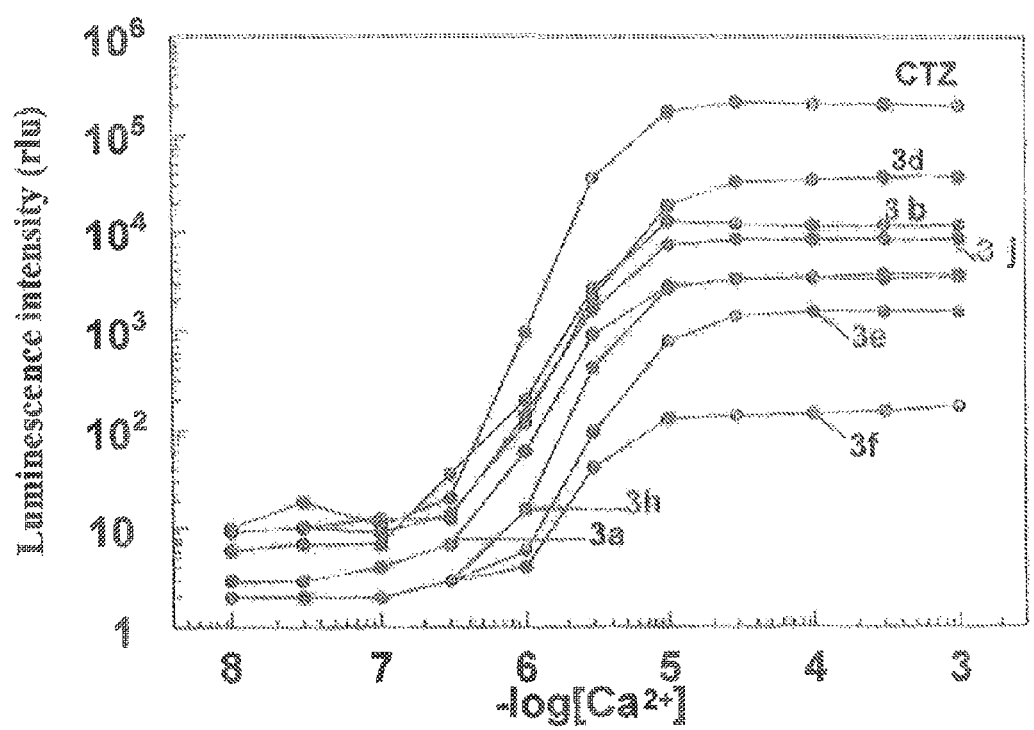
FIG. 3 shows the relationship between the initial luminescence intensities of semi-synthetic aequorins and various concentrations of calcium ion.
Figure 4:
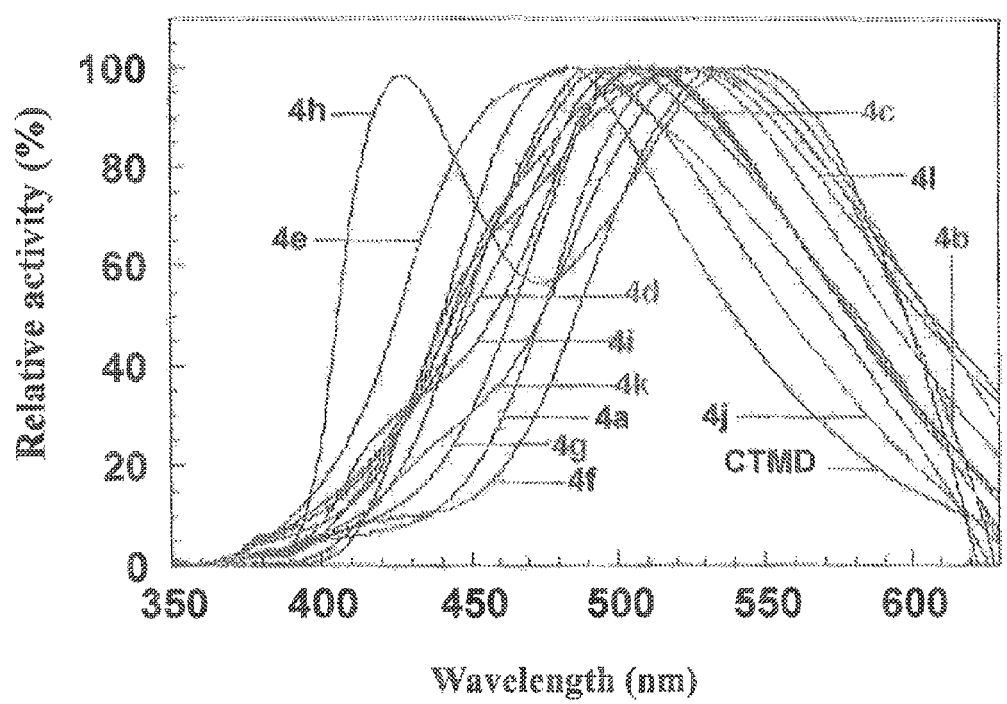
FIG. 4 shows the fluorescence spectra of semi-synthetic gFP prepared from coelenteramide analogs (4a to 4l) and apoaequorin in the presence of EDTA.
Figure 5:
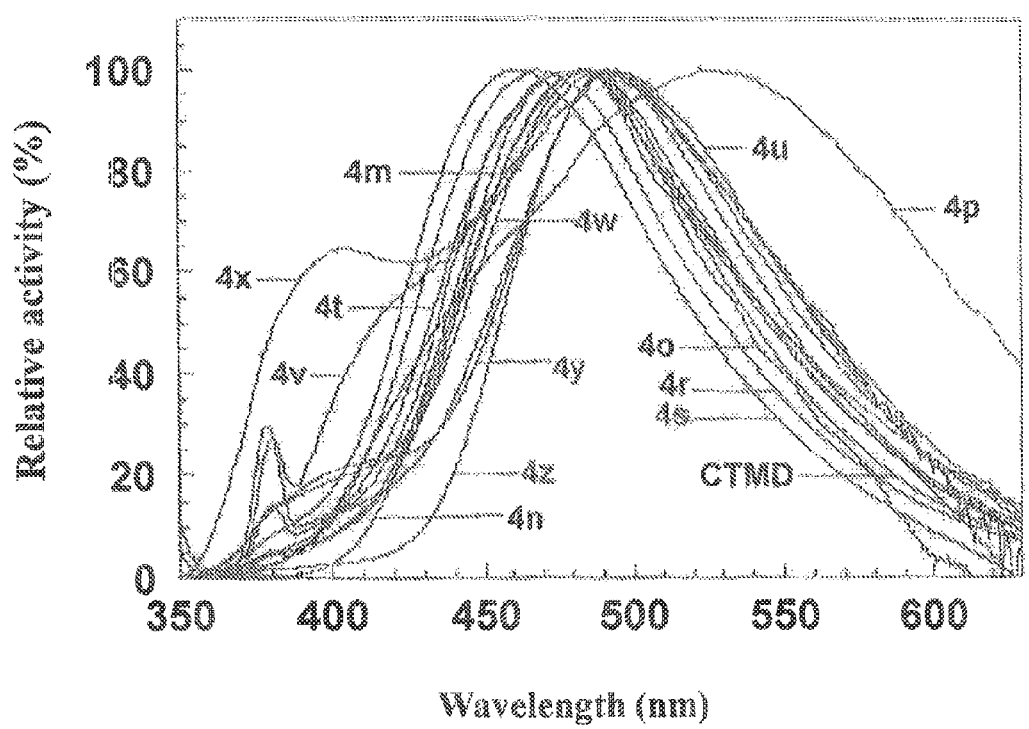
FIG. 5 shows the fluorescence spectra of semi-synthetic gFP prepared from coelenteramide analogs (4m to 4z) and apoaequorin in the presence of EDTA.
Figure 6:
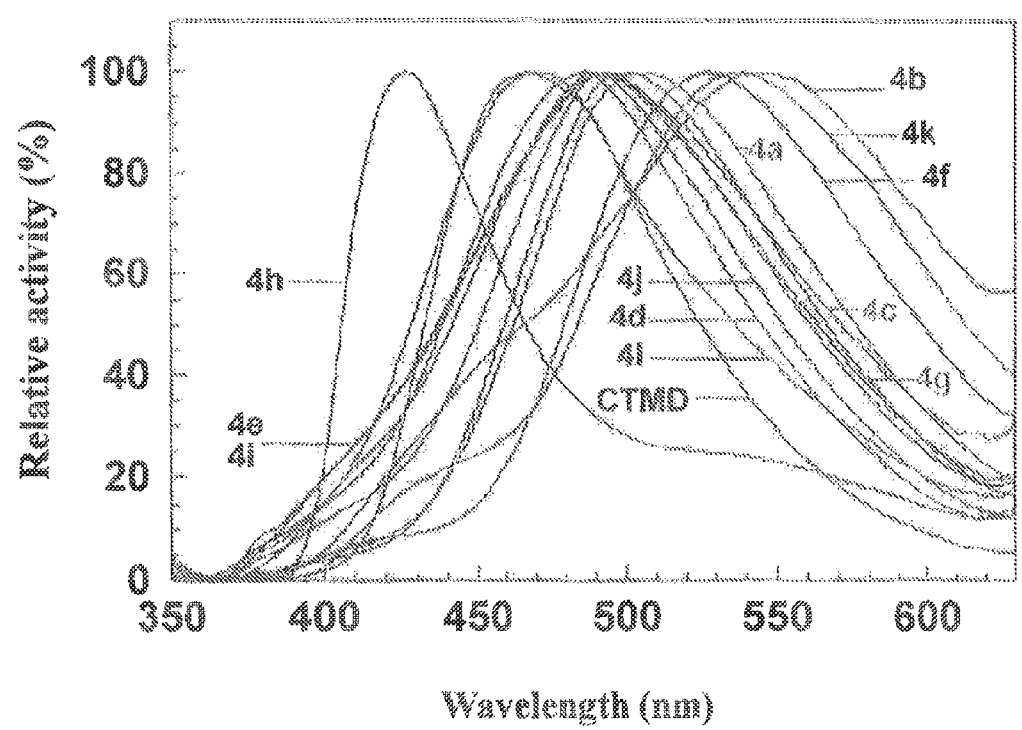
FIG. 6 shows the fluorescence spectra of semi-synthetic BFP prepared from coelenteramide analogs (4a to 4l) and apoaequorin in the presence of calcium ions.
Figure 7:
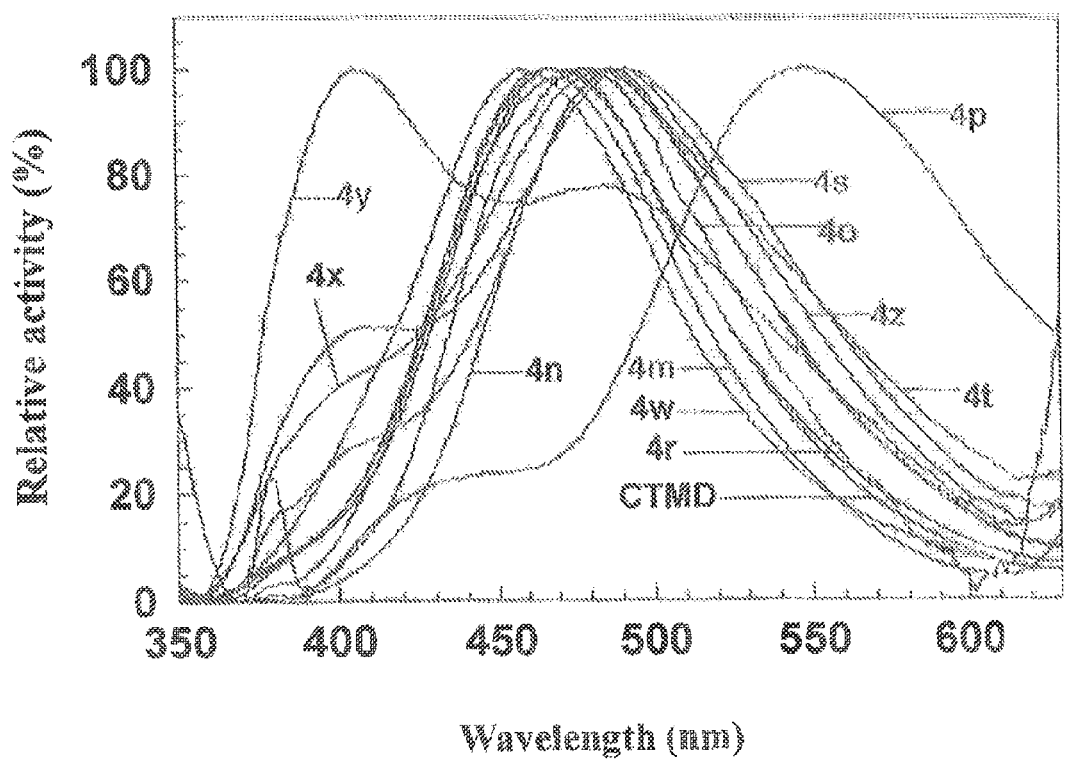
FIG. 7 shows the fluorescence spectra of semi-synthetic BFP prepared from coelenteramide analogs (4m to 4z) and apoaequorin in the presence of calcium ions.

The results are shown in FIG. 3. As shown in FIG. 3, the calcium standard curve can be prepared using semi-synthetic aequorins prepared from coelenterazine analogs (3a, 3b, 3d, 3e, 3f, 3h and 3j) of the present invention, indicating that the photoprotein of the present invention can be used for the detection, quantification and the like of calcium ions.

Example 8

Determination of Substrate Specificity and Luminescence Activity of the 19 kDa Protein from *Oplophorus luciferase*

The 19 kDa protein from *Oplophorus luciferase* was purified by the method described in Inouye, S. and Sasaki, S., Protein Express. Purif. (2007) 56: 261-268 and provided for use.

After 1 μl of the 19 kDa protein (2.3 mg/ml) from *Oplophorus luciferase* containing 1 mM DTT was dissolved in 100 μl of 30 mM Tris-HCl (pH 7.6) containing 10 mM EDTA, 1 μl of a solution of coelenterazine or its analog (1 μg/μl) in ethanol was added to the solution to start the luminescence reaction, and the luminescence activity was measured for 60 seconds on a luminometer luminescencer-PSN AB2200 (manufactured by Atto Co., Ltd.). The luminescence activity was determined by repeating the measurement described above 3 times and expressed in terms of the maximum luminescence intensity ($I_{max}$) of luminescence activity.

The results are shown in TABLE 3. Coelenterazine analog was not a good substrate for *Oplophorus luciferase*.

TABLE 3

| Luminescence activity of *Oplophorus* luciferase using coelenterazine analogues | |
|---|---|
| Coelenterazine analogue (abbreviation) | Luminescence activity $I_{max}$ (%) |
| Coelenterazine (CTZ) | 100.0 |
| 3a (TMD-296) | 0.4 |
| 3b (TMD-282) | 0.07 |
| 3d (TMD-276) | 0.3 |
| 3e (TMD-277) | 0.07 |
| 3f (TMD-278) | 0.1 |
| 3g (TMD-336) | 0.3 |
| 3h (TMD-281) | 0.07 |
| 3i (TMD-337) | 0.09 |
| 3j (TMD-280) | 0.2 |

Example 9

Determination of Substrate Specificity and Luminescence Activity of *Gaussia luciferase*

*Gaussia luciferase* was purified by the method described in Japanese Patent Application KOKAI No. 2008-099669 and provided for use. After 1 μl of *Gaussia luciferase* (0.024 mg/ml) was dissolved in 100 μl. of phosphate buffered saline (manufactured by Sigma Inc.) containing 0.01% Tween 20 (manufactured by Sigma Inc.) and 10 mM EDTA, 1 μl of a solution of coelenterazine or its analog (1 μg/μl) in ethanol was mixed with the solution to start the luminescence reaction. The luminescence activity was measured for 10 seconds on a luminometer luminescencer-PSN AB2200 (manufactured by Atto Co., Ltd.). The luminescence activity was determined by repeating the measurement described above 3 times and expressed in terms of the maximum luminescence intensity ($I_{max}$) of luminescence activity.

The results are shown in TABLE 4. Coelenterazine analog was not a good substrate for *Gaussia luciferase*.

TABLE 4 luminescence activity of *Gaussia* luciferase
using coelenterazine analogues

| Coelenterazine analogue (abbreviation) | Luminescence activity $I_{max}$ (%) |
|---|---|
| Coelenterazine (CTZ) | 100.0 |
| 3a (TMD-296) | 0.00 |
| 3b (TMD-282) | 0.01 |
| 3d (TMD-276) | 0.00 |
| 3e (TMD-277) | 0.00 |
| 3f (TMD-278) | 0.00 |
| 3g (TMD-336) | 0.00 |
| 3h (TMD-281) | 0.00 |
| 3i (TMD-337) | 0.00 |
| 3j (TMD-280) | 0.01 |

Example 10

Determination of Substrate Specificity and Luminescence Activity of *Renilla luciferase*

*Renilla luciferase* was purified by the method described in Inouye, S. & Shimomura, O. Biochem. Biophys. Res. Commun. (1997) 233: 349-353, and used for assay.

After 1 d of *Renilla luciferase* (0.45 mg/ml) was dissolved in 100 µl of 30 mM Tris-HCl (pH 7.6) containing 10 mM EDTA, 1 µl of a solution of coelenterazine or its analog (1 µg/µl) in ethanol was added to the solution to start the luminescence reaction. The luminescence activity was measured for 10 seconds on a luminometer luminescencer-PSN AB2200 (manufactured by Atto Co., Ltd.). The luminescence activity was determined by repeating the measurement of luminescence activity described above 3 times and expressed in terms of the maximum luminescence intensity ($I_{max}$) of luminescence activity.

The results are shown in TABLE 5. Coelenterazine analog was not a good substrate for *Renilla luciferase*.

TABLE 5

Luminescence activity of *Renilla* luciferase
using coelenterazine analogues

| Coelenterazine analogue (abbreviation) | Luminescence activity $I_{max}$ (%) |
|---|---|
| Coelenterazine (CTZ) | 100.0 |
| 3a (TMD-296) | 0.00 |
| 3b (TMD-282) | 0.00 |
| 3d (TMD-276) | 0.00 |
| 3e (TMD-277) | 0.00 |
| 3f (TMD-278) | 0.00 |
| 3g (TMD-336) | 0.00 |
| 3h (TMD-281) | 0.00 |
| 3i (TMD-337) | 0.00 |
| 3j (TMD-280) | 0.03 |

Example 11

Preparation of Semi-Synthetic gFP from Coelenteramide Analogues and Apoaequorin

Semi-synthetic gFP was prepared from recombinant apoaequorin and coelenteramide analogs as follows. In 1 ml of 50 mM Tris-HCl (pH 7.6) containing 10 mM EDTA and 1 mM DTT, apoaequorin (0.2 mg) was mixed with 8 µl of a coelenteramide analog (1 µg/µl in anhydrous methanol). The mixture was allowed to stand 4° C. for 16 hours to prepare semi-synthetic gFP-like protein (hereinafter sometimes simply referred to as "semi-synthetic gFP").

Example 12

Preparation of Semi-Synthetic BFP from Coelenteramide Analogues and Apoaequorin

Semi-synthetic gFP was prepared from recombinant apoaequorin and coelenteramide analogs as follows. In 1 ml of 50 mM Tris-HC 1 (pH 7.6) containing 10 mM $CaCl_2$ and 1 mM DIT, apoaequorin (0.2 mg) was mixed with 8 µl of a coelenteramide analog (1 µg/µl in anhydrous methanol). The mixture was allowed to stand at 4° C. for 16 hours to prepare semi-synthetic BFP-like protein (hereinafter sometimes simply referred to as "semi-synthetic BFP").

Example 13

Measurement of the Fluorescence Spectra of Coelenteramide Analogues, Semi-Synthetic BFP and Semi-Synthetic gFP The fluorescence spectra were determined as follows. For coelenteramide analog alone, the fluorescence was measured according to the procedures for semi-synthetic gFP and semi-synthetic BFP described in EXAMPLES 11 and 12, except for in the absence of apoaequorin, using 1 ml of 50 mM Tris-HCl (pH 7.6) containing 10 mM EDTA and 1 mM DTT or 1 ml of 50 mM Tris-HCl (pH 7.6) containing 10 mM $CaCl_2$ and 1 mM DTT, in the final concentration of coelenteramide analog adjusted to 8 µg/ml. The fluorescence spectra were measured at 25° C. in a quartz cell (10 mm light path length) using a Jasco FP-6500 spectrofluorometer (excitation wavelength: 337 nm, emission/excitation bandwidth: 3 nm; response: 0.5 sec, scan speed, 1000 nm/min).

The results are shown in TABLES 6 and 7. In addition, the charts of fluorescence spectra are shown in FIGS. 4 to 7.

Many of semi-synthetic BFPs and semi-synthetic gFPs prepared from coelenteramide analogs and apoaequorin showed much higher fluorescence intensities than that of coelenteramide analog alone. Also, most of semi-synthetic BFPs and semi-synthetic gFPs had different fluorescence spectra from the fluorescence spectra of coelenteramide analog alone.

TABLE 6

Fluorescence spectra of coelenteramide analogues
and semi-synthetic gFPs in EDTA-containing buffer

| | Coelenteramide (EDTA-containing buffer) | | Semi-synthetic gFP (EDTA-containing buffer) | |
|---|---|---|---|---|
| Coelenteramide analogue (abbreviation) | Maximum fluorescence wavelength $\lambda_{max}$ (nm) | Fluorescence intensity (rlu) | Maximum fluorescence wavelength $\lambda_{max}$ (nm) | Fluorescence intensity (rlu) |
| Coelenteramide (CTMD) | 458.0 | 4.6 | 482.5 | 165.2 |
| 4a (TMD-344) | 471.0 | 1.9 | 521.5 | 82.9 |
| 4b (TMD-343) | 495.5 | 7.1 | 530.0 | 43.2 |
| 4c (TMD-347) | 475.5 | 11.8 | 499.0 | 32.1 |
| 4d (TMD-338) | 462.5 | 12.4 | 504.5 | 58.8 |
| 4e (TMD-339) | 478.0 | 28.9 | 487.0 | 72.6 |
| 4f (TMD-340) | 448.5 | 2.3 | 536.5 | 70.5 |
| 4g (TMD-345) | 473.0 | 5.5 | 512.5 | 108.5 |
| 4h (TMD-342) | 426.5 | 115.2 | 426.5 | 68.9 |
| | | | 544.0 | 70.0 |
| 4i (TMD-346) | 471.5 | 12.1 | 512.5 | 106.5 |

TABLE 6-continued

Fluorescence spectra of coelenteramide analogues and semi-synthetic gFPs in EDTA-containing buffer

| Coelenteramide analogue (abbreviation) | Coelenteramide (EDTA-containing buffer) | | Semi-synthetic gFP (EDTA-containing buffer) | |
|---|---|---|---|---|
| | Maximum fluorescence wavelength $\lambda_{max}$ (nm) | Fluorescence intensity (rlu) | Maximum fluorescence wavelength $\lambda_{max}$ (nm) | Fluorescence intensity (rlu) |
| 4j (TMD-341) | 482.5 | 22.5 | 492.5 | 69.7 |
| 4k (TMD-373) | 487.5 | 10.3 | 532.0 | 139.9 |
| 4l (TMD-374) | 523.5 | 9.3 | 524.5 | 140.5 |
| 4m (TMD-375) | 429.0 | 9.8 | 482.5 | 163.8 |
| | 499.5 | 11.3 | | |
| 4n (TMD-376) | N.D. | | 485.5 | 151.5 |
| 4o (TMD-377) | 482.5 | 2.1 | 485.0 | 3.4 |
| 4p (TMD-378) | 476.0 | 5.3 | 523.0 | 21.1 |
| 4r (TMD-379) | 481.0 | 10.3 | 468.0 | 176.4 |
| 4s (TMD-348) | 457.5 | 1.9 | 460.0 | 106.4 |
| 4t (TMD-349) | 480.5 | 11.8 | 482.5 | 22.0 |
| 4u (TMD-331) | 440.5 | 0.7 | 494.5 | 11.4 |
| 4v (TMD-332) | 484.0 | 1.4 | 491.0 | 3.6 |
| 4w (TMD-330) | 451.0 | 1.3 | 487.0 | 54.6 |
| 4x (TMD-365) | 449.0 | 1.3 | 404.0 | 15.1 |
| | | | 492.5 | 23.1 |
| 4y (TMD-366) | 456.0 | 1.3 | 492.0 | 44.8 |
| 4z (TMD-368) | 409.5 | 20.2 | 492.5 | 246.3 |

N.D. not detected

TABLE 7

Fluorescence spectra of coelenteramide analogues and semi-synthetic BFPs in calcium ion-containing buffer

| Coelenteramide analogue (abbreviation) | Coelenteramide (Buffer containing CaCl$_2$) | | Semi-synthetic BFP (Buffer containing CaCl$_2$) | |
|---|---|---|---|---|
| | Maximum fluorescence wavelength $\lambda_{max}$ (nm) | Fluorescence wavelength (rlu) | Maximum fluorescence wavelength $\lambda_{max}$ (nm) | Fluorescence wavelength (rlu) |
| Coelenteramide (CTMD) | 457.0 | 5.9 | 468.5 | 151.2 |
| 4a (TMD-344) | 467.5 | 2.0 | 507.5 | 148.9 |
| 4b (TMD-343) | 494.5 | 9.4 | 544.5 | 52.7 |
| 4c (TMD-347) | 471.0 | 12.4 | 492.5 | 25.6 |
| 4d (TMD-338) | 463.5 | 12.9 | 487.0 | 98.3 |
| 4e (TMD-339) | 478.0 | 28.6 | 492.5 | 85.6 |
| 4f (TMD-340) | 447.0 | 2.2 | 527.0 | 96.4 |
| 4g (TMD-345) | 470.5 | 6.1 | 501.5 | 195.7 |
| 4h (TMD-342) | 426.5 | 101.2 | 427.0 | 153.3 |
| 4i (TMD-346) | 468.0 | 11.8 | 494.0 | 80.0 |
| 4j (TMD-341) | 481.0 | 22.4 | 489.0 | 100.5 |
| 4k (TMD-373) | 491.0 | 9.7 | 538.5 | 148.2 |
| 4l (TMD-374) | 523.0 | 8.8 | 468.0 | 63.5 |
| 4m (TMD-375) | 438.5 | 7.3 | 457.5 | 182.4 |
| | 502.0 | 11.6 | | |
| 4n (TMD-376) | N.D. | | 487.5 | 231.3 |
| 4o (TMD-377) | 478.5 | 2.1 | 477.5 | 3.9 |
| 4p (TMD-378) | 484.5 | 5.4 | 548.5 | 70.0 |
| 4r (TMD-379) | 483.0 | 10.2 | 468.0 | 159.9 |
| 4s (TMD-348) | 468.5 | 2.0 | 408.5 | 22.1 |
| 4t (TMD-349) | 482.0 | 12.1 | 479.5 | 29.5 |
| | | | 492.0 | 41.5 |
| 4u (TMD-331) | 445.5 | 0.9 | 402.0 | 6.1 |
| | | | 487.5 | 5.2 |
| 4v (TMD-332) | 466.0 | 1.4 | 430.5 | 3.3 |
| 4w (TMD-330) | 450.5 | 1.4 | 466.0 | 181.4 |
| 4x (TMD-365) | 450.0 | 1.4 | 485.0 | 36.8 |
| 4y (TMD-366) | 457.0 | 1.4 | 405.5 | 15.8 |
| | | | 482.5 | 12.6 |
| 4z (TMD-368) | 410.5 | 13.2 | 487.0 | 24.6 |

N.D. not detected

Example 14

Determination of the Luciferase Activity of Semi-Synthetic BFPs

To confirm that semi-synthetic BFPs prepared from coelenteramide analogs and apoaequorin, which are novel fluorescent proteins having luciferase activity, the luminescence reaction was performed in the presence of calcium ions, using coelenterazine as a light emitting substrate. After 5 μl (corresponding to 1 μg protein) of a solution of semi-synthetic BFP prepared in EXAMPLE 12 was added to 100 μl of 50 mM Tris-HC 1 (pH 7.6) containing 10 mM CaCl$_2$, 1 μl of a solution of coelenterazine (1 μg/μl) in ethanol was mixed with the solution to start the luminescence reaction. The luminescence activity was measured for 10 seconds on a luminometer luminescencer-PSN AB2200 (manufactured by Atto Co., Ltd.). The luminescence activity was determined by repeating the measurement of luminescence activity described above twice and expressed in terms of the maximum luminescence intensity ($I_{max}$) of luminescence activity. The results are shown in TABLE 8.

It became clear that semi-synthetic BFP has a sufficient luciferase activity. That is, semi-synthetic BFP was able to prepare various fluorescent proteins having the fluorescence activity and luciferase activity.

TABLE 8

Luciferase activity of semi-synthetic BFP using coelenterazine as a substrate

| Coelenteramide analogue used to prepare semi-synthetic BFP | Luciferase activity of semi-synthetic BFP (%) |
|---|---|
| CTMD | 100.0 |
| 4a (TMD-344) | 80.0 |
| 4b (TMD-343) | 104.3 |
| 4c (TMD-347) | 79.5 |
| 4d (TMD-338) | 104.1 |
| 4e (TMD-339) | 75.2 |
| 4f (TMD-340) | 40.0 |
| 4g (TMD-345) | 69.1 |
| 4h (TMD-342) | 107.8 |
| 4i (TMD-346) | 89.8 |
| 4j (TMD-341) | 71.3 |
| 4k (TMD-373) | 39.0 |
| 4l (TMD-374) | 75.4 |
| 4m (TMD-375) | 42.2 |
| 4n (TMD-376) | 147.4 |
| 4o (TMD-377) | 119.5 |
| 4p (TMD-378) | 159.7 |
| 4r (TMD-379) | 100.4 |
| 4s (TMD-348) | 96.8 |
| 4t (TMD-349) | 90.0 |
| 4u (TMD-331) | 89.3 |
| 4v (TMD-332) | 96.8 |
| 4w (TMD-330) | 65.9 |
| 4x (TMD-365) | 122.9 |
| 4y (TMD-366) | 125.5 |
| 4z (TMD-368) | 121.6 |

[Sequence Listing Free Text]
[SEQ ID NO: 1]
This is the nucleotide sequence of native apoacquorin.
[SEQ ID NO: 2]
This is the amino acid sequence of native apoaequorin.
[SEQ ID NO: 3]
This shows the nucleotide sequence of native apoclytin-I.
[SEQ ID NO: 4]
This shows the amino acid sequence of native apoclytin-I.
[SEQ ID NO: 5]

This shows the nucleotide sequence of native apoclytin-II.
[SEQ ID NO: 6]
This shows the amino acid sequence of native apoclytin-II.
[SEQ ID NO: 7]
This shows the nucleotide sequence of native apomitrocomin.
[SEQ ID NO: 8]
This shows the amino acid sequence of native apomitrocomin.

[SEQ ID NO: 9]
This shows the nucleotide sequence of native apobelin.
[SEQ ID NO: 10]
This shows the amino acid sequence of native apobelin.
[SEQ ID NO: 11]
This shows the nucleotide sequence of native apobervoin.
[SEQ ID NO: 12]
This shows the amino acid sequence of native apobervoin.

The invention claimed is:

1. A compound represented by general formula (IV) below:

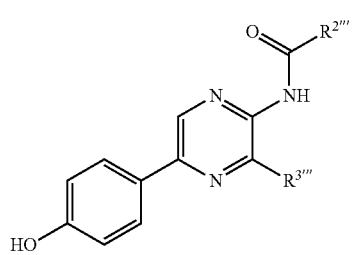

(IV)

wherein R²''' is a group selected from the groups below:

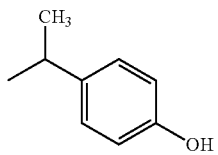 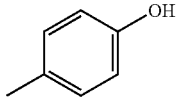

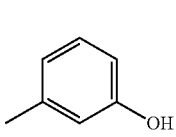 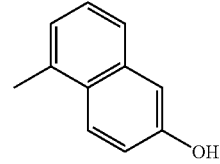

and R³''' hydrogen atom, bromine atom, a substituted or unsubstituted aryl, a substituted or unsubstituted arylalkyl, a substituted or unsubstituted arylalkenyl, a substituted or unsubstituted arylalkynyl, an alkyl which may optionally be substituted with an alicyclic group, an alkenyl which may optionally be substituted with an alicyclic group, an alkynyl which may optionally be substituted with an alicyclic group, an alicyclic group, or a heterocyclic group.

2. The compound according to claim 1, which is selected from the compounds below:

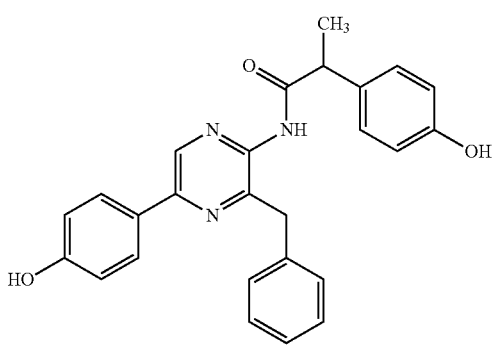

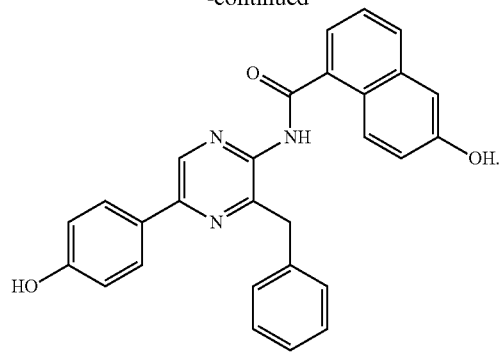

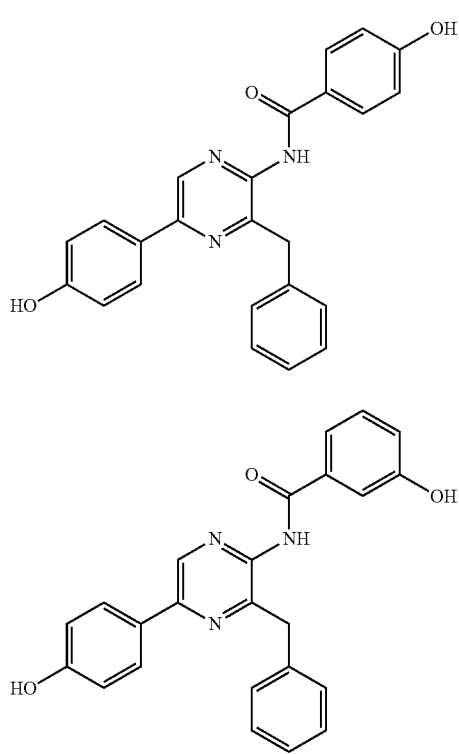

3. A fluorescent protein comprising the compound according to claim 1, an apoprotein of a calcium-binding photoprotein and a calcium ion or a divalent or trivalent ion replaceable for the calcium ion.

4. A method for producing a fluorescent protein, which comprises contacting the compound according to claim 1 with an apoprotein of a calcium-binding photoprotein in the presence of a calcium ion or a divalent or trivalent ion replaceable for the calcium ion to obtain the fluorescent protein.

5. A fluorescent protein comprising the compound according to claim 1 and an apoprotein of a calcium-binding photoprotein.

6. A method for producing a fluorescent protein, which comprises contacting the compound according to claim 1 with an apoprotein of a calcium-binding photoprotein in the presence of a chelating agent for removing a calcium ion or a divalent or trivalent ion replaceable for the calcium ion to obtain the fluorescent protein.

7. A method for producing a fluorescent protein, which comprises treating the fluorescent protein according to claim 3 with a chelating agent for removing a calcium ion or a divalent or trivalent ion replaceable for the calcium ion.

8. The method according to claim 6, wherein the contact is carried out in the presence of a reducing agent.

9. A method for analyzing a physiological function or enzyme activity, which comprises performing the fluorescence resonance energy transfer (FRET) method using the fluorescent protein according to claim 3 as an acceptor or a donor.

* * * * *